US008645115B2

(12) United States Patent
Collins et al.

(10) Patent No.: US 8,645,115 B2
(45) Date of Patent: Feb. 4, 2014

(54) MODULAR NUCLEIC ACID-BASED CIRCUITS FOR COUNTERS, BINARY OPERATIONS, MEMORY AND LOGIC

(75) Inventors: James J Collins, Newton, MA (US); Timothy Lu, Cambridge, MA (US)

(73) Assignees: Trustees of Boston University, Boston, MA (US); Massachusetts Institute of Technology, Cambridge, MA (US)

( * ) Notice: Subject to any disclaimer, the term of this patent is extended or adjusted under 35 U.S.C. 154(b) by 66 days.

(21) Appl. No.: 13/141,165

(22) PCT Filed: Dec. 22, 2009

(86) PCT No.: PCT/US2009/069288
§ 371 (c)(1),
(2), (4) Date: Sep. 19, 2011

(87) PCT Pub. No.: WO2010/075441
PCT Pub. Date: Jul. 1, 2010

(65) Prior Publication Data
US 2012/0003630 A1      Jan. 5, 2012

Related U.S. Application Data

(60) Provisional application No. 61/139,958, filed on Dec. 22, 2008.

(51) Int. Cl.
*G06G 7/48*      (2006.01)
*G06G 7/58*      (2006.01)
*G01N 33/48*     (2006.01)
*G01N 31/00*     (2006.01)

(52) U.S. Cl.
USPC ............... 703/11; 703/12; 702/19; 702/22

(58) Field of Classification Search
None
See application file for complete search history.

(56) References Cited

FOREIGN PATENT DOCUMENTS

| WO | 99/42929 A1 | 8/1999 |
| WO | 00/32748 A1 | 6/2000 |
| WO | 02/48195 A2 | 6/2002 |
| WO | 2008/051854 A2 | 6/2008 |

OTHER PUBLICATIONS

Friedland, A. et al., "Synthetic gene networks that count," Science, May 29, 2009, vol. 324, No. 5931, pp. 1199-1202.
Lu, T. et al., "Next-generation synthetic gene networks," Nature Biotechnology, Dec. 2009, vol. 27, No. 12, pp. 1139-1150.
Gardner, T. et al., "Construction of a genetic toggle switch in *Escherichia coli*," Nature, vol. 403, No. 6767, Jan. 20, 2000, pp. 339-342.

(Continued)

*Primary Examiner* — Larry D Riggs, II
(74) *Attorney, Agent, or Firm* — Nixon Peabody LLP; Ronald I. Eisenstein; Leena H. Karttunen Contarino

(57) ABSTRACT

We have created novel engineered genetic counter designs and methods of use thereof that utilize DNA recombinases to provide modular systems, termed single invertase memory modules (SIMMs), for encoding memory in cells and cellular systems. Our designs are easily extended to compute to high numbers, by utilizing the >100 known recombinases to create subsequent modules. Flexibility in our engineered genetic counter designs is provided by daisy-chaining individual modular components, i.e., SIMMs together. These modular components of the engineered genetic counters can be combined in other network topologies to create circuits that perform, amongst other things, logic and memory. Our novel engineered genetic counter designs allow for the maintenance of memory and provide the ability to count between discrete states by expressing the recombinases between their cognate recognition sites.

28 Claims, 16 Drawing Sheets

(56) References Cited

OTHER PUBLICATIONS

Elowitz, M. et al., "A synthetic oscillartory network of transcriptional regulators," Nature, vol. 403, No. 6767, Jan. 20, 2000, pp. 335-338.
Hasty, J. et al., "Engineered gene circuits," Nature, vol. 420, No. 6912, Nov. 14, 2002, pp. 224-230.
Sayut D. et al., "Engineering and applications of genetic circuits," Molecular Biosystems, vol. 3, No. 12, 2007, pp. 835-840.
Weber, W. et al., "Engineering of synthetic mammalian gene networks," Chemistry & Biology, vol. 16, No. 3, Mar. 27, 2009, pp. 287-297.
Ajo-Franklin et al., Genes Dev., 21:2271-2276 (2007). "Rational design of memory in eukaryotic cells.".
Anderson et al., J. Mol. Biol., 355:619-627 (2006). "Environmentally Controlled Invasion of Cancer Cells by Engineered Bacteria.".
Andrianantoandro et al., Molecular Systems Biology, doi:10.1038/msb4100073, (2006). "Synthetic biology: new engineering rules for an emerging discipline.".
Basu et al., PNAS, 101(17):6355-6360 (2004). "Spatiotemporal control of gene expression with pulse-generating networks.".
Basu et al., Nature, 434:1130-1134 (2005). "A synthetic multicellular system for programmed pattern formation.".
Bayer et al., Nature Biotechnology, 23(3):337-343 (2005). "Programmable ligand-controlled riboregulators of eukaryotic gene expression.".
Brock et al., Genes Dev., 13:1960-1696 (1999). "A cell-counting factor regulating structure size in Dictyostelium.".
Cormack et al., Gene, 173:33-38 (1996). "FACS-optimized mutants of the green fluorescent protein (GFP).".
Datsenko et al., PNAS, 97(12):6640-6645 (2000). "One-step inactivation of chromosomal genes in Escherichia coli K-12 using PCR products.".
Davidson et al., TRENDS in Biotechnology, 23(3):109-112 (2005). "Engineering regulatory RNAs.".
Deans et al., Cell, 130:363-372 (2007). "A Tunable Genetic Switch Based on RNAi and Repressor Proteins for Regulating Gene Expression in Mammalian Cells.".
Groth et al., J. Mol. Biol., 335:667-678 (2004). "Phage Integrases: Biology and Applications.".
Guido et al., Nature, 439:856-860 (2006). "A bottom-up approach to gene regulation.".
Ham et al., Biotechnology and Bioengineering, 94(1):DOI 10.1002/bit.20916 (2006). "A Tightly Regulated Inducible Expression System Utilizing the fim Inversion Recombination Switch.".
Ham et al., PLoS ONE, 3(7):e2815 (2008). "Design and Construction of a Double Inversion Recombination Switch for Heritable Sequential Genetic Memory.".
Haynes et al., Journal of Biological Engineering, 2:8 (2008). "Engineering bacteria to solve the Burnt Pancake Problem.".
Hoess et al., Proc. Natl. Acad. Sci., 79:3398-3402 (1982). "P1 site-specific recombination: Nucleotide sequence of the recombining sites.".
Hooshangi et al., PNAS, 102(10):3581-3586 (2005). "Ultrasensitivity and noise propagation in a synthetic transcriptional cascade.".
Isaacs et al., Nature Biotechnology, 24(5):545-554 (2006). "RNA synthetic biology.".
Kilby et al., TIG, 9(12):413-421 (1993). "Site-specific recombinases: tools for genome engineering.".
Kobayashi et al., PNAS, 101(22):8414-8419 (2004). "Programmable cells: Interfacing natural and engineered gene networks.".
Levskaya et al., Nature, 438:441-442 (2005). "Engineering *Escherichia coli* to see light.".
Lu et al., PNAS, 104(27):11197-11202 (2007). "Dispersing biofilms with engineered enzymatic bacteriophage.".
Mandal et al., Nature Reviews: Molecular Cell Biology, 5:451-463 (2004). "Gene Regulation by Riboswitches.".
Marcand et al., Science, 275:986-990 (1997). "A Protein-Counting Mechanism for Telomere Length Regulation in Yeast.".
No et al., Proc. Natl. Acad. Sci., 93:3346-3351 (1996). "Ecdysone-inducible gene expression in mammalian cells and transgenic mice.".
Pedraza et al., Science, 307(5717):1965-1969 (2005). "Noise Propagation in Gene Networks.".
Pfleger et al., Nature Biotechnology, 24(8):1027-1032 (2006). "Combinatorial engineering of intergenic regions in operons tunes expression of multiple genes.".
Rackham et al., Nature Chemical Biology, 1(3):159-166 (2005). "A network of orthogonal ribosome-mRNA pairs.".
Ray et al., Mol. Cell. Biol., 19(1):31-45 (1999). "The Yeast Telomere Length Counting Machinery Is Sensitive to Sequences at the Telomere-Nontelomere Junction.".
Rinaudo et al., Nature Biotechnology, 25(7):795-801 (2007). "A universal RNAi-based logic evaluator that operates in mammalian cells.".
Roostalu et al., Bmc Microbiology, 8:68 (2008). "Cell division in *Escherichia coli* cultures monitored at single cell resolution.".
Salis et al., Nature Biotechnology, 27(10):946-950 with Supplementary Information (2009). "Automated design of synthetic ribosome binding sites to control protein expression.".
Seelig et al., Science, 314:1585-1588 (2006). "Enzyme-Free Nucleic Acid Logic Circuits.".
Yokobayashi et al., PNAS, 99(26):16587-16591 (2002). "Directed evolution of a genetic circuit.".

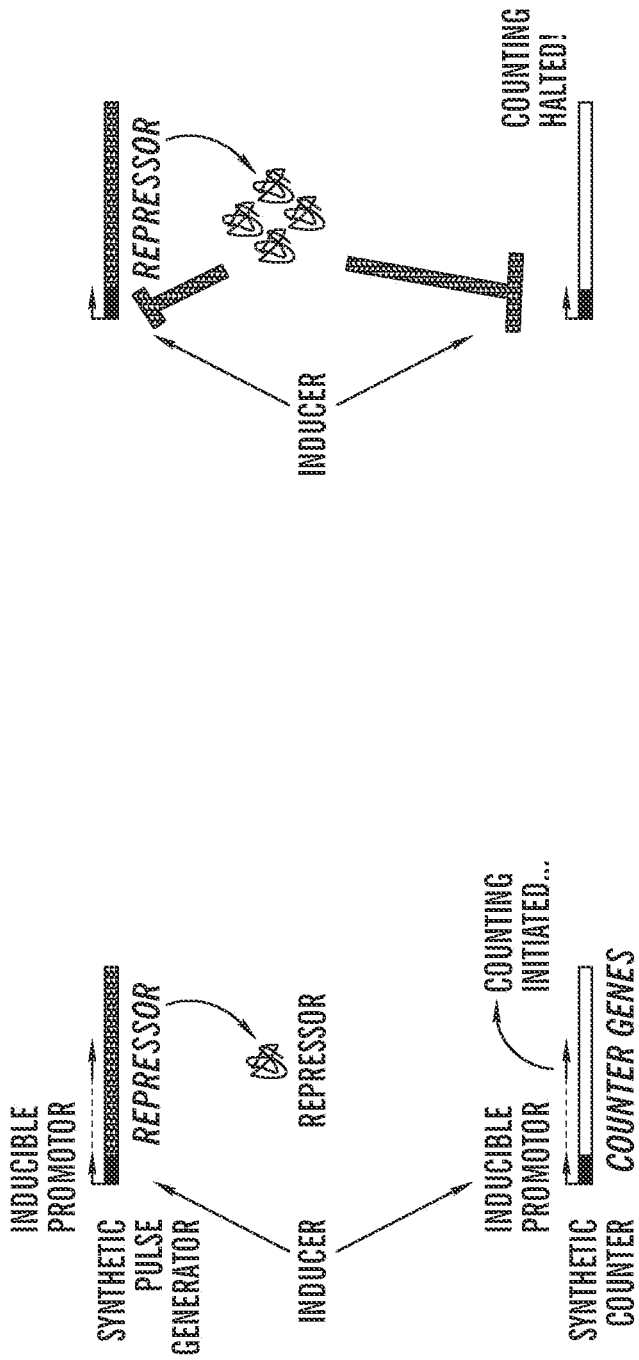

it becomes necessary to have different "parts" for every operation of the circuit, even for relatively elementary operations. Also, implementing all the parts necessary for such operations into a cell can place large energetic requirements on a cell. Finally, in such protein-based systems the various "states" of the circuit are encoded in transient chemical concentrations and cannot be maintained after cell death and cannot be easily transferred from one cell to another.

MODULAR NUCLEIC ACID-BASED CIRCUITS FOR COUNTERS, BINARY OPERATIONS, MEMORY AND LOGIC

CROSS REFERENCE TO RELATED APPLICATIONS

This application is a 35 U.S.C. §371 National Phase Entry Application of International Application No. PCT/US2009/069288 filed Dec. 22, 2009, which designates the United States, and which claims benefit under 35 U.S.C. §119(e) of U.S. Provisional Patent Application Ser. No. 61/139,958 filed on Dec. 22, 2008, the contents of which are incorporated herein in their entirety by reference.

GOVERNMENT SUPPORT

This invention was made with Government Support under Contract No. OD003644 awarded by the National Institutes of Health. The Government has certain rights in the invention.

SEQUENCE LISTING

The instant application contains a Sequence Listing which has been submitted via EFS-Web and is hereby incorporated by reference in its entirety. Said ASCII copy, created on Dec. 17, 2009, is named 70158606.txt, and is 280,108 bytes in size.

FIELD OF THE INVENTION

The present invention relates to engineered genetic counters and methods for uses thereof.

BACKGROUND OF THE INVENTION

Circuits and circuit designs are typically based on electrical and electronic components and properties and are useful for a variety of functions. An electrical circuit is an interconnection of electrical elements, such as resistors, inductors, capacitors, transmission lines, voltage sources, current sources, and switches, and when it also contains active electronic components is known as an electronic circuit. Electronic circuits can usually be categorized as analog, digital or mixed-signal (a combination of analog and digital) electronic circuits. The basic units of analog circuits are passive (resistors, capacitors, inductors, and memristors) and active (independent power sources and dependent power sources). Components such as transistors may be represented by a model containing passive components and dependent sources. In digital electronic circuits, electric signals take on discrete values, which are not dependent upon time, to represent logical and numeric values. These values represent the information that is being processed. The transistor is one of the primary components used in discrete circuits, and combinations of these can be used to create logic gates. These logic gates may then be used in combination to create a desired output from an input.

In contrast, while some biological circuits have been developed, the utility of these circuits has been minimal, and it has been difficult to replicate the versatility and flexibility of standard electronic circuits. Such biological circuits have primarily utilized protein components to represent the state of memory of the cell. Such protein-based biological circuits are difficult to maintain and are unstable, as they require continuous protein expression. When compared to electronic circuits, such protein-based systems resemble DRAM (dynamic random access memory), which encodes volatile memory and requires power to maintain its state. Furthermore, such protein-based systems are not scaleable for use in biological circuits. Unlike electronic circuits, in which wires between physically separated components allow for spatial addressing, it is generally not possible to reuse the same biological component in protein-based systems. Hence, it becomes necessary to have different "parts" for every operation of the circuit, even for relatively elementary operations. Also, implementing all the parts necessary for such operations into a cell can place large energetic requirements on a cell. Finally, in such protein-based systems the various "states" of the circuit are encoded in transient chemical concentrations and cannot be maintained after cell death and cannot be easily transferred from one cell to another.

There is hence interest in the development and design of modular biological parts for the use in the development of biological circuitry. The development of biological systems in which the output depends both on the current inputs, as well as the input history, is a key requisite for complicated computation and information storage. Such biological circuitry can be used for a variety of purposes, including but not limited to, detection of cancers and toxins, counting of events, the design of biological computers, and the coding and reading of DNA fingerprints for engineered organisms.

SUMMARY OF THE INVENTION

We have created novel engineered genetic counter designs and methods of use thereof that utilize DNA recombinases to provide modular systems, termed single invertase memory modules (SIMMs), for encoding memory in cells and cellular systems. Our designs are easily extended to compute to high numbers, by utilizing the >100 known recombinases to create subsequent modules. Flexibility in our engineered genetic counter designs is provided by daisy-chaining individual modular components, i.e., SIMMs together. These modular components of the engineered genetic counters can be combined in other network topologies to create circuits that perform, amongst other things, logic and memory.

Provided herein are modules that constitute a stable switchable bit of memory, termed as a Single Invertase Memory Module (SIMM), and engineered genetic counters comprising such SIMMs. One key improvement of the engineered genetic counters described herein over other described synthetic biological systems is the lack of both "leakiness" and mixtures of inverted and non-inverted states that is caused by expressing the recombinases independently from their cognate recognition sites. Thus, our novel engineered genetic counter designs allow for the maintenance of memory and provide the ability to count between discrete states by expressing the recombinases between their cognate recognition sites. Such SIMMs can further comprise additional components to enhance the ability to regulate and control the activity of a SIMM, such as ribosome binding sites, transcriptional terminator sequences, and protein degradation tag sequences.

Provided herein are engineered genetic counter designs and their uses in cellular and non-cellular systems. These engineered genetic counters are extensible, highly modular and can function with a variety of combinations of various component parts, such as inducible promoters and recombinases. Depending on the combinations of promoters used in the engineered genetic modules described herein, an engineered genetic counter can be used with a single inducer or with multiple inducers. Depending on the type of inducible promoters utilized, the engineered genetic circuits described herein can be used to enumerate physiological events and stimuli, such as activation of gene networks or exposure to nutrients, toxins, or metabolites.

The single inducer engineered genetic counters described herein can be used for counting multiple independent exposures to a single type of inducer, such as arabinose. Thus, such single inducer counters can be used to detect multiple exposures to a single biological agent or inducer, such as a toxin. Such single inducer engineered genetic counters comprise an inducible promoter sequence ($iP_1$), at least one SIMM, and an output gene sequence (OP). In such single inducer engineered genetic counters, the inducible promoter of the counter and the inducible promoters of each SIMM respond to the same inducing or biological agent.

The multiple inducer engineered genetic counters described herein can be used to distinguish multiple input signals occurring in a specific order, such that output gene expression occurs only when a certain number of signals in a specific order are received by the counter. Such multiple inducer engineered genetic counters comprise an inducible promoter sequence ($iP_1$), at least one SIMM, and an output gene sequence (OP). In such multiple inducer engineered genetic counters, at least two inducible promoters in the counter respond to different input signals or biological agents. Further flexibility in the design of such counters can be provided by adding additional components such as ribosome binding sites, transcriptional terminator sequences, and protein degradation tag sequences. For some uses, the counters can further comprise an output gene sequence within a SIMM, thus allowing the regulation of individual output genes within a SIMM based on the state of the SIMM and the activity of the recombinase encoded by that SIMM.

The engineered genetic counters described herein can further be used in cellular or non-cellular systems to allow counting of events or input signals within such systems. The input signal can be an external event or input, such as the presence of a biological agent in the media or environment surrounding the cellular or non-cellular system. The input signal or event can also occur within the cellular or non-cellular system, such that the engineered genetic counter is counting events within the cellular or non-cellular system, such as the activation of certain genes or proteins, or the number of divisions occurring within a cellular or non-cellular system. Examples of non-cellular systems include, but are not limited to, phages, viruses, cell extracts, and can be in, for example, a test tube or cell culture dish. Accordingly, described herein are methods of counting events or inputs occurring within or to a cellular or non-cellular system. Such methods comprise, for example, introducing an engineered genetic counter described herein into a cellular system using a vector, such as a bacterial artificial chromosome (BAC). The engineered genetic counters can also be introduced by directly integrating the nucleic acid sequence encoding the counter into chromosomes of a cellular system.

BRIEF DESCRIPTION OF THE DRAWINGS

FIG. 1 depicts a single-inducer DIC 3-Counter construct design and results.

FIG. 2 depicts a multiple-inducer DIC 3-Counter construct design and results.

FIG. 6 depicts a single-inducer DIC 2-Counter construct design and results.

FIG. 9 depicts that switching times for each SIMM stage in the multiple-inducer DIC 3-Counter were examined by varying the length of exposure to either anhydrotetracycline or arabinose while holding all other inputs constant (aTc followed by Ara followed by IPTG). When not being varied, aTc and Ara pulses were 18 hours in duration and IPTG pulses were 12 hours in duration. The last input to the multiple-inducer DIC 3-Counter, IPTG, does not drive an invertase stage and directly induces the transcriptional GFP output of the system.

FIG. 10 depicts model predictions of the fluorescence output of n-node RTC Counters in response to n, n−1, and n−2 arabinose pulses.

FIG. 11 depicts a synthetic pulse generator that can work with a broad range of engineered nucleic acid-based circuits to provide pulse generation and edge detection. FIG. 11A shows that upon addition of an inducer, the synthetic counter circuit starts to transcribe its genes, and at the same time, the synthetic pulse generator produces a repressor protein. As illustrated in FIG. 11B, once enough repressor protein is produced by the synthetic pulse generator, transcription from the inducible promoter is shut down even in the presence of an inducer.

DETAILED DESCRIPTION

Figure 1A:
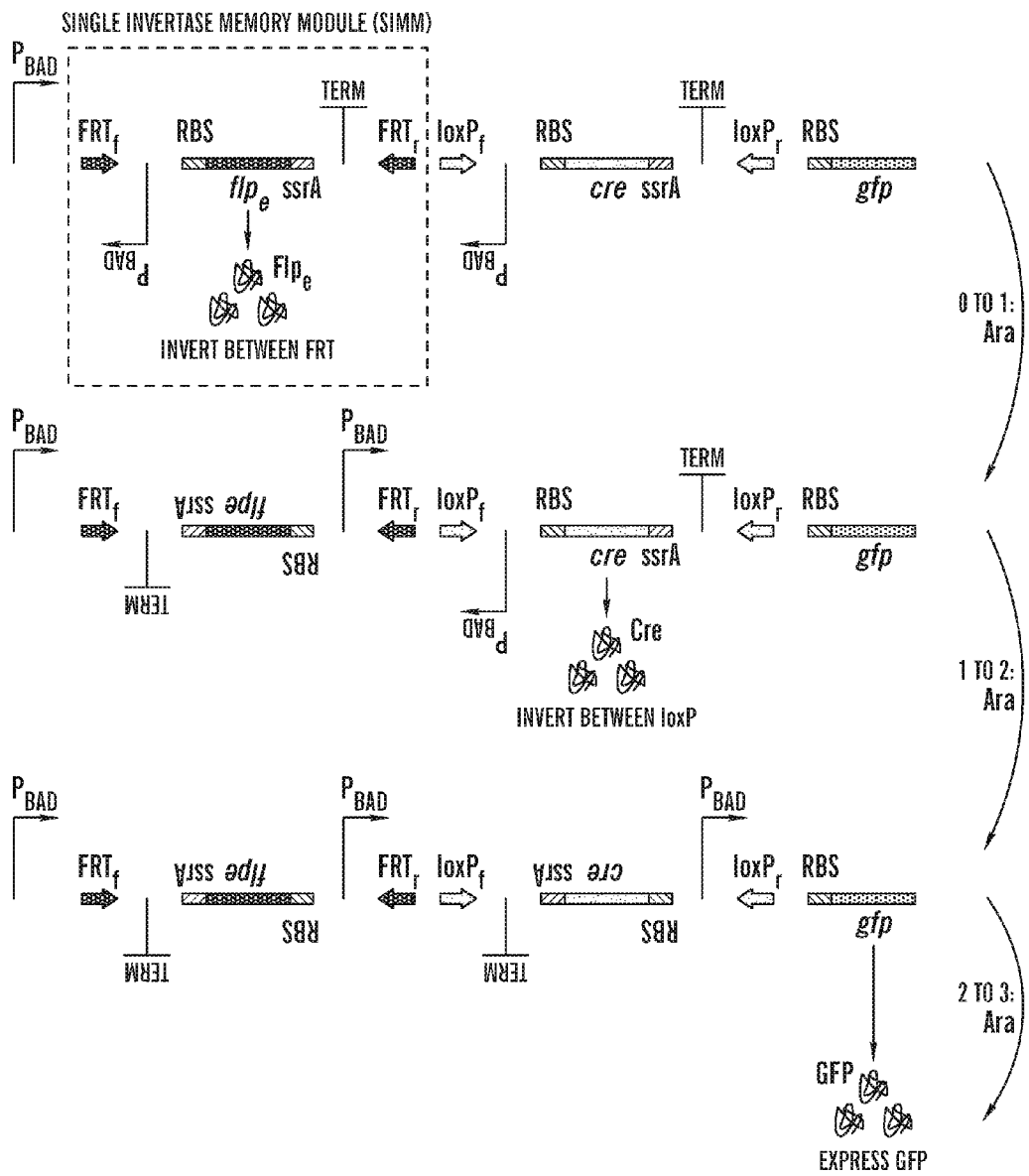
FIG. 1A shows that a single-inducer DIC 3-Counter is built by cascading SIMMs.

We have discovered a nucleic acid-based circuit utilizing DNA recombinases that provides a modular system for encoding memory in cells. Our design is easily extended to compute to high numbers, by utilizing the >100 known recombinases to create subsequent modules. Flexibility in our nucleic acid-based circuit designs is provided by daisy-chaining individual modular components together and utilizing combinations thereof. These modular components of the engineered nucleic acid-based circuits or engineered genetic circuits are combined in other network topologies to create circuits that perform, amongst other things, logic and memory.

While researchers in synthetic biology have developed engineered biological devices that have interesting and well-modeled characteristics (E. Andrianantoandro, Mol Syst Biol 2, 2006.0028 (2006)), many problems exist in the utility of these devices for performing complex computations and information storage. We have discovered that operations on DNA can change the state of a biological circuit in a discrete, Boolean-like fashion, and such states can be maintained without constant energetic input and can persist after cell death. Since the state is encoded in the DNA, it can be inherited and can be transferred through mechanisms of inter-cell DNA transfer, such as conjugation.

We designed our engineered nucleic acid-based or genetic circuits using nucleic acid-based switches instead of the traditionally protein-based systems for several reasons. One example of protein-based memory that can be cascaded to create a counter is the toggle switch (T. S. Gardner, Nature 403, 339 (2000)). The toggle switch requires well-characterized repressors to work properly and is thus much more complicated and more cumbersome than our design, as presented herein. Each of the individual modules of our engineered nucleic acid-based or genetic circuits requires only a single recombinase, whereas protein-based switches utilize two proteins (T. S. Gardner, Nature 403, 339 (2000)). Our nucleic acid-based circuit or engineered genetic circuit designs can be extended readily in a modular fashion with currently known components. Furthermore, our nucleic acid-based system can be used for long periods of time without needing to maintain active transcription and translation of the circuit because our circuit is stable in the absence of inducers. In one embodiment, the engineered nucleic acid-based circuit does not include a toggle switch.

Our invention provides, in part, core modules for engineered nucleic acid-based circuits that can be used for a variety of synthetic circuits and in a modular way to construct memory units. Examples of such synthetic circuits include, but are not limited to, counters, memory, adders, etc. The strength of our modular circuit designs lie in their simplicity, modularity, and extensibility with different recombinase proteins. Therefore, such circuit designs can be used in different means to create basic digital logic in cells.

In one embodiment, the individual modular units used in a genetic counter can be decoupled to each represent a single bit in an engineered memory system rather than a counter. In one embodiment, a pulse generator for the generation of transcriptional pulses is provided that is readily designed by modifying individual modular units to perform inversion events continuously. In some embodiments, the engineered nucleic acid-based circuits and engineered genetic counters described herein essentially comprise AND gates that enforce a particular sequence of inputs. In other embodiments, the design is a cis-based counting system that requires physical proximity of individual counting units for counting transitions. In other embodiments, further functionality, including digital-logic-based computation, is incorporated by adding trans-acting components for coupling to other circuits (K. Rinaudo, Nat Biotechnol 25, 795 (2007)). In other embodiments, the engineered nucleic acid-based circuits can be coupled to quorum-sensing circuits to create a consensus-based counting system.

The ability to count inputs in individual cells is useful for engineering biological organisms and performing basic scientific experiments. Accordingly, described herein are uses of engineered genetic counters in cellular and non-cellular systems, and methods of counting events in cellular and non-cellular systems through the introduction of engineered genetic counters. In a non-limiting example, engineered bacteria can be designed to count exposures to environmental agents, such as toxins or pollutants, and trigger an output, such as population control, only when a discrete threshold has been reached. A yeast cell-cycle counter has been developed to facilitate cell-cycle research (C. M. Ajo-Franklin, Genes Dev 21, 2271 (2007)). Mammalian cells that carry counters can help elucidate the sequence and number of mutations needed to produce cancer cells.

Recombinases and Recombination Recognition Sequences

Described herein are modules that constitute a stable switchable bit of memory, termed as a Single Invertase Memory Module (SIMM), and engineered genetic counters comprising such SIMMs. An improvement of the engineered nucleic acid-based circuits described herein over other described synthetic biological systems is the lack of both "leakiness" and mixtures of inverted and non-inverted states that is caused by expressing the recombinases independently from their cognate recognition sites. Thus, our invention allows for the maintenance of memory and the ability to count between discrete states by expressing the recombinases between their cognate recognition sites.

The recombinases in the engineered nucleic acid-based circuits and engineered genetic counters described herein, are expressed between their cognate recognition sites recombinase recognition site$_{for}$-recombinase-recombinase recognition site$_{rev}$). As a result, upon recombinase expression following activation of an upstream promoter, the recombinase causes a single inversion of the DNA between the cognate recognition sites, including its own DNA sequence (i.e., recombinase recognition site$_{for}$-inverted recombinase-recombinase recognition site$_{rev}$). Any further transcription from the upstream promoter yields antisense RNA of the recombinase gene rather then sense RNA, and therefore no further recombinase protein will be produced. Thus, the inversion event is discrete and stable and does not result in a mixture of inverted and non-inverted states.

As described herein, the engineered nucleic acid-based circuits and engineered genetic counters can use any recombinase for encoding memory, rather than only unidirectional recombinases, allowing greater flexibility and practicality. In some embodiments, the recombinase is encoded between its cognate recombinase recognition sequences. In some embodiments, the recombinase is encoded outside of its cognate recombinase recognition sequences. In such embodiments, where the recombinase is encoded outside of its cognate recombinase recognition sequences, the engineered nucleic acid-based circuit or engineered genetic counter can be used, for example, as a waveform generator or an analog-to-digital converter, where the inputs that lead to recombinase expression results in constant inversion between the recombinase recognition sequences and can be used to generate pulses of output products, such as a fluorescent protein.

The advantages of the use of recombinases that mediate site-specific inversion for use in the various aspects of the invention are the binary dynamics, the sensitivity of the output, the efficiency of DNA usage, and the persistence of the DNA modification. A "recombinase", as defined herein, is a site-specific enzyme that recognizes short DNA sequence(s), which are typically between about 30 bp and 40 bp, and mediates the recombination between these recombinase recognition sequences that results in the excision, integration, inversion, or exchange of DNA fragments.

Recombinases can be classified into two distinct families, the integrase and invertase/resolvase families, based on distinct biochemical properties. Members of the integrase family cleave one strand of each of the two DNA molecules involved, then exchange this strand, and subsequently cleave the second DNA strand. Integrase family recombinases use a conserved tyrosine residue to establish a transient covalent bond between the recombinase and the target DNA. Members of the invertase/resolvase family of recombinases cleave all 4 DNA strands and then exchange them, and initiate DNA cleavage by utilizing a serine residue as the catalytic residue. Recombinases have been used for numerous standard biological applications, including the creation of gene knockouts and the solving of sorting problems (N. J. Kilby, Trends Genet. 9, 413 (December, 1993); K. A. Haynes, J Biol Eng 2, 8 (2008); T. S. Ham, Biotechnol Bioeng 94, 1 (2006); K. A. Datsenko, Proc Natl Acad Sci USA 97, 6640 (2000)).

Inversion recombination happens between two short inverted repeated DNA sequences, typically less than 30 bp long. The recombinases bind to these inverted repeated sequences, which are specific to each recombinase, and are defined herein as "recombinase recognition sequences" or "recombinase recognition sites." Thus, as used herein, a recombinase is "specific for" a recombinase recognition sequence when the recombinase can mediate an inversion between the inverted repeat DNA sequences. As used herein, a recombinase can also be said to recognize its "cognate recombinase recognition sites." A DNA loop formation, assisted by DNA bending proteins, brings the two repeat sequences together, at which point DNA cleavage and ligation occur. This reaction is ATP independent and requires supercoiled DNA. The end result of such an inversion recombination event is that the stretch of DNA between the repeated site inverts, i.e., the stretch of DNA reverses orientation, such that what was the coding strand is now the non-coding strand and vice versa. In such reactions, the DNA is conserved with no net gain or no loss of DNA.

The recombinases provided herein are not meant to be an exclusive listing. Other examples of recombinases that are useful in the modules and engineered genetic counters described herein are known to those of skill in the art, and furthermore, any new recombinase that is discovered or generated can be used in the different embodiments of the invention.

In some embodiments, the recombinase comprises the sequence of Cre recombinase of Pubmed Gene ID #277747, and the corresponding loxP recombinase recognition sequences comprise the sequences of ATAACTTCGTATA GCATACAT TATACGAAGTTAT (SEQ ID NO:1) or ATAACTTCGTATA ATGTATGC TATACGAAGTTAT (SEQ ID NO:2).

In some embodiments, the recombinase is Flp recombinase comprising the sequences of GenBank ID U46493 or NC_001398. In another embodiment, the recombinase is an enhanced Flp recombinase that comprises the sequence:

```
                                      (SEQ ID NO: 3)
ATGAGCCAATTTGATATATTATGTAAAACACCACCTAAGGTCCTGGTTCG

TCAGTTTGTGGAAAGGTTTGAAAGACCTTCAGGGGAAAAAATAGCATCAT

GTGCTGCTGAACTAACCTATTTATGTTGGATGATTACTCATAACGGAACA

GCAATCAAGAGAGCCACATTCATGAGCTATAATACTATCATAAGCAATTC

GCTGAGTTTCGATATTGTCAACAAATCACTCCAGTTTAAATACAAGACGC

AAAAAGCAACAATTCTGGAAGCCTCATTAAAGAAATTAATTCCTGCTTGG

GAATTTACAATTATTCCTTACAATGGACAAAAACATCAATCTGATATCAC

TGATATTGTAAGTAGTTTGCAATTACAGTTCGAATCATCGGAAGAAGCAG

ATAAGGGAAATAGCCACAGTAAAAAAATGCTTAAAGCACTTCTAAGTGAG

GGTGAAAGCATCTGGGAGATCACTGAGAAAATACTAAATTCGTTTGAGT

ATACCTCGAGATTTACAAAAACAAAAACTTTATACCAATTCCTCTTCCTA

GCTACTTTCATCAATTGTGGAAGATTCAGCGATATTAAGAACGTTGATC

CGAAATCATTTAAATTAGTCCAAAATAAGTATCTGGGAGTAATAATCCA

GTGTTTAGTGACAGAGACAAAGACAAGCGTTAGTAGGCACATATACTT

CTTTAGCGCAAGGGGTAGGATCGATCCACTTGTATATTTGGATGAATTT

TTGAGGAACTCTGAACCAGTCCTAAAACGAGTAAATAGGACCGGCAA

TTCTTCAAGCAACAAACAGGAATACCAATTATTAAAAGATAACTTAGTC

AGATCGTACAACAAGGCTTTGAAGAAAAATGCGCCTTATCCAATCTTT

GCTATAAAGAATGGCCCAAAATCTCACATTGGAAGACATTTGATGAC

CTCATTTCTGTCAATGAAGGGCCTAACGGAGTTGACTAATGTTGTGGG

AAATTGGAGCGATAAGCGTGCTTCTGCCGTGGCCAGGACAACGTATA
```

-continued
CTCATCAGATAACAGCAATACCTGATCACTACTTCGCACTAGTTTCTC

GGTACTATGCATATGATCCAATATCAAAGGAAATGATAGCATTGAAGG

ATGAGACTAATCCAATTGAGGAGTGGCAGCATATAGAACAGCTAAAG

GGTAGTGCTGAAGGAAGCATACGATACCCCGCATGGAATGGGATAA

TATCACAGGAGGTACTAGACTACCTTTCATCCTACATAAATAGACGC

ATATAA

The corresponding recombinase recognition sequences for the Flp and enhanced Flp recombinases comprise FRT sites with sequences comprising (SEQ ID NO: 4)
GAAGTTCCTATTC C GAAGTTCCTATTC TCTAGAAA GTATAGGAACT

TC.

In some embodiments, minimal FRT recombinase recognition sites are used, comprising the sequence of

GAAGTTCCTATTC TCTAGAAA GTATAGGAACTTC (SEQ ID NO: 5)

In some embodiments, the recombinase is R recombinase comprising the sequence of GenBank ID # X02398 and the corresponding recombinase recognition sequence comprising

TTGATGAAAGAA TACGTTA TTCTTTCATCAA. (SEQ ID NO: 6)

In some embodiments, the recombinase comprises the bidirectional FimB recombinase of GeneID: 948832 (SEQ ID NO: 9) and the corresponding recombinase recognition sequences comprise (SEQ ID NO: 7)
AATACAAGACAATTGGGGCCAAACTGTCCATATCAT
and (SEQ ID NO: 8)
CTCTATGAGTCAAAATGGCCCCAAATGTTTCATCTTTTG.

In some embodiments, the recombinase is the unidirectional FimE recombinase of GeneID: 948836 (SEQ ID NO: 10) and the corresponding recombinase recognition sequences comprise SEQ ID NO: 7 and SEQ ID NO: 8.

In some embodiments, the recombinase is an Int recombinase. In some embodiments, the Int recombinase comprises a sequence that encodes for an Int recombinase selected from the group consisting of intE, HP1 Int, and HK022 Int.

In some embodiments, the recombinase is the XerC/XerD recombinase comprising the sequence of GeneID: 5387246 (SEQ ID NO: 11) and the corresponding recombinase recognition sequences comprise cer and dif.

In one embodiment, the recombinase is *Salmonella* Hin recombinase comprising the sequence of GeneID: 1254295 (SEQ ID NO: 12) and the corresponding recombinase recognition sequences comprise hixL and hixR.

The Cre protein has been purified to homogeneity (Abremski et al. (1984) J. Mol. Biol. 259:1509) and the cre gene has been cloned and expressed in a variety of host cells (Abremski et al. (1983)). Purified Cre protein is available from a number of suppliers (e.g., Stratagene, Novagen and New England Nuclear/Du Pont). Cre catalyzes the cleavage of the lox site within the spacer region and creates a six base-pair staggered cut (Hoess and Abremski (1985) J. Mol. Biol. 181: 351). The two 13 bp inverted repeat domains of the lox site represent binding sites for the Cre protein. If two lox sites differ in their spacer regions in such a manner that the overhanging ends of the cleaved DNA cannot reanneal with one another, Cre cannot efficiently catalyze a recombination event using the two different lox sites. For example, it has been reported that Cre cannot recombine (at least not efficiently) a loxP site and a loxP511 site; these two lox sites differ in the spacer region. Two lox sites which differ due to variations in the binding sites (i.e., the 13 bp inverted repeats) may be recombined by Cre provided that Cre can bind to each of the variant binding sites; the efficiency of the reaction between two different lox sites (varying in the binding sites) may be less efficient that between two lox sites having the same sequence (the efficiency will depend on the degree and the location of the variations in the binding sites). For example, the loxC2 site can be efficiently recombined with the loxP site; these two lox sites differ by a single nucleotide in the left binding site.

In addition to the foregoing examples of sequences that the Cre protein recognizes, Cre also recognizes a number of variant or mutant lox sites (variant relative to the loxP sequence), including the loxB, loxL, loxR, loxA86, and lox.DELTA.117 sites which are found in the E. coli chromosome (Hoess et al. (1982)). Other variant lox sites include loxP511 (5'ATAACTTCGTATAGTATACATTATAC-GAAGTTAT-3' (SEQ ID NO: 13)); Hoess et al. (1986), supra), loxC2 (5'-ACAAC TTCGTATAATGTATGCTATAC-GAAGTTAT-3' (SEQ ID NO: 14); U.S. Pat. No. 4,959,317), lox66 (5'CTTGGTATAGCATACATTATACGAACGGTA-3') (SEQ ID NO: 15), lox 71 (5'GTTCGTATACGATACAT-TATACGAAGTTAT 3') (SEQ ID NO: 16), and lox BBa_J61046 (5'CTTCGTATAATGTATGCTATACGAAGT-TAT3') (SEQ ID NO: 17).

Other alternative site-specific recombinases include: 1) the FLP recombinase of the 2 pi plasmid of *Saccharomyces cerevisiae* (Cox (1983), Proc. Natl. Acad. Sci. USA 80:4223) which recognize the frt site which, like the loxP site, comprises two 13 bp inverted repeats separated by an 8 bp spacer (5'-GAAGTTCCTATTCTCTAGAAAGT ATAG-GAACTTC-3' (SEQ ID NO: 18)). The FLP gene has been cloned and expressed in *E. coli* (Cox, supra) and in mammalian cells (PCT International Patent Application PCT/US92/01899, Publication No.: WO 92/15694, the disclosure of which is herein incorporated by reference) and has been purified (Meyer-Lean et al. (1987) Nucleic Acids Res. 15:6469; Babineau et al (1985) J. Biol. Chem. 260:12313; Gronostajski and Sadowski (1985) J. Biol. Chem. 260:12328); 2) the integrase of *Streptomyces* phage .PHI.C31 that carries out efficient recombination between the attP site of the phage genome and the attB site of the host chromosome (Groth et al., 2000 Proc. Natl. Acad. Sci. USA, 97: 5995); 3) the Int recombinase of bacteriophage lambda (lambda-int/attP) (with or without Xis) which recognizes att sites (Weisberg et al. In: Lambda II, supra, pp. 211-250); 4) the xerC and xerD recombinases of *E. coli* which together form a recombinase that recognizes the 28 bp dif site (Leslie and Sherratt (1995) EMBO J. 14:1561); 5) the Int protein from the conjugative transposon Tn916 (Lu and Churchward (1994) EMBO J. 13:1541); 6) TpnI and the β-lactamase transposons (Levesque (1990) J. Bacteriol. 172:3745); 7) the Tn3 resolvase (Flanagan et al. (1989) J. Mol. Biol. 206:295 and Stark et al. (1989) Cell 58:779); 8) the SpoIVC recombinase of *Bacillus subtilis* (Sato et al. J. Bacteriol. 172:1092); 9) the Hin recombinase (Galsgow et al. (1989) J. Biol. Chem. 264: 10072); 10) the Cin recombinase (Hafter et al. (1988) EMBO J. 7:3991); 11) the immunoglobulin recombinases (Malynn et al. Cell (1988) 54:453); and 12) the FIMB and FIME recombinases (Blomfield et al., 1997 Mol. Microbiol. 23:705).

In the natural *Salmonella* system, the Hin DNA recombinase (BBa_J31000, BBa_J31001) catalyzes an inversion reaction that regulates the expression of alternative flagellin genes by switching the orientation of a promoter located on a 1 kb invertible DNA segment. The asymmetrical palindromic sequences hixL and hixR flank the invertible DNA segment and serve as the recognition sites for cleavage and strand exchange. A ~70 bp cis-acting recombinational enhancer (RE) increases efficiency of protein-DNA complex formation. In some embodiments, rather than hixL and hixR, hixC (BBa_J44000), a composite 26 bp symmetrical hix site that shows higher binding affinity for Hin and a 16-fold slower inversion rate than wild type sites hixL and hixR can be used. In addition, a modified Hin/hix DNA recombination system can be used in vivo to manipulate at least two adjacent hixC-flanked DNA segments. Hin recombinase fused to a C-terminus LVA degradation tag (BBa_J31001) and hixC (BBa_J44000) are sufficient for DNA inversion activity. Exemplary sequences for the recombinational enhancer and modified Hin recombinase recognition sequences are provided below:

chromosome. This excision reaction recombines attL with attR to precisely restore the attP and attB sites on the circular λ and *E. coli* DNAs. The phage-encoded λ integrase protein (Int), a tyrosine recombinase, splices together bacterial and phage attachment sites. Int is required for both integration and excision of the λ prophage.

λ recombination has a strong directional bias in response to environmental conditions. Accessory factors, whose expression levels change in response to host physiology, control the action of Int and determine whether the phage genome will remain integrated or be excised. Int has two DNA-binding domains: a C-terminal domain, consisting of a catalytic domain and a core-binding (CB) domain, that interacts with the core recombining sites and an N-terminal domain (N-domain) that recognizes the regulatory arm DNA sites [5]. The heterobivalent Int molecules bridge distant core and arm sites with the help of accessory proteins, such as integration host factor (IHF), which bend the DNA at intervening sites, and appose arm and core sequences for interaction with the Int recombinase. Five arm DNA sites in the regions flanking the core of attP are differentially occupied during integration and excision reactions. The integration products attL and attR cannot revert back to attP and attB without assistance from the phage-encoded factor X is, which bends DNA on its own

TABLE 1

| Name | Description | Sequence | Length |
|---|---|---|---|
| BBa_J3101 | SEQ ID NO: 19 Recombinational Enhancer (RE) for Hin/Hix inverting | . . . ctttctagtgcaaattgtgaccgcattttg | 77 |
| BBa_J44000 | SEQ ID NO: 20 hixC binding site for *Salmonella typhimurium* Hin recombinase | ttatcaaaaaccatggtttttgataa | 26 |

TABLE 2

| Name | Protein | Description | Direction | KEGG | UniProt | E.C. | Length |
|---|---|---|---|---|---|---|---|
| BBa_J31001 | Hin-LVA | DNA invertase Hin tagged with LVA | | stm: STM2772 | P03013 | none | 612 |
| BBa_J31000 | Hin | DNA-invertase Hin from *Salmonella typhimurium* | | stm: STM2772 | P03013 | none | 573 |

Bacteriophage λ has long served as a model system for studies of regulated site-specific recombination. In conditions favorable for bacterial growth, the phage genome is inserted into the *Escherichia coli* genome by an 'integrative' recombination reaction, which takes place between DNA attachment sites called attP and attB in the phage and bacterial genomes, respectively. As a result, the integrated λ DNA is bounded by hybrid attachment sites, termed attL and attR. In response to the physiological state of the bacterial host or to DNA damage, λ phage DNA excises itself from the host or in combination with the host-encoded factor Fis. X is also inhibits integration, and prevents the attP and attB products of excision from reverting the attP and attB products of excision from reverting to attL and attR. Because the cellular levels of IHF and Fis proteins respond to growth conditions, these host-encoded factors have been proposed as the master signals for integration and excision. Additional exemplary λ recombination recognition sequences and recombinases for the practice of the invention described herein are shown below:

TABLE 3

| Name | Description | Sequence | Length |
|---|---|---|---|
| BBa_I11022 | SEQ ID NO: 21 Lambda attB, reverse complement | accactttgtacaagaaagctgggt | 25 |
| BBa_I11023 | SEQ ID NO: 22 Lambda attP | . . . tcactatcagtcaaaataaaatcattattt | 232 |
| BBa_K112141 | SEQ ID NO: 23 attR2 recombination site | . . . gttcagctttcttgtacaaagtggttgatc | 136 |

TABLE 3-continued

| Name | Description | Sequence | Length |
|---|---|---|---|
| BBa_K112142 | SEQ ID NO: 24 attR2 recombination site-reverse orientation | . . . aacacaacatatccagtcactatggtcgac | 136 |

TABLE 4

| Name | Protein | Description | Direction | KEGG | UniProt | E.C. | Length |
|---|---|---|---|---|---|---|---|
| BBa_I11021 | Xis lambda | excisionase from *E. coli* phage lambda (removes prophage from host genome) | Forward | none | P03699 | none | 255 |
| BBa_I11020 | Int lambda | integrase from *E. coli* phage lambda | Forward | none | P03700 | none | 1107 |
| BBa_K112001 | Xis | Xis from bacteriophage lambda, assembly standard 21 | | | | | 216 |
| BBa_K112204 | | {a~xis} The bacteriophage lambda xis gene ready to have rbs attached and stop codon; assembly stand | | | | | 223 |
| BBa_K112200 | | {xis} from bacteriophage lambda; assembly standard 21 | | | | | 219 |

Bacteriophage P22 is a lambdoid phage which infects *Salmonella typhimurium*. P22 can integrate into and excise out of its host chromosome via site-specific recombination. Both integration and excision reactions require the phage-encoded int gene, and excision is dependent on the xis gene as well.

P22 Int is a member of the λ integrase family. The Int proteins of λ and P22 are composed of two domains. The catalytic domain binds to the core region of the phage recombination site, attP, where the actual recombination reactions occur. The smaller amino-terminal domain binds to arm-type sequences which are located on either site of the core within the attP. The active components of λ integrative and excisive recombination are nucleosome-like structures, called intasomes, in which DNA is folded around several molecules of Int and integration host factor (IHF). It has been demonstrated that one monomer of λ integrase can simultaneously occupy both a core-type binding site and an arm-type binding site. Formation of these bridges is facilitated by IHF, which binds to specific sequences and imparts a substantial bend to the DNA.

The attP regions of P22 and λ are also similar in that both contain arm regions, known as the P and P' arms, which contain Int arm-type binding sites and IHF binding sites. However, the arrangement, spacing, and orientation of the Int and IHF binding sites are distinct. The attP region of λ contains two Int arm-type binding sites on the P arm and three on the P' arm. The P arm contains two IHF binding sites, and the P' arm contains a single site. The attP region of P22 contains three Int arm-type binding sites on the P arm and two sites on the P' arm. In addition, IHF binding sites, called H and H', are located on each arm of the P22 attP. Leong et al. showed that the *Escherichia coli* IHF can recognize and bind to these P22 IHF binding sites in vitro. It was also shown that the maximum amount of P22 integrative recombination occurred in the presence of *E. coli* IHF in vitro, whereas in its absence, recombination was detectable but depressed. However, the requirement for IHF or other possible accessory proteins during P22 site-specific recombination in vivo has not been tested. In this study, we assessed the role of IHF in P22 integration and excision in vivo.

Although the attP region of P22 contains strong IHF binding sites, in vivo measurements of integration and excision frequencies showed that infecting P22 phages can perform site-specific recombination to its maximum efficiency in the absence of IHF. In addition, a plasmid integration assay showed that integrative recombination occurs equally well in wild-type and ihfA mutant cells. P22 integrative recombination is also efficient in *Escherichia coli* in the absence of functional IHF. Additional exemplary recombination recognition sequences and recombinases are described below:

TABLE 5

| Name | Description | Sequence | Length |
|---|---|---|---|
| BBa_I11032 | SEQ ID NO: 25 P22 "attB", reverse complement | acgaccttcgcattacgaatgcgctgc | 27 |
| BBa_I11033 | SEQ ID NO: 26 P22 "attP" | . . . gggacatatttgggacagaagtaccaaaaa | 260 |

TABLE 6

| Name | Protein | Description | Direction | KEGG | UniProt | E.C. | Length |
| --- | --- | --- | --- | --- | --- | --- | --- |
| BBa_I11031 | Xis P22 | excisionase from E. coli phage P22 (removes prophage from host genome) | Forward | none | P04889 | none | 387 |
| BBa_I11030 | Int P22 | integrase from E. coli phage P22 | Forward | none | P04890 | none | 1200 |

The FLP system of the yeast 2 mm plasmid is one of the most attractive for genomic manipulation because of its efficiency, simplicity, and demonstrated in vivo activity in a wide range of organisms. The Flp system has been used to construct specific genomic deletions and gene duplications, study gene function, promote chromosomal translocations, promote site-specific chromosome cleavage, and facilitate the construction of genomic libraries in organisms including bacteria, yeast, insects, plants, mice, and humans. Site-specific recombination catalyzed by the FLP recombinase occurs readily in bacterial cells.

The yeast FLP system has been studied intensively. The only requirements for FLP recombination are the FLP protein and the FLP recombination target (FRT) sites on the DNA substrates. The minimal functional FRT site contains only 34 bp. The FLP protein can promote both inter- and intramolecular recombination. Exemplary recombination recognition sequences for use with the yeast FLP system are provided below:

chromosome dimer resolution machinery. Two site-specific recombinases of the tyrosine recombinase family, XerCD, act at a 28 bp recombination site, dif, located in the replication terminus region of the E. coli chromosome to remove the crossover introduced by dimer formation, thereby converting dimers to monomers. A complete dimer resolution reaction during recombination at dif requires the action of the C-terminal domain of FtsK (FtsK$_C$). FtsK is a multifunctional protein whose N-terminal domain acts in cell division, while the C-terminal domain functions in chromosome segregation. Therefore, FtsK is well suited to coordinate chromosome segregation and cell division. A purified protein, FtsK$_{50C}$, containing a functional C-terminal domain, can translocate

TABLE 7

| Name | Description | Sequence | Length |
| --- | --- | --- | --- |
| BBa_J61020 | SEQ ID NO: 27 [FRT] | . . . ttcctatacttttagagaataggaacttc | 34 |
| BBa_J72001 | SEQ ID NO: 28 [FRT] recombination site for flp recombinase in BBb | . . . ttcctatactttctagagaataggaacttc | 36 |

The separation and segregation of newly replicated E. coli circular chromosomes can also be prevented by the formation of circular chromosome dimers, which can arise during crossing over by homologous recombination. In E. coli, these dimers, which arise about once every six generations, are resolved to monomers by the action of the FtsK-XerCD-dif DNA in an ATP-dependent manner and activate Xer recombination at the recombination site dif, thereby reconstituting in vitro the expected in vivo activities of the C-terminal domain of the complete FtsK protein. Additional exemplary recombination recognition sequences for use with the XerCD system are provided below:

TABLE 8

| Name | Description | Sequence | Length |
| --- | --- | --- | --- |
| BBa_I742101 | SEQ ID NO: 29 dif site with forward orientation | . . . tcggtgcgcataatgtatattatgttaaat | 31 |
| BBa_I742102 | SEQ ID NO: 30 dif site with reverse orientation | . . . tcatttaacataatatacattatgcgcacc | 31 |

The fim switch (fimS) consists of a 314 bp DNA element that can be inverted by site-specific recombinases FimB and FimE. In the natural system, fimSc contains a promoter, that when switched to the on orientation, drives transcription of the fim operon. The fim operon is needed for export and structural assembly of type 1 fimbriae. FimB and FimE, required to invert fimS, are members of the λ integrase family of site-specific recombinases. Recombination of fimS is distinct from the related Xer-mediated recombination in that the recombinases act independently to invert fimS. Each inverted repeat (IR) is flanked by overlapping FimB and FimE binding sites, and following occupancy of these sites they recombine the switch within the IR sequence. As for λ phage chromosomal integration and excision, fim recombination also requires accessory proteins, specifically integration host factor (IHF) and the leucine-responsive regulatory protein (Lrp). These proteins are believed to contribute to the overall architecture of the fim switch that facilitates synapse of the 9 bp IRs.

FimB catalyses inversion in both directions, although with a slight bias for the off-to-on orientation, while FimE predominantly catalyses on-to-off inversion. Control of FimE expression is important in bringing about its orientation bias; as the fim switch is located at the end of fimE, the orientation of fimS determines the length and 3' sequence of the fimE transcript. As a consequence, fimE mRNA is likely to be subject to more rapid 3' to 5' degradation when the switch is in the off orientation than when it is in the on orientation. In addition, FimE preferentially binds to fimS in the on orientation, as has been demonstrated in vitro and in vivo, which adds to the directional bias. A further difference between FimB and FimE is that FimB inversion frequencies are markedly lower than those exhibited by FimE, both in vitro and in vivo. Additional exemplary recombination recognition sequences and recombinases for use with the FimB and FimE system are provided below:

TABLE 9

| Name | Description | Sequence | Recombinase | Length |
|---|---|---|---|---|
| BBa_K137008 | SEQ ID NO: 31 fimE IRR | . . . gaaacatttggggccaaactgtccatatta | | 35 |
| BBa_K137010 | SEQ ID NO: 32 fimE IRL | . . . gagtcaaaatggccccaattgtcttgtatt | | 35 |

TABLE 10

| Name | Protein | Description | Length |
|---|---|---|---|
| BBa_K137007 | | fimE | 558 |

Promoters

Described herein are promoter sequences for use in the engineered genetic counters and modules. In some aspects, the promoters used in the engineered genetic counters and modules drives expression of an operably linked recombinase, thus regulating expression and consequent enzymatic activity of said recombinase.

The term "promoter" as used herein refers to any nucleic acid sequence that regulates the expression of another nucleic acid sequence by driving transcription of the nucleic acid sequence, which can be a heterologous target gene, encoding a protein or RNA. Promoters can be constitutive, inducible, activatable, repressible, tissue-specific, or any combination thereof. A promoter is a control region of a nucleic acid sequence at which initiation and rate of transcription of the remainder of a nucleic acid sequence are controlled. A promoter may also contain genetic elements at which regulatory proteins and molecules may bind, such as RNA polymerase and other transcription factors. In some embodiments of the aspects, a promoter may drive the expression of a transcription factor that regulates the expression of the promoter itself, or that of another promoter used in another modular component of the invention.

A promoter can be said to drive expression or drive transcription of the nucleic acid sequence that it regulates. The phrases "operably linked", "operatively positioned," "operatively linked," "under control," and "under transcriptional control" indicate that a promoter is in a correct functional location and/or orientation in relation to a nucleic acid sequence it regulates to control transcriptional initiation and/or expression of that sequence. An "inverted promoter" is a promoter in which the nucleic acid sequence is in the reverse orientation, such that what was the coding strand is now the non-coding strand, and vice versa. Inverted promoter sequences can be used in various embodiments of the invention to regulate the state of a module or a switch. Thus, inversion of an inverted promoter sequence due, for example, to recombinase activity, orients the promoter in a direction such that it can drive expression of an operably linked sequence. In some embodiments of the aspects described herein, the promoter is an inverted inducible promoter that, upon inversion to the correct orientation, can drive expression of an operably linked sequence upon receiving the appropriate inducer signal. In addition, in various embodiments of the invention, a promoter may or may not be used in conjunction with an "enhancer", which refers to a cis-acting regulatory sequence involved in the transcriptional activation of a nucleic acid sequence downstream of the promoter. The enhancer may be located at any functional location before or after the promoter, and/or the encoded nucleic acid.

A promoter may be one naturally associated with a gene or sequence, as may be obtained by isolating the 5' non-coding sequences located upstream of the coding segment and/or exon of a given gene or sequence. Such a promoter can be referred to as "endogenous." Similarly, an enhancer may be one naturally associated with a nucleic acid sequence, located either downstream or upstream of that sequence.

Alternatively, certain advantages will be gained by positioning a coding nucleic acid segment under the control of a recombinant or heterologous promoter, which refers to a promoter that is not normally associated with the encoded nucleic acid sequence in its natural environment. A recombinant or heterologous enhancer refers to an enhancer not normally associated with a nucleic acid sequence in its natural environment. Such promoters or enhancers may include promoters or enhancers of other genes; promoters or enhancers isolated from any other prokaryotic, viral, or eukaryotic cell; and synthetic promoters or enhancers that are not "naturally occurring", i.e., contain different elements of different transcriptional regulatory regions, and/or mutations that alter expression through methods of genetic engineering that are known in the art. In addition to producing nucleic acid sequences of promoters and enhancers synthetically, sequences may be produced using recombinant cloning and/or nucleic acid amplification technology, including PCR, in connection with the biological converter switches and modules disclosed herein (see U.S. Pat. Nos. 4,683,202, 5,928,906, each incorporated herein by reference). Furthermore, it is contemplated the control sequences that direct transcription and/or expression of sequences within non-nuclear organelles such as mitochondria, chloroplasts, and the like, can be employed as well.

Inducible Promoters

As described herein, an "inducible promoter" is one that is characterized by initiating or enhancing transcriptional activity when in the presence of, influenced by, or contacted by an inducer or inducing agent. An "inducer" or "inducing agent" may be endogenous, or a normally exogenous compound or protein that is administered in such a way as to be active in inducing transcriptional activity from the inducible promoter. In some embodiments, the inducer or inducing agent, i.e., a chemical, a compound or a protein, can itself be the result of transcription or expression of a nucleic acid sequence (i.e., an inducer can be a transcriptional repressor protein), which itself may be under the control or an inducible promoter. In some embodiments, an inducible promoter is induced in the absence of certain agents, such as a repressor. Examples of inducible promoters include but are not limited to, tetracycline, metallothionine, ecdysone, mammalian viruses (e.g., the adenovirus late promoter; and the mouse mammary tumor virus long terminal repeat (MMTV-LTR)) and other steroid-responsive promoters, rapamycin responsive promoters and the like.

Inducible promoters useful in the methods and systems of the present invention are capable of functioning in both prokaryotic and eukaryotic host organisms. In some embodiments of the different aspects of the invention, mammalian inducible promoters are included, although inducible promoters from other organisms, as well as synthetic promoters designed to function in a prokaryotic or eukaryotic host may be used. One important functional characteristic of the inducible promoters of the present invention is their ultimate inducibility by exposure to an externally applied inducer, such as an environmental inducer. Appropriate environmental inducers include exposure to heat (i.e., thermal pulses or constant heat exposure), various steroidal compounds, divalent cations (including $Cu^{2+}$ and $Zn^{2+}$), galactose, tetracycline, IPTG (isopropyl-β-D thiogalactoside), as well as other naturally occurring and synthetic inducing agents and gratuitous inducers.

The promoters for use in the biological circuit chemotactic converters and modules described herein encompass the inducibility of a prokaryotic or eukaryotic promoter by, in part, either of two mechanisms. In particular embodiments of the present invention, the engineered genetic counters and their component modules comprise suitable inducible promoters that can be dependent upon transcriptional activators that, in turn, are reliant upon an environmental inducer. In other embodiments, the inducible promoters can be repressed by a transcriptional repressor which itself is rendered inactive by an environmental inducer, such as the product of a sequence driven by another promoter. Thus, unless specified otherwise, an inducible promoter can be either one that is induced by an inducing agent that positively activates a transcriptional activator, or one which is derepressed by an inducing agent that negatively regulates a transcriptional repressor. In such embodiments of the various aspects described herein, where it is required to distinguish between an activating and a repressing inducing agent, explicit distinction will be made.

Inducible promoters that are useful in the engineered biological counters and methods of use described herein include those controlled by the action of latent transcriptional activators that are subject to induction by the action of environmental inducing agents. Some non-limiting examples include the copper-inducible promoters of the yeast genes CUP1, CRS5, and SOD1 that are subject to copper-dependent activation by the yeast ACE1 transcriptional activator (see e.g. Strain and Culotta, 1996; Hottiger et al., 1994; Lapinskas et al., 1993; and Gralla et al., 1991). Alternatively, the copper inducible promoter of the yeast gene CTT1 (encoding cytosolic catalase T), which operates independently of the ACE1 transcriptional activator (Lapinskas et al., 1993), can be utilized. The copper concentrations required for effective induction of these genes are suitably low so as to be tolerated by most cell systems, including yeast and Drosophila cells. Alternatively, other naturally occurring inducible promoters can be used in the present invention including: steroid inducible gene promoters (see e.g. Oligino et al. (1998) Gene Ther. 5: 491-6); galactose inducible promoters from yeast (see e.g. Johnston (1987) Microbiol Rev 51: 458-76; Ruzzi et al. (1987) Mol Cell Biol 7: 991-7); and various heat shock gene promoters. Many eukaryotic transcriptional activators have been shown to function in a broad range of eukaryotic host cells, and so, for example, many of the inducible promoters identified in yeast can be adapted for use in a mammalian host cell as well. For example, a unique synthetic transcriptional induction system for mammalian cells has been developed based upon a GAL4-estrogen receptor fusion protein that induces mammalian promoters containing GAL4 binding sites (Braselmann et al. (1993) Proc Natl Acad Sci USA 90: 1657-61). These and other inducible promoters responsive to transcriptional activators that are dependent upon specific inducers are suitable for use with the present invention.

Inducible promoters useful in the modules and methods disclosed herein also include those that are repressed by "transcriptional repressors" that are subject to inactivation by the action of environmental, external agents, or the product of another gene. Such inducible promoters may also be termed "repressible promoters" where it is required to distinguish between other types of promoters in a given module or component of an engineered genetic counter described herein. Examples include prokaryotic repressors that can transcriptionally repress eukaryotic promoters that have been engineered to incorporate appropriate repressor-binding operator sequences. Preferred repressors for use in the present invention are sensitive to inactivation by physiologically benign agent. Thus, where a lac repressor protein is used to control the expression of a promoter sequence that has been engineered to contain a lacO operator sequence, treatment of the host cell with IPTG will cause the dissociation of the lac repressor from the engineered promoter containing a lacO operator sequence and allow transcription to occur. Similarly, where a tet repressor is used to control the expression of a promoter sequence that has been engineered to contain a tetO operator sequence, treatment of the host cell with tetracycline will cause the dissociation of the tet repressor from the engineered promoter and allow transcription of the sequence downstream of the engineered promoter to occur.

An inducible promoter useful in the methods and systems as disclosed herein can be induced by one or more physiological conditions, such as changes in pH, temperature, radiation, osmotic pressure, saline gradients, cell surface binding, and the concentration of one or more extrinsic or intrinsic inducing agents. The extrinsic inducer or inducing agent may comprise amino acids and amino acid analogs, saccharides and polysaccharides, nucleic acids, protein transcriptional activators and repressors, cytokines, toxins, petroleum-based compounds, metal containing compounds, salts, ions, enzyme substrate analogs, hormones, and combinations thereof. In specific embodiments, the inducible promoter is activated or repressed in response to a change of an environmental condition, such as the change in concentration of a chemical, metal, temperature, radiation, nutrient or change in pH. Thus, an inducible promoter useful in the methods and systems as disclosed herein can be a phage inducible promoter, nutrient inducible promoter, temperature inducible promoter, radiation inducible promoter, metal inducible promoter, hormone inducible promoter, steroid inducible promoter, and/or hybrids and combinations thereof.

Promoters that are inducible by ionizing radiation can be used in certain embodiments, where gene expression is induced locally in a cell by exposure to ionizing radiation such as UV or x-rays. Radiation inducible promoters include the non-limiting examples of fos promoter, c-jun promoter or at least one CArG domain of an Egr-1 promoter. Further non-limiting examples of inducible promoters include promoters from genes such as cytochrome P450 genes, inducible heat shock protein genes, metallothionein genes, hormone-inducible genes, such as the estrogen gene promoter, and such. In further embodiments, an inducible promoter useful in the methods and systems as disclosed herein can be $Zn^{2+}$ metallothionein promoter, metallothionein-1 promoter, human metallothionein IIA promoter, lac promoter, lacO promoter, mouse mammary tumor virus early promoter, mouse mammary tumor virus LTR promoter, triose dehydrogenase promoter, herpes simplex virus thymidine kinase promoter, simian virus 40 early promoter or retroviral myeloproliferative sarcoma virus promoter. Examples of inducible promoters also include mammalian probasin promoter, lactalbumin promoter, GRP78 promoter, or the bacterial tetracycline-inducible promoter. Other examples include phorbol ester, adenovirus E1A element, interferon, and serum inducible promoters.

Inducible promoters useful in the modules and engineered genetic counters as disclosed herein for in vivo uses may include those responsive to biologically compatible agents, such as those that are usually encountered in defined animal tissues. An example is the human PAI-1 promoter, which is inducible by tumor necrosis factor. Further suitable examples include cytochrome P450 gene promoters, inducible by various toxins and other agents; heat shock protein genes, inducible by various stresses; hormone-inducible genes, such as the estrogen gene promoter, and such.

The administration or removal of an inducer or repressor as disclosed herein results in a switch between the "on" or "off" states of the transcription of the operably linked heterologous target gene. Thus, as defined herein the "on" state of a promoter operably linked to a nucleic acid sequence, refers to the state when the promoter is actively driving transcription of the operably linked nucleic acid sequence, i.e., the linked nucleic acid sequence is expressed. Several small molecule ligands have been shown to mediate regulated gene expressions, either in tissue culture cells and/or in transgenic animal models. These include the FK1012 and rapamycin immunosuppressive drugs (Spencer et al., 1993; Magari et al., 1997), the progesterone antagonist mifepristone (RU486) (Wang, 1994; Wang et al., 1997), the tetracycline antibiotic derivatives (Gossen and Bujard, 1992; Gossen et al., 1995; Kistner et al., 1996), and the insect steroid hormone ecdysone (No et al., 1996). All of these references are herein incorporated by reference. By way of further example, Yao discloses in U.S. Pat. No. 6,444,871, which is incorporated herein by reference, prokaryotic elements associated with the tetracycline resistance (tet) operon, a system in which the tet repressor protein is fused with polypeptides known to modulate transcription in mammalian cells. The fusion protein is then directed to specific sites by the positioning of the tet operator sequence. For example, the tet repressor has been fused to a transactivator (VP16) and targeted to a tet operator sequence positioned upstream from the promoter of a selected gene (Gussen et al., 1992; Kim et al., 1995; Hennighausen et al., 1995). The tet repressor portion of the fusion protein binds to the operator thereby targeting the VP16 activator to the specific site where the induction of transcription is desired. An alternative approach has been to fuse the tet repressor to the KRAB repressor domain and target this protein to an operator placed several hundred base pairs upstream of a gene. Using this system, it has been found that the chimeric protein, but not the tet repressor alone, is capable of producing a 10 to 15-fold suppression of CMV-regulated gene expression (Deuschle et al., 1995).

One example of a repressible promoter useful in the modules and engineered genetic counters as described herein is the Lac repressor (lacR)/operator/inducer system of E. coli that has been used to regulate gene expression by three different approaches: (1) prevention of transcription initiation by properly placed lac operators at promoter sites (Hu and Davidson, 1987; Brown et al., 1987; Figge et al., 1988; Fuerst et al., 1989; Deuschle et al., 1989; (2) blockage of transcribing RNA polymerase II during elongation by a LacR/operator complex (Deuschle et al. (1990); and (3) activation of a promoter responsive to a fusion between LacR and the activation domain of herpes simples virus (HSV) virion protein 16 (VP16) (Labow et al., 1990; Baim et al., 1991). In one version of the Lac system, expression of lac operator-linked sequences is constitutively activated by a LacR-VP16 fusion protein and is turned off in the presence of isopropyl-β-D-1-thiogalactopyranoside (IPTG) (Labow et al. (1990), cited supra). In another version of the system, a lacR-VP16 variant is used that binds to lac operators in the presence of IPTG, which can be enhanced by increasing the temperature of the cells (Baim et al. (1991), cited supra). Thus, in some embodiments of the present invention, components of the Lac system are utilized. For example, a lac operator (LacO) may be operably linked to tissue specific promoter, and control the transcription and expression of the heterologous target gene and another repressor protein, such as the TetR. Accordingly, the expression of the heterologous target gene is inversely regulated as compared to the expression or presence of Lac repressor in the system.

Components of the tetracycline (Tc) resistance system of E. coli have also been found to function in eukaryotic cells and have been used to regulate gene expression. For example, the Tet repressor (TetR), which binds to tet operator (tetO) sequences in the absence of tetracycline and represses gene transcription, has been expressed in plant cells at sufficiently high concentrations to repress transcription from a promoter containing tet operator sequences (Gatz, C. et al. (1992) Plant J. 2:397-404). In some embodiments of the present invention, the Tet repressor system is similarly utilized in the engineered genetic counters.

A temperature- or heat-inducible gene regulatory system may also be used in the present invention, such as the exemplary TIGR system comprising a cold-inducible transactivator in the form of a fusion protein having a heat shock responsive regulator, rheA, fused to the VP16 transactivator (Weber et al., 2003a). The promoter responsive to this fusion thermosensor comprises a rheO element operably linked to a minimal promoter, such as the minimal version of the human cytomegalovirus immediate early promoter. At the permissive temperature of 37° C., the cold-inducible transactivator transactivates the exemplary rheO-CMVmin promoter, permitting expression of the target gene. At 41° C., the cold-inducible transactivator no longer transactivates the rheO promoter. Any such heat-inducible or -regulated promoter can be used in accordance with the methods of the present invention, including but not limited to a heat-responsive element in a heat shock gene (e.g., hsp20-30, hsp27, hsp40, hsp60, hsp70, and hsp90). See Easton et al. (2000) Cell Stress Chaperones 5(4):276-290; Csermely et al. (1998) Pharmacol Ther 79(2): 129-1 68; Ohtsuka & Hata (2000) Int J Hyperthermia 16(3): 231-245; and references cited therein. Sequence similarity to heat shock proteins and heat-responsive promoter elements have also been recognized in genes initially characterized with respect to other functions, and the DNA sequences that confer heat inducibility are suitable for use in the disclosed gene therapy vectors. For example, expression of glucose-responsive genes (e.g., grp94, grp78, mortalin/grp75) (Merrick et al. (1997) Cancer Lett 119(2): 185-1 90; Kiang et al. (1998) FASEB J 12(14):1571-16-579), calreticulin (Szewczenko-Pawlikowski et al. (1997) Mol Cell Biochem 177(1-2): 145-1 52); clusterin (Viard et al. (1999) J Invest Dermatol 112(3):290-296; Michel et al. (1997) Biochem J 328(Pt1):45-50; Clark & Griswold (1997) J Androl 18(3):257-263), histocompatibility class I gene (HLA-G) (Ibrahim et al. (2000) Cell Stress Chaperones 5(3):207-218), and the Kunitz protease isoform of amyloid precursor protein (Shepherd et al. (2000) Neuroscience 99(2):31 7-325) are upregulated in response to heat. In the case of clusterin, a 14 base pair element that is sufficient for heat-inducibility has been delineated (Michel et al. (1997) Biochem J 328(Pt1):45-50). Similarly, a two sequence unit comprising a 10- and a 14-base pair element in the calreticulin promoter region has been shown to confer heat-inducibility (Szewczenko-Pawlikowski et al. (1997) Mol Cell Biochem 177(1-2): 145-1 52).

Other inducible promoters useful in the engineered genetic counters described herein include the erythromycin-resistance regulon from *E. coli*, having repressible ($E_{off}$) and inducible ($E_{on}$) systems responsive to macrolide antibiotics, such as erythromycin, clarithromycin, and roxithromycin (Weber et al., 2002). The $E_{off}$ system utilizes an erythromycin-dependent transactivator, wherein providing a macrolide antibiotic represses transgene expression. In the $E_{on}$ system, the binding of the repressor to the operator results in repression of transgene expression. Therein, in the presence of macrolides gene expression is induced.

Fussenegger et al. (2000) describe repressible and inducible systems using a Pip (pristinamycin-induced protein) repressor encoded by the streptogramin resistance operon of *Streptomyces coelicolor*, wherein the systems are responsive to streptogramin-type antibiotics (such as, for example, pristinamycin, virginiamycin, and Synercid). The Pip DNA-binding domain is fused to a VP16 transactivation domain or to the KRAB silencing domain, for example. The presence or absence of, for example, pristinamycin, regulates the PipON and PipOFF systems in their respective manners, as described therein.

Another example of a promoter expression system useful for the modules and switches of the invention utilizes a quorum-sensing (referring to particular prokaryotic molecule communication systems having diffusible signal molecules that prevent binding of a repressor to an operator site, resulting in derepression of a target regulon) system. For example, Weber et al. (2003b) employ a fusion protein comprising the *Streptomyces coelicolor* quorum-sending receptor to a transactivating domain that regulates a chimeric promoter having a respective operator that the fusion protein binds. The expression is fine-tuned with non-toxic butyrolactones, such as SCB1 and MP133.

In some embodiments, multiregulated, multigene gene expression systems that are functionally compatible with one another are utilized in the present invention (see, for example, Kramer et al. (2003)). For example, in Weber et al. (2002), the macrolide-responsive erythromycin resistance regulon system is used in conjunction with a streptogramin (PIP)-regulated and tetracycline-regulated expression systems.

Other promoters responsive to non-heat stimuli can also be used. For example, the mortalin promoter is induced by low doses of ionizing radiation (Sadekova (1997) Int J Radiat Biol 72(6):653-660), the hsp27 promoter is activated by 17-β-estradiol and estrogen receptor agonists (Porter et al. (2001) J Mol Endocrinol 26(1):31-42), the HLA-G promoter is induced by arsenite, hsp promoters can be activated by photodynamic therapy (Luna et al. (2000) Cancer Res 60(6): 1637-1 644). A suitable promoter can incorporate factors such as tissue-specific activation. For example, hsp70 is transcriptionally impaired in stressed neuroblastoma cells (Drujan & De Maio (1999) 12(6):443-448) and the mortalin promoter is up-regulated in human brain tumors (Takano et al. (1997) Exp Cell Res 237(1):38-45). A promoter employed in methods of the present invention can show selective up-regulation in tumor cells as described, for example, for mortalin (Takano et al. (1997) Exp Cell Res 237(1):38-45), hsp27 and calreticulin (Szewczenko-Pawlikowski et al. (1997) Mol Cell Biochem 177(1-2): 145-1 52; Yu et al. (2000) Electrophoresis 2 1(14):3058-3068)), grp94 and grp78 (Gazit et al. (1999) Breast Cancer Res Treat 54(2): 135-146), and hsp27, hsp70, hsp73, and hsp90 (Cardillo et al. (2000) Anticancer Res 20(6B):4579-4583; Strik et al. (2000) Anticancer Res 20(6B):4457-4552).

In some embodiments, the promoter is a SOS-responsive promoter that allows the module to count the number of times that the SOS network is activated. In one embodiment, the promoter is an iron-responsive promoter that allows the module to count the number of times that iron is encountered.

In some embodiments, the inducible promoter comprises an Anhydrotetracycline (aTc)-inducible promoter as provided in PLtetO-1 (Pubmed Nucleotide# U66309) with the sequence comprising

```
                                         (SEQ ID NO: 33)
GCATGCTCCCTATCAGTGATAGAGATTGACATCCCTATCAGTGATAGAGA

TACTGAGCACATCAGCAGGACGCACTGACCAGGA.
```

In some embodiments, the inducible promoter is an arabinose-inducible promoter $P_{BAD}$ comprising the sequence

```
                                         (SEQ ID NO: 34)
AAGAAACCAATTGTCCATATTGCATCAGACATTGCCGTCACTGCGTCTTT

TACTGGCTCTTCTCGCTAACCAAACCGGTAACCCCGCTTATTAAAAGCAT

TCTGTAACAAAGCGGGACCAAAGCCATGACAAAAACGCGTAACAAAAGTG

TCTATAATCACGGCAGAAAAGTCCACATTGATTATTTGCACGGCGTCACA

CTTTGCTATGCCATAGCATTTTTATCCATAAGATTAGCGGATCCTACCTG

ACGCTTTTTATCGCAACTCTCTACTGTTTCTCCATA.
```

In some embodiments, the inducible promoter is an isopropyl β-D-1-thiogalactopyranoside (IPTG) inducible promoter. In one embodiment, the IPTG-inducible promoter comprises the P$_{TAC}$ sequence found in the vector encoded by PubMed Accession ID #EU546824. In one embodiment, the IPTG-inducible promoter sequence comprises the P$_{Trc-2}$ sequence (SEQ ID NO: 35)
CCATCGAATGGCTGAAATGAGCTGTTGACAATTAATCATCCGGCTCGTAT

AATGTGTGGAATTGTGAGCGGATAACAATTTCACACAGGA.

In some embodiments, the IPTG-inducible promoter comprises the P$_{Trc-2}$ sequence found in the vector encoded by PubMed Accession ID #EU546816.

In some embodiments, the IPTG-inducible promoter comprises the P$_{LlacO-1}$ sequence:

(SEQ ID NO: 36)
ATAAATGTGAGCGGATAACATTGACATTGTGAGCGGATAACAAGATAC

TGAGCACTCAGCAGGACGCACTGACC.

In some embodiments, the IPTG-inducible promoter comprises the P$_{A1lacO-1}$ sequence (SEQ ID NO: 37)
AAAATTTATCAAAAAGAGTGTTGACTTGTGAGCGGATAACAATGATACTT

AGATTCAATTGTGAGCGGATAACAATTTCACACA.

In some embodiments, the IPTG-inducible promoter comprises the P$_{lac/ara-1}$ sequence (SEQ ID NO: 38)
CATAGCATTTTTATCCATAAGATTAGCGGATCCTAAGCTTTACAATTGTG

AGCGCTCACAATTATGATAGATTCAATTGTGAGCGGATAACAATTTCACA

CA.

In some embodiments, the inducible promoter sequence comprises the P$_{Lslcon}$ sequence (SEQ ID NO: 39)
GCATGCACAGATAACCATCTGCGGTGATAAATTATCTCTGGCGGTGTTGA CATAAATACCACTGGCGGTtATAaTGAGCACATCAGCAGG//GTATGCAA

AGGA

Other non-limiting examples of promoters that are useful for use in the modules and engineered genetic counters described herein are presented in Tables 11-47.

TABLE 11

Examples of Constitutive *E. coli* σ$^{70}$ Promoters

| Name | Description | Promoter Sequence |
|---|---|---|
| BBa_I14018 | SEQ ID NO: 40 P(Bla) | . . . gtttatacataggcgagtactctgttatgg |
| BBa_I14033 | SEQ ID NO: 41 P(Cat) | . . . agaggttccaactttcaccataatgaaaca |
| BBa_I14034 | SEQ ID NO: 42 P(Kat) | . . . taaacaactaacggacaattctacctaaca |
| BBa_I732021 | SEQ ID NO: 43 Template for Building Primer Family Member | . . . acatcaagccaaattaaacaggattaacac |
| BBa_I742126 | SEQ ID NO: 44 Reverse lambda cI-regulated promoter | . . . gaggtaaaatagtcaacacgcacggtgtta |
| BBa_J01006 | SEQ ID NO: 45 Key Promoter absorbs 3 | . . . caggccggaataactccctataatgcgcca |
| BBa_J23100 | SEQ ID NO: 46 constitutive promoter family member | . . . ggctagctcagtcctaggtacagtgctagc |
| BBa_J23101 | SEQ ID NO: 47 constitutive promoter family member | . . . agctagctcagtcctaggtattatgctagc |
| BBa_J23102 | SEQ ID NO: 48 constitutive promoter family member | . . . agctagctcagtcctaggtactgtgctagc |
| BBa_J23103 | SEQ ID NO: 49 constitutive promoter family member | . . . agctagctcagtcctagggattatgctagc |
| BBa_J23104 | SEQ ID NO: 50 constitutive promoter family member | . . . agctagctcagtcctaggtattgtgctagc |
| BBa_J23105 | SEQ ID NO: 51 constitutive promoter family member | . . . ggctagctcagtcctaggtactatgctagc |
| BBa_J23106 | SEQ ID NO: 52 constitutive promoter family member | . . . ggctagctcagtcctaggtatagtgctagc |
| BBa_J23107 | SEQ ID NO: 53 constitutive promoter family member | . . . ggctagctcagccctaggtattatgctagc |
| BBa_J23108 | SEQ ID NO: 54 constitutive promoter family member | . . . agctagctcagtcctaggtataatgctagc |

TABLE 11-continued

Examples of Constitutive *E. coli* σ[70] Promoters

| Name | Description | Promoter Sequence |
| --- | --- | --- |
| BBa_J23109 | SEQ ID NO: 55 constitutive promoter family member | . . . agctagctcagtcctagggactgtgctagc |
| BBa_J23110 | SEQ ID NO: 56 constitutive promoter family member | . . . ggctagctcagtcctaggtacaatgctagc |
| BBa_J23111 | SEQ ID NO: 57 constitutive promoter family member | . . . ggctagctcagtcctaggtatagtgctagc |
| BBa_J23112 | SEQ ID NO: 58 constitutive promoter family member | . . . agctagctcagtcctagggattatgctagc |
| BBa_J23113 | SEQ ID NO: 59 constitutive promoter family member | . . . ggctagctcagtcctagggattatgctagc |
| BBa_J23114 | SEQ ID NO: 60 constitutive promoter family member | . . . ggctagctcagtcctaggtacaatgctagc |
| BBa_J23115 | SEQ ID NO: 61 constitutive promoter family member | . . . agctagctcagcccttggtacaatgctagc |
| BBa_J23116 | SEQ ID NO: 62 constitutive promoter family member | . . . agctagctcagtcctagggactatgctagc |
| BBa_J23117 | SEQ ID NO: 63 constitutive promoter family member | . . . agctagctcagtcctagggattgtgctagc |
| BBa_J23118 | SEQ ID NO: 64 constitutive promoter family member | . . . ggctagctcagtcctaggtattgtgctagc |
| BBa_J23119 | SEQ ID NO: 65 constitutive promoter family member | . . . agctagctcagtcctaggtataatgctagc |
| BBa_J23150 | SEQ ID NO: 66 1bp mutant from J23107 | . . . ggctagctcagtcctaggtattatgctagc |
| BBa_J23151 | SEQ ID NO: 67 1bp mutant from J23114 | . . . ggctagctcagtcctaggtacaatgctagc |
| BBa_J44002 | SEQ ID NO: 68 pBAD reverse | . . . aaagtgtgacgccgtgcaaataatcaatgt |
| BBa_J48104 | SEQ ID NO: 69 NikR promoter, a protein of the ribbon helix-helix family of transcription factors that repress expre | . . . gacgaatacttaaaatcgtcatacttattt |
| BBa_J54200 | SEQ ID NO: 70 lacq_Promoter | . . . aaacctttcgcggtatggcatgatagcgcc |
| BBa_J56015 | SEQ ID NO: 71 lacIQ-promoter sequence | . . . tgatagcgcccggaagagagtcaattcagg |
| BBa_J64951 | SEQ ID NO: 72 *E. coli* CreABCD phosphate sensing operon promoter | . . . ttatttaccgtgacgaactaattgctcgtg |
| BBa_K088007 | SEQ ID NO: 73 GlnRS promoter | . . . catacgccgttatacgttgtttacgctttg |
| BBa_K119000 | SEQ ID NO: 74 Constitutive weak promoter of lacZ | . . . ttatgcttccggctcgtatgttgtgtggac |
| BBa_K119001 | SEQ ID NO: 75 Mutated LacZ promoter | . . . ttatgcttccggctcgtatggtgtgtggac |
| BBa_K137029 | SEQ ID NO: 76 constitutive promoter with (TA)10 between −10 and −35 elements | . . . atatatatatatatataatggaagcgtttt |
| BBa_K137030 | SEQ ID NO: 77 constitutive promoter with (TA)9 between −10 and −35 elements | . . . atatatatatatatataatggaagcgtttt |
| BBa_K137031 | SEQ ID NO: 78 constitutive promoter with (C)10 between −10 and −35 elements | . . . ccccgaaagcttaagaatataattgtaagc |
| BBa_K137032 | SEQ ID NO: 79 constitutive promoter with (C)12 between −10 and −35 elements | . . . ccccgaaagcttaagaatataattgtaagc |
| BBa_K137085 | SEQ ID NO: 80 optimized (TA) repeat constitutive promoter with 13 bp between −10 and −35 elements | . . . tgacaatatatatatatatataatgctagc |

TABLE 11-continued

Examples of Constitutive *E. coli* σ⁷⁰ Promoters

| Name | Description | Promoter Sequence |
|---|---|---|
| BBa_K137086 | SEQ ID NO: 81 optimized (TA) repeat constitutive promoter with 15 bp between -10 and -35 elements | . . . acaatatatatatatatatataatgctagc |
| BBa_K137087 | SEQ ID NO: 82 optimized (TA) repeat constitutive promoter with 17 bp between -10 and -35 elements | . . . aatatatatatatatatatataatgctagc |
| BBa_K137088 | SEQ ID NO: 83 optimized (TA) repeat constitutive promoter with 19 bp between -10 and -35 elements | . . . tatatatatatatatatatataatgctagc |
| BBa_K137089 | SEQ ID NO: 84 optimized (TA) repeat constitutive promoter with 21 bp between -10 and -35 elements | . . . tatatatatatatatatatataatgctagc |
| BBa_K137090 | SEQ ID NO: 85 optimized (A) repeat constitutive promoter with 17 bp between -10 and -35 elements | . . . aaaaaaaaaaaaaaaaaatataatgctagc |
| BBa_K137091 | SEQ ID NO: 86 optimized (A) repeat constitutive promoter with 18 bp between -10 and -35 elements | . . . aaaaaaaaaaaaaaaaaatataatgctagc |
| BBa_K256002 | SEQ ID NO: 87 J23101:GFP | . . . caccttcgggtgggcctttctgcgtttata |
| BBa_K256018 | SEQ ID NO: 88 J23119:IFP | . . . caccttcgggtgggcctttctgcgtttata |
| BBa_K256020 | SEQ ID NO: 89 J23119:HO1 | . . . caccttcgggtgggcctttctgcgtttata |
| BBa_K256033 | SEQ ID NO: 90 Infrared signal reporter (J23119:IFP:J23119:HO1) | . . . caccttcgggtgggcctttctgcgtttata |
| BBa_K292000 | SEQ ID NO: 91 Double terminator + constitutive promoter | . . . ggctagctcagtcctaggtacagtgctagc |
| BBa_K292001 | SEQ ID NO: 92 Double terminator + Constitutive promoter + Strong RBS | . . . tgctagctactagagattaaagaggagaaa |
| BBa_M13101 | SEQ ID NO: 93 M13K07 gene I promoter | . . . cctgtttttatgttattctctctgtaaagg |
| BBa_M13102 | SEQ ID NO: 94 M13K07 gene II promoter | . . . aaatatttgcttatacaatcttcctgttttt |
| BBa_M13103 | SEQ ID NO: 95 M13K07 gene III promoter | . . . gctgataaaccgatacaattaaaggctcct |
| BBa_M13104 | SEQ ID NO: 96 M13K07 gene IV promoter | . . . ctcttctcagcgtcttaatctaagctatcg |
| BBa_M13105 | SEQ ID NO: 97 M13K07 gene V promoter | . . . atgagccagttcttaaaatcgcataaggta |
| BBa_M13106 | SEQ ID NO: 98 M13K07 gene VI promoter | . . . ctattgattgtgacaaaataaacttattcc |
| BBa_M13108 | SEQ ID NO: 99 M13K07 gene VIII promoter | . . . gtttcgcgcttggtataatcgctgggggtc |
| BBa_M13110 | SEQ ID NO: 100 M13110 | . . . ctttgcttctgactataatagtcagggtaa |
| BBa_M31519 | SEQ ID NO: 101 Modified promoter sequence of g3. | . . . aaaccgatacaattaaaggctcctgctagc |
| BBa_R1074 | SEQ ID NO: 102 Constitutive Promoter I | . . . gccggaataactccctataatgcgccacca |
| BBa_R1075 | SEQ ID NO: 103 Constitutive Promoter II | . . . gccggaataactccctataatgcgccacca |
| BBa_S03331 | SEQ ID NO: 104 | ttgacaagcttttcctcagctccgtaaact |

TABLE 12

**Examples of Constitutive *E. coli* $\sigma^{70}$ Promoters**

| Identifier | | Sequence | |
|---|---|---|---|
| BBa_J23119 | SEQ ID NO: 105 | ttgacagctagctcagtcctaggtataatgctagc | n/a |
| BBa_J23100 | SEQ ID NO: 106 | ttgacggctagctcagtcctaggtacagtgctagc | 1 |
| BBa_J23101 | SEQ ID NO: 107 | tttacagctagctcagtcctaggtattatgctagc | 0.70 |
| BBa_J23102 | SEQ ID NO: 108 | ttgacagctagctcagtcctaggtactgtgctagc | 0.86 |
| BBa_J23103 | SEQ ID NO: 109 | ctgatagctagctcagtcctagggattatgctagc | 0.01 |
| BBa_J23104 | SEQ ID NO: 110 | ttgacagctagctcagtcctaggtattgtgctagc | 0.72 |
| BBa_J23105 | SEQ ID NO: 111 | tttacggctagctcagtcctaggtactatgctagc | 0.24 |
| BBa_J23106 | SEQ ID NO: 112 | tttacggctagctcagtcctaggtatagtgctagc | 0.47 |
| BBa_J23107 | SEQ ID NO: 113 | tttacggctagctcagccctaggtattatgctagc | 0.36 |
| BBa_J23108 | SEQ ID NO: 114 | ctgacagctagctcagtcctaggtataatgctagc | 0.51 |
| BBa_J23109 | SEQ ID NO: 115 | tttacagctagctcagtcctagggactgtgctagc | 0.04 |
| BBa_J23110 | SEQ ID NO: 116 | tttacggctagctcagtcctaggtacaatgctagc | 0.33 |
| BBa_J23111 | SEQ ID NO: 117 | ttgacggctagctcagtcctaggtatagtgctagc | 0.58 |
| BBa_J23112 | SEQ ID NO: 118 | ctgatagctagctcagtcctagggattatgctagc | 0.00 |
| BBa_J23113 | SEQ ID NO: 119 | ctgatggctagctcagtcctagggattatgctagc | 0.01 |
| BBa_J23114 | SEQ ID NO: 120 | tttatggctagctcagtcctaggtacaatgctagc | 0.10 |
| BBa_J23115 | SEQ ID NO: 121 | tttatagctagctcagcccttggtacaatgctagc | 0.15 |
| BBa_J23116 | SEQ ID NO: 122 | ttgacagctagctcagtcctagggactatgctagc | 0.16 |
| BBa_J23117 | SEQ ID NO: 123 | ttgacagctagctcagtcctagggattgtgctagc | 0.06 |
| BBa_J23118 | SEQ ID NO: 124 | ttgacggctagctcagtcctaggtattgtgctagc | 0.56 |

TABLE 13

**Examples of Constitutive *E. coli* $\sigma^{S}$ Promoters**

| Name | Description | | Promoter Sequence |
|---|---|---|---|
| BBa_J45992 | SEQ ID NO: 125 | Full-length stationary phase osmY promoter | . . . ggtttcaaaattgtgatctatatttaacaa |
| BBa_J45993 | SEQ ID NO: 126 | Minimal stationary phase osmY promoter | . . . ggtttcaaaattgtgatctatatttaacaa |

TABLE 14

**Examples of Constitutive *E. coli* $\sigma^{32}$ Promoters**

| Name | Description | | Promoter Sequence |
|---|---|---|---|
| BBa_J45504 | SEQ ID NO: 127 | htpG Heat Shock Promoter | . . . tctattccaataaagaaatcttcctgcgtg |

TABLE 15

Examples of Constitutive *B. subtilis* σ$^A$ Promoters

| Name | Description | Promoter Sequence |
|---|---|---|
| BBa_K143012 | SEQ ID NO: 128 Promoter veg a constitutive promoter for *B. subtilis* | . . . aaaaatgggctcgtgttgtacaataaatgt |
| BBa_K143013 | SEQ ID NO: 129 Promoter 43 a constitutive promoter for *B. subtilis* | . . . aaaaaaagcgcgcgattatgtaaaatataa |

TABLE 16

Examples of Constitutive *B. subtilis* σ$^B$ Promoters

| Name | Description | Promoter Sequence |
|---|---|---|
| BBa_K143010 | SEQ ID NO: 130 Promoter ctc for *B. subtilis* | . . . atccttatcgttatgggtattgtttgtaat |
| BBa_K143011 | SEQ ID NO: 131 Promoter gsiB for *B. subtilis* | . . . taaaagaattgtgagcgggaatacaacaac |
| BBa_K143013 | SEQ ID NO: 132 Promoter 43 a constitutive promoter for *B. subtilis* | . . . aaaaaaagcgcgcgattatgtaaaatataa |

TABLE 17

Examples of Constitutive Promoters from Miscellaneous Prokaryotes

| Name | Description | Promoter Sequence |
|---|---|---|
| BBa_K112706 | SEQ ID NO: 133 Pspv2 from *Salmonella* | . . . tacaaaataattcccctgcaaacattatca |
| BBa_K112707 | SEQ ID NO: 134 Pspv from *Salmonella* | . . . tacaaaataattcccctgcaaacattatcg |

TABLE 18

Examples of Constitutive Promoters from bacteriophage T7

| Name | Description | Promoter Sequence |
|---|---|---|
| BBa_I712074 | SEQ ID NO: 135 T7 promoter (strong promoter from T7 bacteriophage) | . . . agggaatacaagctacttgttcttttttgca |
| BBa_I719005 | SEQ ID NO: 136 T7 Promoter | taatacgactcactatagggaga |
| BBa_J34814 | SEQ ID NO: 137 T7 Promoter | gaatttaatacgactcactatagggaga |
| BBa_J64997 | SEQ ID NO: 138 T7 consensus -10 and rest | taatacgactcactatagg |
| BBa_K113010 | SEQ ID NO: 139 overlapping T7 promoter | . . . gagtcgtattaatacgactcactataggg |
| BBa_K113011 | SEQ ID NO: 140 more overlapping T7 promoter | . . . agtgagtcgtactacgactcactataggg |
| BBa_K113012 | SEQ ID NO: 141 weaken overlapping T7 promoter | . . . gagtcgtattaatacgactctctataggg |
| BBa_R0085 | SEQ ID NO: 142 T7 Consensus Promoter Sequence | taatacgactcactatagggaga |
| BBa_R0180 | SEQ ID NO: 143 T7 RNAP promoter | ttatacgactcactatagggaga |
| BBa_R0181 | SEQ ID NO: 144 T7 RNAP promoter | gaatacgactcactatagggaga |
| BBa_R0182 | SEQ ID NO: 145 T7 RNAP promoter | taatacgtctcactatagggaga |

TABLE 18-continued

Examples of Constitutive Promoters from bacteriophage T7

| Name | Description | Promoter Sequence |
| --- | --- | --- |
| BBa_R0183 | SEQ ID NO: 146 T7 RNAP promoter | tcatacgactcactatagggaga |
| BBa_Z0251 | SEQ ID NO: 147 T7 strong promoter | . . . taatacgactcactatagggagaccacaac |
| BBa_Z0252 | SEQ ID NO: 148 T7 weak binding and processivity | . . . taattgaactcactaaagggagaccacagc |
| BBa_Z0253 | SEQ ID NO: 149 T7 weak binding promoter | . . . cgaagtaatacgactcactattagggaaga |
|  | SEQ ID NO: 150 T7 14.3 m | attaaccctcactaaagggaga |

TABLE 19

Examples of Constitutive Promoters from bacteriophage SP6

| Name | Description | Promoter Sequence |
| --- | --- | --- |
| BBa_J64998 | SEQ ID NO: 151 consensus -10 and rest from SP6 | atttaggtgacactataga |

TABLE 20

Examples of Constitutive Promoters from Yeast

| Name | Description | Promoter Sequence |
| --- | --- | --- |
| BBa_I766555 | SEQ ID NO: 152 pCyc (Medium) Promoter | . . . acaaacacaaatacacacactaaattaata |
| BBa_I766556 | SEQ ID NO: 153 pAdh (Strong) Promoter | . . . ccaagcatacaatcaactatctcatataca |
| BBa_I766557 | SEQ ID NO: 154 pSte5 (Weak) Promoter | . . . gatacaggatacagcggaaacaacttttaa |
| BBa_J63005 | SEQ ID NO: 155 yeast ADH1 promoter | . . . tttcaagctataccaagcatacaatcaact |
| BBa_K105027 | SEQ ID NO: 156 cyc100 minimal promoter | . . . cctttgcagcataaattactatacttctat |
| BBa_K105028 | SEQ ID NO: 157 cyc70 minimal promoter | . . . cctttgcagcataaattactatacttctat |
| BBa_K105029 | SEQ ID NO: 158 cyc43 minimal promoter | . . . cctttgcagcataaattactatacttctat |
| BBa_K105030 | SEQ ID NO: 159 cyc28 minimal promoter | . . . cctttgcagcataaattactatacttctat |
| BBa_K105031 | SEQ ID NO: 160 cyc16 minimal promoter | . . . cctttgcagcataaattactatacttctat |
| BBa_K122000 | SEQ ID NO: 161 pPGK1 | . . . ttatctacttttacaacaaatataaaaca |
| BBa_K124000 | SEQ ID NO: 162 pCYC Yeast Promoter | . . . acaaacacaaatacacacactaaattaata |
| BBa_K124002 | SEQ ID NO: 163 Yeast GPD (TDH3) Promoter | . . . gtttcgaataaacacacataaacaaacaaa |
| BBa_M31201 | SEQ ID NO: 164 Yeast CLB1 promoter region, G2/M cell cycle specific | . . . accatcaaaggaagctttaatcttctcata |

TABLE 21

Examples of Constitutive Promoters from Miscellaneous Eukaryotes

| Name | Description | Promoter Sequence |
| --- | --- | --- |
| BBa_I712004 | SEQ ID NO: 165 CMV promoter | . . . agaacccactgcttactggcttatcgaaat |
| BBa_K076017 | SEQ ID NO: 166 Ubc Promoter | . . . ggccgttttggctttttgttagacgaag |

TABLE 22

Examples of Cell Signaling Promoters

| Name | Description | Promoter Sequence |
| --- | --- | --- |
| BBa_I1051 | SEQ ID NO: 167 Lux cassette right promoter | . . . tgttatagtcgaatacctctggcggtgata |
| BBa_I14015 | SEQ ID NO: 168 P(Las) TetO | . . . ttttggtacactccctatcagtgatagaga |
| BBa_I14016 | SEQ ID NO: 169 P(Las) CIO | . . . cttttggtacactacctctggcggtgata |
| BBa_I14017 | SEQ ID NO: 170 P(Rhl) | . . . tacgcaagaaaatggtttgttatagtcgaa |
| BBa_I739105 | SEQ ID NO: 171 Double Promoter (LuxR/HSL, positive/cI, negative) | . . . cgtgcgtgttgataacaccgtgcgtgttga |
| BBa_I746104 | SEQ ID NO: 172 P2 promoter in agr operon from *S. aureus* | . . . agattgtactaaatcgtataatgacagtga |
| BBa_I751501 | SEQ ID NO: 173 plux-cI hybrid promoter | . . . gtgttgatgcttttatcaccgccagtggta |
| BBa_I751502 | SEQ ID NO: 174 plux-lac hybrid promoter | . . . agtgtgtggaattgtgagcggataacaatt |
| BBa_I761011 | SEQ ID NO: 175 CinR, CinL and glucose controlled promoter | . . . acatcttaaaagttttagtatcatattcgt |
| BBa_J06403 | SEQ ID NO: 176 RhlR promoter repressible by CI | . . . tacgcaagaaaatggtttgttatagtcgaa |
| BBa_J64000 | SEQ ID NO: 177 rhlI promoter | . . . atcctcctttagtcttcccctcatgtgtg |
| BBa_J64010 | SEQ ID NO: 178 lasI promoter | . . . taaaattatgaaatttgcataaattcttca |
| BBa_J64067 | SEQ ID NO: 179 LuxR + 3OC6HSL independent R0065 | . . . gtgttgactattttacctctggcggtgata |
| BBa_J64712 | SEQ ID NO: 180 LasR/LasI Inducible & RHLR/RHLI repressible Promoter | . . . gaaatctggcagtttttggtacacgaaagc |
| BBa_K091107 | SEQ ID NO: 181 pLux/cI Hybrid | . . . acaccgtgcgtgttgatatagtcgaataaa |
| BBa_K091117 | SEQ ID NO: 182 pLas promoter | . . . aaaattatgaaatttgtataaattcttcag |
| BBa_K091143 | SEQ ID NO: 183 pLas/cI Hybrid Promoter | . . . ggttcttttggtacctctggcggtgataa |
| BBa_K091146 | SEQ ID NO: 184 pLas/Lux Hybrid Promoter | . . . tgtaggatcgtacaggtataaattcttcag |
| BBa_K091156 | SEQ ID NO: 185 pLux | . . . caagaaaatggtttgttatagtcgaataaa |
| BBa_K091157 | SEQ ID NO: 186 pLux/Las Hybrid Promoter | . . . ctatctcatttgctagtatagtcgaataaa |
| BBa_K145150 | SEQ ID NO: 187 Hybrid promoter: HSL-LuxR activated, P22 C2 repressed | . . . tagtttataatttaagtgttctttaatttc |
| BBa_K266000 | SEQ ID NO: 188 PAI + LasR -> LuxI (AI) | . . . caccttcgggtgggcctttctgcgtttata |
| BBa_K266005 | SEQ ID NO: 189 PAI + LasR -> LasI & AI + LuxR --\| LasI | . . . aataactctgatagtgctagtgtagatctc |
| BBa_K266006 | SEQ ID NO: 190 PAI + LasR -> LasI + GFP & AI + LuxR --\| LasI + GFP | . . . caccttcgggtgggcctttctgcgtttata |

TABLE 22-continued

Examples of Cell Signaling Promoters

| Name | Description | Promoter Sequence |
|---|---|---|
| BBa_K266007 | SEQ ID NO: 191 Complex QS -> LuxI & LasI circuit | . . . caccttcgggtgggccttctgcgtttata |
| BBa_R0061 | SEQ ID NO: 192 Promoter (HSL-mediated luxR repressor) | ttgacacctgtaggatcgtacaggtataat |
| BBa_R0062 | SEQ ID NO: 193 Promoter (luxR & HSL regulated -- lux pR) | . . . caagaaaatggtttgttatagtcgaataaa |
| BBa_R0063 | SEQ ID NO: 194 Promoter (luxR & HSL regulated -- lux pL) | . . . cacgcaaaacttgcgacaaacaataggtaa |
| BBa_R0071 | SEQ ID NO: 195 Promoter (RhlR & C4-HSL regulated) | . . . gttagctttcgaattggctaaaaagtgttc |
| BBa_R0078 | SEQ ID NO: 196 Promoter (cinR and HSL regulated) | . . . ccattctgctttccacgaacttgaaaacgc |
| BBa_R0079 | SEQ ID NO: 197 Promoter (LasR & PAI regulated) | . . . ggccgcgggttcttttggtacacgaaagc |
| BBa_R1062 | SEQ ID NO: 198 Promoter, Standard (luxR and HSL regulated -- lux pR) | . . . aagaaaatggtttgttgatactcgaataaa |

TABLE 23

Examples of Metal Inducible Promoters

| Name | Description | Promoter Sequence |
|---|---|---|
| BBa_I721001 | SEQ ID NO: 199 Lead Promoter | . . . gaaaaccttgtcaatgaagagcgatctatg |
| BBa_I731004 | SEQ ID NO: 200 FecA promoter | . . . ttctcgttcgactcatagctgaacacaaca |
| BBa_I760005 | SEQ ID NO: 201 Cu sensitive promoter | atgacaaaattgtcat |
| BBa_I765000 | SEQ ID NO: 202 Fe promoter | . . . accaatgctgggaacggccagggcacctaa |
| BBa_I765007 | SEQ ID NO: 203 Fe and UV promoters | . . . ctgaaagcgcataccgctatggaggggggtt |
| BBa_J3902 | SEQ ID NO: 204 PrFe (PI + PII rus operon) | . . . tagatatgcctgaaagcgcataccgctatg |

TABLE 24

Examples of T7 Promoters

| Name | Description | Promoter Sequence |
|---|---|---|
| BBa_I712074 | SEQ ID NO: 205 T7 promoter (strong promoter from T7 bacteriophage) | . . . agggaatacaagctacttgttcttttttgca |
| BBa_I719005 | SEQ ID NO: 206 T7 Promoter | taatacgactcactataggaga |
| BBa_J34814 | SEQ ID NO: 207 T7 Promoter | gaatttaatacgactcactataggaga |
| BBa_J64997 | SEQ ID NO: 208 T7 consensus -10 and rest | taatacgactcactatagg |
| BBa_J64998 | SEQ ID NO: 209 consensus -10 and rest from SP6 | atttaggtgacactataga |
| BBa_K113010 | SEQ ID NO: 210 overlapping T7 promoter | . . . gagtcgtattaatacgactcactatagggg |

TABLE 24-continued

Examples of T7 Promoters

| Name | Description | Promoter Sequence |
|---|---|---|
| BBa_K113011 | SEQ ID NO: 211 more overlapping T7 promoter | . . . agtgagtcgtactacgactcactatagggg |
| BBa_K113012 | SEQ ID NO: 212 weaken overlapping T7 promoter | . . . gagtcgtattaatacgactctctatagggg |
| BBa_R0085 | SEQ ID NO: 213 T7 Consensus Promoter Sequence | taatacgactcactatagggaga |
| BBa_R0180 | SEQ ID NO: 214 T7 RNAP promoter | ttatacgactcactatagggaga |
| BBa_R0181 | SEQ ID NO: 215 T7 RNAP promoter | gaatacgactcactatagggaga |
| BBa_R0182 | SEQ ID NO: 216 T7 RNAP promoter | taatacgtctcactatagggaga |
| BBa_R0183 | SEQ ID NO: 217 T7 RNAP promoter | tcatacgactcactatagggaga |
| BBa_R0184 | SEQ ID NO: 218 T7 promoter (lacI repressible) | . . . atagggaattgtgagcggataacaattcc |
| BBa_R0185 | SEQ ID NO: 219 T7 promoter (lacI repressible) | . . . atagggaattgtgagcggataacaattcc |
| BBa_R0186 | SEQ ID NO: 220 T7 promoter (lacI repressible) | . . . atagggaattgtgagcggataacaattcc |
| BBa_R0187 | SEQ ID NO: 221 T7 promoter (lacI repressible) | . . . atagggaattgtgagcggataacaattcc |
| BBa_Z0251 | SEQ ID NO: 222 T7 strong promoter | . . . taatacgactcactatagggagaccacaac |
| BBa_Z0252 | SEQ ID NO: 223 T7 weak binding and processivity | . . . taattgaactcactaaagggagaccacagc |
| BBa_Z0253 | SEQ ID NO: 224 T7 weak binding promoter | . . . cgaagtaatacgactcactattagggaaga |

TABLE 25

Examples of Stress Kit Promoters

| Name | Description | Promoter Sequence |
|---|---|---|
| BBa_K086017 | SEQ ID NO: 225 unmodified Lutz-Bujard LacO promoter | . . . ttgtgagcggataacaagatactgagcaca |
| BBa_K086018 | SEQ ID NO: 226 modified Lutz-Bujard LacO promoter, with alternative sigma factor σ24 | . . . ttgtgagcggataacaattctgaagaacaa |
| BBa_K086019 | SEQ ID NO: 227 modified Lutz-Bujard LacO promoter, with alternative sigma factor σ24 | . . . ttgtgagcggataacaattctgataaaaca |
| BBa_K086020 | SEQ ID NO: 228 modified Lutz-Bujard LacO promoter, with alternative sigma factor σ24 | . . . ttgtgagcggataacatctaacccttttaga |
| BBa_K086021 | SEQ ID NO: 229 modified Lutz-Bujard LacO promoter, with alternative sigma factor σ24 | . . . ttgtgagcggataacatagcagataagaaa |
| BBa_K086022 | SEQ ID NO: 230 modified Lutz-Bujard LacO promoter, with alternative sigma factor σ28 | . . . gtttgagcgagtaacgccgaaaatcttgca |
| BBa_K086023 | SEQ ID NO: 231 modified Lutz-Bujard LacO promoter, with alternative sigma factor σ28 | . . . gtgtgagcgagtaacgacgaaaatcttgca |

TABLE 25-continued

Examples of Stress Kit Promoters

| Name | Description | Promoter Sequence |
|---|---|---|
| BBa_K086024 | SEQ ID NO: 232 modified Lutz-Bujard LacO promoter, with alternative sigma factor σ28 | . . . tttgagcgagtaacagccgaaaatcttgca |
| BBa_K086025 | SEQ ID NO: 233 modified Lutz-Bujard LacO promoter, with alternative sigma factor σ28 | . . . tgtgagcgagtaacagccgaaaatcttgca |
| BBa_K086026 | SEQ ID NO: 234 modified Lutz-Bujard LacO promoter, with alternative sigma factor σ32 | . . . ttgtgagcgagtggcaccattaagtacgta |
| BBa_K086027 | SEQ ID NO: 235 modified Lutz-Bujard LacO promoter, with alternative sigma factor σ32 | . . . ttgtgagcgagtgacaccattaagtacgta |
| BBa_K086028 | SEQ ID NO: 236 modified Lutz-Bujard LacO promoter, with alternative sigma factor σ32 | . . . ttgtgagcgagtaacaccattaagtacgta |
| BBa_K086029 | SEQ ID NO: 237 modified Lutz-Bujard LacO promoter, with alternative sigma factor σ32 | . . . ttgtgagcgagtaacaccattaagtacgta |
| BBa_K086030 | SEQ ID NO: 238 modified Lutz-Bujard LacO promoter, with alternative sigma factor σ38 | . . . cagtgagcgagtaacaactacgctgtttta |
| BBa_K086031 | SEQ ID NO: 239 modified Lutz-Bujard LacO promoter, with alternative sigma factor σ38 | . . . cagtgagcgagtaacaactacgctgtttta |
| BBa_K086032 | SEQ ID NO: 240 modified Lutz-Bujard LacO promoter, with alternative sigma factor σ38 | . . . atgtgagcggataacactataattaataga |
| BBa_K086033 | SEQ ID NO: 241 modified Lutz-Bujard LacO promoter, with alternative sigma factor σ38 | . . . atgtgagcggataacactataattaataga |

TABLE 26

Examples of Logic Promoters

| Name | Description | Promoter Sequence |
|---|---|---|
| BBa_I732200 | SEQ ID NO: 242 NOT Gate Promoter Family Member (D00101wt1) | . . . gaattgtgagcggataacaattggatccgg |
| BBa_I732201 | SEQ ID NO: 243 NOT Gate Promoter Family Member (D001011) | . . . ggaattgtgagcgctcacaattggatccgg |
| BBa_I732202 | SEQ ID NO: 244 NOT Gate Promoter Family Member (D001022) | . . . ggaattgtaagcgcttacaattggatccgg |
| BBa_I732203 | SEQ ID NO: 245 NOT Gate Promoter Family Member (D001033) | . . . ggaattgtaaacgtttacaattggatccgg |
| BBa_I732204 | SEQ ID NO: 246 NOT Gate Promoter Family Member (D001044) | . . . ggaattgtgaacgttcacaattggatccgg |
| BBa_I732205 | SEQ ID NO: 247 NOT Gate Promoter Family Member (D001055) | . . . ggaatttgagcgctcaaaattggatccgg |
| BBa_I732206 | SEQ ID NO: 248 NOT Gate Promoter Family Member (D001066) | . . . ggaattatgagcgctcataattggatccgg |
| BBa_I732207 | SEQ ID NO: 249 NOT Gate Promoter Family Member (D001077) | . . . gggacgactgtatacagtcgtcggatccgg |

TABLE 26-continued

Examples of Logic Promoters

| Name | Description | Promoter Sequence |
|---|---|---|
| BBa_I732270 | SEQ ID NO: 250 Promoter Family Member with Hybrid Operator (D001012) | . . . ggaattgtgagcgcttacaattggatccgg |
| BBa_I732271 | SEQ ID NO: 251 Promoter Family Member with Hybrid Operator (D001016) | . . . ggaattgtgagcgctcataattggatccgg |
| BBa_I732272 | SEQ ID NO: 252 Promoter Family Member with Hybrid Operator (D001017) | . . . ggaattgtgagctacagtcgtcggatccgg |
| BBa_I732273 | SEQ ID NO: 253 Promoter Family Member with Hybrid Operator (D001021) | . . . ggaattgtaagcgctcacaattggatccgg |
| BBa_I732274 | SEQ ID NO: 254 Promoter Family Member with Hybrid Operator (D001024) | . . . ggaattgtaagcgttcacaattggatccgg |
| BBa_I732275 | SEQ ID NO: 255 Promoter Family Member with Hybrid Operator (D001026) | . . . ggaattgtaagcgctcataattggatccgg |
| BBa_I732276 | SEQ ID NO: 256 Promoter Family Member with Hybrid Operator (D001027) | . . . ggaattgtaagctacagtcgtcggatccgg |
| BBa_I732277 | SEQ ID NO: 257 Promoter Family Member with Hybrid Operator (D001046) | . . . ggaattgtgaacgctcataattggatccgg |
| BBa_I732278 | SEQ ID NO: 258 Promoter Family Member with Hybrid Operator (D001047) | . . . ggaattgtgaactacagtcgtcggatccgg |
| BBa_I732279 | SEQ ID NO: 259 Promoter Family Member with Hybrid Operator (D001061) | . . . ggaattatgagcgctcacaattggatccgg |
| BBa_I732301 | SEQ ID NO: 260 NAND Candidate (U073026D001016) | . . . ggaattgtgagcgctcataattggatccgg |
| BBa_I732302 | SEQ ID NO: 261 NAND Candidate (U073027D001017) | . . . ggaattgtgagctacagtcgtcggatccgg |
| BBa_I732303 | SEQ ID NO: 262 NAND Candidate (U073022D001046) | . . . ggaattgtgaacgctcataattggatccgg |
| BBa_I732304 | SEQ ID NO: 263 NAND Candidate (U073022D001047) | . . . ggaattgtgaactacagtcgtcggatccgg |
| BBa_I732305 | SEQ ID NO: 264 NAND Candidate (U073022D059046) | . . . taaattgtgaacgctcataattggatccgg |
| BBa_I732306 | SEQ ID NO: 265 NAND Candidate (U073011D002022) | . . . gaaattgtaagcgcttacaattggatccgg |
| BBa_I732351 | SEQ ID NO: 266 NOR Candidate (U037011D002022) | . . . gaaattgtaagcgcttacaattggatccgg |
| BBa_I732352 | SEQ ID NO: 267 NOR Candidate (U035044D001022) | . . . ggaattgtaagcgcttacaattggatccgg |
| BBa_I732400 | SEQ ID NO: 268 Promoter Family Member (U097NUL + D062NUL) | . . . gccaaattaaacaggattaacaggatccgg |
| BBa_I732401 | SEQ ID NO: 269 Promoter Family Member (U097O11 + D062NUL) | . . . gccaaattaaacaggattaacaggatccgg |
| BBa_I732402 | SEQ ID NO: 270 Promoter Family Member (U085O11 + D062NUL) | . . . gccaaattaaacaggattaacaggatccgg |
| BBa_I732403 | SEQ ID NO: 271 Promoter Family Member (U073O11 + D062NUL) | . . . gccaaattaaacaggattaacaggatccgg |

TABLE 26-continued

Examples of Logic Promoters

| Name | Description | Promoter Sequence |
|------|-------------|-------------------|
| BBa_I732404 | SEQ ID NO: 272 Promoter Family Member (U061O11 + D062NUL) | . . . gccaaattaaacaggattaacaggatccgg |
| BBa_I732405 | SEQ ID NO: 273 Promoter Family Member (U049O11 + D062NUL) | . . . gccaaattaaacaggattaacaggatccgg |
| BBa_I732406 | SEQ ID NO: 274 Promoter Family Member (U037O11 + D062NUL) | . . . gccaaattaaacaggattaacaggatccgg |
| BBa_I732407 | SEQ ID NO: 275 Promoter Family Member (U097NUL + D002O22) | . . . gaaattgtaagcgcttacaattggatccgg |
| BBa_I732408 | SEQ ID NO: 276 Promoter Family Member (U097NUL + D014O22) | . . . taaattgtaagcgcttacaattggatccgg |
| BBa_I732409 | SEQ ID NO: 277 Promoter Family Member (U097NUL + D026O22) | . . . gtaattgtaagcgcttacaattggatccgg |
| BBa_I732410 | SEQ ID NO: 278 Promoter Family Member (U097NUL + D038O22) | . . . tcaattgtaagcgcttacaattggatccgg |
| BBa_I732411 | SEQ ID NO: 279 Promoter Family Member (U097NUL + D050O22) | . . . aaaattgtaagcgcttacaattggatccgg |
| BBa_I732412 | SEQ ID NO: 280 Promoter Family Member (U097NUL + D062O22) | . . . caaattgtaagcgcttacaattggatccgg |
| BBa_I732413 | SEQ ID NO: 281 Promoter Family Member (U097O11 + D002O22) | . . . gaaattgtaagcgcttacaattggatccgg |
| BBa_I732414 | SEQ ID NO: 282 Promoter Family Member (U097O11 + D014O22) | . . . taaattgtaagcgcttacaattggatccgg |
| BBa_I732415 | SEQ ID NO: 283 Promoter Family Member (U097O11 + D026O22) | . . . gtaattgtaagcgcttacaattggatccgg |
| BBa_I732416 | SEQ ID NO: 284 Promoter Family Member (U097O11 + D038O22) | . . . tcaattgtaagcgcttacaattggatccgg |
| BBa_I732417 | SEQ ID NO: 285 Promoter Family Member (U097O11 + D050O22) | . . . aaaattgtaagcgcttacaattggatccgg |
| BBa_I732418 | SEQ ID NO: 286 Promoter Family Member (U097O11 + D062O22) | . . . caaattgtaagcgcttacaattggatccgg |
| BBa_I732419 | SEQ ID NO: 287 Promoter Family Member (U085O11 + D002O22) | . . . gaaattgtaagcgcttacaattggatccgg |
| BBa_I732420 | SEQ ID NO: 288 Promoter Family Member (U085O11 + D014O22) | . . . taaattgtaagcgcttacaattggatccgg |
| BBa_I732421 | SEQ ID NO: 289 Promoter Family Member (U085O11 + D026O22) | . . . gtaattgtaagcgcttacaattggatccgg |
| BBa_I732422 | SEQ ID NO: 290 Promoter Family Member (U085O11 + D038O22) | . . . tcaattgtaagcgcttacaattggatccgg |
| BBa_I732423 | SEQ ID NO: 291 Promoter Family Member (U085O11 + D050O22) | . . . aaaattgtaagcgcttacaattggatccgg |
| BBa_I732424 | SEQ ID NO: 292 Promoter Family Member (U085O11 + D062O22) | . . . caaattgtaagcgcttacaattggatccgg |
| BBa_I732425 | SEQ ID NO: 293 Promoter Family Member (U073O11 + D002O22) | . . . gaaattgtaagcgcttacaattggatccgg |
| BBa_I732426 | SEQ ID NO: 294 Promoter Family Member (U073O11 + D014O22) | . . . taaattgtaagcgcttacaattggatccgg |
| BBa_I732427 | SEQ ID NO: 295 Promoter Family Member (U073O11 + D026O22) | . . . gtaattgtaagcgcttacaattggatccgg |
| BBa_I732428 | SEQ ID NO: 296 Promoter Family Member (U073O11 + D038O22) | . . . tcaattgtaagcgcttacaattggatccgg |

TABLE 26-continued

Examples of Logic Promoters

| Name | Description | Promoter Sequence |
|---|---|---|
| BBa_I732429 | SEQ ID NO: 297 Promoter Family Member (U073O11 + D050O22) | . . . aaaattgtaagcgcttacaattggatccgg |
| BBa_I732430 | SEQ ID NO: 298 Promoter Family Member (U073O11 + D062O22) | . . . caaattgtaagcgcttacaattggatccgg |
| BBa_I732431 | SEQ ID NO: 299 Promoter Family Member (U061O11 + D002O22) | . . . gaaattgtaagcgcttacaattggatccgg |
| BBa_I732432 | SEQ ID NO: 300 Promoter Family Member (U061O11 + D014O22) | . . . taaattgtaagcgcttacaattggatccgg |
| BBa_I732433 | SEQ ID NO: 301 Promoter Family Member (U061O11 + D026O22) | . . . gtaattgtaagcgcttacaattggatccgg |
| BBa_I732434 | SEQ ID NO: 302 Promoter Family Member (U061O11 + D038O22) | . . . tcaattgtaagcgcttacaattggatccgg |
| BBa_I732435 | SEQ ID NO: 303 Promoter Family Member (U061O11 + D050O22) | . . . aaaattgtaagcgcttacaattggatccgg |
| BBa_I732436 | SEQ ID NO: 304 Promoter Family Member (U061O11 + D062O22) | . . . caaattgtaagcgcttacaattggatccgg |
| BBa_I732437 | SEQ ID NO: 305 Promoter Family Member (U049O11 + D002O22) | . . . gaaattgtaagcgcttacaattggatccgg |
| BBa_I732438 | SEQ ID NO: 306 Promoter Family Member (U049O11 + D014O22) | . . . taaattgtaagcgcttacaattggatccgg |
| BBa_I732439 | SEQ ID NO: 307 Promoter Family Member (U049O11 + D026O22) | . . . gtaattgtaagcgcttacaattggatccgg |
| BBa_I732440 | SEQ ID NO: 308 Promoter Family Member (U049O11 + D038O22) | . . . tcaattgtaagcgcttacaattggatccgg |
| BBa_I732441 | SEQ ID NO: 309 Promoter Family Member (U049O11 + D050O22) | . . . aaaattgtaagcgcttacaattggatccgg |
| BBa_I732442 | SEQ ID NO: 310 Promoter Family Member (U049O11 + D062O22) | . . . caaattgtaagcgcttacaattggatccgg |
| BBa_I732443 | SEQ ID NO: 311 Promoter Family Member (U037O11 + D002O22) | . . . gaaattgtaagcgcttacaattggatccgg |
| BBa_I732444 | SEQ ID NO: 312 Promoter Family Member (U037O11 + D014O22) | . . . taaattgtaagcgcttacaattggatccgg |
| BBa_I732445 | SEQ ID NO: 313 Promoter Family Member (U037O11 + D026O22) | . . . gtaattgtaagcgcttacaattggatccgg |
| BBa_I732446 | SEQ ID NO: 314 Promoter Family Member (U037O11 + D038O22) | . . . tcaattgtaagcgcttacaattggatccgg |
| BBa_I732447 | SEQ ID NO: 315 Promoter Family Member (U037O11 + D050O22) | . . . aaaattgtaagcgcttacaattggatccgg |
| BBa_I732448 | SEQ ID NO: 316 Promoter Family Member (U037O11 + D062O22) | . . . caaattgtaagcgcttacaattggatccgg |
| BBa_I732450 | SEQ ID NO: 317 Promoter Family Member (U073O26 + D062NUL) | . . . gccaaattaaacaggattaacaggatccgg |
| BBa_I732451 | SEQ ID NO: 318 Promoter Family Member (U073O27 + D062NUL) | . . . gccaaattaaacaggattaacaggatccgg |
| BBa_I732452 | SEQ ID NO: 319 Promoter Family Member (U073O26 + D062O61) | . . . caaattatgagcgctcacaattggatccgg |

TABLE 27

Examples of Positively Regulated *E. coli* σ70 Promoters

| Name | Description | Promoter Sequence |
|---|---|---|
| BBa_I0500 | SEQ ID NO: 320 Inducible pBad/araC promoter | . . . gtttctccatacccgttttttgggctagc |
| BBa_I1051 | SEQ ID NO: 321 Lux cassette right promoter | . . . tgttatagtcgaatacctctggcggtgata |
| BBa_I12006 | SEQ ID NO: 322 Modified lamdba Prm promoter (repressed by 434 cI) | . . . attacaaactttcttgtatagatttaacgt |
| BBa_I12007 | SEQ ID NO: 323 Modified lambda Prm promoter (OR-3 obliterated) | . . . atttataaatagtggtgatagatttaacgt |
| BBa_I12036 | SEQ ID NO: 324 Modified lamdba Prm promoter (cooperative repression by 434 cI) | . . . tttcttgtatagatttacaatgtatcttgt |
| BBa_I12040 | SEQ ID NO: 325 Modified lambda P(RM) promoter: -10 region from P(L) and cooperatively repressed by 434 cI | . . . tttcttgtagatacttacaatgtatcttgt |
| BBa_I12210 | SEQ ID NO: 326 plac Or2-62 (positive) | . . . ctttatgcttccggctcgtatgttgtgtgg |
| BBa_I13406 | SEQ ID NO: 327 Pbad/AraC with extra REN sites | . . . tttttggggctagcaagctttaccatggat |
| BBa_I13453 | SEQ ID NO: 328 Pbad promoter | . . . tgtttctccatacccgttttttgggctagc |
| BBa_I14015 | SEQ ID NO: 329 P(Las) TetO | . . . ttttggtacactccctatcagtgatagaga |
| BBa_I14016 | SEQ ID NO: 330 P(Las) CIO | . . . cttttggtacactacctctggcggtgata |
| BBa_I14017 | SEQ ID NO: 331 P(Rhl) | . . . tacgcaagaaaatggtttgttatagtcgaa |
| BBa_I721001 | SEQ ID NO: 332 Lead Promoter | . . . gaaaaccttgtcaatgaagagcgatctatg |
| BBa_I723020 | SEQ ID NO: 333 Pu | . . . ctcaaagcgggccagccgtagccgttacgc |
| BBa_I731004 | SEQ ID NO: 334 FecA promoter | . . . ttctcgttcgactcatagctgaacacaaca |
| BBa_I739104 | SEQ ID NO: 335 Double Promoter (LuxR/HSL, positive/P22 cII, negative) | . . . gttctttaattatttaagtgttctttaatt |
| BBa_I739105 | SEQ ID NO: 336 Double Promoter (LuxR/HSL, positive/cI, negative) | . . . cgtgcgtgttgataacaccgtgcgtgttga |
| BBa_I741018 | SEQ ID NO: 337 Right facing promoter (for xylF) controlled by xylR and CRP-cAMP | . . . gttacgtttatcgcggtgattgttacttat |
| BBa_I741019 | SEQ ID NO: 338 Right facing promoter (for xylA) controlled by xylR and CRP-cAMP | . . . gcaaaataaaatggaatgatgaaactgggt |
| BBa_I741020 | SEQ ID NO: 339 promoter to xylF without CRP and several binding sites for xylR | . . . gttacgtttatcgcggtgattgttacttat |
| BBa_I741021 | SEQ ID NO: 340 promoter to xylA without CRP and several binding sites for xylR | . . . atttcacactgctattgagataattcacaa |
| BBa_I746104 | SEQ ID NO: 341 P2 promoter in agr operon from *S. aureus* | . . . agattgtactaaatcgtataatgacagtga |
| BBa_I746360 | SEQ ID NO: 342 PF promoter from P2 phage | . . . gacatctccggcgcaactgaaaataccact |
| BBa_I746361 | SEQ ID NO: 343 PO promoter from P2 phage | . . . gaggatgcgcatcgtcgggaaactgatgcc |

TABLE 27-continued

Examples of Positively Regulated *E. coli* σ70 Promoters

| Name | Description | Promoter Sequence |
|---|---|---|
| BBa_I746362 | SEQ ID NO: 344 PP promoter from P2 phage | . . . catccgggactgatggcggaggatgcgcat |
| BBa_I746363 | SEQ ID NO: 345 PV promoter from P2 phage | . . . aacttttatatattgtgcaatctcacatgc |
| BBa_I746364 | SEQ ID NO: 346 Psid promoter from P4 phage | . . . tgttgtccggtgtacgtcacaattttctta |
| BBa_I746365 | SEQ ID NO: 347 PLL promoter from P4 phage | . . . aatggctgtgtgttttttgttcatctccac |
| BBa_I751501 | SEQ ID NO: 348 plux-cI hybrid promoter | . . . gtgttgatgcttttatcaccgccagtggta |
| BBa_I751502 | SEQ ID NO: 349 plux-lac hybrid promoter | . . . agtgtgtggaattgtgagcggataacaatt |
| BBa_I760005 | SEQ ID NO: 350 Cu-sensitive promoter | atgacaaaattgtcat |
| BBa_I761011 | SEQ ID NO: 351 CinR, CinL and glucose controlled promoter | . . . acatcttaaaagttttagtatcatattcgt |
| BBa_I765001 | SEQ ID NO: 352 UV promoter | . . . ctgaaagcgcataccgctatggaggggtt |
| BBa_I765007 | SEQ ID NO: 353 Fe and UV promoters | . . . ctgaaagcgcataccgctatggaggggtt |
| BBa_J01005 | SEQ ID NO: 354 pspoIIE promoter (spo0A J01004, positive) | . . . aacgaatataacaggtgggagatgagagga |
| BBa_J03007 | SEQ ID NO: 355 Maltose specific promoter | . . . aatatttcctcatttccacagtgaagtga |
| BBa_J06403 | SEQ ID NO: 356 RhIR promoter repressible by CI | . . . tacgcaagaaaatggtttgttatagtcgaa |
| BBa_J07007 | SEQ ID NO: 357 ctx promoter | . . . atttaattgttttgatcaattattttctg |
| BBa_J13210 | SEQ ID NO: 358 pOmpR dependent POPS producer | . . . attattctgcatttttggggagaatggact |
| BBa_J15502 | SEQ ID NO: 359 copA promoter | . . . ccttgctggaaggtttaacctttatcacag |
| BBa_J16101 | SEQ ID NO: 360 BanAp - Banana-induced Promoter | atgatgtgtccatggatta |
| BBa_J16105 | SEQ ID NO: 361 HelPp - "Help" Dependant promoter | atgatagacgatgtgcggacaacgtg |
| BBa_J45503 | SEQ ID NO: 362 hybB Cold Shock Promoter | . . . cattagccgccaccatgggggttaagtagca |
| BBa_J58100 | SEQ ID NO: 363 AND-type promoter synergistically activated by cI and CRP | . . . atttataaatagtggtgatagatttaacgt |
| BBa_J61051 | SEQ ID NO: 364 [Psal1] | . . . ataaagccatcacgagtaccatagaggatc |
| BBa_J61054 | SEQ ID NO: 365 [HIP-1] Promoter | . . . tttgtcttttcttgcttaataatgttgtca |
| BBa_J61055 | SEQ ID NO: 366 [HIP-1fnr] Promoter | . . . tttgtcttttcttgcttaataatgttgtca |
| BBa_J64000 | SEQ ID NO: 367 rhlI promoter | . . . atcctcctttagtcttccccctcatgtgtg |
| BBa_J64010 | SEQ ID NO: 368 lasI promoter | . . . taaaattatgaaatttgcataaattcttca |
| BBa_J64712 | SEQ ID NO: 369 LasR/LasI Inducible & RHLR/RHLI repressible Promoter | . . . gaaatctggcagttttggtacacgaaagc |

TABLE 27-continued

Examples of Positively Regulated *E. coli* σ70 Promoters

| Name | Description | Promoter Sequence |
|---|---|---|
| BBa_J64800 | SEQ ID NO: 370 RHLR/RHLI Inducible & LasR/LasI repressible Promoter | . . . tgccagttctggcaggtctaaaaagtgttc |
| BBa_J64804 | SEQ ID NO: 371 The promoter region (inclusive of regulator binding sites) of the *B. subtilis* RocDEF operon | . . . cacagaacttgcatttatataaagggaaag |
| BBa_K091107 | SEQ ID NO: 372 pLux/cI Hybrid Promoter | . . . acaccgtgcgtgttgatatagtcgaataaa |
| BBa_K091117 | SEQ ID NO: 373 pLas promoter | . . . aaaattatgaaatttgtataaattcttcag |
| BBa_K091143 | SEQ ID NO: 374 pLas/cI Hybrid Promoter | . . . ggttcttttggtacctctggcggtgataa |
| BBa_K091146 | SEQ ID NO: 375 pLas/Lux Hybrid Promoter | . . . tgtaggatcgtacaggtataaattcttcag |
| BBa_K091156 | SEQ ID NO: 376 pLux | . . . caagaaaatggtttgttatagtcgaataaa |
| BBa_K091157 | SEQ ID NO: 377 pLux/Las Hybrid Promoter | . . . ctatctcatttgctagtatagtcgaataaa |
| BBa_K100000 | SEQ ID NO: 378 Natural Xylose Regulated Bi-Directional Operator | . . . gttacgtttatcgcggtgattgttacttat |
| BBa_K100001 | SEQ ID NO: 379 Edited Xylose Regulated Bi-Directional Operator 1 | . . . gttacgtttatcgcggtgattgttacttat |
| BBa_K100002 | SEQ ID NO: 380 Edited Xylose Regulated Bi-Directional Operator 2 | . . . gttacgtttatcgcggtgattgttacttat |
| BBa_K112118 | SEQ ID NO: 381 rrnB P1 promoter | . . . ataaatgcttgactctgtagcgggaaggcg |
| BBa_K112320 | SEQ ID NO: 382 {<ftsAZ promoter>} in BBb format | . . . aaaactggtagtaggactggagattggtac |
| BBa_K112322 | SEQ ID NO: 383 {Pdps} in BBb format | . . . gggacacaaacatcaagaggatatgagatt |
| BBa_K112402 | SEQ ID NO: 384 promoter for FabA gene - Membrane Damage and Ultrasound Sensitive | . . . gtcaaaatgaccgaaacgggtggtaacttc |
| BBa_K112405 | SEQ ID NO: 385 Promoter for CadA and CadB genes | . . . agtaatcttatcgccagtttggtctggtca |
| BBa_K112406 | SEQ ID NO: 386 cadC promoter | . . . agtaatcttatcgccagtttggtctggtca |
| BBa_K112701 | SEQ ID NO: 387 has promoter | . . . aattctgaacaacatccgtactcttcgtgc |
| BBa_K112900 | SEQ ID NO: 388 Pbad | . . . tcgataagattaccgatcttacctgaagct |
| BBa_K116001 | SEQ ID NO: 389 nhaA promoter, which can be regulated by pH and nhaR protein. | . . . cgatctattcacctgaaagagaaataaaaa |
| BBa_K116401 | SEQ ID NO: 390 external phosphate sensing promoter | . . . atcgcaacctatttattacaacactagtgc |
| BBa_K116500 | SEQ ID NO: 391 OmpF promoter that is activated or repressed by OmpR according to osmolarity. | . . . aaacgttagtttgaatggaaagatgcctgc |
| BBa_K116603 | SEQ ID NO: 392 pRE promoter from λ phage | . . . tttgcacgaaccatatgtaagtatttcctt |
| BBa_K117002 | SEQ ID NO: 393 LsrA promoter (indirectly activated by AI-2) | . . . taacacttatttaattaaaagaggagaaa |
| BBa_K118011 | SEQ ID NO: 394 PcstA (glucose-repressible promoter) | . . . tagaaacaaaatgtaacatctctatggaca |

TABLE 27-continued

Examples of Positively Regulated *E. coli* σ70 Promoters

| Name | Description | Promoter Sequence |
| --- | --- | --- |
| BBa_K121011 | SEQ ID NO: 395 promoter (lacI regulated) | . . . acaggaaacagctatgaccatgattacgcc |
| BBa_K135000 | SEQ ID NO: 396 pCpxR (CpxR responsive promoter) | . . . agcgacgtctgatgacgtaatttctgcctc |
| BBa_K136010 | SEQ ID NO: 397 fliA promoter | . . . gttcactctataccgctgaaggtgtaatgg |
| BBa_K145150 | SEQ ID NO: 398 Hybrid promoter: HSL-LuxR activated, P22 C2 repressed | . . . tagtttataatttaagtgttctttaatttc |
| BBa_K180000 | SEQ ID NO: 399 Hybrid promoter (trp & lac regulated -- tac pR) | . . . cgagcacttcaccaacaaggaccatagcat |
| BBa_K180002 | SEQ ID NO: 400 tac pR testing plasmid (GFP) | . . . caccttcgggtgggcctttctgcgtttata |
| BBa_K180003 | SEQ ID NO: 401 PTAC testing plasmid (GFP) - basic | . . . catggcatggatgaactatacaaataataa |
| BBa_K180004 | SEQ ID NO: 402 Game of Life - Primary plasmid | . . . caccttcgggtgggcctttctgcgtttata |
| BBa_K180005 | SEQ ID NO: 403 GoL - Primary plasmid (part 1)/RPS - Paper primary plasmid (part 1) [LuxR generator] | . . . caccttcgggtgggcctttctgcgtttata |
| BBa_K180006 | SEQ ID NO: 404 Game of Life - Primary plasmid (part 2) [lux pR, GFP and LacI generator] | . . . caccttcgggtgggcctttctgcgtttata |
| BBa_K180007 | SEQ ID NO: 405 Game of Life - Secondary plasmid [tac pR, LuxI generator] | . . . caccttcgggtgggcctttctgcgtttata |
| BBa_K180010 | SEQ ID NO: 406 Rock-paper-scissors - Rock primary plasmid | . . . caccttcgggtgggcctttctgcgtttata |
| BBa_K180011 | SEQ ID NO: 407 Rock - Primary plasmid (part 1) [RhlR generator] | . . . caccttcgggtgggcctttctgcgtttata |
| BBa_K180012 | SEQ ID NO: 408 Rock - Primary plasmid (part 2) [tac pR, mCherry and LasI generator] | . . . caccttcgggtgggcctttctgcgtttata |
| BBa_K180013 | SEQ ID NO: 409 Rock-paper-scissors - Rock secondary plasmid [rhl pR, LacI generator] | . . . caccttcgggtgggcctttctgcgtttata |
| BBa_K180014 | SEQ ID NO: 410 Rock-paper-scissors - Paper primary plasmid | . . . caccttcgggtgggcctttctgcgtttata |
| BBa_K180015 | SEQ ID NO: 411 Paper - Primary plasmid (part 2) [tac pR, GFP and RhlI generator] | . . . caccttcgggtgggcctttctgcgtttata |
| BBa_K180016 | SEQ ID NO: 412 Rock-paper-scissors - Paper secondary plasmid [lux pR, LacI generator] | . . . caccttcgggtgggcctttctgcgtttata |
| BBa_K180017 | SEQ ID NO: 413 Rock-paper-scissors - Scissors primary plasmid | . . . caccttcgggtgggcctttctgcgtttata |
| BBa_K180018 | SEQ ID NO: 414 Scissors - Primary plasmid (part 1) [LasR generator] | . . . caccttcgggtgggcctttctgcgtttata |
| BBa_K180019 | SEQ ID NO: 415 Scissors - Primary plasmid (part 2) [tac pR, mBanana and LuxI generator] | . . . caccttcgggtgggcctttctgcgtttata |
| BBa_K180020 | SEQ ID NO: 416 Rock-paper-scissors - Scissors secondary plasmid [las pR, LacI generator] | . . . caccttcgggtgggcctttctgcgtttata |

TABLE 27-continued

Examples of Positively Regulated *E. coli* σ70 Promoters

| Name | Description | Promoter Sequence |
|---|---|---|
| BBa_K206000 | SEQ ID NO: 417 pBAD strong | ... tgtttctccataccgttttttttgggctagc |
| BBa_K206001 | SEQ ID NO: 418 pBAD weak | ... tgtttctccataccgttttttttgggctagc |
| BBa_K259005 | SEQ ID NO: 419 AraC Rheostat Promoter | ... ttttatcgcaactctctactgtttctccat |
| BBa_K259007 | SEQ ID NO: 420 AraC Promoter fused with RBS | ... gtttctccattactagagaaagaggggaca |
| BBa_K266000 | SEQ ID NO: 421 PAI + LasR -> LuxI (AI) | ... caccttcgggtgggcctttctgcgtttata |
| BBa_K266005 | SEQ ID NO: 422 PAI + LasR -> LasI & AI + LuxR --\| LasI | ... aataactctgatagtgctagtgtagatctc |
| BBa_K266006 | SEQ ID NO: 423 PAI + LasR -> LasI + GFP & AI + LuxR --\| LasI + GFP | ... caccttcgggtgggcctttctgcgtttata |
| BBa_K266007 | SEQ ID NO: 424 Complex QS -> LuxI & LasI circuit | ... caccttcgggtgggcctttctgcgtttata |

TABLE 28

Examples of Positively regulated *E. coli* σS promoters

| Name | Description | Promoter Sequence |
|---|---|---|
| BBa_K112322 | SEQ ID NO: 425 {Pdps} in BBb format | ... gggacacaaaca tcaagaggatatgagatt |

TABLE 29

Examples of Positively regulated *E. coli* σ32 promoters

| Name | Description | Promoter Sequence |
|---|---|---|
| BBa_K112400 | SEQ ID NO: 426 Promoter for grpE gene - Heat Shock | ... ataataagcgaagtt agcgagatgaatgcg |

TABLE 29-continued

Examples of Positively regulated *E. coli* σ32 promoters

| Name | Description | Promoter Sequence |
|---|---|---|
| | and Ultrasound Sensitive | |

TABLE 30

Examples of Positively regulated *E. coli* σ54 promoters

| Name | Description | Promoter Sequence |
|---|---|---|
| BBa_J64979 | SEQ ID NO: 427 glnAp2 | ... agttggcacagatttcgc tttatcttttt |

TABLE 31

Examples of Positively regulated *B. subtilis* σA promoters

| Name | Description | Promoter Sequence |
|---|---|---|
| BBa_R0062 | SEQ ID NO: 428 Promoter (luxR & HSL regulated -- lux pR) | ... caagaaaatggtttgttatagtcgaataaa |
| BBa_R0065 | SEQ ID NO: 429 Promoter (lambda cI and luxR regulated -- hybrid) | ... gtgttgactattttacctctggcggtgata |
| BBa_R0071 | SEQ ID NO: 430 Promoter (RhlR & C4-HSL regulated) | ... gttagctttcgaattggctaaaaagtgttc |
| BBa_R0078 | SEQ ID NO: 431 Promoter (cinR and HSL regulated) | ... ccattctgctttccacgaacttgaaaacgc |
| BBa_R0079 | SEQ ID NO: 432 Promoter (LasR & PAI regulated) | ... ggccgcgggttcttttttggtacacgaaagc |
| BBa_R0080 | SEQ ID NO: 433 Promoter (AraC regulated) | ... ttttatcgcaactctctactgtttctccat |
| BBa_R0082 | SEQ ID NO: 434 Promoter (OmpR, positive) | ... attattctgcatttttggggagaatggact |
| BBa_R0083 | SEQ ID NO: 435 Promoter (OmpR, positive) | ... attattctgcatttttggggagaatggact |

TABLE 31-continued

Examples of Positively regulated *B. subtilis* σA promoters

| Name | Description | Promoter Sequence |
|---|---|---|
| BBa_R0084 | SEQ ID NO: 436 Promoter (OmpR, positive) | . . . aacgttagtttgaatggaaagatgcctgca |
| BBa_R1062 | SEQ ID NO: 437 Promoter, Standard (luxR and HSL regulated -- lux pR) | . . . aagaaaatggtttgttgatactcgaataaa |

TABLE 32

Examples of Miscellaneous Prokaryotic Induced Promoters

| Name | Description | Promoter Sequence |
|---|---|---|
| BBa_J64001 | SEQ ID NO: 438 psicA from *Salmonella* | . . . aacgcagtcgttaagttc tacaaagtcggt |
| BBa_J64750 | SEQ ID NO: 439 SPI-1 TTSS secretion-linked promoter from *Salmonella* | . . . gtcggtgacagataa caggagtaagtaatg |
| BBa_K112149 | SEQ ID NO: 440 PmgtCB Magnesium promoter from *Salmonella* | . . . tattggctgactataat aagcgcaaattca |
| BBa_K116201 | SEQ ID NO: 441 ureD promoter from *P mirabilis* | |
| BBa_K125100 | SEQ ID NO: 442 nir promoter from *Synechocystis* sp. PCC6803 | . . . cgaaacgggaaccta tattgatctctact |
| BBa_K131017 | SEQ ID NO: 443 p_qrr4 from *Vibrio harveyi* | . . . aagttggcacgcatcgtg ctttatacagat |

TABLE 33

Examples of Yeast Positive (Activatible) Promoters

| Name | Description | Promoter Sequence |
|---|---|---|
| BBa_J63006 | SEQ ID NO: 444 yeast GAL1 promoter | . . . gaggaaactagacccgccgccaccatggag |
| BBa_K284002 | SEQ ID NO: 445 JEN1 Promoter from *Kluyveromyces lactis* | . . . gagtaaccaaaaccaaaacagatttcaacc |
| BBa_K106699 | SEQ ID NO: 446 Gal1 Promoter | . . . aaagtaagaattttttgaaaattcaatataa |
| BBa_K165041 | SEQ ID NO: 447 Zif268-HIV binding sites + TEF constitutive yeast promoter | . . . atacggtcaacgaactataattaactaaac |
| BBa_K165034 | SEQ ID NO: 448 Zif268-HIV bs + LexA bs + mCYC promoter | . . . cacaaatacacacactaaattaataactag |
| BBa_K165031 | SEQ ID NO: 449 mCYC promoter plus LexA binding sites | . . . cacaaatacacacactaaattaataactag |
| BBa_K165030 | SEQ ID NO: 450 mCYC promoter plus Zif268-HIV binding sites | . . . cacaaatacacacactaaattaataactag |
| BBa_K165001 | SEQ ID NO: 451 pGAL1 + w/XhoI sites | . . . atactttaacgtcaaggagaaaaaactata |
| BBa_K110016 | SEQ ID NO: 452 A-Cell Promoter STE2 (backwards) | . . . accgttaagaaccatatccaagaatcaaaa |

TABLE 33-continued

Examples of Yeast Positive (Activatible) Promoters

| Name | Description | Promoter Sequence |
| --- | --- | --- |
| BBa_K110015 | SEQ ID NO: 453 A-Cell Promoter MFA1 (RtL) | . . . cttcatatataaaccgccagaaatgaatta |
| BBa_K110014 | SEQ ID NO: 454 A-Cell Promoter MFA2 (backwards) | . . . atcttcatacaacaataactaccaacctta |
| BBa_K110006 | SEQ ID NO: 455 Alpha-Cell Promoter MF(ALPHA)1 | . . . tttcatacacaatataaacgattaaaagaa |
| BBa_K110005 | SEQ ID NO: 456 Alpha-Cell Promoter MF(ALPHA)2 | . . . aaattccagtaaattcacatattggagaaa |
| BBa_K110004 | SEQ ID NO: 457 Alpha-Cell Promoter Ste3 | . . . gggagccagaacgcttctggtggtgtaaat |
| BBa_J24813 | SEQ ID NO: 458 URA3 Promoter from *S. cerevisiae* | . . . gcacagacttagattggtatatatacgcat |
| BBa_K284003 | SEQ ID NO: 459 Partial DLD Promoter from *Kluyveromyces lactis* | . . . aagtgcaagaaagaccagaaacgcaactca |

TABLE 34

Examples of Eukaryotic Positive (Activatible) Promoters

| Name | Description | Promoter Sequence |
| --- | --- | --- |
| BBa_I10498 | SEQ ID NO: 460 Oct-4 promoter | . . . taaaaaaaaaaaa aaaaaaaaaaaaaaa |
| BBa_J05215 | SEQ ID NO: 461 Regulator for R1-CREBH | . . . ggggcgagggccccg cctccggaggcgggg |
| BBa_J05216 | SEQ ID NO: 462- Regulator for R3ATF6 | . . . gaggggacggctccgg ccccggggccggag |
| BBa_J05217 | SEQ ID NO: 463 Regulator for R2-YAP7 | . . . ggggcgagggctccgg ccccggggccggag |
| BBa_J05218 | SEQ ID NO: 464 Regulator for R4-cMaf | . . . gaggggacggccccg cctccggaggcgggg |

TABLE 35

Examples of Negatively regulated (repressible) *E. coli* σ70 promoters

| Name | Description | Promoter Sequence |
| --- | --- | --- |
| BBa_I1051 | SEQ ID NO: 465 Lux cassette right promoter | . . . tgttatagtcgaatacctctggcggtgata |
| BBa_I12001 | SEQ ID NO: 466 Promoter (PRM+) | . . . gatttaacgtatcagcacaaaaaagaaacc |
| BBa_I12006 | SEQ ID NO: 467 Modified lamdba Prm promoter (repressed by 434 cI) | . . . attacaaactttcttgtatagatttaacgt |
| BBa_I12036 | SEQ ID NO: 468 Modified lamdba Prm promoter (cooperative repression by 434 cI) | . . . tttcttgtatagatttacaatgtatcttgt |
| BBa_I12040 | SEQ ID NO: 469 Modified lambda P(RM) promoter: -10 region from P(L) and cooperatively repressed by 434 cI | . . . tttcttgtagatacttacaatgtatcttgt |
| BBa_I12212 | SEQ ID NO: 470 TetR - TetR-4C heterodimer promoter (negative) | . . . actctgtcaatgatagagtggattcaaaaa |
| BBa_I14015 | SEQ ID NO: 471 P(Las) TetO | . . . ttttggtacactccctatcagtgatagaga |
| BBa_I14016 | SEQ ID NO: 472 P(Las) CIO | . . . cttttggtacactacctctggcggtgata |
| BBa_I14032 | SEQ ID NO: 473 promoter P(Lac) IQ | . . . aaaccttttcgcggtatggcatgatagcgcc |
| BBa_I714889 | SEQ ID NO: 474 OR21 of PR and PRM | . . . tattttacctctggcggtgataatggttgc |
| BBa_I714924 | SEQ ID NO: 475 RecA_DlexO_DLacO1 | . . . actctcggcatggacgagctgtacaagtaa |

TABLE 35-continued

Examples of Negatively regulated (repressible) *E. coli* σ70 promoters

| Name | Description | Promoter Sequence |
|---|---|---|
| BBa_I715003 | SEQ ID NO: 476 hybrid pLac with UV5 mutation | . . . ttgtgagcggataacaatatgttgagcaca |
| BBa_I718018 | SEQ ID NO: 477 dapAp promoter | . . . cattgagacacttgtttgcacagaggatgg |
| BBa_I731004 | SEQ ID NO: 478 FecA promoter | . . . ttctcgttcgactcatagctgaacacaaca |
| BBa_I732200 | SEQ ID NO: 479 NOT Gate Promoter Family Member (D00101wt1) | . . . gaattgtgagcggataacaattggatccgg |
| BBa_I732201 | SEQ ID NO: 480 NOT Gate Promoter Family Member (D001011) | . . . ggaattgtgagcgctcacaattggatccgg |
| BBa_I732202 | SEQ ID NO: 481 NOT Gate Promoter Family Member (D001022) | . . . ggaattgtaagcgcttacaattggatccgg |
| BBa_I732203 | SEQ ID NO: 482 NOT Gate Promoter Family Member (D001033) | . . . ggaattgtaaacgtttacaattggatccgg |
| BBa_I732204 | SEQ ID NO: 483 NOT Gate Promoter Family Member (D001044) | . . . ggaattgtgaacgttcacaattggatccgg |
| BBa_I732205 | SEQ ID NO: 484 NOT Gate Promoter Family Member (D001055) | . . . ggaattttgagcgctcaaaattggatccgg |
| BBa_I732206 | SEQ ID NO: 485 NOT Gate Promoter Family Member (D001066) | . . . ggaattatgagcgctcataattggatccgg |
| BBa_I732207 | SEQ ID NO: 486 NOT Gate Promoter Family Member (D001077) | . . . gggacgactgtatacagtcgtcggatccgg |
| BBa_I732270 | SEQ ID NO: 487 Promoter Family Member with Hybrid Operator (D001012) | . . . ggaattgtgagcgcttacaattggatccgg |
| BBa_I732271 | SEQ ID NO: 488 Promoter Family Member with Hybrid Operator (D001016) | . . . ggaattgtgagcgctcataattggatccgg |
| BBa_I732272 | SEQ ID NO: 489 Promoter Family Member with Hybrid Operator (D001017) | . . . ggaattgtgagctacagtcgtcggatccgg |
| BBa_I732273 | SEQ ID NO: 490 Promoter Family Member with Hybrid Operator (D001021) | . . . ggaattgtaagcgctcacaattggatccgg |
| BBa_I732274 | SEQ ID NO: 491 Promoter Family Member with Hybrid Operator (D001024) | . . . ggaattgtaagcgttcacaattggatccgg |
| BBa_I732275 | SEQ ID NO: 492 Promoter Family Member with Hybrid Operator (D001026) | . . . ggaattgtaagcgctcataattggatccgg |
| BBa_I732276 | SEQ ID NO: 493 Promoter Family Member with Hybrid Operator (D001027) | . . . ggaattgtaagctacagtcgtcggatccgg |
| BBa_I732277 | SEQ ID NO: 494 Promoter Family Member with Hybrid Operator (D001046) | . . . ggaattgtgaacgctcataattggatccgg |
| BBa_I732278 | SEQ ID NO: 495 Promoter Family Member with Hybrid Operator (D001047) | . . . ggaattgtgaactacagtcgtcggatccgg |
| BBa_I732279 | SEQ ID NO: 496 Promoter Family Member with Hybrid Operator (D001061) | . . . ggaattatgagcgctcacaattggatccgg |
| BBa_I732301 | SEQ ID NO: 497 NAND Candidate (U073026D001016) | . . . ggaattgtgagcgctcataattggatccgg |
| BBa_I732302 | SEQ ID NO: 498 NAND Candidate (U073027D001017) | . . . ggaattgtgagctacagtcgtcggatccgg |
| BBa_I732303 | SEQ ID NO: 499 NAND Candidate (U073022D001046) | . . . ggaattgtgaacgctcataattggatccgg |
| BBa_I732304 | SEQ ID NO: 500 NAND Candidate (U073022D001047) | . . . ggaattgtgaactacagtcgtcggatccgg |
| BBa_I732305 | SEQ ID NO: 501 NAND Candidate (U073022D059046) | . . . taaattgtgaacgctcataattggatccgg |

TABLE 35-continued

Examples of Negatively regulated (repressible) *E. coli* σ70 promoters

| Name | Description | Promoter Sequence |
|---|---|---|
| BBa_I732306 | SEQ ID NO: 502 NAND Candidate (U073O11D002O22) | ... gaaattgtaagcgcttacaattggatccgg |
| BBa_I732351 | SEQ ID NO: 503 NOR Candidate (U037O11D002O22) | ... gaaattgtaagcgcttacaattggatccgg |
| BBa_I732352 | SEQ ID NO: 504 NOR Candidate (U035O44D001O22) | ... ggaattgtaagcgcttacaattggatccgg |
| BBa_I732400 | SEQ ID NO: 505 Promoter Family Member (U097NUL + D062NUL) | ... gccaaattaaacaggattaacaggatccgg |
| BBa_I732401 | SEQ ID NO: 506 Promoter Family Member (U097O11 + D062NUL) | ... gccaaattaaacaggattaacaggatccgg |
| BBa_I732402 | SEQ ID NO: 507 Promoter Family Member (U085O11 + D062NUL) | ... gccaaattaaacaggattaacaggatccgg |
| BBa_I732403 | SEQ ID NO: 508 Promoter Family Member (U073O11 + D062NUL) | ... gccaaattaaacaggattaacaggatccgg |
| BBa_I732404 | SEQ ID NO: 509 Promoter Family Member (U061O11 + D062NUL) | ... gccaaattaaacaggattaacaggatccgg |
| BBa_I732405 | SEQ ID NO: 510 Promoter Family Member (U049O11 + D062NUL) | ... gccaaattaaacaggattaacaggatccgg |
| BBa_I732406 | SEQ ID NO: 511 Promoter Family Member (U037O11 + D062NUL) | ... gccaaattaaacaggattaacaggatccgg |
| BBa_I732407 | SEQ ID NO: 512 Promoter Family Member (U097NUL + D002O22) | ... gaaattgtaagcgcttacaattggatccgg |
| BBa_I732408 | SEQ ID NO: 513 Promoter Family Member (U097NUL + D014O22) | ... taaattgtaagcgcttacaattggatccgg |
| BBa_I732409 | SEQ ID NO: 514 Promoter Family Member (U097NUL + D026O22) | ... gtaattgtaagcgcttacaattggatccgg |
| BBa_I732410 | SEQ ID NO: 515 Promoter Family Member (U097NUL + D038O22) | ... tcaattgtaagcgcttacaattggatccgg |
| BBa_I732411 | SEQ ID NO: 516 Promoter Family Member (U097NUL + D050O22) | ... aaaattgtaagcgcttacaattggatccgg |
| BBa_I732412 | SEQ ID NO: 517 Promoter Family Member (U097NUL + D062O22) | ... caaattgtaagcgcttacaattggatccgg |
| BBa_I732413 | SEQ ID NO: 518 Promoter Family Member (U097O11 + D002O22) | ... gaaattgtaagcgcttacaattggatccgg |
| BBa_I732414 | SEQ ID NO: 519 Promoter Family Member (U097O11 + D014O22) | ... taaattgtaagcgcttacaattggatccgg |
| BBa_I732415 | SEQ ID NO: 520 Promoter Family Member (U097O11 + D026O22) | ... gtaattgtaagcgcttacaattggatccgg |
| BBa_I732416 | SEQ ID NO: 521 Promoter Family Member (U097O11 + D038O22) | ... tcaattgtaagcgcttacaattggatccgg |
| BBa_I732417 | SEQ ID NO: 522 Promoter Family Member (U097O11 + D050O22) | ... aaaattgtaagcgcttacaattggatccgg |
| BBa_I732418 | SEQ ID NO: 523 Promoter Family Member (U097O11 + D062O22) | ... caaattgtaagcgcttacaattggatccgg |
| BBa_I732419 | SEQ ID NO: 524 Promoter Family Member (U085O11 + D002O22) | ... gaaattgtaagcgcttacaattggatccgg |
| BBa_I732420 | SEQ ID NO: 525 Promoter Family Member (U085O11 + D014O22) | ... taaattgtaagcgcttacaattggatccgg |
| BBa_I732421 | SEQ ID NO: 526 Promoter Family Member (U085O11 + D026O22) | ... gtaattgtaagcgcttacaattggatccgg |

TABLE 35-continued

Examples of Negatively regulated (repressible) *E. coli* σ70 promoters

| Name | Description | Promoter Sequence |
|---|---|---|
| BBa_I732422 | SEQ ID NO: 527 Promoter Family Member (U085O11 + D038O22) | ...tcaattgtaagcgcttacaattggatccgg |
| BBa_I732423 | SEQ ID NO: 528 Promoter Family Member (U085O11 + D050O22) | ...aaaattgtaagcgcttacaattggatccgg |
| BBa_I732424 | SEQ ID NO: 529 Promoter Family Member (U085O11 + D062O22) | ...caaattgtaagcgcttacaattggatccgg |
| BBa_I732425 | SEQ ID NO: 530 Promoter Family Member (U073O11 + D002O22) | ...gaaattgtaagcgcttacaattggatccgg |
| BBa_I732426 | SEQ ID NO: 531 Promoter Family Member (U073O11 + D014O22) | ...taaattgtaagcgcttacaattggatccgg |
| BBa_I732427 | SEQ ID NO: 532 Promoter Family Member (U073O11 + D026O22) | ...gtaattgtaagcgcttacaattggatccgg |
| BBa_I732428 | SEQ ID NO: 533 Promoter Family Member (U073O11 + D038O22) | ...tcaattgtaagcgcttacaattggatccgg |
| BBa_I732429 | SEQ ID NO: 534 Promoter Family Member (U073O11 + D050O22) | ...aaaattgtaagcgcttacaattggatccgg |
| BBa_I732430 | SEQ ID NO: 535 Promoter Family Member (U073O11 + D062O22) | ...caaattgtaagcgcttacaattggatccgg |
| BBa_I732431 | SEQ ID NO: 536 Promoter Family Member (U061O11 + D002O22) | ...gaaattgtaagcgcttacaattggatccgg |
| BBa_I732432 | SEQ ID NO: 537 Promoter Family Member (U061O11 + D014O22) | ...taaattgtaagcgcttacaattggatccgg |
| BBa_I732433 | SEQ ID NO: 538 Promoter Family Member (U061O11 + D026O22) | ...gtaattgtaagcgcttacaattggatccgg |
| BBa_I732434 | SEQ ID NO: 539 Promoter Family Member (U061O11 + D038O22) | ...tcaattgtaagcgcttacaattggatccgg |
| BBa_I732435 | SEQ ID NO: 540 Promoter Family Member (U061O11 + D050O22) | ...aaaattgtaagcgcttacaattggatccgg |
| BBa_I732436 | SEQ ID NO: 541 Promoter Family Member (U061O11 + D062O22) | ...caaattgtaagcgcttacaattggatccgg |
| BBa_I732437 | SEQ ID NO: 542 Promoter Family Member (U049O11 + D002O22) | ...gaaattgtaagcgcttacaattggatccgg |
| BBa_I732438 | SEQ ID NO: 543 Promoter Family Member (U049O11 + D014O22) | ...taaattgtaagcgcttacaattggatccgg |
| BBa_I732439 | SEQ ID NO: 544 Promoter Family Member (U049O11 + D026O22) | ...gtaattgtaagcgcttacaattggatccgg |
| BBa_I732440 | SEQ ID NO: 545 Promoter Family Member (U049O11 + D038O22) | ...tcaattgtaagcgcttacaattggatccgg |
| BBa_I732441 | SEQ ID NO: 546 Promoter Family Member (U049O11 + D050O22) | ...aaaattgtaagcgcttacaattggatccgg |
| BBa_I732442 | SEQ ID NO: 547 Promoter Family Member (U049O11 + D062O22) | ...caaattgtaagcgcttacaattggatccgg |
| BBa_I732443 | SEQ ID NO: 548 Promoter Family Member (U037O11 + D002O22) | ...gaaattgtaagcgcttacaattggatccgg |
| BBa_I732444 | SEQ ID NO: 549 Promoter Family Member (U037O11 + D014O22) | ...taaattgtaagcgcttacaattggatccgg |
| BBa_I732445 | SEQ ID NO: 550 Promoter Family Member (U037O11 + D026O22) | ...gtaattgtaagcgcttacaattggatccgg |
| BBa_I732446 | SEQ ID NO: 551 Promoter Family Member (U037O11 + D038O22) | ...tcaattgtaagcgcttacaattggatccgg |

TABLE 35-continued

Examples of Negatively regulated (repressible) E. coli σ70 promoters

| Name | Description | Promoter Sequence |
|---|---|---|
| BBa_I732447 | SEQ ID NO: 552 Promoter Family Member (U037011 + D050022) | . . . aaaattgtaagcgcttacaattggatccgg |
| BBa_I732448 | SEQ ID NO: 553 Promoter Family Member (U037011 + D062022) | . . . caaattgtaagcgcttacaattggatccgg |
| BBa_I732450 | SEQ ID NO: 554 Promoter Family Member (U073026 + D062NUL) | . . . gccaaattaaacaggattaacaggatccgg |
| BBa_I732451 | SEQ ID NO: 555 Promoter Family Member (U073027 + D062NUL) | . . . gccaaattaaacaggattaacaggatccgg |
| BBa_I732452 | SEQ ID NO: 556 Promoter Family Member (U073026 + D062061) | . . . caaattatgagcgctcacaattggatccgg |
| BBa_I739101 | SEQ ID NO: 557 Double Promoter (constitutive/TetR, negative) | . . . tgatagagattccctatcagtgatagagat |
| BBa_I739102 | SEQ ID NO: 558 Double Promoter (cI, negative/TetR, negative) | . . . tgatagagattccctatcagtgatagagat |
| BBa_I739103 | SEQ ID NO: 559 Double Promoter (lacI, negative/P22 cII, negative) | . . . gttctttaattatttaagtgttctttaatt |
| BBa_I739104 | SEQ ID NO: 560 Double Promoter (LuxR/HSL, positive/P22 cII, negative) | . . . gttctttaattatttaagtgttctttaatt |
| BBa_I739105 | SEQ ID NO: 561 Double Promoter (LuxR/HSL, positive/cI, negative) | . . . cgtgcgtgttgataacaccgtgcgtgttga |
| BBa_I739106 | SEQ ID NO: 562 Double Promoter (TetR, negative/P22 cII, negative) | . . . gtgttctttaatatttaagtgttctttaat |
| BBa_I739107 | SEQ ID NO: 563 Double Promoter (cI, negative/LacI, negative) | . . . ggaattgtgagcggataacaatttcacaca |
| BBa_I746665 | SEQ ID NO: 564 Pspac-hy promoter | . . . tgtgtgtaattgtgagcggataacaattaa |
| BBa_I751500 | SEQ ID NO: 565 pcI (for positive control of pcI-lux hybrid promoter) | . . . ttttacctctggcggtgataatggttgcag |
| BBa_I751501 | SEQ ID NO: 566 plux-cI hybrid promoter | . . . gtgttgatgcttttatcaccgccagtggta |
| BBa_I751502 | SEQ ID NO: 567 plux-lac hybrid promoter | . . . agtgtgtggaattgtgagcggataacaatt |
| BBa_I756014 | SEQ ID NO: 568 LexAoperator-MajorLatePromoter | . . . aggggtggggcgcgttggcgcgccacac |
| BBa_I761011 | SEQ ID NO: 569 CinR, CinL and glucose controlled promoter | . . . acatcttaaaagttttagtatcatattcgt |
| BBa_J05209 | SEQ ID NO: 570 Modified Pr Promoter | . . . tattttacctctggcggtgataatggttgc |
| BBa_J05210 | SEQ ID NO: 571 Modified Prm + Promoter | . . . atttataaatagtggtgatagatttaacgt |
| BBa_J07019 | SEQ ID NO: 572 FecA Promoter (with Fur box) | . . . acccttctcgttcgactcatagctgaacac |
| BBa_J15301 | SEQ ID NO: 573 Pars promoter from Escherichia coli chromosomal ars operon. | . . . tgacttatccgcttcgaagagagacactac |
| BBa_J22052 | SEQ ID NO: 574 Pcya | . . . aggtgttaaattgatcacgttttagaccat |
| BBa_J22106 | SEQ ID NO: 575 rec A (SOS) Promoter | . . . caatttggtaaaggctccatcatgtaataa |
| BBa_J22126 | SEQ ID NO: 576 Rec A (SOS) promoter | . . . gagaaacaatttggtaaaggctccatcatg |
| BBa_J31013 | SEQ ID NO: 577 pLac Backwards [cf. BBa_R0010] | . . . aacgcgcggggagaggcggtttgcgtattg |
| BBa_J34800 | SEQ ID NO: 578 Promoter tetracycline inducible | . . . cagtgatagagatactgagcacatcagcac |
| BBa_J34806 | SEQ ID NO: 579 promoter lac induced | . . . ttatgcttccggctcgtataatgtttcaaa |
| BBa_J34809 | SEQ ID NO: 580 promoter lac induced | . . . ggctcgtatgttgtgtcgaccgagctgcgc |

TABLE 35-continued

Examples of Negatively regulated (repressible) *E. coli* σ70 promoters

| Name | Description | Promoter Sequence |
|---|---|---|
| BBa_J54016 | SEQ ID NO: 581 promoter_lacq | . . . aaacctttcgcggtatggcatgatagcgcc |
| BBa_J54120 | SEQ ID NO: 582 EmrR_regulated promoter | . . . atttgtcactgtcgttactatatcggctgc |
| BBa_J54130 | SEQ ID NO: 583 BetI_regulated promoter | . . . gtccaatcaataaccgctttaatagataaa |
| BBa_J56012 | SEQ ID NO: 584 Invertible sequence of dna includes Ptrc promoter | . . . actttattatcaataagttaaatcggtacc |
| BBa_J64065 | SEQ ID NO: 585 cI repressed promoter | . . . gtgttgactattttacctctggcggtgata |
| BBa_J64067 | SEQ ID NO: 586 LuxR + 3OC6HSL independent R0065 | . . . gtgttgactattttacctctggcggtgata |
| BBa_J64068 | SEQ ID NO: 587 increased strength R0051 | . . . atacctctggcggtgatatataatggttgc |
| BBa_J64069 | SEQ ID NO: 588 R0065 with lux box deleted | . . . gtgttgactattttacctctggcggtgata |
| BBa_J64712 | SEQ ID NO: 589 LasR/LasI Inducible & RHLR/RHLI repressible Promoter | . . . gaaatctggcagtttttggtacacgaaagc |
| BBa_J64800 | SEQ ID NO: 590 RHLR/RHLI Inducible & LasR/LasI repressible Promoter | . . . tgccagttctggcaggtctaaaaagtgttc |
| BBa_J64981 | SEQ ID NO: 591 OmpR-P strong binding, regulatory region for Team Challenge03-2007 | . . . agcgctcacaatttaatacgactcactata |
| BBa_J64987 | SEQ ID NO: 592 LacI Consensus Binding Site in sigma 70 binding region | . . . taataattgtgagcgctcacaattttgaca |
| BBa_J72005 | SEQ ID NO: 593 {Ptet} promoter in BBb | . . . atccctatcagtgatagagatactgagcac |
| BBa_K086017 | SEQ ID NO: 594 unmodified Lutz-Bujard LacO promoter | . . . ttgtgagcggataacaagatactgagcaca |
| BBa_K091100 | SEQ ID NO: 595 pLac_lux hybrid promoter | . . . ggaattgtgagcggataacaatttcacaca |
| BBa_K091101 | SEQ ID NO: 596 pTet_Lac hybrid promoter | . . . ggaattgtgagcggataacaatttcacaca |
| BBa_K091104 | SEQ ID NO: 597 pLac/Mnt Hybrid Promoter | . . . ggaattgtgagcggataacaatttcacaca |
| BBa_K091105 | SEQ ID NO: 598 pTet/Mnt Hybrid Promoter | . . . agaactgtaatccctatcagtgatagagat |
| BBa_K091106 | SEQ ID NO: 599 LsrA/cI hybrid promoter | . . . tgttgatttatctaacaccgtgcgtgttga |
| BBa_K091107 | SEQ ID NO: 600 pLux/cI Hybrid Promoter | . . . acaccgtgcgtgttgatatagtcgaataaa |
| BBa_K091110 | SEQ ID NO: 601 LacI Promoter | . . . ctttcgcggtatggcatgatagcgcccgg |
| BBa_K091111 | SEQ ID NO: 602 LacIQ promoter | . . . cctttcgcggtatggcatgatagcgcccgg |
| BBa_K091112 | SEQ ID NO: 603 pLacIQ1 promoter | . . . cctttcgcggtatggcatgatagcgcccgg |
| BBa_K091143 | SEQ ID NO: 604 pLas/cI Hybrid Promoter | . . . ggttcttttggtacctctggcggtgataa |
| BBa_K091146 | SEQ ID NO: 605 pLas/Lux Hybrid Promoter | . . . tgtaggatcgtacaggtataaattcttcag |
| BBa_K091157 | SEQ ID NO: 606 pLux/Las Hybrid Promoter | . . . ctatctcatttgctagtatagtcgaataaa |
| BBa_K093000 | SEQ ID NO: 607 pRecA with LexA binding site | . . . gtatatatatacagtataattgcttcaaca |
| BBa_K093008 | SEQ ID NO: 608 reverse BBa_R0011 | . . . cacaatgtcaattgttatccgctcacaatt |
| BBa_K094120 | SEQ ID NO: 609 pLacI/ara-1 | . . . aattgtgagcggataacaatttcacacaga |
| BBa_K094140 | SEQ ID NO: 610 pLacIq | . . . ccggaagagagtcaattcagggtggtgaat |
| BBa_K101000 | SEQ ID NO: 611 Dual-Repressed Promoter for p22 mnt and TetR | . . . acggtgacctagatctccgatactgagcac |
| BBa_K101001 | SEQ ID NO: 612 Dual-Repressed Promoter for LacI and LambdacI | . . . tggaattgtgagcggataaaatttcacaca |

TABLE 35-continued

Examples of Negatively regulated (repressible) *E. coli* σ70 promoters

| Name | Description | Promoter Sequence |
|---|---|---|
| BBa_K101002 | SEQ ID NO: 613 Dual-Repressed Promoter for p22 cII and TetR | . . . tagtagataatttaagtgttctttaatttc |
| BBa_K101017 | SEQ ID NO: 614 MioC Promoter (DNAa-Repressed Promoter) | . . . ccaacgcgttcacagcgtacaattactagt |
| BBa_K109200 | SEQ ID NO: 615 AraC and TetR promoter (hybrid) | . . . aacaaaaaaacggatcctctagttgcggcc |
| BBa_K112118 | SEQ ID NO: 616 rrnB P1 promoter | . . . ataaatgcttgactctgtagcgggaaggcg |
| BBa_K112318 | SEQ ID NO: 617 {<bolA promoter>} in BBb format | . . . atttcatgatgatacgtgagcggatagaag |
| BBa_K112401 | SEQ ID NO: 618 Promoter for recA gene - SOS and Ultrasound Sensitive | . . . caaacagaaagcgttggcggcagcactggg |
| BBa_K112402 | SEQ ID NO: 619 promoter for FabA gene - Membrane Damage and Ultrasound Sensitive | . . . gtcaaaatgaccgaaacgggtggtaacttc |
| BBa_K112405 | SEQ ID NO: 620 Promoter for CadA and CadB genes | . . . agtaatcttatcgccagtttggtctggtca |
| BBa_K112406 | SEQ ID NO: 621 cadC promoter | . . . agtaatcttatcgccagtttggtctggtca |
| BBa_K112701 | SEQ ID NO: 622 hns promoter | . . . aattctgaacaacatccgtactcttcgtgc |
| BBa_K112708 | SEQ ID NO: 623 PfhuA | . . . tttacgttatcattcactttacatcagagt |
| BBa_K113009 | SEQ ID NO: 624 pBad/araC | . . . gtttctccatacccgttttttttgggctagc |
| BBa_K116001 | SEQ ID NO: 625 nhaA promoter that can be regulated by pH and nhaR protein. | . . . cgatctattcacctgaaagagaaataaaaa |
| BBa_K116500 | SEQ ID NO: 626 OmpF promoter that is activated or repressed by OmpR according to osmolarity. | . . . aaacgttagtttgaatggaaagatgcctgc |
| BBa_K119002 | SEQ ID NO: 627 RcnR operator (represses RcnA) | . . . attgccgaattaatactaagaattattatc |
| BBa_K121011 | SEQ ID NO: 628 promoter (lacI regulated) | . . . acaggaaacagctatgaccatgattacgcc |
| BBa_K121014 | SEQ ID NO: 629 promoter (lambda cI regulated) | . . . actggcggttataatgagcacatcagcagg |
| BBa_K137046 | SEQ ID NO: 630 150 bp inverted tetR promoter | . . . caccgacaaacaacagataaaacgaaaggc |
| BBa_K137047 | SEQ ID NO: 631 250 bp inverted tetR promoter | . . . agtgttattaagctactaaagcgtagtttt |
| BBa_K137048 | SEQ ID NO: 632 350 bp inverted tetR promoter | . . . gaataagaaggctggctctgcaccttggtg |
| BBa_K137049 | SEQ ID NO: 633 450 bp inverted tetR promoter | . . . ttagcgacttgatgctcttgatcttccaat |
| BBa_K137050 | SEQ ID NO: 634 650 bp inverted tetR promoter | . . . acatctaaaacttttagcgttattacgtaa |
| BBa_K137051 | SEQ ID NO: 635 850 bp inverted tetR promoter | . . . ttccgacctcattaagcagctctaatgcgc |
| BBa_K137124 | SEQ ID NO: 636 LacI-repressed promoter A81 | . . . caattttaaacctgtaggatcgtacaggt |
| BBa_K137125 | SEQ ID NO: 637 LacI-repressed promoter B4 | . . . caattttaaaattaaaggcgttacccaac |
| BBa_K145150 | SEQ ID NO: 638 Hybrid promoter: HSL-LuxR activated, P22 C2 repressed | . . . tagtttataatttaagtgttctttaatttc |
| BBa_K145152 | SEQ ID NO: 639 Hybrid promoter: P22 c2, LacI NOR gate | . . . gaaaatgtgagcgagtaacaacctcacaca |
| BBa_K256028 | SEQ ID NO: 640 placI:CHE | . . . caccttcgggtgggcctttctgcgtttata |
| BBa_K259005 | SEQ ID NO: 641 AraC Rheostat Promoter | . . . ttttatcgcaactctctactgtttctccat |
| BBa_K259007 | SEQ ID NO: 642 AraC Promoter fused with RBS | . . . gtttctccattactagagaaagaggggaca |

TABLE 35-continued

Examples of Negatively regulated (repressible) *E. coli* σ70 promoters

| Name | Description | Promoter Sequence |
|---|---|---|
| BBa_K266001 | SEQ ID NO: 643 Inverter TetR -> LuxR | . . . caccttcgggtgggcctttctgcgtttata |
| BBa_K266003 | SEQ ID NO: 644 POPS -> Lac Inverter -> LasR | . . . caccttcgggtgggcctttctgcgtttata |
| BBa_K266004 | SEQ ID NO: 645 Const Lac Inverter -> LasR | . . . caccttcgggtgggcctttctgcgtttata |
| BBa_K266005 | SEQ ID NO: 646 PAI + LasR -> LasI & | . . . aataactctgatagtgctagtgtagatctc |
| BBa_K266006 | SEQ ID NO: 647 PAI + LasR -> LasI + GFP & AI + LuxR --\| LasI + GFP | . . . caccttcgggtgggcctttctgcgtttata |
| BBa_K266007 | SEQ ID NO: 648 Complex QS -> LuxI & LasI circuit | . . . caccttcgggtgggcctttctgcgtttata |
| BBa_K266008 | SEQ ID NO: 649 J23100 + Lac inverter | . . . ttgtgagcggataacaagatactgagcaca |
| BBa_K266009 | SEQ ID NO: 650 J23100 + Lac inverter + RBS | . . . actgagcacatactagagaaagaggagaaa |
| BBa_K266011 | SEQ ID NO: 651 Lac Inverter and strong RBS | . . . actgagcacatactagagaaagaggagaaa |
| BBa_K292002 | SEQ ID NO: 652 pLac (LacI regulated) + Strong RBS | . . . tcacacatactagagattaaagaggagaaa |
| BBa_M31370 | SEQ ID NO: 653 tacI Promoter | . . . ggaattgtgagcggataacaatttcacaca |
| BBa_R0010 | SEQ ID NO: 654 promoter (lacI regulated) | . . . ggaattgtgagcggataacaatttcacaca |
| BBa_R0011 | SEQ ID NO: 655 Promoter (lacI regulated, lambda pL hybrid) | . . . ttgtgagcggataacaagatactgagcaca |
| BBa_R0040 | SEQ ID NO: 656 TetR repressible promoter | . . . atccctatcagtgatagagatactgagcac |
| BBa_R0050 | SEQ ID NO: 657 Promoter (HK022 cI regulated) | . . . ccgtcataatatgaaccataagttcaccac |
| BBa_R0051 | SEQ ID NO: 658 promoter (lambda cI regulated) | . . . tattttacctctggcggtgataatggttgc |
| BBa_R0052 | SEQ ID NO: 659 Promoter (434 cI regulated) | . . . attgtatgaaaatacaagaaagtttgttga |
| BBa_R0053 | SEQ ID NO: 660 Promoter (p22 cII regulated) | . . . tagtagataatttaagtgttctttaatttc |
| BBa_R0061 | SEQ ID NO: 661 Promoter (HSL-mediated luxR repressor) | ttgacacctgtaggatcgtacaggtataat |
| BBa_R0063 | SEQ ID NO: 662 Promoter (luxR & HSL regulated -- lux pL) | . . . cacgcaaaacttgcgacaaacaataggtaa |
| BBa_R0065 | SEQ ID NO: 663 Promoter (lambda cI and luxR regulated -- hybrid) | . . . gtgttgactattttacctctggcggtgata |
| BBa_R0073 | SEQ ID NO: 664 Promoter (Mnt regulated) | . . . tagatctcctatagtgagtcgtattaattt |
| BBa_R0074 | SEQ ID NO: 665 Promoter (PenI regulated) | . . . tactttcaaagactacatttgtaagatttg |
| BBa_R0075 | SEQ ID NO: 666 Promoter (TP901 cI regulated) | . . . cataaagttcatgaaacgtgaactgaaatt |
| BBa_R1050 | SEQ ID NO: 667 Promoter, Standard (HK022 cI regulated) | . . . ccgtgatactatgaaccataagttcaccac |
| BBa_R1051 | SEQ ID NO: 668 Promoter, Standard (lambda cI regulated) | . . . aattttacctctggcggtgatactggttgc |
| BBa_R1052 | SEQ ID NO: 669 Promoter, Standard (434 cI regulated) | . . . attgtatgatactacaagaaagtttgttga |
| BBa_R1053 | SEQ ID NO: 670 Promoter, Standard (p22 cII regulated) | . . . tagtagatactttaagtgttctttaatttc |
| BBa_R2000 | SEQ ID NO: 671 Promoter, Zif23 regulated, test: between | . . . tggtcccacgcgcgtgggatactacgtcag |
| BBa_R2001 | SEQ ID NO: 672 Promoter, Zif23 regulated, test: after | . . . attacggtgagatactcccacgcgcgtggg |

TABLE 35-continued

Examples of Negatively regulated (repressible) E. coli σ70 promoters

| Name | Description | Promoter Sequence |
|---|---|---|
| BBa_R2002 | SEQ ID NO: 673 Promoter, Zif23 regulated, test: between and after | . . . acgcgcgtgggatactcccacgcgcgtggg |
| BBa_R2108 | SEQ ID NO: 674 Promoter with operator site for C2003 | . . . gattagattcataaatttgagagaggagtt |
| BBa_R2109 | SEQ ID NO: 675 Promoter with operator site for C2003 | . . . acttagattcataaatttgagagaggagtt |
| BBa_R2110 | SEQ ID NO: 676 Promoter with operator site for C2003 | . . . ggttagattcataaatttgagagaggagtt |
| BBa_R2111 | SEQ ID NO: 677 Promoter with operator site for C2003 | . . . acttagattcataaatttgagagaggagtt |
| BBa_R2112 | SEQ ID NO: 678 Promoter with operator site for C2003 | . . . aattagattcataaatttgagagaggagtt |
| BBa_R2113 | SEQ ID NO: 679 Promoter with operator site for C2003 | . . . acttagattcataaatttgagagaggagtt |
| BBa_R2114 | SEQ ID NO: 680 Promoter with operator site for C2003 | . . . atttagattcataaatttgagagaggagtt |
| BBa_R2201 | SEQ ID NO: 681 C2006-repressible promoter | . . . cacgcgcgtgggaatgttataatacgtcag |
| BBa_S04209 | SEQ ID NO: 682 R0051:Q04121:B0034:C0079: B0015 | . . . actgagcacatactagagaaagaggagaaa |

TABLE 36

Examples of Negatively regulated (repressible) E. coli $\sigma^S$ promoters

| Name | Description | Promoter Sequence |
|---|---|---|
| BBa_K086030 | SEQ ID NO: 683 modified Lutz-Bujard LacO promoter, with alternative sigma factor σ38 | . . . cagtgagcgagtaacaactacgctgtttta |
| BBa_K086031 | SEQ ID NO: 684 modified Lutz-Bujard LacO promoter, with alternative sigma factor σ38 | . . . cagtgagcgagtaacaactacgctgtttta |
| BBa_K086032 | SEQ ID NO: 685 modified Lutz-Bujard LacO promoter, with alternative sigma factor σ38 | . . . atgtgagcggataacactataattaataga |
| BBa_K086033 | SEQ ID NO: 686 modified Lutz-Bujard LacO promoter, with alternative sigma factor σ38 | . . . atgtgagcggataacactataattaataga |
| BBa_K112318 | SEQ ID NO: 687 {<bolA promoter>} in BBb format | . . . atttcatgatgatacgtgagcggatagaag |

TABLE 37

Examples of Negatively regulated (repressible) E. coli σ32 promoters

| Name | Description | Promoter Sequence |
|---|---|---|
| BBa_K086026 | SEQ ID NO: 688 modified Lutz-Bujard LacO promoter, with alternative sigma factor σ32 | . . . ttgtgagcgagtggcaccattaagtacgta |
| BBa_K086027 | SEQ ID NO: 689 modified Lutz-Bujard LacO promoter, with alternative sigma factor σ32 | . . . ttgtgagcgagtgacaccattaagtacgta |

TABLE 37-continued

Examples of Negatively regulated (repressible) E. coli σ32 promoters

| Name | Description | Promoter Sequence |
|---|---|---|
| BBa_K086028 | SEQ ID NO: 690 modified Lutz-Bujard LacO promoter, with alternative sigma factor σ32 | . . . ttgtgagcgagtaacaccattaagtacgta |
| BBa_K086029 | SEQ ID NO: 691 modified Lutz-Bujard LacO promoter, with alternative sigma factor σ32 | . . . ttgtgagcgagtaacaccattaagtacgta |

TABLE 38

Examples of Negatively regulated (repressible) E. coli σ54 promoters

| Name | Description | Promoter Sequence |
|---|---|---|
| BBa_J64979 | SEQ ID NO: 692 glnAp2 | . . . agttggcacagatttcg ctttatctttttt |

TABLE 39

Examples of Repressible B. subtilis σ⁴ promoters

| Name | Description | Promoter Sequence |
|---|---|---|
| BBa_K090501 | SEQ ID NO: 693 Gram-Positive IPTG-Inducible Promoter | . . . tggaattgtgagc ggataacaattaagctt |

TABLE 39-continued

Examples of Repressible B. subtilis σ⁴ promoters

| Name | Description | Promoter Sequence |
|---|---|---|
| BBa_K143014 | SEQ ID NO: 694 Promoter Xyl for B. subtilis | . . . agtttgtttaaa caacaaactaataggtga |
| BBa_K143015 | SEQ ID NO: 695 Promoter hyper-spank for B. subtilis | . . . aatgtgtgtaat tgtgagcggataacaatt |

TABLE 40

Examples of T7 Repressible Promoters

| Name | Description | Promoter Sequence |
|---|---|---|
| BBa_R0184 | SEQ ID NO: 696 T7 promoter (lacI repressible) | . . . atagggaattgtgagcggataacaattcc |
| BBa_R0185 | SEQ ID NO: 697 T7 promoter (lacI repressible) | . . . atagggaattgtgagcggataacaattcc |
| BBa_R0186 | SEQ ID NO: 698 T7 promoter (lacI repressible) | . . . atagggaattgtgagcggataacaattcc |
| BBa_R0187 | SEQ ID NO: 699 T7 promoter (lacI repressible) | . . . atagggaattgtgagcggataacaattcc |

TABLE 41

Examples of Yeast Repressible Promoters

| Name | Description | Promoter Sequence |
|---|---|---|
| BBa_I766558 | SEQ ID NO: 700 pFig1 (Inducible) Promoter | . . . aaacaaacaaacaaaaaaaaaaaaaaaaa |
| BBa_I766214 | SEQ ID NO: 701 pGal1 | . . . atactttaacgtcaaggagaaaaaactata |
| BBa_K165000 | SEQ ID NO: 702 MET 25 Promoter | . . . tagatacaattctattaccccccatccatac |

TABLE 42

Examples of Eukaryotic Repressible Promoters

| Name | Description | Promoter Sequence |
|---|---|---|
| BBa_I756015 | SEQ ID NO: 703 CMV Promoter with lac operator sites | . . . ttagtgaaccgtcagatcactagtctgcag |
| BBa_I756016 | SEQ ID NO: 704 CMV-tet promoter | . . . ttagtgaaccgtcagatcactagtctgcag |
| BBa_I756017 | SEQ ID NO: 705 U6 promoter with tet operators | . . . ggaaaggacgaaacaccgactagtctgcag |
| BBa_I756018 | SEQ ID NO: 706 Lambda Operator in SV-40 intron | . . . attgtttgtgtattttagactagtctgcag |
| BBa_I756019 | SEQ ID NO: 707 Lac Operator in SV-40 intron | . . . attgtttgtgtattttagactagtctgcag |
| BBa_I756020 | SEQ ID NO: 708 Tet Operator in SV-40 intron | . . . attgtttgtgtattttagactagtctgcag |
| BBa_I756021 | SEQ ID NO: 709 CMV promoter with Lambda Operator | . . . ttagtgaaccgtcagatcactagtctgcag |

TABLE 43

Examples of Combination Inducible & Repressible *E. coli* Promoters

| Name | Description | Promoter Sequence |
|---|---|---|
| BBa_I1051 | SEQ ID NO: 710 Lux cassette right promoter | . . . tgttatagtcgaatacctctggcggtgata |
| BBa_I12006 | SEQ ID NO: 711 Modified lamdba Prm promoter (repressed by 434 cI) | . . . attacaaactttcttgtatagatttaacgt |
| BBa_I12036 | SEQ ID NO: 712 Modified lamdba Prm promoter (cooperative repression by 434 cI) | . . . tttcttgtatagatttacaatgtatcttgt |
| BBa_I12040 | SEQ ID NO: 713 Modified lambda P(RM) promoter: -10 region from P(L) and cooperatively repressed by 434 cI | . . . tttcttgtagatacttacaatgtatcttgt |
| BBa_I14015 | SEQ ID NO: 714 P(Las) TetO | . . . ttttggtacactccctatcagtgatagaga |
| BBa_I14016 | SEQ ID NO: 715 P(Las) CIO | . . . cttttggtacactacctctggcggtgata |
| BBa_I714924 | SEQ ID NO: 716 RecA_DlexO_DLacO1 | . . . actctcggcatggacgagctgtacaagtaa |
| BBa_I731004 | SEQ ID NO: 717 FecA promoter | . . . ttctcgttcgactcatagctgaacacaaca |
| BBa_I732301 | SEQ ID NO: 718 NAND Candidate (U073026D001016) | . . . ggaattgtgagcgctcataattggatccgg |
| BBa_I732302 | SEQ ID NO: 719 NAND Candidate (U073027D001017) | . . . ggaattgtgagctacagtcgtcggatccgg |
| BBa_I732303 | SEQ ID NO: 720 NAND Candidate (U073022D001046) | . . . ggaattgtgaacgctcataattggatccgg |
| BBa_I732304 | SEQ ID NO: 721 NAND Candidate (U073022D001047) | . . . ggaattgtgaactacagtcgtcggatccgg |
| BBa_I732305 | SEQ ID NO: 722 NAND Candidate (U073022D059046) | . . . taaattgtgaacgctcataattggatccgg |
| BBa_I732306 | SEQ ID NO: 723 NAND Candidate (U073011D002022) | . . . gaaattgtaagcgcttacaattggatccgg |
| BBa_I732351 | SEQ ID NO: 724 NOR Candidate (U037011D002022) | . . . gaaattgtaagcgcttacaattggatccgg |
| BBa_I732352 | SEQ ID NO: 725 NOR Candidate (U035044D001022) | . . . ggaattgtaagcgcttacaattggatccgg |

TABLE 43-continued

Examples of Combination Inducible & Repressible *E. coli* Promoters

| Name | Description | Promoter Sequence |
|---|---|---|
| BBa_I732400 | SEQ ID NO: 726 Promoter Family Member (U097NUL + D062NUL) | . . . gccaaattaaacaggattaacaggatccgg |
| BBa_I732401 | SEQ ID NO: 727 Promoter Family Member (U097O11 + D062NUL) | . . . gccaaattaaacaggattaacaggatccgg |
| BBa_I732402 | SEQ ID NO: 728 Promoter Family Member (U085O11 + D062NUL) | . . . gccaaattaaacaggattaacaggatccgg |
| BBa_I732403 | SEQ ID NO: 729 Promoter Family Member (U073O11 + D062NUL) | . . . gccaaattaaacaggattaacaggatccgg |
| BBa_I732404 | SEQ ID NO: 730 Promoter Family Member (U061O11 + D062NUL) | . . . gccaaattaaacaggattaacaggatccgg |
| BBa_I732405 | SEQ ID NO: 731 Promoter Family Member (U049O11 + D062NUL) | . . . gccaaattaaacaggattaacaggatccgg |
| BBa_I732406 | SEQ ID NO: 732 Promoter Family Member (U037O11 + D062NUL) | . . . gccaaattaaacaggattaacaggatccgg |
| BBa_I732407 | SEQ ID NO: 733 Promoter Family Member (U097NUL + D002O22) | . . . gaaattgtaagcgcttacaattggatccgg |
| BBa_I732408 | SEQ ID NO: 734 Promoter Family Member (U097NUL + D014O22) | . . . taaattgtaagcgcttacaattggatccgg |
| BBa_I732409 | SEQ ID NO: 735 Promoter Family Member (U097NUL + D026O22) | . . . gtaattgtaagcgcttacaattggatccgg |
| BBa_I732410 | SEQ ID NO: 736 Promoter Family Member (U097NUL + D038O22) | . . . tcaattgtaagcgcttacaattggatccgg |
| BBa_I732411 | SEQ ID NO: 737 Promoter Family Member (U097NUL + D050O22) | . . . aaaattgtaagcgcttacaattggatccgg |
| BBa_I732412 | SEQ ID NO: 738 Promoter Family Member (U097NUL + D062O22) | . . . caaattgtaagcgcttacaattggatccgg |
| BBa_I732413 | SEQ ID NO: 739 Promoter Family Member (U097O11 + D002O22) | . . . gaaattgtaagcgcttacaattggatccgg |
| BBa_I732414 | SEQ ID NO: 740 Promoter Family Member (U097O11 + D014O22) | . . . taaattgtaagcgcttacaattggatccgg |
| BBa_I732415 | SEQ ID NO: 741 Promoter Family Member (U097O11 + D026O22) | . . . gtaattgtaagcgcttacaattggatccgg |
| BBa_I732416 | SEQ ID NO: 742 Promoter Family Member (U097O11 + D038O22) | . . . tcaattgtaagcgcttacaattggatccgg |
| BBa_I732417 | SEQ ID NO: 743 Promoter Family Member (U097O11 + D050O22) | . . . aaaattgtaagcgcttacaattggatccgg |
| BBa_I732418 | SEQ ID NO: 744 Promoter Family Member (U097O11 + D062O22) | . . . caaattgtaagcgcttacaattggatccgg |
| BBa_I732419 | SEQ ID NO: 745 Promoter Family Member (U085O11 + D002O22) | . . . gaaattgtaagcgcttacaattggatccgg |
| BBa_I732420 | SEQ ID NO: 746 Promoter Family Member (U085O11 + D014O22) | . . . taaattgtaagcgcttacaattggatccgg |
| BBa_I732421 | SEQ ID NO: 747 Promoter Family Member (U085O11 + D026O22) | . . . gtaattgtaagcgcttacaattggatccgg |
| BBa_I732422 | SEQ ID NO: 748 Promoter Family Member (U085O11 + D038O22) | . . . tcaattgtaagcgcttacaattggatccgg |
| BBa_I732423 | SEQ ID NO: 749 Promoter Family Member (U085O11 + D050O22) | . . . aaaattgtaagcgcttacaattggatccgg |
| BBa_I732424 | SEQ ID NO: 750 Promoter Family Member (U085O11 + D062O22) | . . . caaattgtaagcgcttacaattggatccgg |

TABLE 43-continued

Examples of Combination Inducible & Repressible E. coli Promoters

| Name | Description | Promoter Sequence |
|---|---|---|
| BBa_I732425 | SEQ ID NO: 751 Promoter Family Member (U073011 + D002022) | . . . gaaattgtaagcgcttacaattggatccgg |
| BBa_I732426 | SEQ ID NO: 752 Promoter Family Member (U073011 + D014022) | . . . taaattgtaagcgcttacaattggatccgg |
| BBa_I732427 | SEQ ID NO: 753 Promoter Family Member (U073011 + D026022) | . . . gtaattgtaagcgcttacaattggatccgg |
| BBa_I732428 | SEQ ID NO: 754 Promoter Family Member (U073011 + D038022) | . . . tcaattgtaagcgcttacaattggatccgg |
| BBa_I732429 | SEQ ID NO: 755 Promoter Family Member (U073011 + D050022) | . . . aaaattgtaagcgcttacaattggatccgg |
| BBa_I732430 | SEQ ID NO: 756 Promoter Family Member (U073011 + D062022) | . . . caaattgtaagcgcttacaattggatccgg |
| BBa_I732431 | SEQ ID NO: 757 Promoter Family Member (U061011 + D002022) | . . . gaaattgtaagcgcttacaattggatccgg |
| BBa_I732432 | SEQ ID NO: 758 Promoter Family Member (U061011 + D014022) | . . . taaattgtaagcgcttacaattggatccgg |
| BBa_I732433 | SEQ ID NO: 759 Promoter Family Member (U061011 + D026022) | . . . gtaattgtaagcgcttacaattggatccgg |
| BBa_I732434 | SEQ ID NO: 760 Promoter Family Member (U061011 + D038022) | . . . tcaattgtaagcgcttacaattggatccgg |
| BBa_I732435 | SEQ ID NO: 761 Promoter Family Member (U061011 + D050022) | . . . aaaattgtaagcgcttacaattggatccgg |
| BBa_I732436 | SEQ ID NO: 762 Promoter Family Member (U061011 + D062022) | . . . caaattgtaagcgcttacaattggatccgg |
| BBa_I732437 | SEQ ID NO: 763 Promoter Family Member (U049011 + D002022) | . . . gaaattgtaagcgcttacaattggatccgg |
| BBa_I732438 | SEQ ID NO: 764 Promoter Family Member (U049011 + D014022) | . . . taaattgtaagcgcttacaattggatccgg |
| BBa_I732439 | SEQ ID NO: 765 Promoter Family Member (U049011 + D026022) | . . . gtaattgtaagcgcttacaattggatccgg |
| BBa_I732440 | SEQ ID NO: 766 Promoter Family Member (U049011 + D038022) | . . . tcaattgtaagcgcttacaattggatccgg |
| BBa_I732441 | SEQ ID NO: 767 Promoter Family Member (U049011 + D050022) | . . . aaaattgtaagcgcttacaattggatccgg |
| BBa_I732442 | SEQ ID NO: 768 Promoter Family Member (U049011 + D062022) | . . . caaattgtaagcgcttacaattggatccgg |
| BBa_I732443 | SEQ ID NO: 769 Promoter Family Member (U037011 + D002022) | . . . gaaattgtaagcgcttacaattggatccgg |
| BBa_I732444 | SEQ ID NO: 770 Promoter Family Member (U037011 + D014022) | . . . taaattgtaagcgcttacaattggatccgg |
| BBa_I732445 | SEQ ID NO: 771 Promoter Family Member (U037011 + D026022) | . . . gtaattgtaagcgcttacaattggatccgg |
| BBa_I732446 | SEQ ID NO: 772 Promoter Family Member (U037011 + D038022) | . . . tcaattgtaagcgcttacaattggatccgg |
| BBa_I732447 | SEQ ID NO: 773 Promoter Family Member (U037011 + D050022) | . . . aaaattgtaagcgcttacaattggatccgg |
| BBa_I732448 | SEQ ID NO: 774 Promoter Family Member (U037011 + D062022) | . . . caaattgtaagcgcttacaattggatccgg |
| BBa_I732450 | SEQ ID NO: 775 Promoter Family Member (U073026 + D062NUL) | . . . gccaaattaaacaggattaacaggatccgg |

TABLE 43-continued

Examples of Combination Inducible & Repressible E. coli Promoters

| Name | Description | Promoter Sequence |
|---|---|---|
| BBa_I732451 | SEQ ID NO: 776 Promoter Family Member (U073027 + D062NUL) | . . . gccaaattaaacaggattaacaggatccgg |
| BBa_I732452 | SEQ ID NO: 777 Promoter Family Member (U073026 + D062061) | . . . caaattatgagcgctcacaattggatccgg |
| BBa_I739102 | SEQ ID NO: 778 Double Promoter (cI, negative/TetR, negative) | . . . tgatagagattccctatcagtgatagagat |
| BBa_I739103 | SEQ ID NO: 779 Double Promoter (lacI, negative/P22 cII, negative) | . . . gttctttaattatttaagtgttctttaatt |
| BBa_I739104 | SEQ ID NO: 780 Double Promoter (LuxR/HSL, positive/P22 cII, negative) | . . . gttctttaattatttaagtgttctttaatt |
| BBa_I739105 | SEQ ID NO: 781 Double Promoter LuxR/HSL, positive/cI, negative) | . . . cgtgcgtgttgataacaccgtgcgtgttga |
| BBa_I739106 | SEQ ID NO: 782 Double Promoter (TetR, negative/P22 cII, negative) | . . . gtgttctttaatatttaagtgttctttaat |
| BBa_I739107 | SEQ ID NO: 783 Double Promoter (cI, negative/LacI, negative) | . . . ggaattgtgagcggataacaatttcacaca |
| BBa_I741018 | SEQ ID NO: 784 Right facing promoter (for xylF) controlled by xylR and CRP-cAMP | . . . gttacgtttatcgcggtgattgttacttat |
| BBa_I741019 | SEQ ID NO: 785 Right facing promoter (for xylA) controlled by xylR and CRP-cAMP | . . . gcaaataaaatggaatgatgaaactgggt |
| BBa_I742124 | SEQ ID NO: 786 Reverse complement Lac promoter | . . . aacgcgcggggagaggcggtttgcgtattg |
| BBa_I751501 | SEQ ID NO: 787 plux-cI hybrid promoter | . . . gtgttgatgcttttatcaccgccagtggta |
| BBa_I751502 | SEQ ID NO: 788 plux-lac hybrid promoter | . . . agtgtgtggaattgtgagcggataacaatt |
| BBa_I761011 | SEQ ID NO: 789 CinR, CinL and glucose controlled promoter | . . . acatcttaaaagttttagtatcatattcgt |
| BBa_I765007 | SEQ ID NO: 790 Fe and UV promoters | . . . ctgaaagcgcataccgctatggaggggtt |
| BBa_J05209 | SEQ ID NO: 791 Modified Pr Promoter | . . . tatttacctctggcggtgataatggttgc |
| BBa_J05210 | SEQ ID NO: 792 Modified Prm+ Promoter | . . . atttataaatagtggtgatagatttaacgt |
| BBa_J58100 | SEQ ID NO: 793 AND-type promoter synergistically activated by cI and CRP | . . . atttataaatagtggtgatagatttaacgt |
| BBa_J64712 | SEQ ID NO: 794 LasR/LasI Inducible & RHLR/RHLI repressible Promoter | . . . gaaatctggcagttttggtacacgaaagc |
| BBa_J64800 | SEQ ID NO: 795 RHLR/RHLI Inducible & LasR/LasI repressible Promoter | . . . tgccagttctggcaggtctaaaaagtgttc |
| BBa_J64804 | SEQ ID NO: 796 The promoter region (inclusive of regulator binding sites) of the B. subtilis RocDEF operon | . . . cacagaacttgcatttatataaagggaaag |
| BBa_J64979 | SEQ ID NO: 797 glnAp2 | . . . agttggcacagatttcgctttatctttttt |
| BBa_J64981 | SEQ ID NO: 798 OmpR-P strong binding, regulatory region for Team Challenge03-2007 | . . . agcgctcacaatttaatacgactcactata |
| BBa_K091100 | SEQ ID NO: 799 pLac_lux hybrid promoter | . . . ggaattgtgagcggataacaatttcacaca |
| BBa_K091101 | SEQ ID NO: 800 pTet_Lac hybrid promoter | . . . ggaattgtgagcggataacaatttcacaca |
| BBa_K091104 | SEQ ID NO: 801 pLac/Mnt Hybrid Promoter | . . . ggaattgtgagcggataacaatttcacaca |

TABLE 43-continued

Examples of Combination Inducible & Repressible E. coli Promoters

| Name | Description | Promoter Sequence |
|---|---|---|
| BBa_K091105 | SEQ ID NO: 802 pTet/Mnt Hybrid Promoter | . . . agaactgtaatccctatcagtgatagagat |
| BBa_K091106 | SEQ ID NO: 803 LsrA/cI hybrid promoter | . . . tgttgatttatctaacaccgtgcgtgttga |
| BBa_K091107 | SEQ ID NO: 804 pLux/cI Hybrid Promoter | . . . acaccgtgcgtgttgatatagtcgaataaa |
| BBa_K091143 | SEQ ID NO: 805 pLas/cI Hybrid Promoter | . . . ggttcttttggtacctctggcggtgataa |
| BBa_K091146 | SEQ ID NO: 806 pLas/Lux Hybrid Promoter | . . . tgtaggatcgtacaggtataaattcttcag |
| BBa_K091157 | SEQ ID NO: 807 pLux/Las Hybrid Promoter | . . . ctatctcatttgctagtatagtcgaataaa |
| BBa_K094120 | SEQ ID NO: 808 pLacI/ara-1 | . . . aattgtgagcggataacaatttcacacaga |
| BBa_K100000 | SEQ ID NO: 809 Natural Xylose Regulated Bi-Directional Operator | . . . gttacgtttatcgcggtgattgttacttat |
| BBa_K101000 | SEQ ID NO: 810 Dual-Repressed Promoter for p22 mnt and TetR | . . . acggtgacctagatctccgatactgagcac |
| BBa_K101001 | SEQ ID NO: 811 Dual-Repressed Promoter for LacI and LambdacI | . . . tggaattgtgagcggataaaatttcacaca |
| BBa_K101002 | SEQ ID NO: 812 Dual-Repressed Promoter for p22 cII and TetR | . . . tagtagataaatttaagtgttctttaattc |
| BBa_K109200 | SEQ ID NO: 813 AraC and TetR promoter (hybrid) | . . . aacaaaaaaacggatcctctagttgcggcc |
| BBa_K112118 | SEQ ID NO: 814 rrnB P1 promoter | . . . ataaatgcttgactctgtagcgggaaggcg |
| BBa_K112318 | SEQ ID NO: 815 {<bolA promoter>} in BBb format | . . . atttcatgatgatacgtgagcggatagaag |
| BBa_K112322 | SEQ ID NO: 816 {Pdps} in BBb format | . . . gggacacaaacatcaagaggatatgagatt |
| BBa_K112402 | SEQ ID NO: 817 promoter for FabA gene - Membrane Damage and Ultrasound Sensitive | . . . gtcaaaatgaccgaaacgggtggtaacttc |
| BBa_K112405 | SEQ ID NO: 818 Promoter for CadA and CadB genes | . . . agtaatcttatcgccagtttggtctggtca |
| BBa_K112406 | SEQ ID NO: 819 cadC promoter | . . . agtaatcttatcgccagtttggtctggtca |
| BBa_K112701 | SEQ ID NO: 820 hns promoter | . . . aattctgaacaacatccgtactcttcgtgc |
| BBa_K116001 | SEQ ID NO: 821 nhaA promoter, that can be regulated by pH and nhaR protein. | . . . cgatctattcacctgaaagagaaataaaaa |
| BBa_K116500 | SEQ ID NO: 822 OmpF promoter that is activated or repressed by OmpR according to osmolarity. | . . . aaacgttagtttgaatggaaagatgcctgc |
| BBa_K121011 | SEQ ID NO: 823 promoter (lacI regulated) | . . . acaggaaacagctatgaccatgattacgcc |
| BBa_K136010 | SEQ ID NO: 824 fliA promoter | . . . gttcactctataccgctgaaggtgtaatgg |
| BBa_K145150 | SEQ ID NO: 825 Hybrid promoter: HSL-LuxR activated, P22 C2 repressed | . . . tagtttataatttaagtgttctttaatttc |
| BBa_K145152 | SEQ ID NO: 826 Hybrid promoter: P22 c2, LacI NOR gate | . . . gaaaatgtgagcgagtaacaacctcacaca |
| BBa_K259005 | SEQ ID NO: 827 AraC Rheostat Promoter | . . . ttttatcgcaactctctactgtttctccat |
| BBa_K259007 | SEQ ID NO: 828 AraC Promoter fused with RBS | . . . gtttctccattactagagaaagaggggaca |
| BBa_K266005 | SEQ ID NO: 829 PAI + LasR -> LasI & AI + LuxR --\| LasI | . . . aataactctgatagtgctagtgtagatctc |

TABLE 43-continued

Examples of Combination Inducible & Repressible *E. coli* Promoters

| Name | Description | Promoter Sequence |
|---|---|---|
| BBa_K266006 | SEQ ID NO: 830 PAI + LasR -> LasI + GFP & AI + LuxR --\| LasI + GFP | . . . caccttcgggtgggcctttctgcgtttata |
| BBa_K266007 | SEQ ID NO: 831 Complex QS -> LuxI & LasI circuit | . . . caccttcgggtgggcctttctgcgtttata |
| BBa_R0065 | SEQ ID NO: 832 Promoter (lambda cI and luxR regulated -- hybrid) | . . . gtgttgactattttacctctggcggtgata |

TABLE 44

Examples of Combination Inducible & Repressible Miscellaneous Prokaryotic Promoters

| Name | Description | Promoter Sequence |
|---|---|---|
| BBa_K125100 | SEQ ID NO: 833 nir promoter from *Synechocystis* sp. PCC6803 | . . . cgaaacgggaaccctatattgatctctact |

TABLE 45

Examples of Combination Inducible & Repressible Miscellaneous Yeast Promoters

| Name | Description | Promoter Sequence |
|---|---|---|
| BBa_I766200 | SEQ ID NO: 834 pSte2 | . . . accgttaagaaccatatccaagaatcaaaa |
| BBa_K110016 | SEQ ID NO: 835 A-Cell Promoter STE2 (backwards) | . . . accgttaagaaccatatccaagaatcaaaa |
| BBa_K165034 | SEQ ID NO: 836 Zif268-HIV bs + LexA bs + mCYC promoter | . . . cacaaatacacacactaaattaataactag |
| BBa_K165041 | SEQ ID NO: 837 Zif268-HIV binding sites + TEF constitutive yeast promoter | . . . atacggtcaacgaactataattaactaaac |
| BBa_K165043 | SEQ ID NO: 838 Zif268-HIV binding sites + MET25 constitutive yeast promoter | . . . tagatacaattctattaccccatccatac |

TABLE 46

Examples of Combination Inducible & Repressible Miscellaneous Eukaryotic Promoters

| Name | Description | Promoter Sequence |
|---|---|---|
| BBa_J05215 | SEQ ID NO: 839 Regulator for R1- CREBH | . . . ggggcgagggccccgcctccggaggcgggg |
| BBa_J05216 | SEQ ID NO: 840 Regulator for R3- ATF6 | . . . gaggggacggctccggccccggggccggag |
| BBa_J05217 | SEQ ID NO: 841 Regulator for R2- YAP7 | . . . ggggcgagggctccggccccggggccggag |
| BBa_J05218 | SEQ ID NO: 842 Regulator for R4- cMaf | . . . gaggggacggccccgcctccggaggcgggg |

Ribosome Binding Sites

Ribosome binding sites (RBS) are sequences that promote efficient and accurate translation of mRNAs for protein synthesis, and are also provided for use in the modules and biological converter switches of the invention to enable modulation of the efficiency and rates of synthesis of the proteins encoded by the switches, such as recombinases and repressors. The RBS affects the translation rate of an open reading frame in two main ways—i) the rate at which ribosomes are recruited to the mRNA and initiate translation is dependent on the sequence of the RBS, and ii) the RBS can also affect the stability of the mRNA, thereby affecting the number of proteins made over the lifetime of the mRNA. Accordingly, one or more ribosome binding site (RBS) can be added to the modules and engineered genetic counters described herein to control expression of proteins, such as recombinases.

Translation initiation in prokaryotes is a complex process involving the ribosome, the mRNA, and several other proteins, such as initiation factors, as described in Laursen B S, et al., Microbiol Mol Biol Rev 2005 March; 69(1) 101-23. Translation initiation can be broken down into two major steps—i) binding of the ribosome and associated factors to the mRNA, and ii) conversion of the bound ribosome into a translating ribosome lengthening processing along the mRNA. The rate of the first step can be increased by making the RBS highly complementary to the free end of the 16s rRNA and by ensuring that the start codon is AUG. The rate of ribosome binding can also be increased by ensuring that there is minimal secondary structure in the neighborhood of the RBS. Since binding between the RBS and the ribosome is mediated by base-pairing interactions, competition for the RBS from other sequences on the mRNA, can reduce the rate of ribosome binding. The rate of the second step in translation initiation, conversion of the bound ribosome into an initiation complex is dependent on the spacing between the RBS and the start codon being optimal (5-6 bp).

Thus, a "ribosome binding site" (RBS), as defined herein, is a segment of the 5' (upstream) part of an mRNA molecule that binds to the ribosome to position the message correctly for the initiation of translation. The RBS controls the accuracy and efficiency with which the translation of mRNA begins. In prokaryotes (such as E. coli) the RBS typically lies about 7 nucleotides upstream from the start codon (i.e., the first AUG). The sequence itself in general is called the "Shine-Dalgarno" sequence after its discoverers, regardless of the exact identity of the bases. Strong Shine-Dalgarno sequences are rich in purines (A's,G's), and the "Shine-Dalgarno consensus" sequence—derived statistically from lining up many well-characterized strong ribosome binding sites—has the sequence AGGAGG. The complementary sequence (CCUCCU) occurs at the 3'-end of the structural RNA ("16S") of the small ribosomal subunit and it base-pairs with the Shine-Dalgarno sequence in the mRNA to facilitate proper initiation of protein synthesis. In some embodiments of aspects described herein, a ribosome binding site (RBS) is added to an engineered genetic counter to regulate expression of a recombinase.

For protein synthesis in eukaryotes and eukaryotic cells, the 5' end of the mRNA has a modified chemical structure ("cap") recognized by the ribosome, which then binds the mRNA and moves along it ("scans") until it finds the first AUG codon. A characteristic pattern of bases (called a "Kozak sequence") is sometimes found around that codon and assists in positioning the mRNA correctly in a manner reminiscent of the Shine-Dalgarno sequence, but does not involve base pairing with the ribosomal RNA.

RBSs can include only a portion of the Shine-Dalgarno sequence. When looking at the spacing between the RBS and the start codon, the aligned spacing rather than just the absolute spacing is important. In essence, if only a portion of the Shine-Dalgarno sequence is included in the RBS, the spacing that matters is between wherever the center of the full Shine-Dalgarno sequence would be and the start codon rather than between the included portion of the Shine-Dalgarno sequence and the start codon.

While the Shine-Dalgarno portion of the RBS is critical to the strength of the RBS, the sequence upstream of the Shine-Dalgarno sequence is also important. One of the ribosomal proteins, S1, is known to bind to adenine bases upstream from the Shine-Dalgarno sequence. As a result, in some embodiments of the modules and engineered genetic counters described herein, an RBS can be made stronger by adding more adenines to the sequence upstream of the RBS. A promoter may add some bases onto the start of the mRNA that may affect the strength of the RBS by affecting S1 binding.

In addition, the degree of secondary structure can affect the translation initiation rate. This fact can be used to produce regulated translation initiation rates, as described in Isaacs F J et al., Nat Biotechnol 2004 July; 22(7) 841-7.

In addition to affecting the translation rate per unit time, an RBS affects the level of protein synthesis in a second way. That is because the stability of the mRNA affects the steady state level of mRNA, i.e., a stable mRNA will have a higher steady state level than an unstable mRNA that is being produced as an identical rate. Since the primary sequence and the secondary structure of an RBS (for example, the RBS could introduce an RNase site) can affect the stability of the mRNA, the RBS can affect the amount of mRNA and hence the amount of protein that is synthesized.

A "regulated RBS" is an RBS for which the binding affinity of the RBS and the ribosome can be controlled, thereby changing the RBS strength. One strategy for regulating the strength of prokaryotic RBSs is to control the accessibility of the RBS to the ribosome. By occluding the RBS in RNA secondary structure, translation initiation can be significantly reduced. By contrast, by reducing secondary structure and revealing the RBS, translation initiation rate can be increased. Isaacs and coworkers engineered mRNA sequences with an upstream sequence partially complementary to the RBS. Base-pairing between the upstream sequence and the RBS 'locks' the RBS off. A 'key' RNA molecule that disrupts the mRNA secondary structure by preferentially base-pairing with the upstream sequence can be used to expose the RBS and increase translation initiation rate. In some embodiments, the ribosome binding site (RBS) comprises a sequence that is selected from the group consisting of SEQ ID NO: 843-SEQ ID NO: 850 presented in Table 47. In some embodiments, the ribosome binding site (RBS) is selected from the ribosome binding site sequences presented in Tables 48-53. In some embodiments, novel ribosome binding sites can be generated using automated design of synthetic ribosome sites, as described in Salis H M et al., Nature Biotechnology 27, 946-950 (2009).

TABLE 47

| | | |
|---|---|---|
| SEQ ID NO: 843 | RBS-A | AGGAGGAAAAAAATG |
| SEQ ID NO: 844 | RBS-B | AGGAATTTAAATG |
| SEQ ID NO: 845 | RBS-C | AGGAAACAGACCATG |
| SEQ ID NO: 846 | RBS-D | AGGAAACCGGTTCGATG |

TABLE 47-continued

| SEQ ID NO: 847 | RBS-E | AGGAAACCGGTTATG |
| SEQ ID NO: 848 | RBS-F | AGGACGGTTCGATG |

TABLE 47-continued

| SEQ ID NO: 849 | RBS-G | AGGAAAGGCCTCGATG |
| SEQ ID NO: 850 | RBS-H | AGGACGGCCGGATG |

TABLE 48

Examples of RBS Sequences (underlines indicate consensus sequence)

| Identifier | Sequence |
| --- | --- |
| SEQ ID NO: 851 Master Sequence | TCTAGAGAAAGANNNGANNNACTAGATG |
| SEQ ID NO: 852 BBa_J61100 | TCTAGAGAAAGAGGGGACAAACTAGATG |
| SEQ ID NO: 853 BBa_J61101 | TCTAGAGAAAGACAGGACCCACTAGATG |
| SEQ ID NO: 854 BBa_J61102 | TCTAGAGAAAGATCCGATGTACTAGATG |
| SEQ ID NO: 855 BBa_J61103 | TCTAGAGAAAGATTAGACAAACTAGATG |
| SEQ ID NO: 856 BBa_J61104 | TCTAGAGAAAGAAGGGACAGACTAGATG |
| SEQ ID NO: 857 BBa_J61105 | TCTAGAGAAAGACATGACGTACTAGATG |
| SEQ ID NO: 858 BBa_J61106 | TCTAGAGAAAGATAGGAGACACTAGATG |
| SEQ ID NO: 859 BBa_J61107 | TCTAGAGAAAGAAGAGACTCACTAGATG |
| SEQ ID NO: 860 BBa_J61108 | TCTAGAGAAAGACGAGATATACTAGATG |
| SEQ ID NO: 861 BBa_J61109 | TCTAGAGAAAGACTGGAGACACTAGATG |
| SEQ ID NO: 862 BBa_J61110 | TCTAGAGAAAGAGGCGAATTACTAGATG |
| SEQ ID NO: 863 BBa_J61111 | TCTAGAGAAAGAGGCGATACACTAGATG |
| SEQ ID NO: 864 BBa_J61112 | TCTAGAGAAAGAGGTGACATACTAGATG |
| SEQ ID NO: 865 BBa_J61113 | TCTAGAGAAAGAGTGGAAAAACTAGATG |
| SEQ ID NO: 866 BBa_J61114 | TCTAGAGAAAGATGAGAAGAACTAGATG |
| SEQ ID NO: 867 BBa_J61115 | TCTAGAGAAAGAAGGGATACACTAGATG |
| SEQ ID NO: 868 BBa_J61116 | TCTAGAGAAAGACATGAGGCACTAGATG |
| SEQ ID NO: 869 BBa_J61117 | TCTAGAGAAAGACATGAGTTACTAGATG |
| SEQ ID NO: 870 BBa_J61118 | TCTAGAGAAAGAGACGAATCACTAGATG |
| SEQ ID NO: 871 BBa_J61119 | TCTAGAGAAAGATTTGATATACTAGATG |
| SEQ ID NO: 872 BBa_J61120 | TCTAGAGAAAGACGCGAGAAACTAGATG |
| SEQ ID NO: 873 BBa_J61121 | TCTAGAGAAAGAGACGAGTCACTAGATG |
| SEQ ID NO: 874 BBa_J61122 | TCTAGAGAAAGAGAGGAGCCACTAGATG |
| SEQ ID NO: 875 BBa_J61123 | TCTAGAGAAAGAGATGACTAACTAGATG |
| SEQ ID NO: 876 BBa_J61124 | TCTAGAGAAAGAGCCGACATACTAGATG |
| SEQ ID NO: 877 BBa_J61125 | TCTAGAGAAAGAGCCGAGTTACTAGATG |
| SEQ ID NO: 878 BBa_J61126 | TCTAGAGAAAGAGGTGACTCACTAGATG |
| SEQ ID NO: 879 BBa_J61127 | TCTAGAGAAAGAGTGGAACTACTAGATG |
| SEQ ID NO: 880 BBa_J61128 | TCTAGAGAAAGATAGGACTCACTAGATG |
| SEQ ID NO: 881 BBa_J61129 | TCTAGAGAAAGATTGGACGTACTAGATG |
| SEQ ID NO: 882 BBa_J61130 | TCTAGAGAAAGAAACGACATACTAGATG |
| SEQ ID NO: 883 BBa_J61131 | TCTAGAGAAAGAACCGAATTACTAGATG |

TABLE 48-continued

Examples of RBS Sequences (underlines indicate consensus sequence)

| Identifier | | Sequence |
|---|---|---|
| SEQ ID NO: 884 | BBa_J61132 | TCTAGAG<u>AAAGACAGGATTA</u>ACTAGATG |
| SEQ ID NO: 885 | BBa_J61133 | TCTAGAG<u>AAAGACCCGAGAC</u>ACTAGATG |
| SEQ ID NO: 886 | BBa_J61134 | TCTAGAG<u>AAAGACCGGAAAT</u>ACTAGATG |
| SEQ ID NO: 887 | BBa_J61135 | TCTAGAG<u>AAAGACCGGAGAC</u>ACTAGATG |
| SEQ ID NO: 888 | BBa_J61136 | TCTAGAG<u>AAAGAGCTGAGCA</u>ACTAGATG |
| SEQ ID NO: 889 | BBa_J61137 | TCTAGAG<u>AAAGAGTAGATCA</u>ACTAGATG |
| SEQ ID NO: 890 | BBa_J61138 | TCTAGAG<u>AAAGATATGAATA</u>ACTAGATG |
| SEQ ID NO: 891 | BBa_J61139 | TCTAGAG<u>AAAGATTAGAGTC</u>ACTAGATG |

TABLE 49

Examples of Community RBS Sequences

| Identifier | | Sequence | Measured Strength Set 1 | Measured Strength Set 2 |
|---|---|---|---|---|
| SEQ ID NO: 892 | BBa_B0029 | TCTAGA<u>GTTCACACAGGAAACC</u>TACTAGATG | — | 0.764 |
| SEQ ID NO: 893 | BBa_B0030 | TCTAGA<u>GATTAAAGAGGAGAAA</u>TACTAGATG | 0.6 | — |
| SEQ ID NO: 894 | BBa_B0031 | TCTAGAG<u>TCACACAGGAAACC</u>TACTAGATG | 0.07 | — |
| SEQ ID NO: 895 | BBa_B0032 | TCTAGAG<u>TCACACAGGAAAG</u>TACTAGATG | 0.3 | 0.376 |
| SEQ ID NO: 896 | BBa_B0033 | TCTAGAG<u>TCACACAGGAC</u>TACTAGATG | 0.01 | 0.002 |
| SEQ ID NO: 897 | BBa_B0034 | TCTAGAG<u>AAAGAGGAGAAA</u>TACTAGATG | 1 | 1 |
| SEQ ID NO: 898 | BBa_B0035 | TCTAGAG<u>ATTAAAGAGGAGAA</u>TACTAGATG | — | 1.124 |
| SEQ ID NO: 899 | BBa_B0064 | TCTAGAG<u>AAAGAGGGGAAA</u>TACTAGATG | 0.35 | — |

TABLE 50

Examples Miscellaneous Constitutive Prokaryotic RBS

| Name | | Sequence | Description |
|---|---|---|---|
| SEQ ID NO: 900 | BBa_B0036 | gtgtg | Specialized RBS |
| SEQ ID NO: 901 | BBa_B0037 | gtgtgtctag | Specialized RBS |
| SEQ ID NO: 902 | BBa_B0038 | tcacacaggaaaccggttcgatg | RBS 1 |
| SEQ ID NO: 903 | BBa_B0039 | tcacacaggaaaggcctcgatg | RBS 2 |
| SEQ ID NO: 904 | BBa_B0041 | tcacacaggacggccggatg | RBS 3 |
| SEQ ID NO: 905 | BBa_B0070 | tctcacgtgtgtcaag | Specialized RBS modified from that of B0036 (Brink et al.) |
| SEQ ID NO: 906 | BBa_B0071 | tctcacgtgtgt | Specialized RBS |
| SEQ ID NO: 907 | BBa_B0076 | catccct | Specialized RBS |
| SEQ ID NO: 908 | BBa_B0077 | tcacatccct | Specialized RBS |

TABLE 50-continued

Examples Miscellaneous Constitutive Prokaryotic RBS

| Name | Sequence | Description |
|---|---|---|
| SEQ ID NO: 909 BBa_B0078 | tcacatccctcc | Specialized RBS |
| SEQ ID NO: 910 BBa_B2001 | actgcacgaggtaacacaag | T7 RBS 0.3 |
| SEQ ID NO: 911 BBa_B2002 | tacgaggaggatgaagagta | T7 RBS 0.4 |
| SEQ ID NO: 912 BBa_B2003 | actttacttatgagggagta | T7 RBS 0.5 |
| SEQ ID NO: 913 BBa_B2017 | acgaagacggagacttctaa | 2.8 RBS from T7 |
| SEQ ID NO: 914 BBa_B2022 | aaccctcaggaggtaaacca | 4B RBS from T7 |
| SEQ ID NO: 915 BBa_B2040 | aagacatggagacacattta | 8 RBS from T7 |
| SEQ ID NO: 916 BBa_B2101 | . . . gcacgaggtaacacaagatgtgaagagctg | T7 RBS 0.3 + SapI (rev) |
| SEQ ID NO: 917 BBa_B2102 | . . . gaggaggatgaagagtaatgtgaagagctg | T7 RBS 0.4 + SapI (rev) |
| SEQ ID NO: 918 BBa_I11010 | aggaggtcatc | RBS |
| SEQ ID NO: 919 BBa_I723012 | gcaagctcttttttcagttgtctc | Estimated RBS for DntR |
| SEQ ID NO: 920 BBa_I723014 | ctgatagttaaaatcaccagcatga | Estimated RBS for DntA |
| SEQ ID NO: 921 BBa_I723019 | taaaaacaagaggaaaacaa | RBS for XylR |
| SEQ ID NO: 922 BBa_I742130 | tctcctcttt | Reverse RBS |
| SEQ ID NO: 923 BBa_I742145 | acggagaagcagcgaa | sam5 native rbs |
| SEQ ID NO: 924 BBa_I742146 | gaggttgggacaag | sam8 native rbs |
| SEQ ID NO: 925 BBa_I742150 | . . . taaatgtatccgtttataaggacagcccga | crtE native rbs |
| SEQ ID NO: 926 BBa_I742153 | ctcttaagtgggagcggct | crtY native rbs |
| SEQ ID NO: 927 BBa_I742156 | ctctaccggagaaatt | crtZ native rbs |
| SEQ ID NO: 928 BBa_I742159 | ctcatcgttaaagagcgactac | crtI native rbs |
| SEQ ID NO: 929 BBa_I742163 | ctcagcctgtacctggagagcctttc | native ftsK rbs |
| SEQ ID NO: 930 BBa_J15001 | ctcaaggagg | strong synthetic E. coli ribosome binding site with SacI site. |
| SEQ ID NO: 931 BBa_J26002 | gagagg | Mario Binding Site |
| SEQ ID NO: 932 BBa_J29048 | aggaggattacaa | RBS |
| SEQ ID NO: 933 BBa_J34801 | aaagaggagaaa | ribosome binding site |
| SEQ ID NO: 934 BBa_J34803 | tcacacaggaaag | ribosome binding site |
| SEQ ID NO: 935 BBa_J34810 | ggaagagg | ribosome binding site |
| SEQ ID NO: 936 BBa_J44001 | tttctcctctttaat | Reverse RBS (RBS$_{rev}$) -- corresponds to BBa_B0030 |
| SEQ ID NO: 937 BBa_J56013 | tcacacaggaaaggcctcg | Rbs2 ribosome binding site |
| SEQ ID NO: 938 BBa_J56016 | attaaagaggagaaattaagc | Rbs-orig - ribosome binding site |
| SEQ ID NO: 939 BBa_J59001 | . . . tcgtttctgaaaaattttcgtttctgaaaa | tuba |
| SEQ ID NO: 940 BBa_J61140 | tggctaacatagggt | {rbs1} Library Member in BBb |

TABLE 50-continued

Examples Miscellaneous Constitutive Prokaryotic RBS

| Name | | Sequence | Description |
|---|---|---|---|
| SEQ ID NO: 941 | BBa_J61141 | tggctaactgaggat | {rbs1} Library Member in BBb |
| SEQ ID NO: 942 | BBa_J61142 | tggctaacccaggat | {rbs1} Library Member in BBb |
| SEQ ID NO: 943 | BBa_J61143 | tggctaactcaggtg | {rbs1} Library Member in BBb |
| SEQ ID NO: 944 | BBa_J61144 | tggctaaccctggta | {rbs1} Library Member in BBb |
| SEQ ID NO: 945 | BBa_J61145 | tggctaacttgggac | {rbs1} Library Member in BBb |
| SEQ ID NO: 946 | BBa_J61146 | tggctaacgcaggtc | {rbs1} Library Member in BBb |
| SEQ ID NO: 947 | BBa_J61147 | tggctaacatcggtg | {rbs1} Library Member in BBb |
| SEQ ID NO: 948 | BBa_J64011 | ttaattaaggaaaagatct | invB RBS |
| SEQ ID NO: 949 | BBa_J64013 | cagaagaggatattaata | sipA RBS |
| SEQ ID NO: 950 | BBa_J64015 | ttgataaggaattgta | sopA RBS |
| SEQ ID NO: 951 | BBa_J64018 | tcagaggagataattta | invJ RBS |
| SEQ ID NO: 952 | BBa_J64020 | tgacacgttgagcggtatga | invI RBS |
| SEQ ID NO: 953 | BBa_J64022 | acagataacaggagtaagta | sicA RBS |
| SEQ ID NO: 954 | BBa_J64024 | taaagggagaaaaat | sipC RBS |
| SEQ ID NO: 955 | BBa_J64026 | gagtcttgaggtaactat | sigE RBS |
| SEQ ID NO: 956 | BBa_J64028 | tcaggaatattaaaaacgct | sopB RBS |
| SEQ ID NO: 957 | BBa_J64030 | atttgaaggaaaatatt | sopD RBS |
| SEQ ID NO: 958 | BBa_J64031 | caaaaacatactgcaggaat | sptP RBS |
| SEQ ID NO: 959 | BBa_J64609 | tgccattgcaaaggagaagact | creD RBS |
| SEQ ID NO: 960 | BBa_J64807 | aaggggaattcaaat | RocD RBS |
| SEQ ID NO: 961 | BBa_J64808 | aaggggtgcagaat | RocE RBS |
| SEQ ID NO: 962 | BBa_J64809 | aggtggaatcacag | RocF RBS |
| SEQ ID NO: 963 | BBa_J64907 | atagataaaaatggtaacaat | creA RBS |
| SEQ ID NO: 964 | BBa_J64908 | gggatatagcctgaggggcctgta | RBS for creC in *e coli* operon |
| SEQ ID NO: 965 | BBa_J64968 | cggcaataacagaggcgattt | RBS on creB |
| SEQ ID NO: 966 | BBa_K082000 | attaaagaggagaaata | reconstruct strong RBS |
| SEQ ID NO: 967 | BBa_K082001 | tcacacaggaaagta | RBS medium |
| SEQ ID NO: 968 | BBa_K090505 | aaaggaggtgt | "*Bacillus subtilis*" consensus RBS |
| SEQ ID NO: 969 | BBa_K090506 | agaggtggtgt | "*Bacillus subtilis*" weak RBS |
| SEQ ID NO: 970 | BBa_K103015 | aggagg | consensus RBS |
| SEQ ID NO: 971 | BBa_K118012 | gagg | Synthetic ribosome binding site added by Son of Babel procedure |
| SEQ ID NO: 972 | BBa_K143020 | taaaggaggaa | GsiB ribosome binding site (RBS) for *B. subtilis* |

TABLE 50-continued

Examples Miscellaneous Constitutive Prokaryotic RBS

| Name | Sequence | Description |
| --- | --- | --- |
| SEQ ID NO: 973 BBa_K143021 | aaaggtggtgaa | SpoVG ribosome binding site (RBS) for B. subtilis |
| SEQ ID NO: 974 BBa_K150005 | aggaaacagaacc | ribosome binding site of pTrc99a |
| SEQ ID NO: 975 BBa_M13501 | gattgggataaataat | M13K07 gene I RBS |
| SEQ ID NO: 976 BBa_M13502 | atcaaccggggtacat | M13K07 gene II RBS |
| SEQ ID NO: 977 BBa_M13503 | tttggagattttcaac | M13K07 gene III RBS |
| SEQ ID NO: 978 BBa_M13504 | aaaaaaggtaattcaa | M13K07 gene IV RBS |
| SEQ ID NO: 979 BBa_M13505 | cataaggtaattcaca | M13K07 gene V RBS |
| SEQ ID NO: 980 BBa_M13506 | ataaggagtcttaatc | M13K07 gene VI RBS |
| SEQ ID NO: 981 BBa_M13507 | gttccggctaagtaac | M13K07 gene VII RBS |
| SEQ ID NO: 982 BBa_M13508 | taatggaaacttcctc | M13K07 gene VIII RBS |
| SEQ ID NO: 983 BBa_M13509 | tcgctgggggtcaaag | M13Ko7 gene IX RBS |
| SEQ ID NO: 984 BBa_M13510 | atttgagggggattca | M13K07 gene X RBS |
| SEQ ID NO: 985 BBa_M13511 | aatttaggtcagaag | M13K07 gene XI RBS |
| SEQ ID NO: 986 BBa_Z0261 | aatcaataggagaaatcaat | Strong T7.2 RBS |
| SEQ ID NO: 987 BBa_Z0262 | ttaaagaggagaaatactag | Medium strength T7.2 RBS |

TABLE 51

Examples of Regulated Prokaryotic RBS

| Identifier | Sequence |
| --- | --- |
| SEQ ID NO: 988 BBa_J01010 | TCTAGAG<u>AACTAGAATCACCTCTT GGATTTGGGTATTAAAGAGGAGA</u>TACTAGATG |
| SEQ ID NO: 989 BBa_J01080 | TCTAGAG<u>AACTAGAATCACCTCTT GCTTTTGGGTAAGAAAGAGGAGA</u>TACTAGATG |

TABLE 52

Examples of Regulated Yeast RBS

| Name | Sequence | Description |
| --- | --- | --- |
| SEQ ID NO: 990 BBa_J63003 | cccgccgccaccatggag | designed yeast Kozak sequence |
| SEQ ID NO: 991 BBa_K165002 | cccgccgccaccatggag | Kozak sequence (yeast RBS) |

TABLE 53

Examples of Eukaryotic RBS

| Identifier | Sequence[a] | Strength[b] |
| --- | --- | --- |
| SEQ ID NO: 992 BBa_B0072 | TCTAGAG<u>CACCAC</u>TACTAGATG | 0.24 |
| SEQ ID NO: 993 BBa_B0073 | TCTAGAG<u>TCACACCAC</u>TACTAGATG | 1 |
| SEQ ID NO: 994 BBa_B0074 | TCTAGAG<u>TCACACCACCC</u>TACTAGATG | 0.84 |

Terminators

In some embodiments, terminator sequences are provided for use in the modules and engineered genetic counters described herein. Terminators are genetic sequences that usually occur at the end of a gene or operon and cause transcription to stop. As described herein, a terminator sequence prevents activation of downstream modules by upstream promoters. A "terminator" or "termination signal", as described herein, is comprised of the DNA sequences involved in specific termination of an RNA transcript by an RNA polymerase. Thus, in certain embodiments a terminator that ends the production of an RNA transcript is contemplated. A terminator may be necessary in vivo to achieve desirable message levels.

In prokaryotes, terminators usually fall into two categories (1) rho-independent terminators and (2) rho-dependent terminators. Rho-independent terminators are generally composed of palindromic sequence that forms a stem loop rich in G-C base pairs followed by several T bases. Without wishing to be bound by a theory, the conventional model of transcriptional termination is that the stem loop causes RNA polymerase to pause, and transcription of the poly-A tail causes the RNA:DNA duplex to unwind and dissociate from RNA polymerase.

The most commonly used type of terminator is a forward terminator. When placed downstream of a nucleic acid sequence that is usually transcribed, a forward transcriptional terminator will cause transcription to abort. In some embodiments, bidirectional transcriptional terminators are provided. Such terminators will usually cause transcription to terminate on both the forward and reverse strand. Finally, In some embodiments, reverse transcriptional terminators are provided that terminate transcription on the reverse strand only.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that a terminator comprises a signal for the cleavage of the RNA, and it is more preferred that the terminator signal promotes polyadenylation of the message. The terminator and/or polyadenylation site elements can serve to enhance message levels and/or to minimize read through between modules of the engineered genetic counters. As disclosed herein, terminators contemplated for use in the modules, engineered genetic counters, and methods of use thereof include any known terminator of transcription described herein or known to one of ordinary skill in the art. Such terminators include, but are not limited to, the termination sequences of genes, such as for example, the bovine growth hormone terminator, or viral termination sequences, such as for example, the SV40 terminator. In certain embodiments, the termination signal may be a lack of transcribable or translatable sequence, such as due to a sequence truncation. The terminator used can be unidirectional or bidirectional.

Terminators of use in the engineered genetic counters described herein can be selected from the non-limiting examples of Tables 54-58.

TABLE 54

Examples of Forward Terminators

| Name | Description | Direction | Efficiency Fwd. | Efficiency Rev. | Length |
|---|---|---|---|---|---|
| BBa_B0010 | T1 from E. coli rrnB | Forward | | | 80 |
| BBa_B0012 | TE from coliphage T7 | Forward | 0.309[CC] | −0.368[CC] | 41 |
| BBa_B0013 | TE from coliphage T7 (+/−) | Forward | 0.6[CC] | −1.06[CC] | 47 |
| BBa_B0015 | double terminator (B0010-B0012) | Forward | 0.984[CC] 0.97[JK] | 0.295[CC] 0.62[JK] | 129 |
| BBa_B0017 | double terminator (B0010-B0010) | Forward | | | 168 |
| BBa_B0053 | Terminator (His) | Forward | | | 72 |
| BBa_B0055 | -- No description -- | | | | 78 |
| BBa_B1002 | Terminator (artificial, small, % T ~= 85%) | Forward | 0.98[CH] | | 34 |
| BBa_B1003 | Terminator (artificial, small, % T ~= 80) | Forward | 0.83[CH] | | 34 |
| BBa_B1004 | Terminator (artificial, small, % T ~= 55) | Forward | 0.93[CH] | | 34 |
| BBa_B1005 | Terminator (artificial, small, % T ~= 25% | Forward | 0.86[CH] | | 34 |
| BBa_B1006 | Terminator (artificial, large, % T ~> 90) | Forward | 0.99[CH] | | 39 |
| BBa_B1010 | Terminator (artificial, large, % T ~< 10) | Forward | 0.95[CH] | | 40 |
| BBa_I11013 | Modification of biobricks part BBa_B0015 | | | | 129 |
| BBa_I51003 | -- No description -- | | | | 110 |
| BBa_J61048 | [rnpB-T1] Terminator | Forward | 0.98[JCA] | | 113 |

TABLE 55

Examples of Bidirectional Terminators

| Name | Description | Direction | Efficiency Fwd. | Efficiency Rev. | Length |
|---|---|---|---|---|---|
| BBa_B0011 | LuxICDABEG (+/−) | Bidirectional | 0.419[CC]/0.95[JK] | 0.636[CC]/0.86[JK] | 46 |
| BBa_B0014 | double terminator (B0012-B0011) | Bidirectional | 0.604[CC]/0.96[JK] | 0.86[JK] | 95 |
| BBa_B0021 | LuxICDABEG (+/−), reversed | Bidirectional | 0.636[CC]/0.86[JK] | 0.419[CC]/0.95[JK] | 46 |
| BBa_B0024 | double terminator (B0012-B0011), reversed | Bidirectional | 0.86[JK] | 0.604[CC]/0.96[JK] | 95 |
| BBa_B0050 | Terminator (pBR322, +/−) | Bidirectional | | | 33 |
| BBa_B0051 | Terminator (yciA/tonA, +/−) | Bidirectional | | | 35 |
| BBa_B1001 | Terminator (artificial, small, % T ~= 90) | Bidirectional | 0.81[CH] | | 34 |

TABLE 55-continued

Examples of Bidirectional Terminators

| Name | Description | Direction | Efficiency Fwd. | Rev. | Length |
|---|---|---|---|---|---|
| BBa_B1007 | Terminator (artificial, large, % T ~= 80) | Bidirectional | 0.83[CH] | | 40 |
| BBa_B1008 | Terminator (artificial, large, % T ~= 70) | Bidirectional | | | 40 |
| BBa_B1009 | Terminator (artificial, large, % T ~= 40%) | Bidirectional | | | 40 |
| BBa_K259006 | GFP-Terminator | Bidirectional | 0.604[CC]/0.96[JK] | 0.86[JK] | 823 |

TABLE 56

Examples of Reverse Terminators

| Name | Description | Direction | Efficiency Fwd. | Rev. | Length |
|---|---|---|---|---|---|
| BBa_B0020 | Terminator (Reverse B0010) | Reverse | | | 82 |
| BBa_B0022 | TE from coliphage T7, reversed | Reverse | −0.368[CC] | 0.309[CC] | 41 |
| BBa_B0023 | TE from coliphage T7, reversed | Reverse | −1.06[CC] | 0.6[CC] | 47 |
| BBa_B0025 | double terminator (B0015), reversed | Reverse | 0.295[CC]/0.62[JK] | 0.984[CC]/0.97[JK] | 129 |
| BBa_B0052 | Terminator (rrnC) | Forward | | | 41 |
| BBa_B0060 | Terminator (Reverse B0050) | Bidirectional | | | 33 |
| BBa_B0061 | Terminator (Reverse B0051) | Bidirectional | | | 35 |
| BBa_B0063 | Terminator (Reverse B0053) | Reverse | | | 72 |

TABLE 57

Examples of Yeast Terminators

| Name | Description | Direction | Efficiency Fwd. | Rev. | Length |
|---|---|---|---|---|---|
| BBa_J63002 | ADH1 terminator from S. cerevisiae | Forward | | | 225 |
| BBa_K110012 | STE2 terminator | Forward | | | 123 |
| BBa_Y1015 | CycE1 | | | | 252 |

TABLE 58

Examples of Eukaryotic Terminators

| Name | Description | Direction | Efficiency Fwd. | Rev. | Chassis | Length |
|---|---|---|---|---|---|---|
| BBa_J52016 | eukaryotic -- derived from SV40 early poly A signal sequence | Forward | | | | 238 |
| BBa_J63002 | ADH1 terminator from S. cerevisiae | Forward | | | | 225 |
| BBa_K110012 | STE2 terminator | Forward | | | | 123 |
| BBa_Y1015 | CycE1 | | | | | 252 |

Degradation Tags

In some embodiments, a nucleic sequence encoding a protein degradation tag is added to the modules and engineered genetic counters in order to enhance protein degradation of a protein, such as a recombinase. As defined herein, a "degradation tag" is a genetic addition to the end of a nucleic acid sequence that modifies the protein that is expressed from that sequence such that the protein undergoes faster degradation by cellular degradation mechanisms. Thus, such protein degradation tags mark a protein for degradation, thus decreasing a protein's half-life.

One of the useful aspects of degradation tags is the ability to detect and regulate gene activity in a time-sensitive manner. Such protein degradation tags can operate through the use of protein-degrading enzymes, such as proteases, within the cell. In some embodiments, the tags encode for a sequence of about eleven amino acids at the C-terminus of a protein, wherein said sequence is normally generated in E. coli when a ribosome gets stuck on a broken ("truncated") mRNA. Without a normal termination codon, the ribosome can't detach from the defective mRNA. A special type of RNA known as ssrA ("small stable RNA A") or tmRNA ("transfer-messenger RNA") rescues the ribosome by adding the degradation tag followed by a stop codon. This allows the ribosome to break free and continue functioning. The tagged, incomplete protein can get degraded by the proteases ClpXP or ClpAP. Although the initial discovery of the number of amino acids encoding for an ssRA/tmRNA tag was eleven, the efficacy of mutating the last three amino acids of that system has been tested. Thus, the tags AAV, ASV, LVA, and LAA are classified by only three amino acids.

In some embodiments, the protein degradation tag is an ssrA tag. In some embodiments, the ssrA tag comprises a sequence that is selected from the group consisting of sequences that encode for the peptides RPAANDENYALAA (SEQ ID NO: 995), RPAANDENYALVA (SEQ ID NO: 996), RPAANDENYAAAV (SEQ ID NO: 997), and RPAANDENYAASV (SEQ ID NO: 998).

In some embodiments, the protein degradation tag is an LAA variant comprising the sequence GCAGCAAACGAC-GAAAACTACGCTTTAGCAGCTTAA (SEQ ID NO: 999). In one embodiment, the protein degradation tag is an AAV variant comprising the sequence GCAGCAAACGAC-GAAAACTACGCTGCAGCAGTTTAA (SEQ ID NO: 1000). In some embodiments, the protein degradation tag is an ASV variant comprising the sequence GCAGCAAAC-GACGAAAACTACGCTGCATCAGTTTAA (SEQ ID NO: 1001).

Output Product Sequences and Output Products

A variety of biological output gene and output product nucleic acid sequences are provided for use in the various modules and engineered genetic counters described herein. The biological outputs, or output gene products, as described herein, refer to gene products that can are used as markers of specific states of the modules and engineered genetic counters described herein. An output gene can encode for a protein or RNA that is used to track or mark the state of the cell upon receiving a particular input. Such output gene products can be used to distinguish between various states of a cell. Representative output products for the engineered genetic counters described herein include, but are not limited to, reporter proteins, transcriptional repressors, transcriptional activators, selection markers, enzymes, receptor proteins, ligand proteins, RNAs, riboswitches or short-hairpin RNAs.

Reporter Outputs

In some embodiments of the aspects described herein, the output gene products are "reporters." As defined herein, reporters are proteins that can be used to measure gene expression and generally produce a measurable signal such as fluorescence, color, or luminescence. Reporter protein coding sequences encode proteins whose presence in the cell or organism is readily observed. For example, fluorescent proteins cause a cell to fluoresce when excited with light of a particular wavelength, luciferases cause a cell to catalyze a reaction that produces light, and enzymes such as β-galactosidase convert a substrate to a colored product. In some embodiments, reporters are used to quantify the strength or activity of the signal received by the modules or biological converter switches of the invention. In some embodiments, reporters can be fused in-frame to other protein coding sequences to identify where a protein is located in a cell or organism.

There are several different ways to measure or quantify a reporter depending on the particular reporter and what kind of characterization data is desired. In some embodiments, microscopy can be a useful technique for obtaining both spatial and temporal information on reporter activity, particularly at the single cell level. In other embodiments, flow cytometers can be used for measuring the distribution in reporter activity across a large population of cells. In some embodiments, plate readers may be used for taking population average measurements of many different samples over time. In other embodiments, instruments that combine such various functions, can be used, such as multiplex plate readers designed for flow cytometers, and combination microscopy and flow cytometric instruments.

Fluorescent proteins are convenient ways to visualize or quantify the output of a module or engineered genetic counter. Fluorescence can be readily quantified using a microscope, plate reader or flow cytometer equipped to excite the fluorescent protein with the appropriate wavelength of light. Since several different fluorescent proteins are available, multiple gene expression measurements can be made in parallel. Non-limiting examples of fluorescent proteins useful for the engineered genetic counters described herein are provided in Table 59.

TABLE 59

Examples of Fluorescent Protein Reporters

| Name | Protein | Description | Tag | Emission | Excitation | Length |
|---|---|---|---|---|---|---|
| BBa_E0030 | EYFP | enhanced yellow fluorescent protein derived from *A. victoria* GFP | None | 527 | 514 | 723 |
| BBa_E0020 | ECFP | engineered cyan fluorescent protein derived from *A. victoria* GFP | None | 476 | 439 | 723 |
| BBa_E1010 | mRFP1 | highly engineered mutant of red fluorescent | None | 607 | 584 | 681 |

TABLE 59-continued

Examples of Fluorescent Protein Reporters

| Name | Protein | Description | Tag | Emission | Excitation | Length |
|---|---|---|---|---|---|---|
| | | protein from *Discosomastriata* (coral) | | | | |
| BBa_E2050 | mOrange | derivative of mRFP1, yeast-optimized | None | 562 | 548 | 744 |
| BBa_E0040 | GFPmut3b | green fluorescent protein derived from jellyfish *Aequeora victoria* wild-type GFP (SwissProt: P42212 | None | 511 | 501 | 720 |
| BBa_J52021 | | dnTraf6-linker-GFP | | | | 1446 |
| BBa_J52026 | | dnMyD88-linker-GFP | | | | 1155 |
| BBa_I715022 | | Amino Portion of RFP | | | | 462 |
| BBa_I715023 | | Carboxyl portion of RFP | | | | 220 |
| BBa_I712028 | | CherryNLS - synthetic construct monomeric red fluorescent protein with nuclear localization sequence | | | | 733 |
| BBa_K125500 | | GFP fusion brick | | | | 718 |
| BBa_K106000 | | GFP, AarI BD part | | | | 714 |
| BBa_K106004 | | mCherry, Aar1 AB part | | | | 708 |
| BBa_K106005 | | mCherry, Aar1 BD part | | | | 708 |
| BBa_K106028 | | GFP, Aar1 AB part | | | | 714 |
| BBa_K165005 | | Venus YFP, yeast optimized for fusion | | | | 744 |
| BBa_K157005 | | Split-Cerulean-cCFP | | | | 261 |
| BBa_K157006 | | Split-Cerulean-nCFP | | | | 483 |
| BBa_K157007 | | Split-Venus-cYFP | | | | 261 |
| BBa_K157008 | | Split-Venus-nYFP | | | | 486 |
| BBa_K125810 | | slr2016 signal sequence + GFP fusion for secretion of GFP | | | | 779 |
| BBa_K082003 | GFP | GFP(+LVA) | | | | 756 |
| BBa_K156009 | | OFP (orange fluorescent protein) | | | | 864 |
| BBa_K156010 | | SBFP2 (strongly enhanced blue fluorescent protein) | | | | 720 |
| BBa_K106671 | | GFP, Aar1 AD part | | | | 714 |
| BBa_K294055 | GFPmut3b | GFP RFP Hybrid | None | 511 | 501 | 720 |
| BBa_K192001 | | CFP + tgt + lva | | | | 858 |
| BBa_K180001 | GFPmut3b | Green fluorescent protein (+LVA) | LVA | | | 754 |
| BBa_K283005 | | lpp_ompA_eGFP_streptavidin | | | | 1533 |
| BBa_K180008 | mCherry | mCherry (rights owned by Clontech) | | | | 708 |
| BBa_K180009 | mBanana | mBanana (rights owned by Clontech) | | | | 708 |

Luminescence can be readily quantified using a plate reader or luminescence counter. Luciferases can be used as output gene products for various embodiments of the invention, for example, measuring low levels of gene expression, because cells tend to have little to no background luminescence in the absence of a luciferase. Non-limiting examples of luciferases are provided in Table 60.

TABLE 60

Examples of Luciferases

| Name | Description | Length |
|---|---|---|
| BBa_J52011 | dnMyD88-linker-Rluc | 1371 |
| BBa_J52013 | dnMyD88-linker-Rluc-linker-PEST191 | 1872 |
| BBa_I712019 | Firefly luciferase - luciferase from *Photinus pyralis* | 1653 |

In other embodiments, enzymes that produce colored substrates can be quantified using spectrophotometers or other instruments that can take absorbance measurements including plate readers. Like luciferases, enzymes like β-galactosidase can be used for measuring low levels of gene expression because they tend to amplify low signals.

TABLE 61

Examples of Enzymes that Produce Colored Substrates

| Name | Protein | Description | Length |
|---|---|---|---|
| BBa_I732006 | | lacZ alpha fragment | 234 |
| BBa_I732005 | | lacZ (encoding beta-galactosidase, full-length) | 3075 |
| BBa_K147002 | | xylE | 924 |

Another reporter gene output product for use in the different aspects described herein include:

TABLE 62

Examples of Other Reporter Genes

| Name | Protein | Description | Length |
|---|---|---|---|
| BBa_K157004 | | Fluoresceine-A-binding | 522 |

Transcriptional Outputs:

In some embodiments of the different aspects described herein, the output gene product of a given module or engineered genetic counter is itself a transcriptional activator or repressor, the production of which by an output gene can result in a further change in state of the cell, and provide additional input signals to subsequent or additional modules or engineered genetic counters. Transcriptional regulators either activate or repress transcription from cognate promoters. Transcriptional activators typically bind nearby to transcriptional promoters and recruit RNA polymerase to directly initiate transcription. Repressors bind to transcriptional promoters and sterically hinder transcriptional initiation by RNA polymerase. Other transcriptional regulators serve as either an activator or a repressor depending on where it binds and cellular conditions. Examples of transcriptional regulators as output gene products are provided in Table 63.

TABLE 63

Examples of Transcriptional Regulators

| Name | Protein | Description | Tag | Direction | Uniprot | Length |
|---|---|---|---|---|---|---|
| BBa_C0079 | lasR-LVA | lasR activator from *P. aeruginosa* PAO1 (+LVA) | LVA | Forward | P25084 | 756 |
| BBa_C0077 | cinR | cinR activator from *Rhizobium leguminosarum* (+LVA) | LVA | Forward | ~Q84HT2 | 762 |
| BBa_C0179 | lasR | lasR activator from *P. aeruginosa* PAO1 (no LVA) | None | Forward | P25084 | 723 |
| BBa_J07009 | ToxR | toxicity-gene activator from *Vibrio cholerae* | None | Forward | P15795 | 630 |
| BBa_K118001 | | appY coding sequence encoding a DNA-binding transcriptional activator | | | | 753 |
| BBa_K137113 | | rcsA | | | | 624 |
| BBa_K131022 | | LuxO D47E, *Vibrio harveyi* | | | | 1362 |
| BBa_K131023 | | LuxO D47A, *Vibrio harveyi* | | | | 1362 |
| BBa_K082006 | | LuxR-G2F | | | | 753 |
| BBa_K294205 | | This is a coding sequence of heat shock protein from *E. coli* | | | | 402 |
| BBa_S04301 | lasR-LVA | C0079:B0015 | LVA | Forward | P25084 | 918 |
| BBa_K266002 | lasR-LVA | LasR + Term | LVA | Forward | P25084 | 918 |
| BBa_C0012 | LacI | lacI repressor from *E. coli* (+LVA) | LVA | Forward | P03023 | 1128 |
| BBa_C0040 | TetR | tetracycline repressor from transposon Tn10 (+LVA) | LVA | Forward | P04483 | 660 |
| BBa_C0050 | CI HK022 | cI repressor from phage HK022 (+LVA?) | LVA | Forward | P18680 | 744 |
| BBa_C0051 | CI lambda | cI repressor from *E. coli* phage lambda (+LVA) | LVA | Forward | P03034 | 750 |
| BBa_C0052 | CI 434-LVA | cI repressor from phage 434 (+LVA) | LVA | Forward | P16117 | 669 |
| BBa_C0053 | C2 P22 | c2 repressor from *Salmonella* phage P22 (+LVA) | LVA | Forward | P69202 | 687 |
| BBa_C0073 | mnt-weak | mnt repressor (weak) from *Salmonella* phage P22 (+LVA) | LVA | Forward | P03049 | 288 |
| BBa_C0075 | cI TP901 | TP901 cI repressor from phage TP901-1 (+LVA) | LVA | Forward | none | 579 |
| BBa_C0074 | penI | penI repressor from *Bacillus licheniformis* (+LVA) | LVA | Forward | P06555 | 423 |
| BBa_C0072 | mnt | mnt repressor (strong) from *Salmonella* phage P22 (+LVA) | LVA | Forward | P03049 | 288 |
| BBa_C2001 | Zif23-GCN4 | Zif23-GCN4 engineered repressor (+LVA, C2000 codon-optimized for *E. coli*) | LVA | Forward | P03069 | 300 |
| BBa_C0056 | CI 434 | cI repressor from phage 434 (no LVA) | None | Forward | P16117 | 636 |
| BBa_J06501 | LacI-mut2 | LacI repressor (temperature-sensitive mut 265) (+LVA) | LVA | Forward | ~P03023 | 1153 |
| BBa_J06500 | LacI-mut1 | LacI repressor (temperature-sensitive mut 241) (+LVA) | LVA | Forward | ~P03023 | 1153 |
| BBa_C2006 | | MalE.FactorXa.Zif268-GCN4 | | | | 1428 |
| BBa_I715032 | | lacIq reverse | | | | 1128 |
| BBa_I732100 | | LacI | | | | 1086 |
| BBa_I732101 | | LRLa | | | | 1086 |
| BBa_I732105 | | ARL2A0101 | | | | 1086 |
| BBa_I732106 | | ARL2A0102 | | | | 1086 |
| BBa_I732107 | | ARL2A0103 | | | | 1086 |
| BBa_I732110 | | ARL2A0203 | | | | 1086 |
| BBa_I732112 | | ARL2A0301 | | | | 1086 |
| BBa_I732115 | | ARL4A0604 | | | | 1086 |
| BBa_K091001 | | LsrR gene | | Forward | | 954 |
| BBa_K091121 | | LacI wild-type gene | | | | 1083 |
| BBa_K091122 | | LacI_I12 protein | | | | 1083 |
| BBa_K143033 | | LacI (Lva−, N-terminal deletion) regulatory protein | | | | 1086 |
| BBa_K142000 | | lacI IS mutant (IPTG unresponsive) R197A | | | | 1128 |

TABLE 63-continued

Examples of Transcriptional Regulators

| Name | Protein | Description | Tag | Direction | Uniprot | Length |
|---|---|---|---|---|---|---|
| BBa_K142001 | | lacI IS mutant (IPTG unresponsive) R197F | | | | 1128 |
| BBa_K142002 | | lacI IS mutant (IPTG unresponsive) T276A | | | | 1128 |
| BBa_K142003 | | lacI IS mutant (IPTG unresponsive) T276F | | | | 1128 |
| BBa_K106666 | | Lac Repressor, AarI AB part | | | | 1104 |
| BBa_K106667 | | Lac Repressor, AarI BD part | | | | 1107 |
| BBa_K142004 | | lacI IS mutant (IPTG unresponsive) R197A T276A | | | | 1128 |
| BBa_K106668 | | Tet Repressor, AarI AB part | | | | 618 |
| BBa_K106669 | | Tet Repressor, AarI BD part | | | | 621 |
| BBa_K142005 | | lacI IS mutant (IPTG unresponsive) R197A T276F | | | | 1128 |
| BBa_K142006 | | lacI IS mutant (IPTG unresponsive) R197F T276A | | | | 1128 |
| BBa_K142007 | | lacI IS mutant (IPTG unresponsive) R197F T276F | | | | 1128 |
| BBa_K082004 | LacI | LacI-wild type | | | | 1083 |
| BBa_K082005 | LacI | LacI-Mutant | | | | 1083 |
| BBa_C0062 | LuxR | luxR repressor/activator, (no LVA?) | None | Forward | P12746 | 756 |
| BBa_C0071 | rhlR-LVA | rhlR repressor/activator from *P. aeruginosa* PA3477 (+LVA) | LVA | Forward | P54292 | 762 |
| BBa_C0080 | araC | araC arabinose operon regulatory protein (repressor/activator) from *E. coli* (+LVA) | LVA | Forward | P0A9E0 | 915 |
| BBa_C0171 | rhIR | rhlR repressor/activator from *P. aeruginosa* PA3477 (no LVA) | None | Forward | P54292 | 729 |
| BBa_K108021 | | Fis | | | | 297 |

Selection Markers

In other embodiments of the various aspects described herein, genes encoding selection markers are used as output genes. "Selection markers", as defined herein, are protein coding sequences that confer a selective advantage or disadvantage to a biological unit, such as a cell. For example, a common type of prokaryotic selection marker is one that confers resistance to a particular antibiotic. Thus, cells that carry the selection marker can grow in media despite the presence of antibiotic. For example, most plasmids contain antibiotic selection markers so that it is ensured that the plasmid is maintained during cell replication and division, as cells that lose a copy of the plasmid will soon either die or fail to grow in media supplemented with antibiotic. A second common type of selection marker, often termed a positive selection marker, are those that are toxic to the cell. Positive selection markers are frequently used during cloning to select against cells transformed with the cloning vector and ensure that only cells transformed with a plasmid containing the insert. Examples of output genes encoding selection markers are provided in Table 64.

TABLE 64

Examples of Selection Markers

| Name | Protein | Description | Tag | Direction | UniProt | KEGG | Length |
|---|---|---|---|---|---|---|---|
| BBa_T9150 | PyrF | orotidine 5 | None | Forward | P08244 | eco:b1281; | 741 |
| BBa_J31002 | AadA-bkw | kanamycin resistance backwards (KanB) [cf. BBa_J23012 & BBa_J31003] | | | P0AG05 | none | 816 |
| BBa_J31003 | AadA2 | kanamycin resistance forward (KanF) [cf. BBa_J23012 & BBa_J31002] | | | P0AG05 | none | 816 |
| BBa_J31004 | CAT-bkw | chloramphenicol acetyltransferase (backwards, CmB) [cf. BBa_J31005] | | | P62577 | none | 660 |
| BBa_J31006 | TetA(C)-bkw | tetracycline resistance protein TetA(C) (backwards) [cf. BBa_J31007] | | | P02981 | | 1191 |
| BBa_J31005 | CAT | chloramphenicol acetyltransferase | | | P62577 | none | 660 |

TABLE 64-continued

Examples of Selection Markers

| Name | Protein | Description | Tag | Direction | UniProt | KEGG | Length |
|------|---------|-------------|-----|-----------|---------|------|--------|
| BBa_J31007 | TetA(C) | (forwards, CmF) [cf. BBa_J31004] tetracycline resistance protein TetA(C) (forward), [cf. BBa_J31006] | | | P02981 | | 1191 |
| BBa_K145151 | | ccdB coding region | | | | | 306 |
| BBa_K143031 | | Aad9 Spectinomycin Resistance Gene | | | | | 771 |
| BBa_K156011 | | aadA (streptomycin 3'-adenyltransferase) | | | | | 789 |

Enzyme Outputs

An output gene sequence can encode an enzyme for use in different embodiments the modules and engineered genetic counters described herein. In some embodiments, an enzyme output is used as a response to a particular input. For example, in response to a particular number of inputs received by one or more engineered genetic counters described herein, such as a certain range of toxin concentration present in the environment, the engineered genetic counter may "turn on" a modular component that encodes as an output gene product an enzyme that can degrade or otherwise destroy the toxin.

In some embodiments, output gene sequences encode "biosynthetic enzymes" that catalyze the conversion of substrates to products. For example, such biosynthetic enzymes can be combined together along with or within the modules and engineered genetic counters of the invention to construct pathways that produce or degrade useful chemicals and materials, in response to specific signals. These combinations of enzymes can reconstitute either natural or synthetic biosynthetic pathways. These enzymes have applications in specialty chemicals, biofuels, and bioremediation. Descriptions of enzymes useful for the modules and engineered genetic counters of the invention are described herein.

N-Acyl Homoserine lactones (AHLs or N-AHLs) are a class of signaling molecules involved in bacterial quorum sensing. Quorum sensing is a method of communication between bacteria that enables the coordination of group based behavior based on population density. In synthetic biology, genetic parts derived from quorum sensing systems have been used to create patterns on a lawn of bacteria and to achieve synchronized cell behavior. AHL can diffuse across cell membranes and is stable in growth media over a range of pH values. AHL can bind to transcriptional activators such as LuxR and stimulate transcription from cognate promoters. Several similar quorum sensing systems exists across different bacterial species; thus, there are several known enzymes that synthesize or degrade different AHL molecules that can be used for the modules and engineered genetic counters of the invention.

TABLE 65

Examples of AHLs

| Name | Protein | Description | Direction | Uniprot | KEGG | E.C. | Length |
|------|---------|-------------|-----------|---------|------|------|--------|
| BBa_C0061 | luxI-LVA | autoinducer synthetase for AHL | Forward | P12747 | none | none | 618 |
| BBa_C0060 | aiiA-LVA | autoinducer inactivation enzyme from *Bacillus*; hydrolyzes acetyl homoserine lactone | Forward | Q1WNZ5 | none | 3.1.1.— | 789 |
| BBa_C0070 | rhlI-LVA | autoinducer synthetase for N-butyryl-HSL (BHL) and HHL | Forward | Q02QW5 | none | none | 642 |
| BBa_C0076 | cinI | autoinducer synthetase | Forward | Q1MDW1 | none | none | 702 |
| BBa_C0078 | lasI | autoinducer synthetase for PAI from *Pseudomonas aeruginosa* | Forward | P33883 | pae:PA1432 | none | 642 |
| BBa_C0161 | luxI | autoinducer synthetase for AHL (no LVA) | Forward | P12747 | none | none | 585 |
| BBa_C0170 | rhlI | autoinducer synthetase for N-butyryl-HSL | Forward | Q02QW5 | none | none | 609 |

TABLE 65-continued

Examples of AHLs

| Name | Protein | Description | Direction | Uniprot | KEGG | E.C. | Length |
|---|---|---|---|---|---|---|---|
| BBa_C0178 | lasI | (BHL) and HHL (no LVA) autoinducer synthetase for PAI from *Pseudomonas aeruginosa* (no LVA) | Forward | P33883 | pae:PA1432 | none | 609 |
| BBa_K091109 | | LuxS | | | | | 516 |
| BBa_C0060 | aiiA-LVA | autoinducer inactivation enzyme from *Bacillus*; hydrolyzes acetyl homoserine lactone | Forward | Q1WNZ5 | none | 3.1.1.— | 789 |
| BBa_C0160 | aiiA | autoinducer inactivation enzyme aiiA (no LVA) | Forward | Q1WNZ5 | none | 3.1.1.— | 756 |

Isoprenoids, also known as terpenoids, are a large and highly diverse class of natural organic chemicals with many functions in plant primary and secondary metabolism. Most are multicyclic structures that differ from one another not only in functional groups but also in their basic carbon skeletons. Isoprenoids are synthesized from common prenyl diphosphate precursors through the action of terpene synthases and terpene-modifying enzymes such as cytochrome P450 monooxygenases. Plant terpenoids are used extensively for their aromatic qualities. They play a role in traditional herbal remedies and are under investigation for antibacterial, antineoplastic, and other pharmaceutical functions. Much effort has been directed toward their production in microbial hosts.

There are two primary pathways for making isoprenoids: the mevalonate pathway and the non-mevalonate pathway.

TABLE 66

Examples of Isoprenoids

| Name | Description | Length |
|---|---|---|
| BBa_K118000 | dxs coding sequence encoding 1-deoxyxylulose-5-phosphate synthase | 1866 |
| BBa_K115050 | A-coA -> AA-coA | 1188 |
| BBa_K115056 | IPP -> OPP or DMAPP -> OPP | 552 |
| BBa_K115057 | OPP -> FPP | 903 |
| BBa_K118002 | crtB coding sequence encoding phytoene synthase | 933 |
| BBa_K118003 | crtI coding sequence encoding phytoene dehydrogenase | 1482 |
| BBa_K118008 | crtY coding sequence encoding lycopene B-cyclase | 1152 |

Odorants are volatile compounds that have an aroma detectable by the olfactory system. Odorant enzymes convert a substrate to an odorant product. Exemplary odorant enzymes are described in Table 67.

TABLE 67

Examples of Odorant Enzymes

| Name | Protein | Description | Uniprot | KEGG | E.C. | Length |
|---|---|---|---|---|---|---|
| BBa_J45001 | SAMT | SAM: salicylic acid carboxyl methyltransferase; converts salicylic acid to methyl salicylate (winter | Q8H6N2 | none | none | 1155 |
| BBa_J45002 | BAMT | SAM: benzoic acid carboxyl methyltransferase; converts benzoic acid to methyl benzoate (floral odor) | Q9FYZ9 | none | 2.1.1.— | 1098 |
| BBa_J45004 | BSMT1 | SAM: benzoic acid/salicylic acid carboxyl methyltransferase I; | Q84UB5 | none | none | 1074 |

TABLE 67-continued

Examples of Odorant Enzymes

| Name | Protein | Description | Uniprot | KEGG | E.C. | Length |
|---|---|---|---|---|---|---|
| BBa_J45008 | BAT2 | converts salicylic acid to methyl sali branched-chain amino acid transaminase (BAT2); converts leucine to alpha-ketoisocaproate | P47176 | sce:YJR148W | 2.6.1.42 | 1134 |
| BBa_J45014 | ATF1-1148 mutant | alcohol acetyltransferase I; converts isoamyl alcohol to isoamyl acetate (banana odor) | P40353 | sce:YOR377W | 2.3.1.84 | 1581 |
| BBa_J45017 | PchA & PchB | isochorismate pyruvate-lyase and isochorismate synthase (pchBA); converts chorismate to salicylate | | | | 1736 |
| BBa_I742107 | | COMT | | | | 1101 |

The following are exemplary enzymes involved in the biosynthesis of plastic, specifically polyhydroxybutyrate.

TABLE 68

Examples of Plastic Biosynthesis Enzymes

| Name | Description | Length |
|---|---|---|
| BBa_K125504 | phaE BioPlastic polyhydroxybutyrate synthesis pathway (origin PCC6803 slr1829) | 996 |
| BBa_K125501 | phaA BioPlastic polyhydroxybutyrate synthesis pathway (origin PCC6803 slr1994) | 1233 |
| BBa_K125502 | phaB BioPlastic polyhydroxybutyrate synthesis pathway (origin PCC6803 slr1993) | 726 |
| BBa_K125503 | phaC BioPlastic polyhydroxybutyrate synthesis pathway (origin PCC6803 slr1830) | 1140 |
| BBa_K156012 | phaA (acetyl-CoA acetyltransferase) | 1182 |
| BBa_K156013 | phaB1 (acetyacetyl-CoA reductase) | 741 |
| BBa_K156014 | phaC1 (Poly(3-hydroxybutyrate) polymerase) | |

The following are exemplary enzymes involved in the biosynthesis of butanol and butanol metabolism.

TABLE 69

Examples of Butanol Biosynthesis Enzymes

| Name | Description | Length |
|---|---|---|
| BBa_I725011 | B-hydroxy butyryl coA dehydrogenase | 870 |
| BBa_I72512 | Enoyl-coa hydratase | 801 |
| BBa_I725013 | Butyryl CoA dehyrogenase | 1155 |
| BBa_I725014 | Butyraldehyde dehydrogenase | 2598 |
| BBa_I725015 | Butanol dehydrogenase | 1188 |

Bisphenol A is a toxin that has been shown to leech from certain types of plastic. Studies have shown this chemical to have detrimental effects in animal studies and is very likely to be harmful to humans as well. The following exemplary bisphenol A degradation protein coding sequences are from *Sphingomonas bisphenolicum* and may aid in the remediation of bisphenol A contamination.

TABLE 70

Examples of Bisphenol A Biosynthesis Enzymes

| Name | Description | Length |
|---|---|---|
| BBa_K123001 | BisdB | 1284 |
| BBa_K123000 | BisdA | 330 |

Other miscellaneous enzymes for use in the invention are provided in Table 71.

TABLE 71

Examples of Miscellaneous Biosynthetic Enzymes

| Name | Description | Direction | Uniprot | KEGG | E.C. | Length |
|---|---|---|---|---|---|---|
| BBa_K118022 | cex coding sequence encoding *Cellulomonas fimi* exoglucanase | | | | | 1461 |
| BBa_K118023 | cenA coding sequence encoding *Cellulomonas fimi* endoglucanase A | | | | | 1353 |
| BBa_K118028 | beta-glucosidase gene bglX (chu_2268) from *Cytophaga hutchinsonii* | | | | | 2280 |
| BBa_C0083 | aspartate ammonia-lyase | Forward | P0AC38 | eco:b4139 | 4.3.1.1 | 1518 |
| BBa_I15008 | heme oxygenase (ho1) from *Synechocystis* | Forward | P72849 | syn:sll1184 | 1.14.99.3 | 726 |
| BBa_I15009 | phycocyanobilin:ferredoxin oxidoreductase (PcyA) from *synechocystis* | Forward | Q55891 | syn:slr0116 | 1.3.7.5 | 750 |

TABLE 71-continued

Examples of Miscellaneous Biosynthetic Enzymes

| Name | Description | Direction | Uniprot | KEGG | E.C. | Length |
|---|---|---|---|---|---|---|
| BBa_T9150 | orotidine 5 | Forward | P08244 | eco:b1281; | 4.1.1.23 | 741 |
| BBa_I716153 | hemB | | | | | 975 |
| BBa_I716154 | hemC | | | | | 942 |
| BBa_I716155 | hemD | | | | | 741 |
| BBa_I716152 | hemA (from CFT703) | | | | | 1257 |
| BBa_I742141 | sam5 (coumarate hydroxylase) coding sequence | | | | | 1542 |
| BBa_I742142 | sam8 (tyrosine-ammonia lyase) coding sequence | | | | | 1536 |
| BBa_I723024 | PhzM | | | | | 1019 |
| BBa_I723025 | PhzS | | | | | 1210 |
| BBa_K137005 | pabA (from pABA synthesis) | | | | | 585 |
| BBa_K137006 | pabB (from pABA synthesis) | | | | | 1890 |
| BBa_K137009 | folB (dihydroneopterin aldolase) | | | | | 354 |
| BBa_K137011 | folKE (GTP Cyclohydrolase I + pyrophosphokinase) | | | | | 1053 |
| BBa_K137017 | Galactose Oxidase | | | | | 1926 |
| BBa_K118015 | glgC coding sequence encoding ADP-glucose pyrophosphorylase | | | | | 1299 |
| BBa_K118016 | glgC16 (glgC with G336D substitution) | | | | | 1299 |
| BBa_K123001 | BisdB | | | | | 1284 |
| BBa_K108018 | PhbAB | | | | | 1997 |
| BBa_K108026 | XylA | | | | | 1053 |
| BBa_K108027 | XylM | | | | | 1110 |
| BBa_K108028 | XylB | | | | | 1101 |
| BBa_K108029 | XylS | | | | | 966 |
| BBa_K147003 | ohbA | | | | | 531 |
| BBa_K123000 | BisdA | | | | | 330 |
| BBa_K284999 | Deletar este | | | | | 1431 |
| BBa_I716253 | HPI, katG | | | | | 2181 |
| BBa_K137000 | katE | | | | | 2265 |
| BBa_K137014 | katE + LAA | | | | | 2298 |
| BBa_K137067 | katG | | | | | 2184 |
| BBa_K078102 | dxnB | | | | | 886 |
| BBa_K078003 | one part of the initial dioxygenase of the dioxin degradation pathway | | | | | 1897 |

Other enzymes of use in the modules and engineered genetic counters of the invention include enzymes that phosphorylate or dephosphorylate either small molecules or other proteins, and enzymes that methylate or demethylate other proteins or DNA.

TABLE 72

Examples of Phosphorylation and Methylation-Related Enzymes

| Name | Protein | Description | Direction | Uniprot | KEGG | E.C. | Length |
|---|---|---|---|---|---|---|---|
| BBa_C0082 | tar-envZ | Receptor, tar-envZ | Forward | | | | 1491 |
| BBa_J58104 | | Fusion protein Trg-EnvZ for signal transduction | | | | | 1485 |
| BBa_J58105 | | Synthetic periplasmic binding protein that docks a vanillin molecule | | | | | 891 |
| BBa_I752001 | | CheZ coding sequence (Chemotaxis protein) | | | | | 639 |
| BBa_K091002 | | LsrK gene | Forward | | | | 1593 |
| BBa_K147000 | | cheZ | | | | | 835 |
| BBa_K118015 | | glgC coding sequence encoding | | | | | 1299 |

TABLE 72-continued

Examples of Phosphorylation and Methylation-Related Enzymes

| Name | Protein | Description | Direction | Uniprot | KEGG | E.C. | Length |
|---|---|---|---|---|---|---|---|
| BBa_K118016 | | ADP-glucose pyrophosphorylase glgC16 (glgC with G336D substitution) | | | | | 1299 |
| BBa_K094100 | | cheZ gene | | | | | 695 |
| BBa_K136046 | | envZ* | | | | | 1353 |
| BBa_K283008 | chez | chez_Histag | | | | | 713 |
| BBa_C0024 | CheB | CheB chemotaxis coding sequence (protein glutamate methylesterase) | Forward | P07330 | JW1872 | 3.1.1.61 | 1053 |
| BBa_K108020 | | Dam | | | | | 837 |

Also useful as output gene products for the purposes of the invention are receptors, ligands, and lytic proteins. Receptors tend to have three domains: an extracellular domain for binding ligands such as proteins, peptides or small molecules, a transmembrane domain, and an intracellular or cytoplasmic domain which frequently can participate in some sort of signal transduction event such as phosphorylation. In some embodiments, transporter, channel, or pump gene sequences are used as output genes. Transporters are membrane proteins responsible for transport of substances across the cell membrane. Channels are made up of proteins that form transmembrane pores through which selected ions can diffuse. Pumps are membrane proteins that can move substances against their gradients in an energy-dependent process known as active transport. In some embodiments, nucleic acid sequences encoding proteins and protein domains whose primary purpose is to bind other proteins, ions, small molecules, and other ligands are used. Exemplary receptors, ligands, and lytic proteins are listed in Table 73.

TABLE 73

Examples of Receptors, Ligands, and Lytic Proteins

| Name | Protein | Description | Tag | Direction | UniProt | Length |
|---|---|---|---|---|---|---|
| BBa_J07009 | ToxR | toxicity-gene activator from *Vibrio cholerae* | None | Forward | P15795 | 630 |
| BBa_K133063 | | (TIR)TLR3 | | | | 453 |
| BBa_K133064 | | (TIR)TLR9 | | | | 585 |
| BBa_K133065 | | (TMTIR)TLR3 | | | | 600 |
| BBa_K133069 | | (TMTIR)TLR3stop | | | | 603 |
| BBa_K133067 | | (TMTIR)TLR4 | | | | 621 |
| BBa_K133060 | | (TMTIR)TLR9 | | | | 645 |
| BBa_K209400 | | AarI B-C part, hM4D | | | | 1434 |
| BBa_K209401 | | AarI B-C part, Rs1.3 | | | | 1407 |
| BBa_I712002 | | CCR5 | | | | 1059 |
| BBa_I712003 | | CCR5-NUb | | | | 1194 |
| BBa_I712010 | | CD4 sequence without signal peptide | | | | 1299 |
| BBa_I712017 | | Chemokine (CXC motif) receptor 4, fused to N-terminal half of ubiquitin. | | | | 1191 |
| BBa_I15010 | Cph8 | cph8 (Cph1/EnvZ fusion) | None | Forward | | 2238 |
| BBa_I728500 | | CPX Terminal Surface Display Protein with Polystyrene-Binding Peptide | | | | 654 |
| BBa_J52035 | | dnMyD88 | | | | 420 |
| BBa_K259000 | | fhuA - Outer membrane transporter for ferrichrome-iron | | | | 2247 |
| BBa_K259001 | | fiu B Outer Membrane Ferric Iron Transporter | | | | 2247 |
| BBa_J58104 | | Fusion protein Trg-EnvZ for signal transduction | | | | 1485 |
| BBa_K137112 | | lamB | | | | 1339 |
| BBa_C0082 | tar-envZ | Receptor, tar-envZ | LVA | Forward | | 1491 |
| BBa_J58105 | | Synthetic periplasmic binding protein that docks a vanillin molecule | | | | 891 |
| BBa_I712012 | | TIR domain of TLR3 | | | | 456 |
| BBa_K143037 | | YtvA Blue Light Receptor for *B. subtilis* | | | | 789 |
| BBa_J07006 | | malE | | | | 1191 |
| BBa_J07017 | | FecA protein | | | | 2325 |
| BBa_K141000 | UCP1 | Ucp1 | | | | 924 |
| BBa_K141002 | | Ucp 175 deleted | | | | 921 |
| BBa_K141003 | | Ucp 76 deleted | | | | 921 |

TABLE 73-continued

Examples of Receptors, Ligands, and Lytic Proteins

| Name | Protein | Description | Tag | Direction | UniProt | Length |
|---|---|---|---|---|---|---|
| BBa_K190028 | | GlpF | | | | 846 |
| BBa_I746200 | | FepA L8T Mutant - Large Diffusion pore for *E. coli* outer membrane. | | | | 2208 |
| BBa_I765002 | | ExbB membrane spanning protein in TonB-ExbB-ExbD complex [*Escherichia coli* K12] | | | | 735 |
| BBa_I765003 | | TonB ferric siderophore transport system, periplasmic binding protein TonB [*Pseudomonas entomophila* | | | | 735 |
| BBa_K090000 | | Glutamate gated K+ channel | | | | 1194 |
| BBa_K284000 | | Lactate Permease from Kluyveromyces lactis | | | | 1873 |
| BBa_K284997 | | Deletar este | | | | 1069 |
| BBa_J22101 | | Lac Y gene | | | | 1288 |
| BBa_K079015 | | LacY transporter protein from *E. coli* | | | | 1254 |
| BBa_K119003 | | RcnA (YohM) | | | | 833 |
| BBa_K137001 | | LacY | | | | 1254 |
| BBa_I712024 | | CD4 | | | | 1374 |
| BBa_K133061 | | CD4 ecto | | | | 1113 |
| BBa_K136046 | | envZ* | | | | 1353 |
| BBa_K157002 | | Transmembrane region of the EGF-Receptor (ErbB-1) | | | | 87 |
| BBa_K227006 | | puc BA coding region of *R. sphaeroides* | | forward | | 336 |
| BBa_M12067 | | E1 | | | | 264 |
| BBa_I721002 | | Lead Binding Protein | | | | 399 |
| BBa_K126000 | | TE33 Fab L chain | | | | 648 |
| BBa_K133070 | | gyrEC | | | | 660 |
| BBa_K133062 | | gyrHP | | | | 660 |
| BBa_K157003 | | Anti-NIP singlechain Fv-Fragment | | | | 753 |
| BBa_K211001 | | RI7 | | | | 987 |
| BBa_K211002 | | RI7-odr10 chimeric GPCR | | | | 1062 |
| BBa_K103004 | | protein $Z_{SPA-1}$ | | | | 190 |
| BBa_K128003 | | p1025 | | | | 101 |
| BBa_K133059 | | RGD | | | | 9 |
| BBa_K283010 | | Streptavidin | | | | 387 |
| BBa_K103004 | | protein $Z_{SPA-1}$ | | | | 190 |
| BBa_K128003 | | p1025 | | | | 101 |
| BBa_K133059 | | RGD | | | | 9 |
| BBa_K283010 | | Streptavidin | | | | 387 |
| BBa_K112000 | Holin | T4 holin, complete CDS, berkeley standard | | | | 657 |
| BBa_K112002 | Holin | T4 holin, without stop codon, berkeley standard | | | | 654 |
| BBa_K112004 | | a~T4 holin in BBb | | | | 661 |
| BBa_K112006 | | T4 antiholin in BBb | | | | 294 |
| BBa_K112009 | | in BBb | | | | 288 |
| BBa_K112010 | | a~T4 antiholin in BBb | | | | 298 |
| BBa_K112012 | | T4 lysozyme in BBb | | | | 495 |
| BBa_K112015 | | in BBb | | | | 489 |
| BBa_K112016 | | a~T4 lysozyme in BBb | | | | 499 |
| BBa_K117000 | | Lysis gene (promotes lysis in colicin-producing bacteria strain) | | | | 144 |
| BBa_K124014 | | Bacteriophage Holin Gene pS105 | | | | 317 |
| BBa_K108001 | | SRRz | | | | 1242 |
| BBa_K112300 | | {lambda lysozyme} in BBb format | | | | 477 |
| BBa_K112304 | | {a~lambda lysozyme} in BBb format | | | | 481 |
| BBa_K112306 | | {lambda holin} in BBb format | | | | 318 |
| BBa_K112310 | | {a~lambda holin}; adheres to Berkeley standard | | | | 322 |
| BBa_K112312 | | {lambda antiholin}; adheres to Berkeley standard | | | | 324 |
| BBa_K112316 | | {a~lambda antiholin}; adheres to Berkeley standard | | | | 328 |
| BBa_K124017 | | Bacteriophage Lysis Cassette S105, R, and Rz | | | | 1257 |
| BBa_K112806 | | [T4 endolysin] | | | | 514 |
| BBa_K284001 | | Lysozyme from *Gallus gallus* | | | | 539 |

Single Invertase Memory Modules

In some aspects, different components, such as promoters, promoter activators promoter repressors, recombinases, and output gene products, are provided to create novel biological modules to be used in the engineered genetic counters described herein. The ability to create and modulate various combinations of the different components and modules provides flexibility in the designs and uses of the engineered genetic counters described herein.

One exemplary module for use in the engineered genetic counters described herein is the "single invertase memory module." As defined herein, a "single invertase memory module (SIMM)," is a stable, switchable bit of memory that uses recombinases, such as Cre and $flp_e$, which can invert DNA between two oppositely oriented cognate recombinase recognition sites. A unique feature and advantage of SIMMs, of relevance to their use in the engineered genetic counters described herein, is the lack of both "leakiness" and mixtures of inverted and non-inverted states that can be caused by expressing recombinases independently from their cognate recognition sites. Thus, the use of SIMMs in the engineered genetic counters described herein allows for the maintenance of memory, and provides the ability to count between discrete states by expressing the recombinases between their cognate recognition sites.

A SIMM is a nucleic acid-based module comprising a recombinase sequence that is located between its cognate recombinase recognition sites, and downstream of an inverted inducible promoter sequence, i.e., $RRS_{for}$-$iP_{inv}$-RC-$RRS_{rev}$, where $RRS_{for}$ is a forward recombinase recognition site, $iP_{inv}$ is an inverted promoter sequence, RC is a recombinase sequence and $RRS_{rev}$ is a reverse recombinase recognition. Upon recombinase expression following activation of an upstream promoter not present within the SIMM, the recombinase causes a single inversion of the DNA between the cognate recognition sites, including its own DNA sequence (i.e., $RRS_{for}$-iP-$RC_{inv}$-$RRS_{rev}$). Any further transcription from the upstream promoter yields antisense RNA of the recombinase gene rather then sense RNA, and therefore no further recombinase protein is produced. Thus, the inversion event is discrete and stable, and does not result in a mixture of inverted and non-inverted states. Further, the inverted promoter is now in the proper orientation to drive transcription of components of downstream modules, such as another SIMM. Similarly, the upstream promoter driving expression of the SIMM can be a promoter within an upstream SIMM or another module.

In some embodiments of the aspects described herein, a SIMM can use any recombinase for encoding memory, rather than only unidirectional recombinases, which can allow greater flexibility and practicality. In some embodiments, the recombinase is encoded between its cognate recombinase recognition sequences. In other embodiments, the recombinase is encoded outside of its cognate recombinase recognition sequences. In those embodiments where the recombinase is encoded outside of its cognate recombinase recognition sequences, the SIMM can be used as, for example, a waveform generator, such that the input or inputs that lead to recombinase expression results in constant inversion between the recombinase recognition sequences and is used to generate pulses of outputs. Such outputs can be any of the output gene products described herein. In some embodiments, the outputs can be a fluorescent protein.

The recombinases and recombination recognition sequences for use in the SIMMs described herein can be selected from any known or variant (engineered) recombinase or recombinase recognition sequences, as determined by a skilled artisan. In some embodiments of the various aspects described herein, the recombinase is a Cre recombinase and the recombinase recognition sites are LoxP sites or variants thereof. Alternative site-specific recombinases include: 1) the Flp recombinase of the 2 µl plasmid of *Saccharomyces cerevisiae* (Cox (1983) Proc. Natl. Acad. Sci. USA 80:4223) which recognize FRT sites and variants thereof; 2) the integrase of *Streptomyces* phage .PHI.C31 that carries out efficient recombination between the attP site of the phage genome and the attB site of the host chromosome (Groth et al., 2000 Proc. Natl. Acad. Sci. USA, 97: 5995); 3) the Int recombinase of bacteriophage lambda (lambda-int/attP) (with or without Xis) which recognizes att sites (Weisberg et al. In: Lambda II, supra, pp. 211-250); 4) the xerC and xerD recombinases of *E. coli* which together form a recombinase that recognizes the 28 by dif site (Leslie and Sherratt (1995) EMBO J. 14:1561); 5) the Int protein from the conjugative transposon Tn916 (Lu and Churchward (1994) EMBO J. 13:1541); 6) TpnI and the β-lactamase transposons (Levesque (1990) J. Bacteriol. 172:3745); 7) the Tn3 resolvase (Flanagan et al. (1989) J. Mol. Biol. 206:295 and Stark et al. (1989) Cell 58:779); 8) the SpoIVC recombinase of *Bacillus subtilis* (Sato et al. J. Bacteriol. 172:1092); 9) the Hin recombinase (Galsgow et al. (1989) J. Biol. Chem. 264: 10072); 10) the Cin recombinase (Hafter et al. (1988) EMBO J. 7:3991); 11) the immunoglobulin recombinases (Malynn et al. Cell (1988) 54:453); and 12) the FIMB and FIME recombinases (Blomfield et al., 1997 Mol. Microbiol. 23:705). Additional non-limiting examples of recombinases and their cognate recombinase recognition sequences that are useful for the SIMMs and engineered genetic counters described herein are provided in Tables 1-10, and in SEQ ID NOs: 1-18.

The inverted promoter sequence in a SIMM can be used to drive transcription of downstream components of that SIMM or other modules upon recombinase activation and inversion of the promoter to the forward direction. Accordingly, an inverted promoter sequence for use in the SIMMs described herein can be a constitutive or inducible promoter, depending upon the requirements of the engineered genetic counters. Non-limiting examples of such promoter sequences for use in the SIMMs described herein are provided in SEQ ID NOs: 33-39 and Tables 11-46.

In other embodiments of the aspects described herein, one or more ribosome binding site sequences (RBSs) can also be added to a SIMM to promote efficient and accurate translation of the mRNA sequences for protein synthesis. RBSs are useful components for modulating the efficiency and rates of synthesis of the proteins encoded by the engineered genetic counters described herein. Non-limiting examples of such RBS sequences for use in the SIMMs described herein are provided in Tables 47-53. Accordingly, in some embodiments of these aspects, a SIMM further comprises a ribosome binding site upstream of the recombinase sequence, i.e., the SIMM comprises $RRS_{for}iP_{inv}$-RBS-RC-$RRS_{rev}$, where RBS is a ribosome binding site.

In other embodiments of the aspects described herein, one or more terminator sequences can be added to a SIMM to prevent activation of downstream genes or modules by an upstream promoter. Terminator sequences can be added to the end of, for example, a recombinase sequence in a SIMM, to prevent further transcription downstream of the recombinase. Thus, terminator sequences are useful in the engineered genetic counters described herein to prevent unwanted transcription driven by activation of the various modules. Non-limiting examples of such terminator sequences for use in the SIMMs described herein are provided in Tables 54-58. Accordingly, in some embodiments of these aspects, a SIMM further comprises a transcriptional terminator sequence downstream of the recombinase sequence, i.e., $RRS_{for}\text{-}iP_{inv}\text{-}RC\text{-}T\text{-}RRS_{rev}$, where T is a terminator sequence.

Degradation tag sequences are also provided for use in the SIMMs and engineered genetic counters described herein to enhance degradation of a protein expressing the tag. The ability to add degradation tags to the proteins encoded by the SIMMs and engineered genetic counters described herein provides for additional layer of regulation and control of the modules. Non-limiting examples of such degradation tag sequences for use in the SIMMs described herein are provided in SEQ ID NOs: 995-1001. Accordingly, in some embodiments of the aspects described herein, a SIMM further comprises a protein degradation tag sequence downstream of the recombinase sequence, i.e., the SIMM comprises i.e., the SIMM comprises $RRS_{for}\text{-}iP_{inv}\text{-}RC\text{-}D\text{-}RRS_{rev}$, where D is a degradation tag sequence.

In further embodiments of these aspects, a SIMM comprises both a ribosome binding site upstream of the recombinase sequence and a protein degradation tag sequence downstream of the recombinase sequence, i.e., the SIMM comprises $RRS_{for}\text{-}iP_{inv}\text{-}RBS\text{-}RC\text{-}D\text{-}RRS_{rev}$. In other embodiments of these aspects, a SIMM comprises a protein degradation tag sequence and a transcriptional terminator sequence downstream of the recombinase sequence, i.e., the SIMM comprises $RRS_{for}\text{-}iP_{inv}\text{-}RC\text{-}D\text{-}T\text{-}RRS_{rev}$. In some embodiments of these aspects, a SIMM comprises a ribosome binding site upstream of the recombinase sequence and a terminator sequence downstream of the recombinase sequence, i.e., the SIMM comprises $RRS_{for}\text{-}iP_{inv}\text{-}RBS\text{-}RC\text{-}T\text{-}RRS_{rev}$.

In some particular embodiments of these aspects, a SIMM can further comprise a ribosome binding site upstream of the recombinase sequence, and protein degradation tag and transcriptional terminator sequences downstream of the recombinase sequence, i.e., $RRS_{for}\text{-}iP_{inv}\text{-}RBS\text{-}RC\text{-}D\text{-}T\text{-}RRS_{rev}$. In such embodiments, the combined addition of an RBS, a transcriptional terminator sequence, and a degradation tag to the SIMM provides an enhanced ability to regulate and control expression of the recombinase encoded by the SIMM.

In some embodiments of these aspects and all such aspects described herein, a SIMM can be designed so that it can be reset by placing an additional promoter sequence in an inverted orientation downstream of the reverse recombinase recognition site, i.e., $RRS_{for}\text{-}iP_{1,inv}\text{-}RBS\text{-}RC\text{-}RRS_{rev}\text{-}iP_{2,inv}$; where $iP_{1,inv}$ is a first inverted inducible promoter sequence and $iP_{2,inv}$ is a second inverted inducible promoter sequence. Upon activation of the reverse promoter, the state of such a SIMM is flipped from its inverted state back to its original state. In some embodiments, the same reverse inducible promoter can be used throughout the entire set of SIMMs within an engineered genetic counter, such that a single inducer can be used to perform a global reset of the memory system.

Engineered Genetic Counters

Described herein are engineered genetic counters that are extensible, highly modular and can function with a variety of combinations of various component parts and modules, such as inducible promoters, recombinases, output products, and SIMMs. The modular architecture of the counters described herein allows for tunable expression of a variety output products. Further, these counters can operate on a variety of time scales, including hours, and retain their "state" based on DNA orientation, due to the use of recombinases expressed within their cognate recognition sequences. Depending on the combinations of promoters used in the engineered genetic modules described herein, an engineered genetic counter can be used with a single inducer or with multiple inducers. Depending on the type of inducible promoters utilized, the engineered genetic circuits described herein can be used to enumerate physiological events and stimuli, such as activation of gene networks or exposure to nutrients, toxins, or metabolites.

Accordingly, in some aspects, single inducer engineered genetic counters are provided. Single inducer counters can be used for counting multiple independent exposures to a single type of inducer, such as arabinose. Thus, such single inducer counters can be used to detect multiple exposures to a biological agent, such as a toxin. Such single inducer engineered genetic counters comprise an inducible promoter sequence ($iP_1$), at least one SIMM, and an output nucleic acid sequence (OP). In such counters, the inverted promoter sequences of each SIMM and the inducible promoter sequence of the counter are the same promoter sequence. In some embodiments of the aspects described herein, the SIMM comprises a ribosome binding site upstream of a recombinase sequence, and protein degradation tag and transcriptional terminator sequences downstream of a recombinase sequence, i.e., the SIMM comprises a forward recombinase recognition sequence ($RRS_{for}$), an inverted inducible promoter sequence ($iP_{1,inv}$), a ribosome binding site (RBS), a recombinase gene sequence (RC), a degradation tag sequence (D), a transcriptional terminator sequence (T), and a reverse recombinase recognition sequence ($RRS_{rev}$). Thus, in such embodiments, the single inducer engineered genetic counter comprises: $iP_1\text{-}[RRS_{for}\text{-}iP_{1,inv}\text{-}RBS\text{-}RC\text{-}D\text{-}T\text{-}RRS_{rev}]_n\text{-}OP$. In such embodiments, the recombinase encoded by each of the at least one SIMMs is a unique recombinase, such that expression of a recombinase in one SIMM does not result in inversion of sequences outside of that SIMM.

In such single inducer engineered genetic counters, upon activation of the inducible promoter of the counter by an inducer or inducing agent, the recombinase encoded within the first SIMM is expressed, resulting in the inversion of the sequence between the two recombinase recognition sites, causing termination of recombinase expression, and allowing for the inverted promoter sequence within the first SIMM (i.e., $iP_{1,inv}$) to be in the appropriate direction to drive expression of a downstream module or component, such as an output nucleic acid sequence, e.g., a gene, or another SIMM, if the counter receives a second same inducer signal.

In some embodiments, a single inducer, 2 input, engineered genetic counter is provided, i.e., $iP_1\text{-}[RRS_{for}\text{-}iP_{1,inv}\text{-}RBS\text{-}RC\text{-}D\text{-}T\text{-}RRS_{rev}]\text{-}OP$. In such single inducer, 2 input, engineered genetic counters, the counter has to receive two discrete input signals of the same inducer for output nucleic acid expression to occur. In some such embodiments, the output nucleic acid sequence encodes a reporter protein, such as a fluorescent or luminescent reporter. In some embodiments, the output nucleic acid sequence further comprises an upstream RBS sequence. In some embodiments, the output nucleic acid sequence further comprises a downstream terminator sequence. In other embodiments, the output nucleic acid sequence further comprises both an upstream RBS sequence and a downstream terminator sequence.

For example, in some embodiments, the single inducer, 2 input engineered genetic counter comprises a $P_{BAD}$ inducible promoter, i.e., $iP_{BAD}=iP_1$; FRT sites as recombinase recognition sites, i.e., $RRS_{for}$ and $RRS_{rev}$ are $FRT_f$ and $FRT_r$ sites respectively; a $flp_e$ recombinase, i.e., $RC=flp_e$, and the output nucleic acid product is GFP, i.e., OP=GFP such that the engineered genetic counter comprises $iP_{BAD}\text{-}[FRT_f\text{-}iP_{BAD,inv}\text{-}RBS\text{-}flp_e\text{-}D\text{-}T\text{-}FRT_r]\text{-}GFP$. In such embodiments, a first arabinose signal causes expression of the $flp_e$ recombinase within the SIMM, resulting in inversion of the recombinase sequence and inversion of the inducible promoter within the SIMM. A second arabinose signal results in expression of GFP driven by the $iP_{BAD}$ promoter of the SIMM. Thus, such a single inducer, 2 input engineered genetic counter gives an output signal only after the receipt of two independent inputs of the same inducer, i.e., the single inducer, 2 input engineered genetic counter "counts to" two.

In other embodiments, a single inducer, 3 input, engineered genetic counter is provided, i.e., $iP_1$-[$RRS_{1,for}$-$iP_{1,inv}$-RBS-$RC_1$-D-T-$RRS_{1,rev}$]-[$RRS_{2,for}$-$iP_{1,inv}$-RBS-$RC_2$-D-T-$RRS_{2,rev}$]-OP. In such single inducer, 3 input, engineered genetic counters, the counter has to receive three discrete input signals of the same inducer for output gene expression to occur. In some such embodiments, the output gene sequence encodes a reporter protein, such as a fluorescent or luminescent reporter. In some embodiments, the output nucleic acid sequence further comprises an upstream RBS sequence. In some embodiments, the output nucleic acid sequence further comprises a downstream terminator sequence. In other embodiments, the output nucleic acid sequence further comprises both an upstream RBS sequence and a downstream terminator sequence.

For example, in some embodiments, the single inducer, 3 input engineered genetic counter comprises a $P_{BAD}$ inducible promoter, i.e., $iP_{BAD}$=$iP_1$; a $flp_e$ recombinase SIMM (i.e., $RRS_{1,for}$=$FRT_f$; $RRS_{1,rev}$=$FRT_r$, and $RC_1$=$flp_e$); a Cre recombinase SIMM (i.e., $RRS_{2,for}$=$loxP_F$; $RRS_{2,rev}$=$loxP_R$ and $RC_2$=Cre), and GFP as an output nucleic acid sequence, such that the engineered genetic counter comprises $iP_{BAD}$-[$FRT_f$-$iP_{BAD,inv}$-RBS-$flp_e$-D-T-$FRT_r$]-[$loxP_F$-$iP_{BAD,inv}$-RBS-Cre-D-T-$loxP_R$]-GFP. In such embodiments, a first arabinose signal causes expression of the $flp_e$ recombinase within the $flp_e$ SIMM, resulting in inversion of the $flp_e$ recombinase sequence and inversion of the inducible promoter within the $flp_e$ SIMM, while the inducible promoter within the Cre SIMM remains inverted. A second arabinose signal results in expression of the Cre recombinase within the Cre SIMM, resulting in inversion of the Cre recombinase sequence and inversion of the inducible promoter within the Cre. As the $flp_e$ recombinase is inverted, the second arabinose signal has no effect on the $flp_e$ SIMM. A third such arabinose signal results in expression of GFP driven by the $iP_{BAD}$ promoter of the Cre SIMM. Thus, such a single inducer, 3 input engineered genetic counter gives an output signal only after the receipt of three independent inputs of the same inducer, i.e., the single inducer, 3 input engineered genetic counter "counts to" three.

In all such embodiments of these aspects, the single inducer engineered genetic counter described herein can comprise at least 150 SIMMs, where the number of SIMMs "n" in a counter is an integer that ranges between and includes 1 to 150, such that the single inducer engineered genetic counter "counts to" n+1, i.e., the number of input signal required for the output gene product to be expressed is n+1. For example, in one embodiment n equals 1, and the single inducer engineered genetic counter "counts to" 2. In another embodiment, n equals 2 and the single inducer engineered genetic counter "counts to" 3. In another embodiment, n equals 3 and the single inducer engineered genetic counter "counts to" 4. In another embodiment, n equals 4 and the single inducer engineered genetic counter "counts to" 5. In another embodiment, n equals 5 and the single inducer engineered genetic counter "counts to" 6. In another embodiment, n equals 6 and the single inducer engineered genetic counter "counts to" 7. In another embodiment, n equals 7 and the single inducer engineered genetic counter "counts to" 8. In another embodiment, n equals 8 and the single inducer engineered genetic counter "counts to" 9. In another embodiment, n equals 9 and the single inducer engineered genetic counter "counts to" 10. In another embodiment, n equals 10 and the single inducer engineered genetic counter "counts to" 11. In another embodiment, n equals any one of 11 . . . 25 . . . 45 . . . 90 . . . 99 . . . 105 . . . 125 . . . 150. For example, n equals 12. In another embodiment, n equals 117. In another embodiment, n is an integer value ranging between 10-150. In another embodiment, n is an integer value ranging between 10 and 15. In another embodiment, n is an integer value ranging between 15 and 20. In another embodiment, n is an integer value ranging between 25 and 30. In another embodiment, n is an integer value ranging between 30 and 35. In another embodiment, n is an integer value ranging between 35 and 40. In another embodiment, n is an integer value ranging between 40 and 45. In another embodiment, n is an integer value ranging between 45 and 50. In another embodiment, n is an integer value ranging between 50 and 55. In another embodiment, n is an integer value ranging between 55 and 60. In another embodiment, n is an integer value ranging between 60 and 65. In another embodiment, n is an integer value ranging between 65 and 70. In another embodiment, n is an integer value ranging between 70 and 75. In another embodiment, n is an integer value ranging between 75 and 80. In another embodiment, n is an integer value ranging between 80 and 85. In another embodiment, n is an integer value ranging between 85 and 90. In another embodiment, n is an integer value ranging between 90 and 95. In another embodiment, n is an integer value ranging between 95 and 100. In another embodiment, n is an integer value ranging between 100 and 105. In another embodiment, n is an integer value ranging between 105 and 110. In another embodiment, n is an integer value ranging between 110 and 115. In another embodiment, n is an integer value ranging between 115 and 120. In another embodiment, n is an integer value ranging between 120 and 125. In another embodiment, n is an integer value ranging between 125 and 130. In another embodiment, n is an integer value ranging between 130 and 135. In another embodiment, n is an integer value ranging between 135 and 140. In another embodiment, n is an integer value ranging between 140 and 145. In another embodiment, n is an integer value ranging between 145 and 150. In all the ranges described herein, both the lower and upper values of the range are included. In other aspects, the single inducer engineered genetic counter can be extended with more sophisticated designs to count in binary, thus allowing the maximum countable number to be $2^n-1$.

In other aspects, multiple inducer engineered genetic counters are provided. Multiple inducer engineered genetic counters can be used to distinguish multiple input signals occurring in a specific order, such that output nucleic acid expression occurs only when a certain number of signals in a specific order are received by the counter. Such multiple inducer engineered genetic counters comprise an inducible promoter sequence ($iP_A$), at least one SIMM, and an output nucleic acid sequence (OP). In such counters, the inverted promoter sequences of at least one SIMM and the inducible promoter sequence of the counter are different promoter sequences, or are responsive to at least two different inducers. In some embodiments of the aspects described herein, the SIMM comprises a ribosome binding site upstream of a recombinase sequence, and protein degradation tag and transcriptional terminator sequences downstream of a recombinase sequence, i.e., the SIMM comprises a forward recombinase recognition sequence ($RRS_{for}$), an inverted inducible promoter sequence ($iP_{1,inv}$), a ribosome binding site (RBS), a recombinase gene sequence (RC), a degradation tag sequence (D), a transcriptional terminator sequence (T), and a reverse recombinase recognition sequence ($RRS_{rev}$). Thus, in such embodiments, the multiple inducer engineered genetic counter comprises: $iP_A\text{-}[RRS_{for}\text{-}iP_{1,inv}\text{-}RBS\text{-}RC\text{-}D\text{-}T\text{-}RRS_{rev}]_n\text{-}OP$. In such embodiments, the recombinase encoded by each of the at least one SIMMs is a unique recombinase, such that expression of a recombinase in one SIMM does not result in inversion of sequences outside of that SIMM.

In some embodiments of such aspects, a multiple inducer, 2 input, engineered genetic counter is provided, i.e., $iP_A\text{-}[RRS_{for}\text{-}iP_{1,inv}\text{-}RBS\text{-}RC\text{-}D\text{-}T\text{-}RRS_{rev}]\text{-}OP$. In such multiple inducers, 2 input, engineered genetic counters, the counter has to receive two discrete input signals of different inducers for output nucleic acid expression to occur. In some such embodiments, the output nucleic acid sequence encodes a reporter protein, such as a fluorescent or luminescent reporter. In some embodiments, the output nucleic acid sequence further comprises a downstream terminator sequence. In other embodiments, the output nucleic acid sequence further comprises both an upstream RBS sequence and a downstream terminator sequence.

For example, in some embodiments, the multiple inducer, 2 input engineered genetic counter comprises a $P_{LtetO\text{-}1}$ inducible promoter, i.e., $iP_{LtetO\text{-}1}=iP_A$; an inverted $P_{BAD}$ promoter that drives expression of the SIMM, i.e., $iP_{BAD,inv}=iP_{1,inv}$; FRT sites as recombinase recognition sites in the SIMM, i.e., $RRS_{for}$ and $RRS_{rev}$ are $FRT_f$ and $FRT_r$ sites respectively; a $flp_e$ recombinase, i.e., $RC=flp_e$, and the output nucleic acid product is GFP, i.e., OP=GFP. In such embodiments, the engineered genetic counter comprises $iP_{LtetO\text{-}1}\text{-}[FRT_f\text{-}iP_{BAD,inv}\text{-}RBS\text{-}flp_e\text{-}D\text{-}T\text{-}FRT_r]\text{-}GFP$. In such embodiments, exposure to anhydrotetracycline causes expression of the $flp_e$ recombinase within the SIMM, resulting in inversion of the recombinase sequence and inversion of the inducible promoter $P_{BAD}$ within the SIMM. Exposure to an arabinose signal results in expression of GFP driven by the $iP_{BAD}$ promoter of the SIMM. Thus, such a multiple inducer, 2 input engineered genetic counter gives an output signal only after the receipt of two independent inputs of two different inducers, i.e., the multiple inducer, 2 input engineered genetic counter "counts to" two.

In other embodiments, a multiple inducer, 3 input, engineered genetic counter is provided, i.e., $iP_A\text{-}[RRS_{1,for}\text{-}iP_{1,inv}\text{-}RBS\text{-}RC_1\text{-}D\text{-}T\text{-}RRS_{1,rev}]\text{-}[RRS_{2,for}\text{-}iP_{2,inv}\text{-}RBS\text{-}RC_2\text{-}D\text{-}T\text{-}RRS_{2,rev}]\text{-}OP$. In such multiple inducers, 3 input, engineered genetic counters, the counter has to receive three discrete input signals of at least two different inducers for output nucleic acid expression to occur. In some embodiments, each inducible promoter in the engineered genetic counter is responsive to a different inducer, i.e., all the inducible promoters are different. In other embodiments, at least one inducible promoter in the engineered genetic counter is responsive to a different inducer from the other inducible promoters. Specific combinations of inducible promoters can be used to create engineered genetic counters that receive specific patterns of multiple inducers. For example, an engineered genetic counter can be designed so that every other inducible promoter is responsive to the same inducer or inducing agent, such that the counter detects alternate exposures to a combination of inducers, for example, arabinose followed by anyhydrotetracycline.

In some such embodiments, the output nucleic acid sequence encodes a reporter protein, such as a fluorescent or luminescent reporter. In some embodiments, the output nucleic acid sequence further comprises an upstream RBS sequence. In some embodiments, the output nucleic acid sequence further comprises a downstream terminator sequence. In other embodiments, the output nucleic acid sequence further comprises both an upstream RBS sequence and a downstream terminator sequence.

For example, in some embodiments, the multiple inducer, 3 input engineered genetic counter comprises a $P_{LtetO\text{-}1}$ inducible promoter that receives the first signal of the engineered genetic counter i.e., $iP_{LtetO\text{-}1}=iP_A$, and the output nucleic acid product is GFP, i.e., OP=GFP. The first SIMM comprises an inverted $P_{BAD}$ promoter that drives expression of the first SIMM, i.e., $iP_{BAD,inv}=iP_{1,inv}$; FRT sites as recombinase recognition sites in the first SIMM, i.e., $RRS_{for}$ and $RRS_{rev}$ are $FRT_f$ and $FRT_r$ sites respectively; a $flp_e$ recombinase, i.e., $RC=flp_e$. The second SIMM comprises an inverted $iP_{A1lacO\text{-}1}$ promoter that drives expression of the second SIMM, i.e., $iP_{A1lacO\text{-}1,inv}=iP_{2,inv}$; LoxP sites as recombinase recognition sites in the second SIMM, i.e., $RRS_{2,for}=loxP_F$; $RRS_{2,rev}=loxP_R$; and a Cre recombinase as the recombinase of the second SIMM. In such embodiments, the engineered genetic counter comprises $iP_{BAD}\text{-}[FRT_f\text{-}iP_{BAD,inv}\text{-}RBS\text{-}flp_e\text{-}D\text{-}T\text{-}FRT_r]\text{-}[loxP_F\text{-}iP_{A1lacO\text{-}1,inv}\text{-}RBS\text{-}Cre\text{-}D\text{-}T\text{-}loxP_R]\text{-}GFP$. In such embodiments, exposure to anhydrotetracycline causes expression of the $flp_e$ recombinase within the first SIMM, resulting in inversion of the $flp_e$ recombinase sequence and inversion of the inducible promoter $P_{BAD}$ within the first SIMM. Exposure to an arabinose signal results in expression of the Cre recombinase within the second SIMM, resulting in inversion of the Cre recombinase sequence and inversion of the inducible promoter $iP_{A1lacO\text{-}1}$ within the second SIMM. Exposure to IPTG then drives expression of the output nucleic acid sequence resulting in GFP expression. Thus, such a multiple inducer, 3 input engineered genetic counter gives an output signal only after the receipt of three independent inputs of at least two different inducers, i.e., the multiple inducer, 3 input engineered genetic counter "counts to" three.

In all embodiments of the aspects described herein, the multiple inducer engineered genetic counters can comprise at least 150 SIMMs, where the number of SIMMs "n" in a counter is an integer that ranges between and includes 1 to 150, such that the multiple inducer engineered genetic counter "counts to" n+1, i.e., the number of input signals required for the output product to be expressed is n+1. For example, in one embodiment n equals 1, and the multiple inducer engineered genetic counter "counts to" 2. In another embodiment, n equals 2 and the multiple inducer engineered genetic counter "counts to" 3. In another embodiment, n equals 3 and the multiple inducer engineered genetic counter "counts to" 4. In another embodiment, n equals 4 and the multiple inducer engineered genetic counter "counts to" 5. In another embodiment, n equals 5 and the multiple inducer engineered genetic counter "counts to" 6. In another embodiment, n equals 6 and the multiple inducer engineered genetic counter "counts to" 7. In another embodiment, n equals 7 and the multiple inducer engineered genetic counter "counts to" 8. In another embodiment, n equals 8 and the multiple inducer engineered genetic counter "counts to" 9. In another embodiment, n equals 9 and the multiple inducer engineered genetic counter "counts to" 10. In another embodiment, n equals 10 and the multiple inducer engineered genetic counter "counts to" 11. In another embodiment, n equals any one of 11 . . . 25 . . . 45 . . . 90 . . . 99 . . . 105 . . . 125 . . . 150. For example, n equals 12. In another embodiment, n equals 117. In another embodiment, n is an integer value ranging between 10-150. In another embodiment, n is an integer value ranging between 10 and 15. In another embodiment, n is an integer value ranging between 15 and 20. In another embodiment, n is an integer value ranging between 25 and 30. In another embodiment, n is an integer value ranging between 30 and 35. In another embodiment, n is an integer value ranging between 35 and 40. In another embodiment, n is an integer value ranging between 40 and 45. In another embodiment, n is an integer value ranging between 45 and 50. In another embodiment, n is an integer value ranging between 50 and 55. In another embodiment, n is an integer value ranging between 55 and 60. In another embodiment, n is an integer value ranging between 60 and 65. In another embodiment, n is an integer value ranging between 65 and 70. In another embodiment, n is an integer value ranging between 70 and 75. In another embodiment, n is an integer value ranging between 75 and 80. In another embodiment, n is an integer value ranging between 80 and 85. In another embodiment, n is an integer value ranging between 85 and 90. In another embodiment, n is an integer value ranging between 90 and 95. In another embodiment, n is an integer value ranging between 95 and 100. In another embodiment, n is an integer value ranging between 100 and 105. In another embodiment, n is an integer value ranging between 105 and 110. In another embodiment, n is an integer value ranging between 110 and 115. In another embodiment, n is an integer value ranging between 115 and 120. In another embodiment, n is an integer value ranging between 120 and 125. In another embodiment, n is an integer value ranging between 125 and 130. In another embodiment, n is an integer value ranging between 130 and 135. In another embodiment, n is an integer value ranging between 135 and 140. In another embodiment, n is an integer value ranging between 140 and 145. In another embodiment, n is an integer value ranging between 145 and 150. In all the ranges described herein, both the lower and upper values of the range are included. In other aspects, the multiple inducer engineered nucleic acid-based circuit can be extended with more sophisticated designs to count in binary, thus allowing the maximum countable number to be $2^n-1$.

In some embodiments of the different aspects of the invention described herein, additional components can be added to the SIMMs to increase the utility and functionality of the SIMM in the engineered genetic counters. In some embodiments, output nucleic acid sequences can be included within an individual SIMM, such that an individual SIMM regulates its own output nucleic acid expression. Regulation of an output nucleic acid sequence within a SIMM is dependent on the placement and orientation of the output nucleic acid sequence within the SIMM. For example, in some embodiments, the output nucleic acid sequence is placed in an inverted orientation between the recombinase recognition sites, such that upon expression of the recombinase encoded by the SIMM, the output nucleic acid sequence is inverted and can be driven by the promoter sequence of the SIMM upon receipt of the appropriate input signal by the SIMM, i.e., the SIMM comprises ($RRS_{for}$-$iP_{inv}$-RBS-RC-D-T-$OP_{inv}$-$RRS_{rev}$). In some embodiments, regulation of output nucleic acid sequence transcription within the SIMM can be enhanced through the addition of an RBS sequence, a terminator sequence, or a combination thereof, such that the RBS sequence and/or terminator sequence are also placed in the inverted orientation.

In other embodiments where an output nucleic acid sequence is included within an individual SIMM, the output nucleic acid sequence can be placed in the forward orientation between the recombinase recognition sites, i.e., ($RRS_{for}$-$iP_{inv}$-RBS-RC-D-T-OP-$RRS_{rev}$). In such embodiments, upon activation of the promoter sequence that drives expression of that SIMM, for example, the promoter sequence of an upstream SIMM, expression of both the recombinase and the output nucleic acid product occurs. Inversion of the sequence within the two recombinase recognition sites then occurs due to the activity of the recombinase, resulting in inversion of the output nucleic acid sequence, thus shutting off expression of the output nucleic acid product. Thus, in such embodiments, an individual SIMM can creates a single pulse of expression of an output nucleic acid product. When multiple such SIMMs are used in the engineered genetic counters described herein, each "count" is represented by a single pulse of output nucleic acid expression, thus achieving enumeration of each count recorded by the engineered genetic counters described herein. In some such embodiments, regulation of output nucleic acid sequence transcription within the SIMM can be enhanced through the addition of an RBS sequence, a terminator sequence, or a combination thereof, such that the RBS sequence and/or terminator sequence.

In some embodiments, the engineered genetic counters are designed so that they can reset by placing an additional inverted promoter sequence downstream of the reverse recombinase recognition site within a SIMM, i.e., $iP_A$-($RRS_{for}$-$iP_{1,inv}$-RBS-RC-D-T-$RRS_{rev}$-$iP_{reset,inv}$)$_n$-OP, where $iP_{reset,inv}$ is the inverted sequence of the reset promoter. In such embodiments, upon activation of the reverse promoter, all recombinases in the reverse orientation are expressed and flipped back to their original position. Thus, the state of the system is flipped from its inverted state back to its original state. If the same reverse promoter is used throughout the entire set of SIMMs within a counter, a single inducer can be used to perform a global reset of the memory system, which has great utility for regulating the counters described herein In some embodiments of these aspects, one or more of any of the SIMMs described herein can be "daisy-chained" together on an *E. coli* chromosome, with a promoter placed upstream of the first SIMM. In some embodiments of these aspects, the designs utilized in the engineered genetic counters described herein are cis-based counting systems that require physical proximity of the individual counting units, or SIMMs, for counting transitions. In other embodiments of these aspects, further functionality is provided by incorporating trans-acting components to couple the counters to other engineered genetic and biological circuit designs. In one such embodiment, the engineered genetic counter is coupled to a toggle switch. For example, in some embodiments, the engineered genetic counters can be coupled to quorum-sensing engineered biological circuits to create consensus-based counting systems.

Some non-limiting examples of output products for use in the engineered genetic counters described herein are fluorescent proteins, such as GFP, RFP and YFP, transcription factors, transcriptional repressors, or RNAs, such as riboswitches in prokaryotic and mammalian cells, as well as short-hairpin RNAs in mammalian cells (F. J. Isaacs, Nat Biotechnol 22, 841 (2004)). Further non-limiting examples of output gene sequences and output products for use in the SIMMs, as described herein, are provided in the foregoing section entitled "*Output Nucleic Acid Sequences and Output Products*" and in Tables 59-73, and include, but are not limited to, reporter proteins, transcriptional repressors, transcriptional activators, selection markers, enzymes, receptor proteins, ligand proteins, RNAs, riboswitches or short-hairpin RNAs. The choice of an output nucleic acid sequence for use in the engineered genetic counters described herein is dependent on a variety of factors, including whether an output nucleic acid product should be detected by the skilled artisan, or whether the output nucleic acid product is itself responsive to a particular set of inputs. For example, an engineered genetic counter can be designed so that the output nucleic acid product is an enzyme that is produced only when the counter receives a certain number of inputs, such as a toxin.

Uses of Engineered Genetic Counters

The engineered genetic counters described herein are useful for engineering complex behavioral phenotypes in cellular systems, such as prokaryotic, eukaryotic, or synthetic cells, or in non-cellular systems, including test tubes, viruses and phages. The novel engineered genetic counters described herein combine the power of nucleic acid-based engineering methods with systems biology approaches to elicit targeted responses in cellular and non-cellular systems, such as the ability to count specific inputs, and respond to such inputs.

In some of the aspects described herein, an engineered genetic counter is provided for use in cellular systems, such as bacteria, to count input signals received by the cellular system. In some aspects, engineered genetic counters are provided for use in non-cellular systems, such as viruses or phages, to count input signals received by the non-cellular system. In other aspects, methods are provided for counting at least 1 event in a cellular or non-cellular system comprising introducing an engineered genetic counter into a cellular or non-cellular system for use in counting events in the cellular or non-cellular system. In one aspect, a method is provided for counting at least 2 events in a cellular system comprising introducing an engineered genetic counter into a cellular system for use in counting events or inputs. In one embodiment, a method is provided for counting at least 1 . . . 3 . . . 26 . . . 45 . . . 76 . . . 96 . . . 121 . . . 150 events in a cellular or non-cellular system, the method comprising introducing an engineered genetic counter into a cellular or non-cellular system for use in counting events. Such an engineered counter can be a multiple inducer or single inducer counter.

The engineered genetic counters described herein can be used for a variety of applications and in many different types of methods, including, but not limited to, bioremediation, biosensing, and biomedical therapeutics. For example, in some embodiments, an engineered genetic counter is coupled to the cell cycle for use in a cellular system. In such embodiments, the output gene product can be a toxin or agent that causes cell death, such that the cellular system dies after a certain number of events is counted by the counter. Such embodiments of the engineered counters described herein are useful in biosensing and bioremediation applications. In other embodiments, the engineered genetic counters described herein can be modified to perform continuous inversion events. In one such embodiment, the engineered genetic counters can be introduced into a cellular system to provide transcriptional pulses. In addition, such embodiments where an engineered genetic counter is coupled to the cell cycle can be useful in biomedical or therapeutic applications, such as in therapies for cancer or other proliferative disorders. In some embodiments of the aspects described herein, an engineered genetic counter can be introduced into a mammalian cell to count the number of mutations that are required to produce a cancer cell. In other embodiments of the aspects described herein, the engineered genetic counters can be introduced into cellular systems, such as ex vivo or in vivo mammalian cells to maintain genetic memory of low frequency events. Such embodiments are useful for therapeutic applications or research purposes, such as the study of neural circuits.

The methods and uses of the engineered genetic counters described herein can involve in vivo, ex vivo, or in vitro systems. The term "in vivo" refers to assays or processes that occur in or within an organism, such as a multicellular animal. In some of the aspects described herein, a method or use can be said to occur "in vivo" when a unicellular organism, such as a bacteria, is used. The term "ex vivo" refers to methods and uses that are performed using a living cell with an intact membrane that is outside of the body of a multicellular animal or plant, e.g., explants, cultured cells, including primary cells and cell lines, transformed cell lines, and extracted tissue or cells, including blood cells, among others. The term "in vitro" refers to assays and methods that do not require the presence of a cell with an intact membrane, such as cellular extracts, and can refer to the introducing an engineered genetic counter in a non-cellular system, such as a media not comprising cells or cellular systems, such as cellular extracts.

A cell to be engineered for use with the engineered genetic counters described herein can be any cell or host cell. As defined herein, a "cell" or "cellular system" is the basic structural and functional unit of all known independently living organisms. It is the smallest unit of life that is classified as a living thing, and is often called the building block of life. Some organisms, such as most bacteria, are unicellular (consist of a single cell). Other organisms, such as humans, are multicellular. A "natural cell," as defined herein, refers to any prokaryotic or eukaryotic cell found naturally. A "prokaryotic cell" can comprise a cell envelope and a cytoplasmic region that contains the cell genome (DNA) and ribosomes and various sorts of inclusions.

In some embodiments, the cell is a eukaryotic cell. A eukaryotic cell comprises membrane-bound compartments in which specific metabolic activities take place, such as a nucleus. In other embodiments, the cell or cellular system is an artificial or synthetic cell. As defined herein, an "artificial cell" or a "synthetic cell" is a minimal cell formed from artificial parts that can do many things a natural cell can do, such as transcribe and translate proteins and generate ATP.

Host cells of use in the aspects of the invention upon transformation or transfection with the engineered genetic counters include any host cell that is capable of supporting the activation and expression of the engineered genetic counters. In some embodiments of the aspects described herein, the cells are bacterial cells. The term "bacteria" as used herein is intended to encompass all variants of bacteria, for example, prokaryotic organisms and cyanobacteria. Bacteria are small (typical linear dimensions of around 1 m), non-compartmentalized, with circular DNA and ribosomes of 70S. The term bacteria also includes bacteria subdivisions of Eubacteria and Archaebacteria. Eubacteria can be further subdivided on the basis of their staining using Gram stain, and both gram-positive and gram-negative eubacteria, which depends upon a difference in cell wall structure are also included, as well as classified based on gross morphology alone (into cocci, bacilli, etc.).

In some embodiments, the bacterial cells are gram-negative cells and in alternative embodiments, the bacterial cells are gram-positive cells. Non-limiting examples of species of bacterial cells useful for engineering with the engineered genetic counters of the invention include, without limitation, cells from *Escherichia coli, Bacillus subtilis, Salmonella typhimurium* and various species of *Pseudomonas, Streptomyces*, and *Staphylococcus*. Other examples of bacterial cells that can be genetically engineered for use with the biological circuit chemotactic converters of the invention include, but are not limited to, cells from *Yersinia* spp., *Escherichia* spp., *Klebsiella* spp., *Bordetella* spp., *Neisseria* spp., *Aeromonas* spp., *Franciesella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Salmonella* spp., *Vibrio* spp., *Bacillus* spp., and *Erysipelothrix* spp. In some embodiments, the bacterial cells are *E. coli* cells. Other examples of organisms from which cells may be transformed or transfected with the engineered genetic counters of the present invention include, but are not limited to the following: *Staphylococcus aureus, Bacillus subtilis, Clostridium butyricum, Brevibacterium lactofermentum, Streptococcus agalactiae, Lactococcus lactis, Leuconostoc lactis, Streptomyces, Actinobacillus actinobycetemcomitans, Bacteroides,* cyanobacteria, *Escherichia coli, Helobacter pylori, Selnomonas ruminatium, Shigella sonnei, Zymomonas mobilis, Mycoplasma mycoides,* or *Treponema denticola, Bacillus thuringiensis, Staphlococcus lugdunensis, Leuconostoc oenos, Corynebacterium xerosis, Lactobacillus* planta rum, *Streptococcus faecalis, Bacillus coagulans, Bacillus ceretus, Bacillus popillae, Synechocystis* strain PCC6803, *Bacillus liquefaciens, Pyrococcus abyssi, Selenomonas nominantium, Lactobacillus hilgardii, Streptococcus ferus, Lactobacillus pentosus, Bacteroides fragilis, Staphylococcus epidermidis, Staphylococcus epidermidis, Zymomonas mobilis, Streptomyces* phaechromogenes, *Streptomyces* ghanaenis, Halobacterium strain GRB, and *Halobaferax* sp. strain Aa2.2.

In alternative embodiments, the cells can be any cell, for example mammalian cells, plant cells and chimeric cells. In some embodiments, the cells can be from any organism or multi-cell organism. Examples of eukaryotic cells that can be useful in aspects of the invention include eukaryotic cells selected from, e.g., mammalian, insect, yeast, or plant cells. In some embodiments, the eukaryotic cells are from a vertebrate animal. The present invention contemplates the use of any such vertebrate cells for the engineered genetic counters, including, but not limited to, reproductive cells including sperm, ova and embryonic cells, and non-reproductive cells, such as kidney, lung, spleen, lymphoid, cardiac, gastric, intestinal, pancreatic, muscle, bone, neural, brain, and epithelial cells.

In other embodiments of the aspects described herein, engineered genetic counters can be introduced into a non-cellular system such as a virus or phage, by direct integration of the engineered genetic counter nucleic acid, for example, into the viral genome. A virus for use with the engineered genetic counters described herein can be a dsDNA virus (e.g. Adenoviruses, Herpesviruses, Poxviruses), a ssDNA viruses ((+)sense DNA) (e.g. Parvoviruses); a dsRNA virus (e.g. Reoviruses); a (+)ssRNA viruses ((+)sense RNA) (e.g. Picornaviruses, Togaviruses); (−)ssRNA virus ((−)sense RNA) (e.g. Orthomyxoviruses, Rhabdoviruses); a ssRNA-Reverse Transcriptase viruses ((+)sense RNA with DNA intermediate in life-cycle) (e.g. Retroviruses); or a dsDNA-Reverse Transcriptase virus (e.g. Hepadnaviruses).

Viruses can also include plant viruses and bacteriophages or phages. Examples of phage families that can be used with the engineered genetic counters described herein include, but are not limited to, Myoviridae (T4-like viruses; P1-like viruses; P2-like viruses; Mu-like viruses; SPO1-like viruses; φH-like viruses); Siphoviridaeλ-like viruses (T1-like viruses; T5-like viruses; c2-like viruses; L5-like viruses; ψM1-like viruses; φC31-like viruses; N15-like viruses); Podoviridae (T7-like viruses; φ29-like viruses; P22-like viruses; N4-like viruses); Tectiviridae (Tectivirus); Corticoviridae (Corticovirus); Lipothrixviridae (Alphalipothrixvirus, Betalipothrixvirus, Gammalipothrixvirus, Deltalipothrixvirus); Plasmaviridae (Plasmavirus);Rudiviridae (Rudivirus); Fuselloviridae (Fusellovirus); Inoviridae (Inovirus, Plectrovirus); Microviridae (Microvirus, Spiromicrovirus, Bdellomicrovirus, Chlamydiamicrovirus); Leviviridae (Levivirus, Allolevivirus) and Cystoviridae (Cystovirus). Such phages can be naturally occurring or engineered phages.

In some embodiments of the aspects described herein, the engineered genetic counters are introduced into a cellular or non-cellular system using a vector or plasmid for use in counting events in the system. As used herein, the term "vector" is used interchangeably with "plasmid" to refer to a nucleic acid molecule capable of transporting another nucleic acid to which it has been linked. Vectors capable of directing the expression of genes and/or nucleic acid sequence to which they are operatively linked are referred to herein as "expression vectors.". In general, expression vectors of utility in the methods and engineered genetic counters described herein are often in the form of "plasmids," which refer to circular double stranded DNA loops which, in their vector form are not bound to the chromosome.

Other expression vectors can be used in different embodiments of the invention, for example, but not limited to, plasmids, episomes, bacteriophages or viral vectors, and such vectors can integrate into the host's genome or replicate autonomously in the particular cellular system used. Other forms of expression vectors known by those skilled in the art which serve the equivalent functions can also be used. Expression vectors comprise expression vectors for stable or transient expression encoding the DNA. A vector can be either a self replicating extrachromosomal vector or a vector which integrates into a host genome. One type of vector is a genomic integrated vector, or "integrated vector", which can become integrated into the chromosomal DNA or RNA of a host cell, cellular system, or non-cellular system. In some embodiments, the nucleic acid sequence or sequences encoding the engineered genetic counter integrates into the chromosomal DNA or RNA of a host cell, cellular system, or non-cellular system along with components of the vector sequence. In other embodiments, the nucleic acid sequence encoding the engineered genetic counter directly integrates into chromosomal DNA or RNA of a host cell, cellular system, or non-cellular system, in the absence of any components of the vector by which it was introduced. In such embodiments, the nucleic acid sequence encoding the engineered genetic counter can be integrated using targeted insertions, such as knock-in technologies or homologous recombination techniques, or by non-targeted insertions, such as gene trapping techniques or non-homologous recombination. The number of copies of an engineered genetic counter that integrate into the chromosomal DNA or RNA of a cellular or non-cellular system can impact the fidelity of counting, and thus it is preferred that only one copy is integrated per cellular system. Accordingly, in some embodiments of the aspects described herein, only one copy of an engineered genetic counter is integrated in the chromosomal DNA or RNA of a cellular or non-cellular system. In some embodiments, the number of copies is less than 10, less than 9, less than 8, less than 7, less than 6, less than 6, less than 4, less than 3, or less than 2.

Another type of vector is an episomal vector, i.e., a nucleic acid capable of extra-chromosomal replication. Such plasmids or vectors can include plasmid sequences from bacteria, viruses or phages. Such vectors include chromosomal, episomal and virus-derived vectors e.g., vectors derived from bacterial plasmids, bacteriophages, yeast episomes, yeast chromosomal elements, and viruses, vectors derived from combinations thereof, such as those derived from plasmid and bacteriophage genetic elements, cosmids and phagemids. A vector can be a plasmid, bacteriophage, bacterial artificial chromosome (BAC) or yeast artificial chromosome (YAC). A vector can be a single or double-stranded DNA, RNA, or phage vector. In some embodiments, the engineered genetic counters are introduced into a cellular system using a BAC vector.

The vectors comprising the engineered genetic counters described herein may be "introduced" into cells as polynucleotides, preferably DNA, by techniques well-known in the art for introducing DNA and RNA into cells. The term "transduction" refers to any method whereby a nucleic acid sequence is introduced into a cell, e.g., by transfection, lipofection, electroporation, biolistics, passive uptake, lipid:nucleic acid complexes, viral vector transduction, injection, contacting with naked DNA, gene gun, and the like. The vectors, in the case of phage and viral vectors may also be introduced into cells as packaged or encapsidated virus by well-known techniques for infection and transduction. Viral vectors may be replication competent or replication defective. In the latter case, viral propagation generally occurs only in complementing host cells. In some embodiments, the engineered genetic counters are introduced into a cell using other mechanisms known to one of skill in the art, such as a liposome, microspheres, gene gun, fusion proteins, such as a fusion of an antibody moiety with a nucleic acid binding moiety, or other such delivery vehicle.

The engineered genetic counters or the vectors comprising the engineered genetic counters described herein can be introduced into a cell using any method known to one of skill in the art. The term "transformation" as used herein refers to the introduction of genetic material (e.g., a vector comprising an engineered genetic counter) comprising one or more modules or engineered genetic counters described herein into a cell, tissue or organism. Transformation of a cell may be stable or transient. The term "transient transformation" or "transiently transformed" refers to the introduction of one or more transgenes into a cell in the absence of integration of the transgene into the host cell's genome. Transient transformation may be detected by, for example, enzyme linked immunosorbent assay (ELISA), which detects the presence of a polypeptide encoded by one or more of the transgenes. Alternatively, transient transformation may be detected by detecting the activity of the protein encoded by the transgene. The term "transient transformant" refers to a cell which has transiently incorporated one or more transgenes.

In contrast, the term "stable transformation" or "stably transformed" refers to the introduction and integration of one or more transgenes into the genome of a cell or cellular system, preferably resulting in chromosomal integration and stable heritability through meiosis. Stable transformation of a cell may be detected by Southern blot hybridization of genomic DNA of the cell with nucleic acid sequences, which are capable of binding to one or more of the transgenes. Alternatively, stable transformation of a cell may also be detected by the polymerase chain reaction of genomic DNA of the cell to amplify transgene sequences. The term "stable transformant" refers to a cell or cellular, which has stably integrated one or more transgenes into the genomic DNA. Thus, a stable transformant is distinguished from a transient transformant in that, whereas genomic DNA from the stable transformant contains one or more transgenes, genomic DNA from the transient transformant does not contain a transgene. Transformation also includes introduction of genetic material into plant cells in the form of plant viral vectors involving epichromosomal replication and gene expression, which may exhibit variable properties with respect to meiotic stability. Transformed cells, tissues, or plants are understood to encompass not only the end product of a transformation process, but also transgenic progeny thereof.

Definitions

The terms "nucleic acids" and "nucleotides" refer to naturally occurring or synthetic or artificial nucleic acid or nucleotides. The terms "nucleic acids" and "nucleotides" comprise deoxyribonucleotides or ribonucleotides or any nucleotide analogue and polymers or hybrids thereof in either single- or doublestranded, sense or antisense form. As will also be appreciated by those in the art, many variants of a nucleic acid can be used for the same purpose as a given nucleic acid. Thus, a nucleic acid also encompasses substantially identical nucleic acids and complements thereof. Nucleotide analogues include nucleotides having modifications in the chemical structure of the base, sugar and/or phosphate, including, but not limited to, 5-position pyrimidine modifications, 8-position purine modifications, modifications at cytosine exocyclic amines, substitution of 5-bromo-uracil, and the like; and 2'-position sugar modifications, including but not limited to, sugar-modified ribonucleotides in which the 2'-OH is replaced by a group selected from H, OR, R, halo, SH, SR, NH2, NHR, NR2, or CN. shRNAs also can comprise non-natural elements such as non-natural bases, e.g., ionosin and xanthine, normatural sugars, e.g., 2'-methoxy ribose, or non-natural phosphodiester linkages, e.g., methylphosphonates, phosphorothioates and peptides.

The term "nucleic acid sequence" or "oligonucleotide" or "polynucleotide" are used interchangeably herein and refers to at least two nucleotides covalently linked together. The term "nucleic acid sequence" is also used inter-changeably herein with "gene", "cDNA", and "mRNA". As will be appreciated by those in the art, the depiction of a single nucleic acid sequence also defines the sequence of the complementary nucleic acid sequence. Thus, a nucleic acid sequence also encompasses the complementary strand of a depicted single strand. Unless otherwise indicated, a particular nucleic acid sequence also implicitly encompasses conservatively modified variants thereof (e.g., degenerate codon substitutions) and complementary sequences, as well as the sequence explicitly indicated. As will also be appreciated by those in the art, a single nucleic acid sequence provides a probe that can hybridize to the target sequence under stringent hybridization conditions. Thus, a nucleic acid sequence also encompasses a probe that hybridizes under stringent hybridization conditions. The term "nucleic acid sequence" refers to a single or double-stranded polymer of deoxyribonucleotide or ribonucleotide bases read from the 5'- to the 3'-end. It includes chromosomal DNA, self-replicating plasmids, infectious polymers of DNA or RNA and DNA or RNA that performs a primarily structural role. "Nucleic acid sequence" also refers to a consecutive list of abbreviations, letters, characters or words, which represent nucleotides. Nucleic acid sequences can be single stranded or double stranded, or can contain portions of both double stranded and single stranded sequence. The nucleic acid sequence can be DNA, both genomic and cDNA, RNA, or a hybrid, where the nucleic acid sequence can contain combinations of deoxyribo- and ribonucleotides, and combinations of bases including uracil, adenine, thymine, cytosine, guanine, inosine, xanthine hypoxanthine, isocytosine and isoguanine. Nucleic acid sequences can be obtained by chemical synthesis methods or by recombinant methods. A nucleic acid sequence will generally contain phosphodiester bonds, although nucleic acid analogs can be included that can have at least one different linkage, e.g., phosphoramidate, phosphorothioate, phosphorodithioate, or O-methylphosphoroamidite linkages and peptide nucleic acid backbones and linkages in the nucleic acid sequence. Other analog nucleic acids include those with positive backbones; non-ionic backbones, and non-ribose backbones, including those described in U.S. Pat. Nos. 5,235,033 and 5,034,506, which are incorporated by reference. Nucleic acid sequences containing one or more non-naturally occurring or modified nucleotides are also included within one definition of nucleic acid sequences. The modified nucleotide analog can be located for example at the 5'-end and/or the 3'-end of the nucleic acid sequence. Representative examples of nucleotide analogs can be selected from sugar- or backbone-modified ribonucleotides. It should be noted, however, that also nucleobase-modified ribonucleotides, i.e. ribonucleotides, containing a non naturally occurring nucleobase instead of a naturally occurring nucleobase such as uridines or cytidines modified at the 5-position, e.g. 5-(2-amino)propyl uridine, 5-bromo uridine; adenosines and guanosines modified at the 8-position, e.g. 8-bromo guanosine; deaza nucleotides, e.g. 7 deaza-adenosine; O- and N-alkylated nucleotides, e.g. N6-methyl adenosine are suitable. The 2' OH— group can be replaced by a group selected from H. OR, R. halo, SH, SR, NH2, NHR, NR2 or CN, wherein R is C-C6 alkyl, alkenyl or alkynyl and halo is F, Cl, Br or I. Modifications of the ribose-phosphate backbone can be done for a variety of reasons, e.g., to increase the stability and half-life of such molecules in physiological environments or as probes on a biochip. Mixtures of naturally occurring nucleic acids and analogs can be used; alternatively, mixtures of different nucleic acid analogs, and mixtures of naturally occurring nucleic acids and analogs can be used. Nucleic acid sequences include but are not limited to, nucleic acid sequence encoding proteins, for example that act as transcriptional repressors, antisense molecules, ribozymes, small inhibitory nucleic acid sequences, for example but not limited to RNAi, shRNAi, siRNA, micro RNAi (mRNAi), antisense oligonucleotides etc.

The term "oligonucleotide" as used herein refers to an oligomer or polymer of ribonucleic acid (RNA) or deoxyribonucleic acid (DNA) or mimetics thereof, as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases. An oligonucleotide preferably includes two or more nucleomonomers covalently coupled to each other by linkages (e.g., phosphodiesters) or substitute linkages.

In its broadest sense, the term "substantially complementary", when used herein with respect to a nucleotide sequence in relation to a reference or target nucleotide sequence, means a nucleotide sequence having a percentage of identity between the substantially complementary nucleotide sequence and the exact complementary sequence of said reference or target nucleotide sequence of at least 60%, at least 70%, at least 80% or 85%, at least 90%, at least 93%, at least 95% or 96%, at least 97% or 98%, at least 99% or 100% (the later being equivalent to the term "identical" in this context). For example, identity is assessed over a length of at least 10 nucleotides, or at least 11, 12, 13, 14, 15, 16, 17, 18, 19, 20, 21, 22 or up to 50 nucleotides of the entire length of the nucleic acid sequence to said reference sequence (if not specified otherwise below). Sequence comparisons are carried out using default GAP analysis with the University of Wisconsin GCG, SEQWEB application of GAP, based on the algorithm of Needleman and Wunsch (Needleman and Wunsch (1970) J Mol. Biol. 48: 443-453; as defined above). A nucleotide sequence "substantially complementary" to a reference nucleotide sequence hybridizes to the reference nucleotide sequence under low stringency conditions, preferably medium stringency conditions, most preferably high stringency conditions (as defined above).

In its broadest sense, the term "substantially identical", when used herein with respect to a nucleotide sequence, means a nucleotide sequence corresponding to a reference or target nucleotide sequence, wherein the percentage of identity between the substantially identical nucleotide sequence and the reference or target nucleotide sequence is at least 60%, at least 70%, at least 80% or 85%, at least 90%, at least 93%, at least 95% or 96%, at least 97% or 98%, at least 99% or 100% (the later being equivalent to the term "identical" in this context). For example, identity is assessed over a length of 10-22 nucleotides, such as at least 10, 11, 12, 13, 14, 15, 16, 17, 18, 19, 20, 21, 22 or up to 50 nucleotides of a nucleic acid sequence to said reference sequence (if not specified otherwise below). Sequence comparisons are carried out using default GAP analysis with the University of Wisconsin GCG, SEQWEB application of GAP, based on the algorithm of Needleman and Wunsch (Needleman and Wunsch (1970) J Mol. Biol. 48: 443-453; as defined above). A nucleotide sequence that is "substantially identical" to a reference nucleotide sequence hybridizes to the exact complementary sequence of the reference nucleotide sequence (i.e. its corresponding strand in a double-stranded molecule) under low stringency conditions, preferably medium stringency conditions, most preferably high stringency conditions (as defined above). Homologues of a specific nucleotide sequence include nucleotide sequences that encode an amino acid sequence that is at least 24% identical, at least 35% identical, at least 50% identical, at least 65% identical to the reference amino acid sequence, as measured using the parameters described above, wherein the amino acid sequence encoded by the homolog has the same biological activity as the protein encoded by the specific nucleotide. The term "substantially non-identical" refers to a nucleotide sequence that does not hybridize to the nucleic acid sequence under stringent conditions.

As used herein, the term "gene" refers to a nucleic acid sequence comprising an open reading frame encoding a polypeptide, including both exon and (optionally) intron sequences. A "gene" refers to coding sequence of a gene product, as well as non-coding regions of the gene product, including 5'UTR and 3'UTR regions, introns and the promoter of the gene product. These definitions generally refer to a single-stranded molecule, but in specific embodiments will also encompass an additional strand that is partially, substantially or fully complementary to the single-stranded molecule. Thus, a nucleic acid sequence can encompass a double-stranded molecule or a double-stranded molecule that comprises one or more complementary strand(s) or "complement(s)" of a particular sequence comprising a molecule. As used herein, a single stranded nucleic acid can be denoted by the prefix "ss", a double stranded nucleic acid by the prefix "ds", and a triple stranded nucleic acid by the prefix "ts."

The term "operable linkage" or "operably linked" are used interchangeably herein, are to be understood as meaning, for example, the sequential arrangement of a regulatory element (e.g. a promoter) with a nucleic acid sequence to be expressed and, if appropriate, further regulatory elements (such as, e.g., a terminator) in such a way that each of the regulatory elements can fulfill its intended function to allow, modify, facilitate or otherwise influence expression of the linked nucleic acid sequence. The expression may result depending on the arrangement of the nucleic acid sequences in relation to sense or antisense RNA. To this end, direct linkage in the chemical sense is not necessarily required. Genetic control sequences such as, for example, enhancer sequences, can also exert their function on the target sequence from positions which are further away, or indeed from other DNA molecules. In some embodiments, arrangements are those in which the nucleic acid sequence to be expressed recombinantly is positioned behind the sequence acting as promoter, so that the two sequences are linked covalently to each other. The distance between the promoter sequence and the nucleic acid sequence to be expressed recombinantly can be any distance, and in some embodiments is less than 200 base pairs, especially less than 100 base pairs, less than 50 base pairs. In some embodiments, the nucleic acid sequence to be transcribed is located behind the promoter in such a way that the transcription start is identical with the desired beginning of the chimeric RNA of the invention. Operable linkage, and an expression construct, can be generated by means of customary recombination and cloning techniques as described (e.g., in Maniatis T, Fritsch E F and Sambrook J (1989) Molecular Cloning: A Laboratory Manual, 2nd Ed., Cold Spring Harbor Laboratory, Cold Spring Harbor (NY); Silhavy et al. (1984) Experiments with Gene Fusions, Cold Spring Harbor Laboratory, Cold Spring Harbor (NY); Ausubel et al. (1987) Current Protocols in Molecular Biology, Greene Publishing Assoc and Wiley Interscience; Gelvin et al. (Eds) (1990) Plant Molecular Biology Manual; Kluwer Academic Publisher, Dordrecht, The Netherlands). However, further sequences may also be positioned between the two sequences. The insertion of sequences may also lead to the expression of fusion proteins, or serves as ribosome binding sites. In some embodiments, the expression construct, consisting of a linkage of promoter and nucleic acid sequence to be expressed, can exist in a vector integrated form and be inserted into a plant genome, for example by transformation.

The terms "promoter," "promoter element," or "promoter sequence" are equivalents and as used herein, refers to a DNA sequence which when operatively linked to a nucleotide sequence of interest is capable of controlling the transcription of the nucleotide sequence of interest into mRNA. A promoter is typically, though not necessarily, located 5' (i.e., upstream) of a nucleotide sequence of interest (e.g., proximal to the transcriptional start site of a structural gene) whose transcription into mRNA it controls, and provides a site for specific binding by RNA polymerase and other transcription factors for initiation of transcription. A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g. a genetically engineered coding sequence or an allele from a different ecotype or variety). Suitable promoters can be derived from genes of the host cells where expression should occur or from pathogens for the host cells (e.g., tissue promoters or pathogens like viruses).

If a promoter is an "inducible promoter", as defined herein, then the rate of transcription is modified in response to an inducing agent or inducer. In contrast, the rate of transcription is not regulated by an inducer if the promoter is a constitutive promoter. The term "constitutive" when made in reference to a promoter means that the promoter is capable of directing transcription of an operably linked nucleic acid sequence in the absence of a stimulus (e.g., heat shock, chemicals, agents, light, etc.). Typically, constitutive promoters are capable of directing expression of a nucleic acid sequence in substantially any cell and any tissue. In contrast, the term "regulateable" or "inducible" promoter referred to herein is one which is capable of directing a level of transcription of an operably linked nucleic acid sequence in the presence of a stimulus (e.g., heat shock, chemicals, light, agent etc.) which is different from the level of transcription of the operably linked nucleic acid sequence in the absence of the stimulus.

A promoter may be regulated in a tissue-specific or tissue preferred manner such that it is only active in transcribing the associated coding region in a specific tissue type(s). The term "tissue specific" as it applies to a promoter refers to a promoter that is capable of directing selective expression of a nucleotide sequence of interest to a specific type of tissue (e.g., liver) in the relative absence of expression of the same nucleotide sequence of interest in a different type of tissue (e.g., kidney). Tissue specificity of a promoter may be evaluated by, for example, operably linking a reporter gene to the promoter sequence to generate a reporter construct, introducing the reporter construct into the genome of an organism, e.g. an animal model such that the reporter construct is integrated into every tissue of the resulting transgenic animal, and detecting the expression of the reporter gene (e.g., detecting mRNA, protein, or the activity of a protein encoded by the reporter gene) in different tissues of the transgenic animal. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter, which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., GUS activity staining or immunohistochemical staining. The term "minimal promoter" as used herein refers to the minimal nucleic acid sequence comprising a promoter element while also maintaining a functional promoter. A minimal promoter may comprise an inducible, constitutive or tissue-specific promoter.

The term "expression" as used herein refers to the biosynthesis of a gene product, preferably to the transcription and/or translation of a nucleotide sequence, for example an endogenous gene or a heterologous gene, in a cell. For example, in the case of a heterologous nucleic acid sequence, expression involves transcription of the heterologous nucleic acid sequence into mRNA and, optionally, the subsequent translation of mRNA into one or more polypeptides. Expression also refers to biosynthesis of an RNAi molecule, which refers to expression and transcription of an RNAi agent such as siRNA, shRNA, and antisense DNA but does not require translation to polypeptide sequences. The term "expression construct" and "nucleic acid construct" as used herein are synonyms and refer to a nucleic acid sequence capable of directing the expression of a particular nucleotide sequence, such as the heterologous target gene sequence in an appropriate host cell (e.g., a prokaryotic cell, eukaryotic cell, or mammalian cell). If translation of the desired heterologous target gene is required, it also typically comprises sequences required for proper translation of the nucleotide sequence. The coding region may code for a protein of interest but may also code for a functional RNA of interest, for example antisense RNA, dsRNA, or a nontranslated RNA, in the sense or antisense direction. The nucleic acid construct as disclosed herein can be chimeric, meaning that at least one of its components is heterologous with respect to at least one of its other components.

The term "leakiness" or "leaky" as used in reference to "promoter leakiness" refers to some level of expression of the nucleic acid sequence which is operatively linked to the promoter, even when the promoter is not intended to result in expression of the nucleic acid sequence (i.e. when the promoter is in the "off" state, a background level of expression of the nucleic acid sequence which is operatively linked to such promoter exists). In one illustrative example using inducible promoters, for example a Tet-on promoter, a leaky promoter is where some level of the nucleic acid sequence expression (which is operatively linked to the Tet-on promoter) still occurs in the absence of the inducer agent, tetracycline. Typically, most inducible promoters and tissue-specific promoters have approximately 10%-30% or 10-20% unintended or background nucleic acid sequence expression when the promoter is not active, for example, the background of leakiness of nucleic acid sequence expression is about 10%-20% or about 10-30%. As an illustrative example using a tissue-specific promoter, a "leaky promoter" is one in which expression of the nucleic acid sequence occurs in tissue where a tissue-specific promoter is not active, i.e. expression occurs in a non-specific tissue. Stated in another way using a kidney-specific promoter as an example; if at least some level of the nucleic acid sequence expression occurs in at least one tissue other than the kidney, where the nucleic acid sequence is operably linked to a kidney specific promoter, the kidney specific promoter would be considered a leaky promoter The term "enhancer" refers to a cis-acting regulatory sequence involved in the transcriptional activation of a nucleic acid sequence. An enhancer can function in either orientation and can be upstream or downstream of the promoter. As used herein, the term "gene product(s)" is used to refer to include RNA transcribed from a gene, or a polypeptide encoded by a gene or translated from RNA. A protein and/or peptide or fragment thereof can be any protein of interest, for example, but not limited to; mutated proteins; therapeutic proteins; truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, tribodies, humanized proteins, humanized antibodies, chimeric antibodies, modified proteins and fragments thereof.

The term "nucleic acid construct" as used herein refers to a nucleic acid at least partly created by recombinant methods. The term "DNA construct" refers to a polynucleotide construct consisting of deoxyribonucleotides. The construct can be single or double stranded. The construct can be circular or linear. A person of ordinary skill in the art is familiar with a variety of ways to obtain and generate a DNA construct. Constructs can be prepared by means of customary recombination and cloning techniques as are described, for example, in Maniatis T, Fritsch EF and Sambrook J (1989) Molecular Cloning: A Laboratory Manual, 2nd Ed., Cold Spring Harbor Laboratory, Cold Spring Harbor (NY); Silhavy et al. (1984) Experiments with Gene Fusions, Cold Spring Harbor Laboratory, Cold Spring Harbor (NY); Ausubel et al. (1987) Current Protocols in Molecular Biology, Greene Publishing Assoc and Wiley Interscience; Gelvin et al. (Eds) (1990) Plant Molecular Biology Manual; Kluwer Academic Publisher, Dordrecht, The Netherlands.

The terms "polypeptide", "peptide", "oligopeptide", "polypeptide", "gene product", "expression product" and "protein" are used interchangeably herein to refer to a polymer or oligomer of consecutive amino acid residues.

As used herein, the term "comprising" means that other elements can also be present in addition to the defined elements presented. The use of "comprising" indicates inclusion rather than limitation. Accordingly, the terms "comprising" means "including principally, but not necessary solely". Furthermore, variation of the word "comprising", such as "comprise" and "comprises", have correspondingly the same meanings. The term "consisting essentially of" means "including principally, but not necessary solely at least one", and as such, is intended to mean a "selection of one or more, and in any combination". Stated another way, the term "consisting essentially of" means that an element can be added, subtracted or substituted without materially affecting the novel characteristics of the invention. This applies equally to steps within a described method as well as compositions and components therein. In other embodiments, the inventions, compositions, methods, and respective components thereof, described herein are intended to be exclusive of any element not deemed an essential element to the component, composition or method ("consisting of"). For example, an engineered genetic counter that comprises a sequence encoding a recombinase and a recombinase recognition sequence encompasses both the recombinase and a recombinase recognition sequence of a larger sequence. By way of further example, a composition that comprises elements A and B also encompasses a composition consisting of A, B and C.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, publications, and websites identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

The present invention can be defined in any of the following numbered paragraphs:

1. A single invertase memory module (SIMM) comprising a forward recombinase recognition site ($RRS_{for}$), an inverted promoter sequence ($iP_{inv}$), a recombinase sequence (RC) and a reverse recombinase recognition site ($RRS_{rev}$), [$RRS_{for}$-$iP_{inv}$-RC-$RRS_{rev}$], where the recombinase encoded by the recombinase sequence is specific for the forward and reverse recombination recognition sites.
2. The single invertase memory module of paragraph 1, further comprising a ribosome binding site (RBS).
3. The single invertase memory module of any of the preceding paragraphs, further comprising a transcriptional terminator sequence (T).
4. The single invertase memory module of any of the preceding paragraphs, further comprising a protein degradation tag sequence (D).

5. The single invertase memory module of any of the preceding paragraphs, further comprising a ribosome binding site (RBS) and a transcriptional terminator sequence (T).
6. The single invertase memory module of any of the preceding paragraphs, further comprising a ribosome binding site (RBS) and a protein degradation tag sequence (D).
7. The single invertase memory module of any of the preceding paragraphs, further comprising a protein degradation tag sequence (D) and a transcriptional terminator sequence (T).
8. The single invertase memory module of any of the preceding paragraphs, further comprising a ribosome binding site (RBS), a protein degradation tag sequence (D), and a transcriptional terminator sequence (T).
9. The single invertase memory module of any of the preceding paragraphs, further comprising an output nucleic acid sequence encoding an output product.
10. The single invertase memory module of any of the preceding paragraphs, wherein the output product is a reporter protein, a transcriptional repressor, a transcriptional activator, a selection marker, an enzyme, a receptor protein, a ligand protein, an RNA, a riboswitch or a short-hairpin RNA.
11. A single-inducer engineered genetic counter comprising an inducible promoter sequence ($iP_A$), at least one single invertase memory module (SIMM), and an output nucleic acid sequence encoding an output product (OP), where the SIMM comprises a forward recombinase recognition sequence ($RRS_{for}$), an inverted inducible promoter sequence ($iP_{1,inv}$), a ribosome binding site (RBS), a recombinase gene sequence (RC), a degradation tag sequence (D), a transcriptional terminator sequence (T), and a reverse recombinase recognition sequence ($RRS_{rev}$), such that the single-inducer engineered genetic counter comprises the following components:
$iP_A$-[$RRS_{1,for}$-$iP_{1,inv}$-RBS-$RC_1$-D-T-$RRS_{1,rev}$]$_n$-OP,
wherein $iP_A$ and the $iP_1$ of each SIMM are responsive to the same inducer, wherein the recombinase encoded by each at least one SIMM is specific for the forward and reverse recombinase recognition site of that SIMM, and wherein n is an integer value $\geq 1$.
12. The single-inducer engineered genetic counter of paragraph 11, wherein the recombinase encoded by each at least one SIMM is a different recombinase from each other SIMM.
13. The single-inducer engineered genetic counter of paragraph 11 or 12, further comprising an inverted promoter sequence downstream of the reverse recombination recognition site of at least one SIMM.
14. The single-inducer engineered genetic counter of any of paragraphs 11-13, further comprising an output nucleic acid sequence encoding an output product downstream of the recombinase sequence of at least one SIMM.
15. The single-inducer engineered genetic counter of any of paragraphs 11-14, further comprising an inverted output nucleic acid sequence encoding an output product downstream of the transcriptional terminator sequence of at least one SIMM.
16. A multiple-inducer engineered genetic counter comprising an inducible promoter sequence ($iP_A$), at least one single invertase memory module (SIMM), and an output nucleic sequence encoding an output product (OP), where each at least one SIMM comprises a forward recombinase recognition sequence ($RRS_{for}$), an inverted inducible promoter sequence ($iP_{inv}$), a ribosome binding site (RBS), a recombinase gene sequence (RC), a degradation tag sequence (D), a transcriptional terminator sequence (T), and a reverse recombinase recognition sequence ($RRS_{rev}$), such that the multiple-inducer engineered genetic counter comprises the following components:
$iP_A$-[$RRS_{1,for}$-$iP_{inv}$-RBS-$RC_1$-D-T-$RRS_{1,rev}$]$_n$-OP,
wherein $iP_A$ and the $iP_1$ of at least one SIMM are responsive to different inducers from each other, wherein the recombinase encoded by each at least one SIMM is specific for the forward and reverse recombinase recognition site of that SIMM, and wherein n is an integer value $\geq 1$.
17. The multiple-inducer engineered genetic counter of paragraph 16, wherein the recombinase encoded by each at least one SIMM is a different recombinase from each other SIMM.
18. The multiple-inducer engineered genetic counter of paragraphs 16 or 17, further comprising an inverted promoter sequence downstream of the reverse recombination recognition site of at least one SIMM.
19. The multiple-inducer engineered genetic counter of any of paragraphs 16-18, further comprising an output nucleic acid sequence encoding an output product downstream of the recombinase sequence of at least one SIMM.
20. The multiple-inducer engineered genetic counter of paragraphs 16-19, further comprising an inverted output nucleic acid sequence encoding an output product downstream of the transcriptional terminator sequence of at least one SIMM.
21. The engineered genetic counter of any of paragraphs 11-20, wherein the recombinase sequence and the forward and reverse recombinase recognition sites of at least one SIMM comprise a Cre recombinase sequence of SEQ ID NO: 1002, and LoxP recombinase recognition sites comprising the sequences of SEQ ID NO:1 and SEQ ID NO:2.
22. The engineered genetic counter of any of paragraphs 11-21, wherein the recombinase sequence and the forward and reverse recombinase recognition sites of one SIMM comprise a Flp recombinase sequence of SEQ ID NO:3 or SEQ ID NO:1002 and FRT recombinase recognition sites comprising the sequence of SEQ ID NO: 4.
23. The engineered genetic counter of any of paragraphs 11-22, wherein the recombinase sequence and the forward and reverse recombinase recognition sites of one SIMM comprise a Flp recombinase sequence of SEQ ID NO:3 or SEQ ID NO:1002 and FRT recombinase recognition sites comprising the sequence of SEQ ID NO: 5.
24. The engineered genetic counter of any of paragraphs 11-23, wherein the recombinase sequence and the forward and reverse recombinase recognition sites of one SIMM comprise a FimB recombinase of SEQ ID NO: 9 and recombinase recognition sites comprising the sequence of SEQ ID NO: 7 and SEQ ID NO: 8.
25. The engineered genetic counter of any of paragraphs 11-24, wherein the recombinase sequence and the forward and reverse recombinase recognition sites of one SIMM comprise a FimE recombinase of SEQ ID NO: 10 and recombinase recognition sites comprising the sequence of SEQ ID NO: 7 and SEQ ID NO: 8 respectively.

26. The engineered genetic counter of any of paragraphs 11-25, wherein the recombinase sequence of one SIMM comprises a Cre recombinase of SEQ ID NO: 1002, and the LoxP recombinase recognition sites of that SIMM comprise a sequence selected from the group consisting of SEQ ID NO: 13, SEQ ID NO: 14, SEQ ID NO: 15, SEQ ID NO: 16, and SEQ ID NO: 17.

27. The engineered genetic counter of any of paragraphs 11-26, wherein at least one inducible promoter comprises a sequence selected from the group consisting of a $P_{LtetO-1}$ promoter of SEQ ID NO: 33, a $P_{BAD}$ promoter of SEQ ID NO: 34, a $P_{Trc-2}$ promoter of SEQ ID NO: 35, a $P_{LlacO-1}$ promoter of SEQ ID NO: 36, a $P_{A1LacO-1}$ promoter of SEQ ID NO: 37, a $P_{lac/ara-1}$ promoter of SEQ ID NO: 38, and a $P_{Lslcon}$ promoter of SEQ ID NO: 39.

28. The engineered genetic counter of any of paragraphs 11-27, wherein at least one inducible promoter comprises a sequence selected from the group consisting of SEQ ID NO: 320-SEQ ID NO: 842.

29. The engineered genetic counter of any of paragraphs 11-28, wherein the output product encoded by the output nucleic acid sequence is a reporter protein, a transcriptional repressor, a transcriptional activator, a selection marker, an enzyme, a receptor protein, a ligand protein, an RNA, a riboswitch or a short-hairpin RNA.

30. The engineered genetic counter of any of paragraphs 11-29, further comprising an RBS sequence upstream of the output nucleic acid sequence.

31. The engineered genetic counter of any of paragraphs 11-30, wherein the RBS sequence of at least one SIMM comprises a sequence that is selected from the group consisting of SEQ ID NO: 843-SEQ ID NO: 850.

32. The engineered genetic counter of any of paragraph 11-31, wherein the RBS sequence of at least one SIMM comprises a sequence that is selected from SEQ ID NO: 851-SEQ ID NO: 994.

33. The engineered genetic counter of any of paragraphs 11-32, wherein the protein degradation tag sequence of at least one SIMM comprises a sequence that is selected from the group consisting of sequences that encode for the peptides of SEQ ID NO: 995-SEQ ID NO: 1001.

34. The engineered genetic counters of any of paragraphs 11-34, wherein n is an integer value selected from the group consisting of 1, 2, 3, 4, 5, 6, 7, 8, 9, 10, 11, 12, 13, 14, 15, 16, 17, 18, 19, and 20.

35. A single-inducer engineered genetic counter comprising an inducible promoter sequence ($iP_A$), one single invertase memory module (SIMM), and an output nucleic acid sequence encoding an output product (OP), where the SIMM comprises a forward recombinase recognition sequence ($RRS_{for}$), an inverted inducible promoter sequence ($iP_{1,inv}$), a ribosome binding site (RBS), a recombinase gene sequence (RC), a degradation tag sequence (D), a transcriptional terminator sequence (T), and a reverse recombinase recognition sequence ($RRS_{rev}$), such that the single-inducer engineered genetic counter comprises the following components:
$iP_A$-[$RRS_{1,for}$-$iP_{1,inv}$-RBS-$RC_1$-D-T-$RRS_{1,rev}$]-OP,
wherein $iP_A$ and $iP_1$ are responsive to the same inducer, and wherein the recombinase encoded by the SIMM is specific for the forward and reverse recombinase recognition site of the SIMM.

36. The single-inducer engineered genetic counter of paragraph 35, wherein the inducible promoter sequences $iP_A$ and $iP_1$ are responsive to arabinose.

37. The single-inducer engineered genetic counter of paragraph 35 or 36, wherein the inducible promoter sequences $iP_A$ and $iP_1$ are $P_{BAD}$ promoter sequences.

38. The single-inducer engineered genetic counter of any of paragraphs 35-37, wherein the recombinase gene sequence ($RC_1$) encodes a Flp recombinase and the forward ($RRS_{for}$) and reverse ($RRS_{rev}$) recombinase recognition sites are $FRT_F$ and $FRT_R$ sites.

39. The single-inducer engineered genetic counter of any of paragraphs 35-38, wherein the output nucleic acid sequence encodes green fluorescent protein.

40. A single-inducer engineered genetic counter comprising an inducible promoter sequence ($iP_A$), two single invertase memory modules (SIMMs), and an output nucleic acid sequence encoding an output product (OP), where each SIMM comprises a forward recombinase recognition sequence ($RRS_{for}$), an inverted inducible promoter sequence ($iP_{inv}$), a ribosome binding site (RBS), a recombinase gene sequence (RC), a degradation tag sequence (D), a transcriptional terminator sequence (T), and a reverse recombinase recognition sequence ($RRS_{rev}$), such that the single-inducer engineered genetic counter comprises the following components:
$iP_A$-[$RRS_{1,for}$-$iP_{1,inv}$-RBS-$RC_1$-D-T-$RRS_{1,rev}$]-[$RRS_{2,for}$-$iP_{1,inv}$-RBS-$RC_2$-D-T-$RRS_{2,rev}$]-OP,
wherein $iP_A$ and $iP_1$ are responsive to the same inducer, and wherein the recombinase encoded by each SIMM is specific for the forward and reverse recombinase recognition site of that SIMM.

41. The single-inducer engineered genetic counter of paragraph 40, wherein the inducible promoter sequences $iP_A$ and $iP_1$ are responsive to arabinose.

42. The single-inducer engineered genetic counter of paragraph 40 or 41, wherein the inducible promoter sequences $iP_A$ and $iP_1$ are $P_{BAD}$ promoter sequences.

43. The single-inducer engineered genetic counter of any of paragraphs 40-42, wherein the recombinase gene sequence of the first SIMM ($RC_1$) encodes a Flp recombinase and the forward ($RRS_{1,for}$) and reverse ($RRS_{1,rev}$) recombinase recognition sites of the first SIMM are $FRT_F$ and $FRT_R$ sites.

44. The single-inducer engineered genetic counter of any of paragraphs 40-43, wherein the recombinase gene sequence of the second SIMM ($RC_2$) encodes a Cre recombinase and the forward ($RRS_{2,for}$) and reverse ($RRS_{2,rev}$) recombinase recognition sites of the second SIMM are $loxP_F$ and $loxP_R$ sites.

45. The single-inducer engineered genetic counter of any of paragraphs 40-44, wherein the output nucleic acid sequence encodes green fluorescent protein.

46. A multiple-inducer engineered genetic counter comprising an inducible promoter sequence ($iP_A$), one single invertase memory module (SIMM), and an output nucleic sequence encoding an output product (OP), where the SIMM comprises a forward recombinase recognition sequence ($RRS_{for}$), an inverted inducible promoter sequence ($iP_{1,inv}$), a ribosome binding site (RBS), a recombinase gene sequence (RC), a degradation tag sequence (D), a transcriptional terminator sequence (T), and a reverse recombinase recognition sequence ($RRS_{rev}$), such that the multiple-inducer engineered genetic counter comprises the following components:
$iP_A$-[$RRS_{1,for}$-$iP_{1,inv}$-RBS-$RC_1$-D-T-$RRS_{1,rev}$]-OP,
wherein $iP_A$ and the $iP_1$ of the SIMM are responsive to different inducers from each other, and wherein the recombinase encoded by the SIMM is specific for the forward and reverse recombinase recognition site of the SIMM.

47. The multiple-inducer engineered genetic counter of paragraph 46, wherein the inducible promoter sequence $iP_A$ is responsive to anhydrotetracycline.

48. The multiple-inducer engineered genetic counter of paragraph 46 or 47, wherein the inducible promoter sequence $iP_1$ is responsive to arabinose.

49. The multiple-inducer engineered genetic counter of any of paragraphs 46-48, wherein the inducible promoter sequence $iP_A$ is a $P_{LtetO-1}$ promoter.

50. The multiple-inducer engineered genetic counter of any of paragraphs 46-49, wherein the inducible promoter sequence $iP_1$ is a $P_{BAD}$ promoter.

51. The multiple-inducer engineered genetic counter of any of paragraphs 46-50, wherein the recombinase gene sequence of the SIMM ($RC_1$) encodes a Flp recombinase and the forward ($RRS_{1,for}$) and reverse ($RRS_{1,rev}$) recombinase recognition sites of the SIMM are $FRT_F$ and $FRT_R$ sites.

52. The multiple-inducer engineered genetic counter of any of paragraphs 46-51, wherein the output nucleic acid sequence encodes green fluorescent protein.

53. A multiple-inducer engineered genetic counter comprising an inducible promoter sequence ($iP_A$), two single invertase memory modules (SIMM), and an output nucleic sequence encoding an output product (OP), where each SIMM comprises a forward recombinase recognition sequence ($RRS_{for}$), an inverted inducible promoter sequence ($iP_{inv}$), a ribosome binding site (RBS), a recombinase gene sequence (RC), a degradation tag sequence (D), a transcriptional terminator sequence (T), and a reverse recombinase recognition sequence ($RRS_{rev}$), such that the multiple-inducer engineered genetic counter comprises the following components:

$iP_A$-[$RRS_{1,for}$-$iP_{1,inv}$-RBS-$RC_1$-D-T-$RRS_{1,rev}$]-[$RRS_{2,for}$-$iP_{2,inv}$-RBS-$RC_2$-D-T-$RRS_{2,rev}$] OP, wherein $iP_A$ and the iP of at least one SIMM are responsive to different inducers from each other, and wherein the recombinase encoded by each SIMM is specific for the forward and reverse recombinase recognition site of that SIMM.

54. The multiple-inducer engineered genetic counter of paragraph 53, wherein the inducible promoter sequence $iP_A$ is responsive to anhydrotetracycline.

55. The multiple-inducer engineered genetic counter of paragraph 53 or 54, wherein the inducible promoter sequence $iP_1$ is responsive to arabinose.

56. The multiple-inducer engineered genetic counter of any of paragraphs 53-55, wherein the inducible promoter sequence $iP_2$ is responsive to IPTG (isopropyl-β-D thiogalactoside).

57. The multiple-inducer engineered genetic counter of any of paragraphs 53-56, wherein the inducible promoter sequence $iP_A$ is a $P_{LtetO-1}$ promoter.

58. The multiple-inducer engineered genetic counter of any of paragraphs 53-57, wherein the inducible promoter sequence $iP_1$ is a $P_{BAD}$ promoter.

59. The multiple-inducer engineered genetic counter of any of paragraphs 53-58, wherein the inducible promoter sequence $iP_2$ is a $P_{A1lacO-1}$ promoter.

60. The multiple-inducer engineered genetic counter of any of paragraphs 53-59, wherein the recombinase gene sequence of the first SIMM ($RC_1$) encodes a Flp recombinase and the forward ($R_{RS1,for}$) and reverse ($RRS_{1,rev}$) recombinase recognition sites of the first SIMM are $FRT_F$ and $FRT_R$ sites.

61. The multiple-inducer engineered genetic counter of any of paragraphs 53-60, wherein the recombinase gene sequence of the second SIMM ($RC_2$) encodes a Cre recombinase and the forward ($RRS_{2,for}$) and reverse ($RRS_{2,rev}$) recombinase recognition sites of the second SIMM are $loxP_F$ and $loxP_R$ sites.

62. The multiple-inducer engineered genetic counter of any of paragraphs 53-61, wherein the output nucleic acid sequence encodes green fluorescent protein.

63. The engineered genetic counter of any of paragraphs 11-62, for use in a cellular or non-cellular system in counting inputs.

64. The engineered genetic counter of paragraph 63, wherein the engineered genetic counter is introduced into a cellular or non-cellular system using a vector.

65. The engineered genetic counter of paragraph 63 or 64, wherein the vector is a bacterial artificial chromosome (BAC).

66. The engineered genetic counter of any of paragraphs 63-65, wherein the cellular system is a prokaryotic, eukaryotic, or artificial cell.

67. The engineered genetic counter of any of paragraphs 63-65, wherein the non-cellular system is a virus or bacteriophage.

68. A method for counting at least one event in a cellular system comprising introducing an engineered genetic counter of any of paragraphs 11-62 into a cellular or non-cellular system for use in counting events in the cellular or non-cellular system.

69. The method of paragraph 68, wherein the engineered genetic counter is introduced into a cellular or non-cellular system using a vector.

70. The method of paragraph 68 or 69, wherein the vector is a bacterial artificial chromosome (BAC).

71. The method of any of paragraphs 68-70, wherein the cellular system is a prokaryotic, eukaryotic, or artificial cell.

72. The method of any of paragraphs 68-70, wherein the non-cellular system is a virus or bacteriophage.

73. Any of the above-described paragraphs wherein the SIMM, the invertase memory module, the engineered genetic counter and methods of use thereof consist essentially of the specified components.

EXAMPLES

Example 1

We have developed a novel circuit design using DNA recombinases to enable individual bacterial cells to count. Recombinases have been used for numerous applications, including the creation of gene knockouts and solving sorting problems (N. J. Kilby, Trends Genet. 9, 413 (December, 1993); K. A. Haynes, J Biol Eng 2, 8 (2008); T. S. Ham, Biotechnol Bioeng 94, 1 (2006); K. A. Datsenko, Proc Natl Acad Sci USA 97, 6640 (2000)).

We demonstrate the ability of the counter to count from zero to three events upon exposure to chemical inducers. Our design is composed of simple, modular building blocks composed of recombinases, such as Cre and Flp, which can invert DNA in between two oppositely-oriented recognition sites, such as loxP and FRT, respectively. Each recombinase is placed downstream of an inverted promoter ($P_{inv}$) followed by an upright ribosome-binding site (RBS) and a transcriptional terminator (Term). In addition, each recombinase gene is fused to an ssrA tag that causes rapid degradation of recombinase proteins in order to maintain stability of the counter (J. B. Andersen, Appl Environ Microbiol 64, 2240 (1998)). The $P_{inv}$-RBS-recombinase-ssrA-Term DNA sequences (Coff) are placed between recombinase recognition sites that are oriented in opposite directions to form a single counting unit (Rf-Coff-Rr). Upon expression of the recombinase by an upstream promoter, the entire Coff sequence is inverted between the recombinase recognition sites. In this design, the Coff orientation represents a zero and the inverted $P_{inv}$-RBS-recombinase-ssrA-Term DNA sequence (Con) represents a one. In the inverted orientation (Con), further expression of the recombinase is not achieved because the recombinase DNA is inverted with respect to the upstream promoter. Therefore, the Con DNA sequence is stable and avoids being flipped back to Coff. To achieve counting, these components are daisy-chained together on the *Escherichia coli* chromosome, with a promoter placed upstream of the first $R_f$-$C_{off}$-$R_r$ DNA sequence.

To avoid loss of atomicity, we placed counting circuits on pBAC plasmids which are maintained as single-copy episomes (D. A. Wright, Nat Protoc 1, 1637 (2006)). Upon transcription of the most upstream promoter ($P_{LtetO}$ from R. Lutz, Nucleic Acids Res 25, 1203 (1997)), the first recombinase (Flpe from F. Buchholz, Nat Biotechnol 16, 657 (1998)) is expressed and inverts the DNA located between its cognate recombinase sites. This converts $R_f$-$C_{off}$-$R_r$ to $R_f$-$C_{on}$-$R_r$ and halts further transcription of that same recombinase because there is no active promoter upstream of the $R_f$-$C_{on}$-$R_r$ sequence. This first inversion event results in a logical transition from zero to one. Inversion brings $P_{inv}$, the inverted promoter of $C_{off}$, into the upright orientation. For example, inversion of $FRT_f$-$P_{BADinv}$-RBS-flpe-ssrA-Term-$FRT_r$ produces a forward-facing pBAD promoter that is able to drive expression of the next stage. Transcription from this promoter can thus invert the downstream $R_f$-$C_{off}$-$R_r$, resulting in another transition. To monitor successful counting, an RBS followed by a green fluorescent protein gene (gfp) was placed downstream of the last $R_f$-$C_{off}$-$R_r$ module. Thus, green fluorescence should only be detected when the last $R_f$-$C_{off}$-$R_r$ module is inverted and the appropriate inducer is added to activate the last promoter, which should only be true when the circuit has counted to its maximum. Because there are >100 identified recombinases, our design is readily extendible to count in a modular fashion to higher numbers (A. C. Groth, J Mol Biol 335, 667 (2004)). Recombinases can also be mutagenized to have altered site preferences or thermostabilities, allowing for increased diversity to create our synthetic gene circuits (F. Buchholz, Nat Biotechnol 16, 657 (1998); M. Hartung, J Biol Chem 273, 22884 (1998); S. W. Santoro, Proc Natl Acad Sci USA 99, 4185 (2002)).

To test the modularity and functionality of the genetic counter, we designed a two-stage counter with $P_{LtetO}$-$FRT_f$-$P_{BAD,inv}$-RBS-flpe-ssrA-Term-$FRT_r$-RBS-gfp on a pBAC plasmid. Without any inducers, GFP fluorescence was minimal. When transcription from $P_{LtetO}$ was induced with 400 ng/mL anhydrotetracycline, Hp, was expressed, resulting in an inversion event and resultant DNA containing $P_{LtetO}$-$FRT_f$-$Term_{inv}$-$flp_{e,inv}$-ssrA-RBS¬ inv-$p_{BAD}$-$FRT_r$-RBS-gfp. Upon addition of arabinose, GFP fluorescence was induced, demonstrating that the circuit is able to count to two, where two is defined as anhydrotetracycline (aTc) followed by arabinose. Note that the addition of aTc alone, arabinose alone, or arabinose followed by aTc produced no GFP output.

We tested the ability to count from zero to three by placing $loxP_f$-$P_{A1lacOinv}$-RBS-cre-ssrA-Term-$loxP_r$-RBS-gfp downstream of $P_{LtetO}$-$FRT_f$-$P_{BADinv}$-RBS-$flp_e$-ssrA-Term-$FRT_r$. In the presence of aTc and arabinose followed by IPTG, the circuit counted to three and therefore expressed a high GFP fluorescence. In the presence of no inducer, aTc alone, arabinose alone, or IPTG alone, the circuit did not count to three and had a low fluorescence. In the presence of aTc followed by arabinose, aTc followed by IPTG, and arabinose followed by IPTG, the circuit did not count to three and had a low fluorescence. These results demonstrate that the counter can count events in a defined order and is not activated by any unintended sequence of inputs.

In order to make the genetic counter more user-friendly and allow a global reset to zero, inverted promoters could be placed in between each counting unit. In the presence of an inducer, each flipped counting unit could be reset by driving expression of the recombinases with the inverted promoters. In this initial embodiment, the counter counts pulses of different inducers. However, the counter could be modified in a straightforward way to count multiple events of the same inducer by replacing all the different promoters with the same promoter.

The genetic circuit described herein is a modular, daisy-chained counter built with individual counting units. In one embodiment of this design, the maximum number which can be counted is linearly proportional to the number of counting units, n. In other embodiments, this system can be readily extended with more sophisticated designs to count in binary, allowing the maximum countable number to be $2^n-1$.

We designed the engineered nucleic acid-based circuits for use as genetic counters using DNA-based switches instead of protein-based systems for several reasons. An example of protein-based memory which could be cascaded to create a counter is the toggle switch (T. S. Gardner, Nature 403, 339 (2000)). The toggle switch requires well-characterized repressors to work properly and is thus more complicated than the design presented herein. Each of the individual counting units requires only a single recombinase whereas protein-based switches utilize two proteins (T. S. Gardner, Nature 403, 339 (2000)). The DNA-based design can be extended readily in a modular fashion with currently known components. Furthermore, the DNA-based system can be used across long time scales without needing to maintain active transcription and translation of the circuit because the circuit is stable in the absence of inducers.

In one embodiment, the design is a cis-based counting system that requires physical proximity of individual counting units for counting transitions. In other embodiments, further functionality, including digital-logic-based computation, is incorporated by adding trans-acting components for coupling to other circuits (K. Rinaudo, Nat Biotechnol 25, 795 (2007)). In a non-limiting example, the gfp output gene can be replaced by other proteins, such as transcription factors, transcriptional repressors, or RNAs, such as riboswitches in prokaryotic and mammalian cells as well as short-hairpin RNAs in mammalian cells (F. J. Isaacs, Nat Biotechnol 22, 841 (2004)). In other embodiments, the counter can be coupled to quorum-sensing circuits to create a consensus-based counting system.

The ability to count inputs in individual cells can be useful for engineering biological organisms and performing basic scientific experiments. For example, in some embodiments, engineered bacteria can be designed to count exposures to environmental agents and trigger an output only when a discrete threshold has been reached. A yeast cell-cycle counter has been developed to facilitate cell-cycle research (C. M. Ajo-Franklin, Genes Dev 21, 2271 (2007)). Mammalian cells that carry counters can help elucidate the sequence and number of mutations needed to produce cancer cells.

One strength of our design lies in its simplicity, modularity, and extensibility with different recombinase proteins. Therefore, it can be used in different designs to create basic digital logic in cells. For example, in one embodiment, the counter described herein is essentially an AND gate that enforces a particular sequence of inputs. The individual modular units used in the genetic counter can be decoupled to each represent a single bit in an engineered memory system rather than a counter. A pulse generator for the generation of transcriptional pulses can also be readily designed by modifying individual modular units to perform inversion events continuously.

One issue with counters which utilize transcription as an input is that they will not be able to easily distinguish between one pulse and multiple separate pulses. For example, if the counter is modified so it works with a single promoter, such as $P_{BAD}$, which is arabinose-inducible, then a long single pulse will eventually flip all of the stages in the counter and result in an output. Three separate pulses may cause the same effect as well. The main reason for this issue is that circuits which use transcription to generate proteins to perform counting (such as a recombinase protein to flip a DNA sequence) respond to pulse duration rather than the transition from no inducer to inducer present.

In order to allow counters to recognize edge transitions, or binary operations, such as 0 to 1 or 1 to 0, a circuit has been developed, that can be placed into cells along with a counting circuit. Essentially, the synthetic pulse generator created allows a burst of transcription to take place before shutting down all transcription, thus allowing step transitions in inducer level to produce pulses of transcription rather than constant transcription. The synthetic pulse generator is composed of an inducible promoter that is the same promoter the counter circuit uses. Some non-limiting examples of promoters include $P_{BAD}$, $P_{LtetO}$, and $P_{A1lacO}$, or, alternatively, whatever synthetic circuit one wants to generate pulses of transcription for. This promoter drives expression of a repressor that suppresses its own transcription, thus forming a negative-feedback loop. For optimal performance, in one embodiment, the repressor is a non-inducible repressor.

Upon addition of the appropriate inducer, the synthetic counter circuit begins to transcribe its genes. However, at the same time, the synthetic pulse generator produces repressor protein that suppresses transcription from the inducible promoters in the synthetic pulse generator or the synthetic counter. Eventually, enough repressor protein is produced that transcription from the inducible promoters is shut down, even in the presence of inducer. In one embodiment, a non-inducible repressor is used such that the shutting down of transcription is absolute. In a non-limiting example, non-inducible AraC proteins have been created (Mutational Analysis of Residue Roles in AraC Function, Jennifer J. Ross, Urszula Gryczynski and Robert Schleif, J. Mol. Biol. (2003) 328, 85-93) and (Hemiplegic Mutations in AraC Protein, Wendy L. Reed and Robert F. Schleif, J. Mol. Biol. (1999) 294, 417-425). These non-inducible AraC proteins could be used in the synthetic pulse generator with inducible promoter $P_{BAD}$. Non-inducible versions of TetR and LacI are also available.

Eventually, the inducer is withdrawn and the repressor protein degraded in order to allow transcription from the inducible promoters during the next addition of inducer. This therefore generates pulses of transcription from the inducible promoters and requires that inducer be withdrawn for additional pulses to be generated. Thus, this circuit is a synthetic pulse generator that can work with a broad range of other synthetic circuits to provide pulse generation and edge detection.

Example 2

Synthetic gene networks can be constructed to emulate digital circuits and devices, giving one the ability to program and design cells with some of the principles of modern computing. A counter is one such device that results in a new type of memory and allows for complex synthetic programming and novel behaviors. Here, we describe two complementary synthetic genetic counters in E. coli that can count multiple induction events, shown herein for three events, the first comprised of a riboregulated transcriptional cascade and the second of a recombinase-based cascade of memory units. The modularity of these devices permit counting of varied user-defined inputs over a range of frequencies and their open-ended architectures provide potent biotechnology platforms for counting higher numbers.

A counter is a device that retains memory of events or objects, representing each number of such as a distinct state. A key component in digital circuits and computing, counters can also be useful for cells, which often must have accurate accounting of tightly controlled processes or biomolecules in order to effectively maintain metabolism and growth. Counting mechanisms have been reportedly found in telomere length regulation (S. Marcand et al., Science 275, 986 (1997); A. Ray and K. W. Runge, Mol Cell Biol 19, 31 (1999) and cell aggregation (D. A. Brock, R. H. Gomer, Genes Dev 13, 1960 (1999)), but these system behaviors appear to be the result of a thresholding effect in which some critical molecule number or density must be reached for the observed phenotypic change.

The first type of counter we developed, termed the Riboregulated Transcriptional Cascade (RTC) Counter, is based on a transcriptional cascade with additional translational regulation. The RTC counters represent each number with a unique expression profile, truly counting their inputs, and we have illustrated two such cascades that can count up to 2 and 3, respectively. For the RTC 2-Counter, the constitutive promoter $P_{LtetO-1}$ drives transcription of T7 RNA polymerase (RNAP), whose protein binds the T7 promoter and transcribes the downstream gene, in this case Green Fluorescent Protein (GFP) (B. P. Cormack et al., Gene 173, 33 (1996)). Both genes are additionally regulated by riboregulators (F. J. Isaacs et al., Nat Biotechnol 22, 841 (2004)), whose cis and trans elements silence and activate post-transcriptional gene expression, respectively. The cis-repressor sequence is placed between the transcription start site and the ribosome binding site (RBS), and its complementarity with the RBS causes a stem-loop structure to form upon transcription. This secondary structure prevents binding of the RBS by the 30S ribosomal subunit, inhibiting translation. A short, trans-activating, noncoding RNA (taRNA) driven by the arabinose promoter $P_{BAD}$ binds to the cis-repressor in trans, relieving RBS repression and allowing translation. With this riboregulation, each node in the cascade requires both independent transcription and translation for protein expression and is thus AND-gated. This cascade is able to count brief arabinose pulses by expressing a new protein species in response to each pulse. With cis-repressed T7 RNAP mRNAs in the cell, the first pulse of arabinose drives a short burst of taRNA production and consequently expression of T7 RNAP proteins. At the end of the pulse, arabinose is removed from the cell environment, intracellular arabinose and taRNA are metabolized, and expression of protein halts. The T7 RNAP proteins that have been made go on to transcribe cis-repressed GFP transcripts, but few GFP proteins are made until the next arabinose pulse is delivered and translation is once again fully activated.

We built the RTC 2-Counter construct on a high copy plasmid and transformed it into E. coli strain K-12pro. Cells containing this construct were pulsed with inducer, and mean fluorescence over time was measured. As expected, uninduced cells show no increase in mean fluorescence while cells that received either the first or second pulse show only small increases, indicating some degree of leakage—an effect in which the intended protein is expressed in each arabinose pulse but also some unintended, downstream proteins are expressed as well. Cells that received both arabinose pulses show a significant increase in fluorescence when the second pulse is delivered, precisely when the cells are expected to express GFP proteins. With concentrations of GFP protein switching from low to high as a result of a second pulse, we represent the number "2" in this case with GFP protein.

To extend the RTC counter's capability to count to three, we built a second synthetic construct, the RTC 3-Counter, again with GFP as the quantitative readout. It is similar to the RTC 2-Counter but has three nodes in the cascade instead of two. T7 RNAP is the gene at the first node driving transcription of T3 RNAP, which in turn drives transcription of GFP. All transcripts are likewise cis-repressed with the same riboregulator sequence. When pulsed with arabinose, this counter primarily produces T7 RNAP proteins during the first pulse, T3 RNAP proteins during the second pulse, and GFP proteins during the third pulse.

Our experimental results demonstrate that fluorescence increases substantially only when all three arabinose pulses are delivered. Flow cytometry measurements show this increase beginning at precisely the time of the third pulse, and the considerable slope at this juncture suggests that cells contain a high concentration of cis-repressed GFP transcripts ready for trans-activation. The data also reveal slight leakage in cells that are pulsed only once or twice, but their fluorescence remains comparatively low. This result, in combination with the RTC 2-Counter evidence, shows that the temporal progression of RNA and protein species logically predicted by our counter network architecture design is indeed responsible for the observed effect.

To further support these results, we constructed and analyzed a mathematical model based on the design of the RTC 2-Counter and 3-Counter constructs. This model, with fitted parameters, was able to match both the RTC 2-Counter and 3-Counter experimental results. We used the model to investigate the effects of pulse frequency and pulse length on the performance of the RTC 3-Counter and guide our experimental search for optimal combinations. The mathematical model predictions, shown as contour lines, indicate that maximum expression occurs with pulse lengths of approximately 20 to 30 minutes and pulse intervals of 10 to 40 minutes. The absolute difference in fluorescence after three pulses and two pulses is described, with optimal counting behavior requiring similar pulse length and interval combinations noted above.

Experimentally, we sampled various pulse lengths and intervals, plotting these results as circles. These results are consistent with the model predictions across a wide range of temporal conditions, and confirm that the RTC 3-Counter has a sizeable temporal region in which its counting behavior is robust. Within this region, the counter is also capable of counting irregular pulses; for example, it is able to distinguish between two short pulses followed by a long pulse and two long pulses, as predicted by the model. However, when pulse length or frequency is either too high or low the RTC 3-Counter is unable to count properly due to the intrinsic kinetic limits of the biochemical processes involved, such as transcription and mRNA degradation.

Our second counter design, termed the DNA Invertase Cascade (DIC) Counter, is built by daisy-chaining modular DNA-based counting units (FIG. 1A). The DIC Counter utilizes recombinases, such as cre and flp$_e$ F. Buchholz, et al., Nat Biotechnol 16, 657 (1998)), which can invert DNA between two oppositely-oriented cognate recognition sites, such as loxP and FRT, respectively.

Figure 2A:
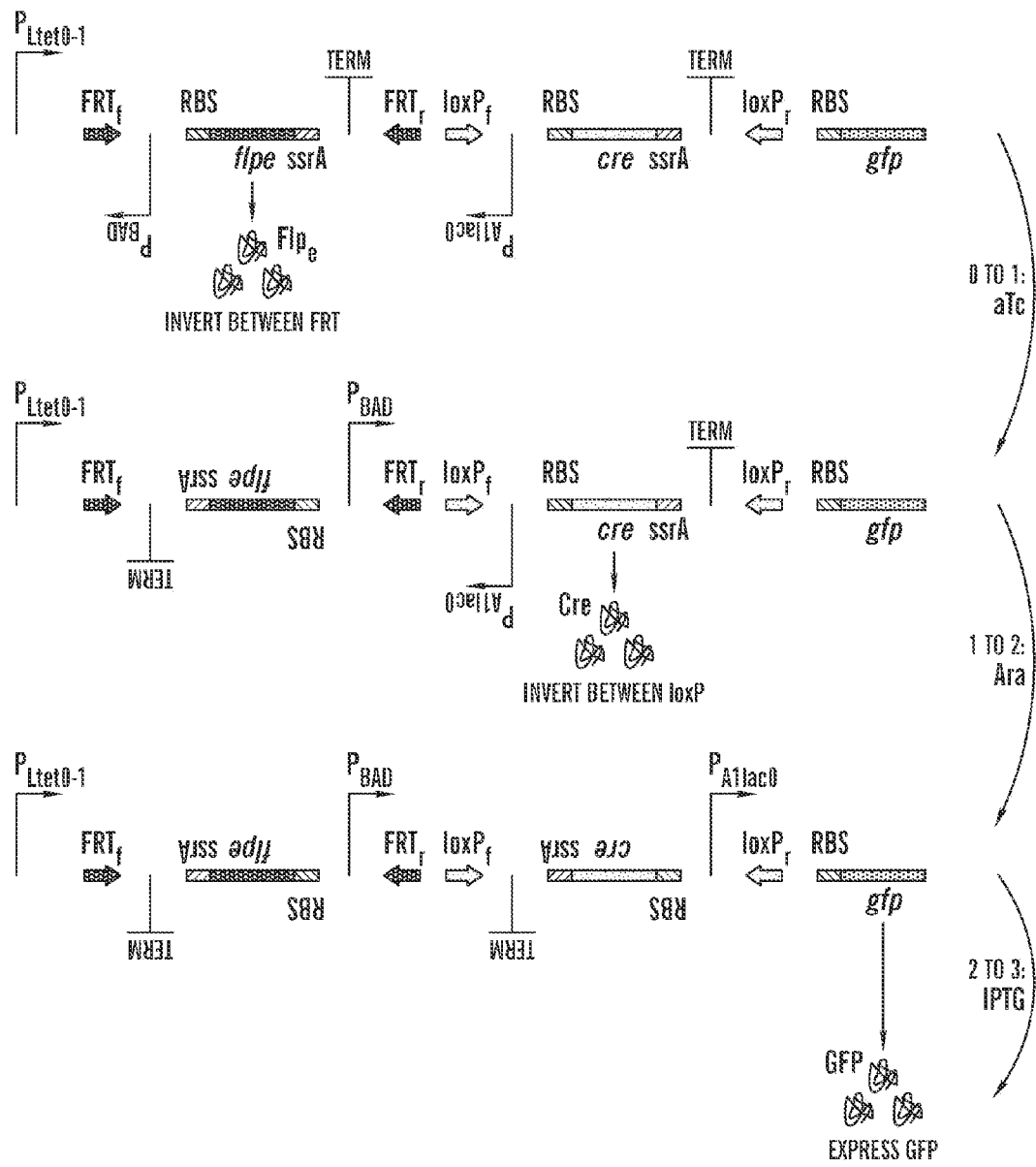
FIG. 2A depicts a multiple-inducer DIC 3-Counter where each promoter is a unique inducible promoter: $P_{LtetO-1}$, $P_{BAD}$, and $P_{A1lacO}$ that respond to anhydrotetracycline (aTc), arabinose, and IPTG, respectively.
Figure 3:
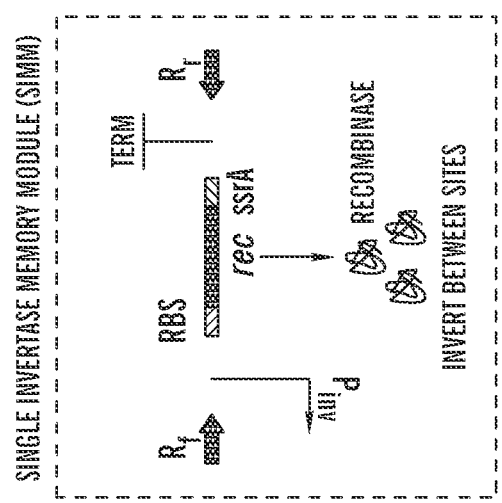
FIG. 3 depicts a schematic design of a Single Invertase Memory Module (SIMM) used in the DIC counters. The SIMMs are composed of opposing recombinase recognition sites ($R_f$ and $R_r$) which contain between them an inverted promoter ($P_{inv}$), a synthetic ribosome-binding-sequence (RBS), a recombinase gene (rec), an ssrA-based degradation tag, and a transcriptional terminator (Term). The SIMM maintains memory based on its DNA orientation, which can be inverted when the recombinase is expressed.

Recombinases have been used for numerous applications, including the creation of gene knockouts, solving sorting problems, and constructing inheritable genetic memory (A. C. Groth, M. P. Calos, J Mol Biol 335, 667 (2004); T. S. Ham, et al., Biotechnol Bioeng 94, 1 (2006); and K. A. Haynes et al., J Biol Eng 2, 8 (2008)). In our counter design, each recombinase gene (rec) is downstream of an inverted promoter ($P_{inv}$), fused to an ssrA-based tag that causes rapid protein degradation (J. B. Andersen et al., Appl Environ Microbiol 64, 2240 (1998)), and followed by a transcriptional terminator (Term) (FIG. 1A, FIG. 2A, and FIG. 3). The $P_{inv}$-rec-ssrA-Term DNA sequences are placed between recombinase recognition sites ($R_f$ and $R_r$), forming a single counting unit which we have named a Single Invertase Memory Module (SIMM) (FIG. 1A and FIG. 3). Upon expression of recombinase by an upstream promoter, the entire SIMM is inverted between the recognition sites, representing the flipping of a digital bit. Due to the inverted orientation of the recombinase gene with respect to the upstream promoter, further expression of recombinase protein ceases and DNA orientation is fixed.

Figure 1B:
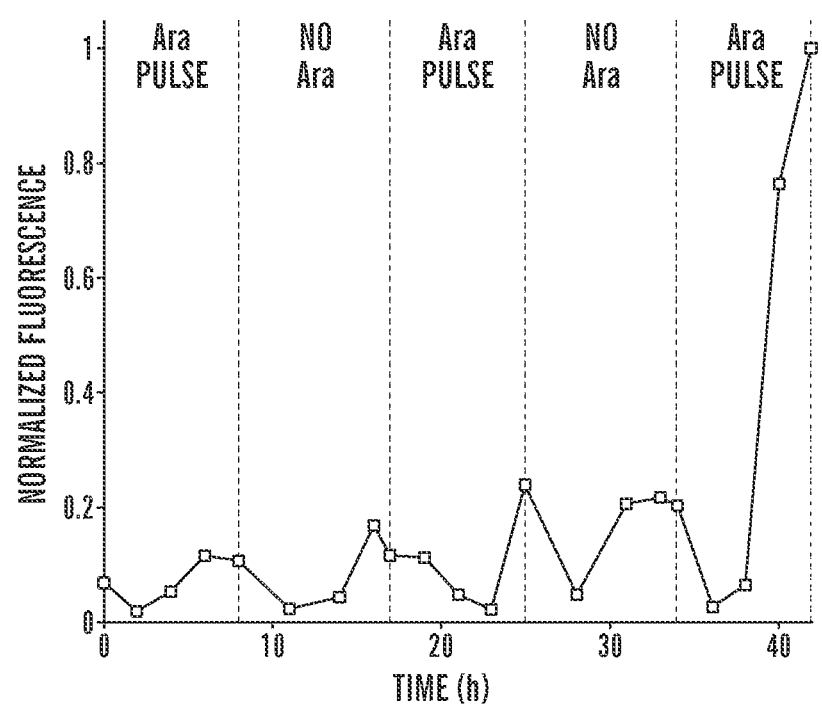
FIG. 1B depicts mean fluorescence of single-inducer DIC 3-Counter cell populations over time, measured by a flow cytometer.
Figure 1C:
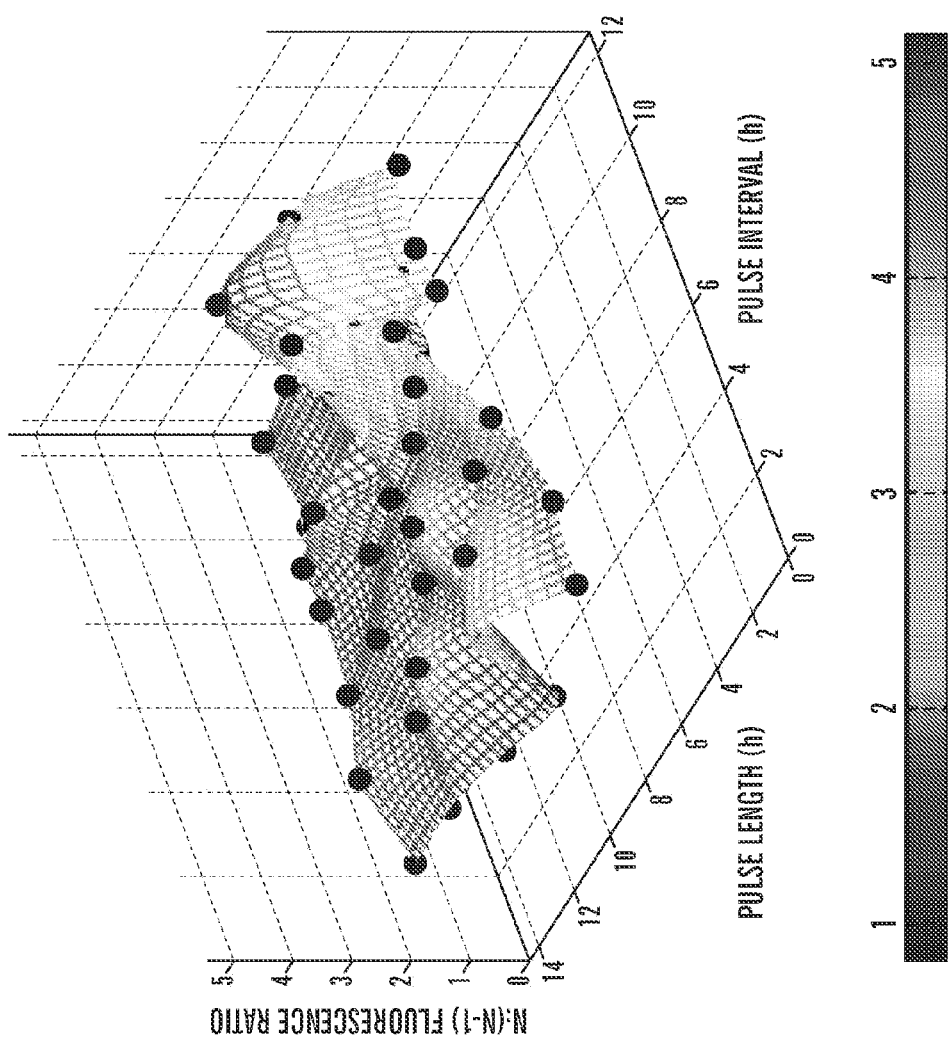
FIG. 1C depicts GFP fluorescence ratios between a single-inducer DIC 3-Counter exposed to three pulses of arabinose (N) versus two pulses of arabinose (N−1), with varying arabinose pulse lengths and intervals.
Figure 4:
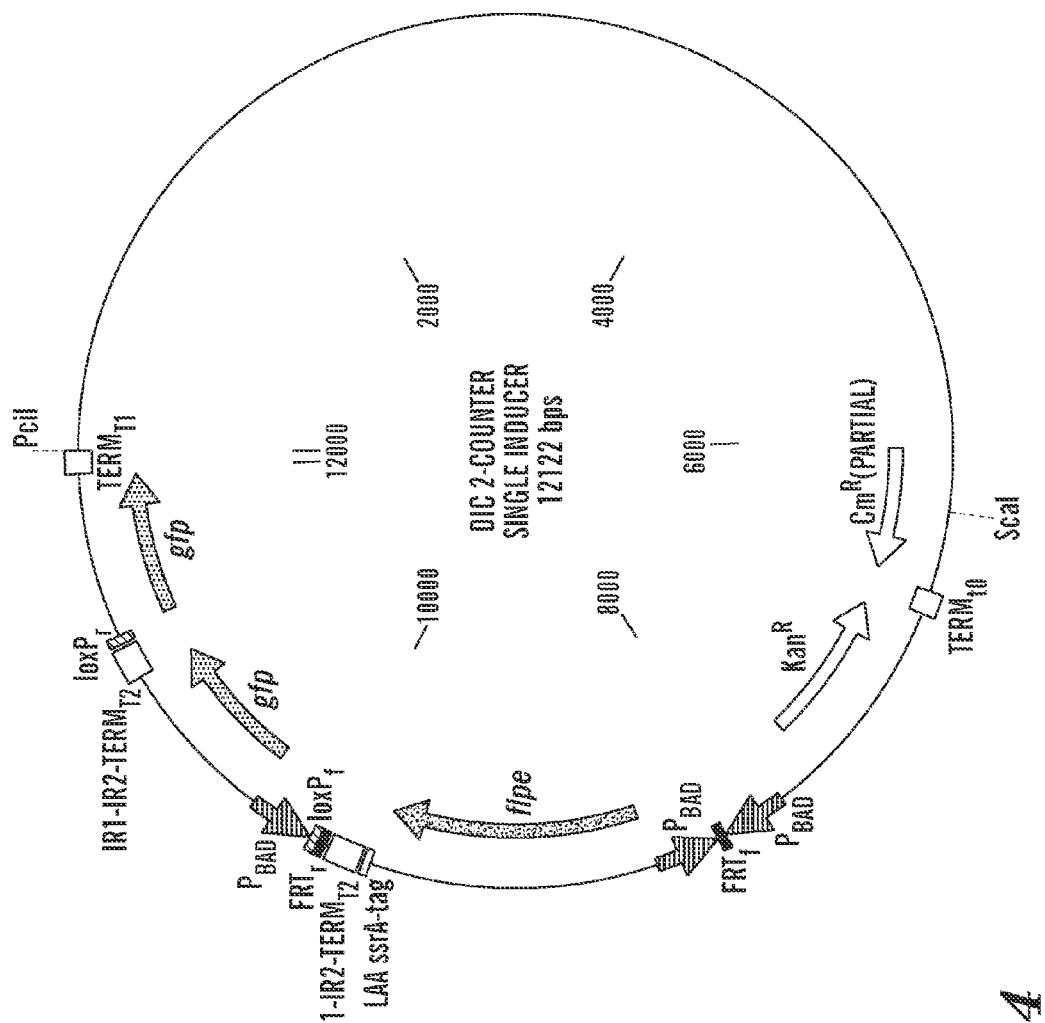
FIG. 4 shows a single-inducer DIC 2-Counter plasmid. Genes are denoted by arrows within the plasmid circle, promoters by arrows on the plasmid circle, transcriptional terminators by light rectangles, ssrA-based degradation tags by darker rectangles, and recombinase recognition sites by rectangles of other shades.
Figure 5:
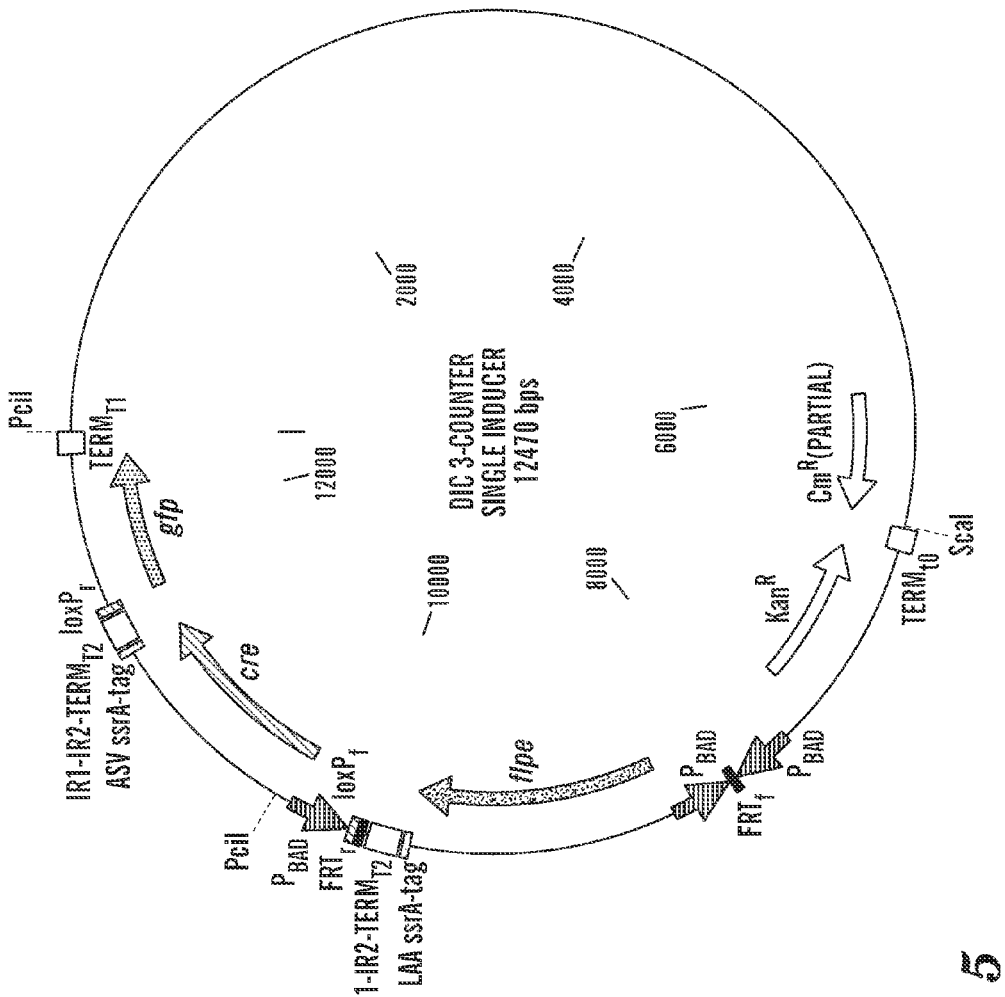
FIG. 5 shows a single-inducer DIC 3-Counter Plasmid. Genes are denoted by arrows within the plasmid circle, promoters by arrows on the plasmid circle, transcriptional terminators by light rectangles, ssrA-based degradation tags by darker rectangles, and recombinase recognition sites by rectangles of other shades.
Figure 6A:
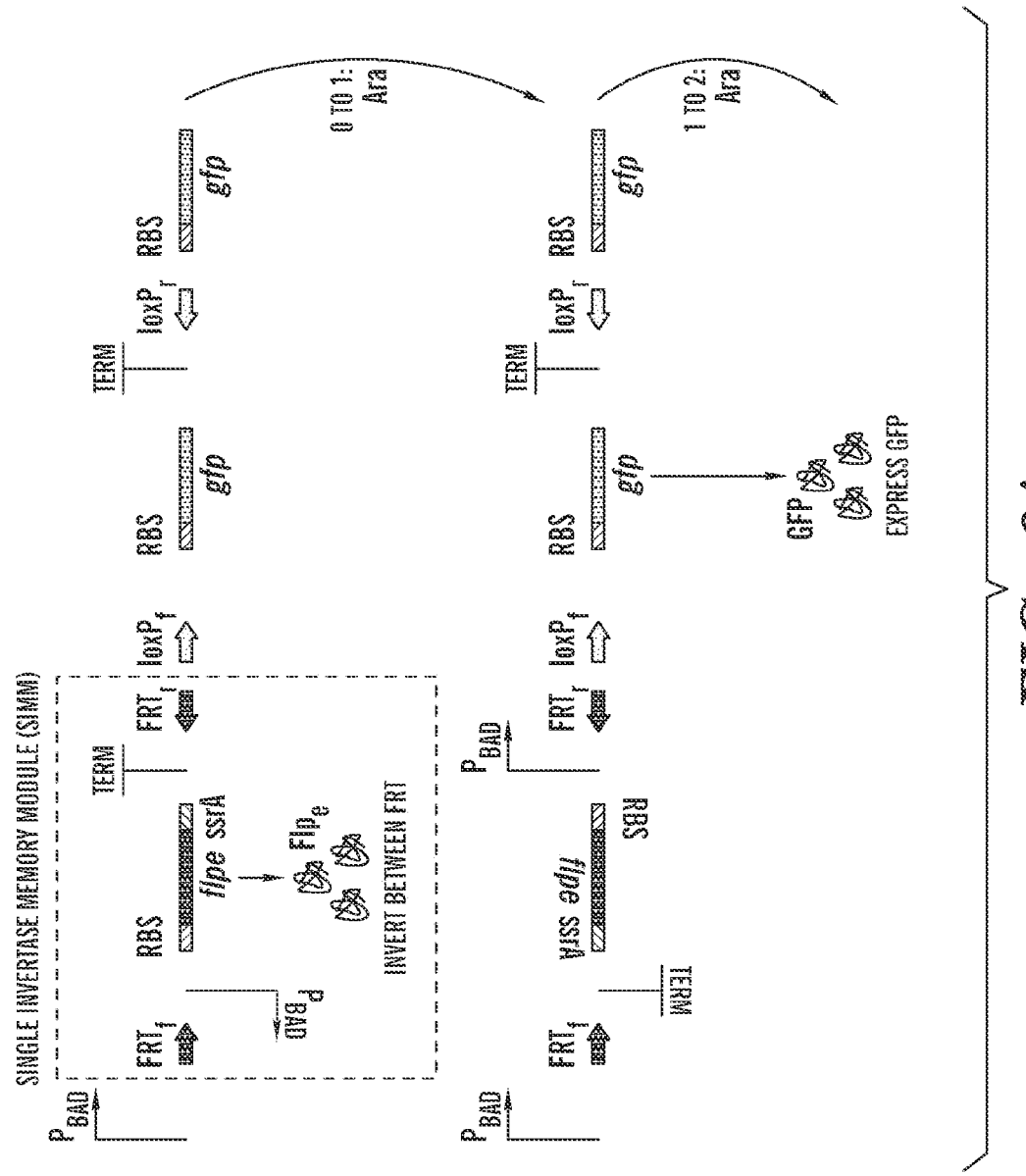
FIG. 6A shows that a single-inducer DIC 2-Counter is characterized by a single Single Invertase Memory Module (SIMM) with $P_{BAD}$ as the inducible upstream promoter and inducible inverted promoter within the SIMM.
Figure 6C:
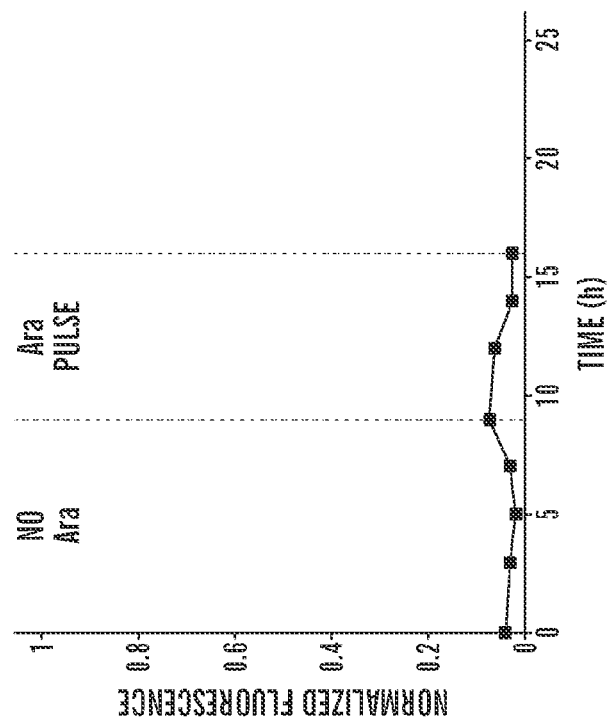
FIG. 6C shows the mean fluorescence of single-inducer DIC 2-Counter cell populations over time, measured by a flow cytometer, and demonstrates that cells grown with no inducer for 9 hours followed by a single pulse of arabinose lasting 7 hours did not show significant GFP expression. Mean fluorescence was normalized against the maximum fluorescence for cells obtained in FIGS. 6B and 6C in order to allow comparison between the two plots.
Figure 6B:
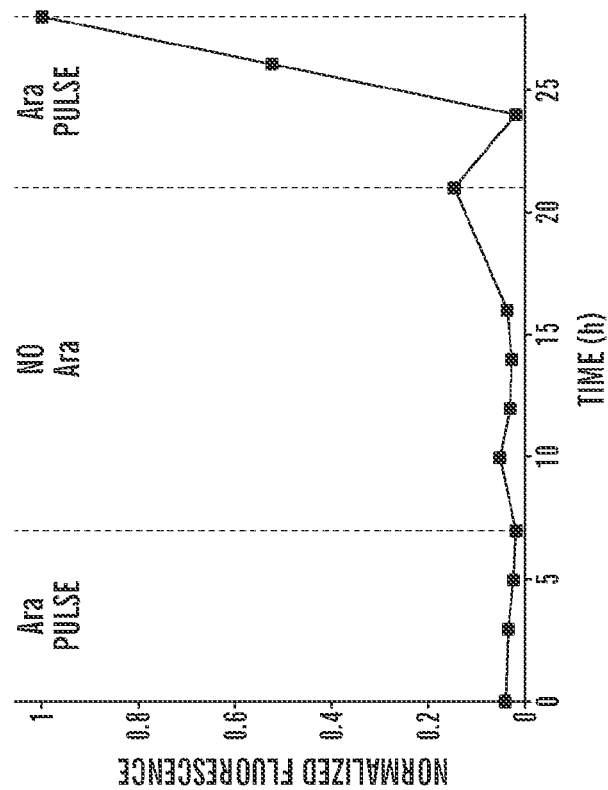
FIG. 6B shows the mean fluorescence of single-inducer DIC 2-Counter cell populations over time, measured by a flow cytometer, and demonstrates a significant increase in GFP fluorescence after exposure to two pulses of arabinose.
Figure 7:
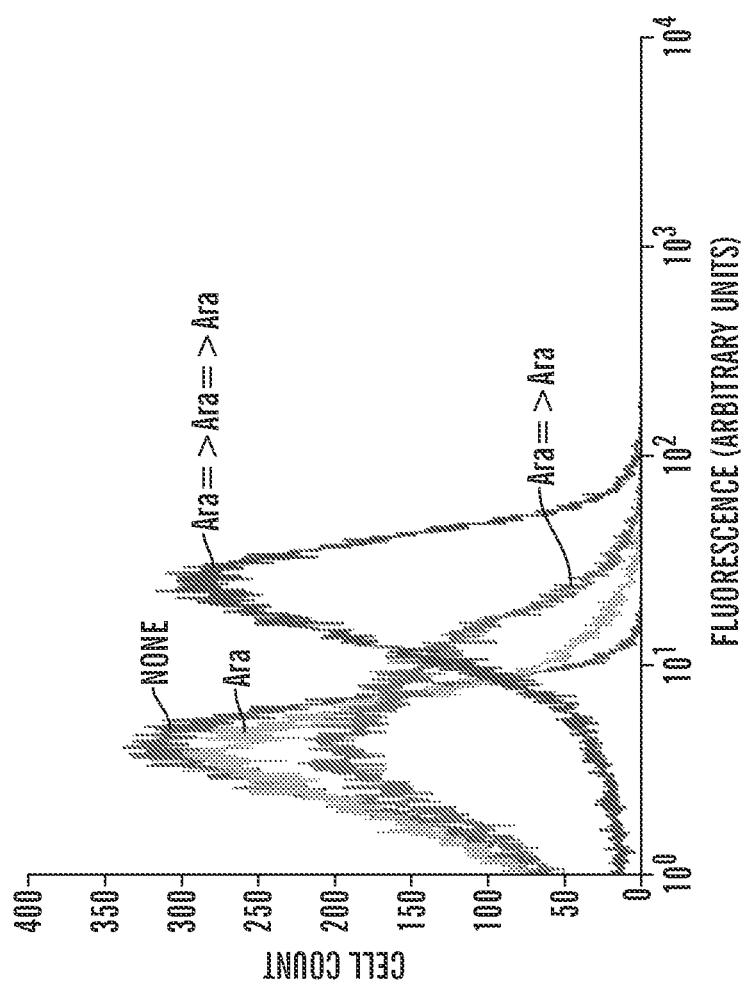
FIG. 7 shows flow cytometry population data for a single-inducer DIC 3-Counter exposed to zero, one, two, or three pulses of arabinose. Each arabinose pulse was 8 hours long and spaced by 9 hours of no arabinose exposure. The data demonstrate that there is no leakage with one pulse ("Ara" in the legend), a small degree of leakage with two pulses ("Ara=>Ara" in the legend), and a large degree of activation after three pulses ("Ara=>Ara=>Ara" in the legend).

To maximize the atomicity of DNA inversion events, we placed our counting circuits on pBAC plasmids that are maintained as single-copy episomes (D. A. Wright et al., Nat Protoc 1, 1637 (2006)). We developed a single-inducer DIC 2-Counter (FIG. 4) and 3-Counter (FIG. 1A and FIG. 5), which are composed of one and two SIMMs, respectively. These circuits utilize $P_{BAD}$ so that pulses of arabinose constitute inputs to the circuit. Each pulse of arabinose results in promoter activation and expression of the next recombinase in the cascade, which then inverts the SIMM in which it is located. This allows the inverted promoter contained within that SIMM to be placed in an upright orientation to drive expression of the next SIMM stage. The single-inducer DIC 2-Counter shows high GFP output after two pulses of arabinose and only low GFP output after one pulse of arabinose, demonstrating that a single SIMM can be inverted to count events (FIG. 6). In the single-inducer DIC 3-Counter, some premature flipping of the cre-based SIMM did occur, resulting in a small amount of leakage, e.g., fluorescence increased after only two arabinose pulses (FIG. 1B and FIG. 7). However, this leakage was small compared to the high GFP output obtained after three pulses of arabinose (FIG. 1B). In order to probe the temporal characteristics of the single-inducer DIC 3-Counter, we varied the pulse lengths and intervals, calculating the ratio of GFP output for cells exposed to three versus two pulses of arabinose (FIG. 1C). This ratio was at least 1.5 for most conditions tested, demonstrating that the single-inducer DIC 3-Counter is able to successfully count pulses whose lengths and intervals range from 2 to 12 hours (FIG. 1C).

Figure 2B:
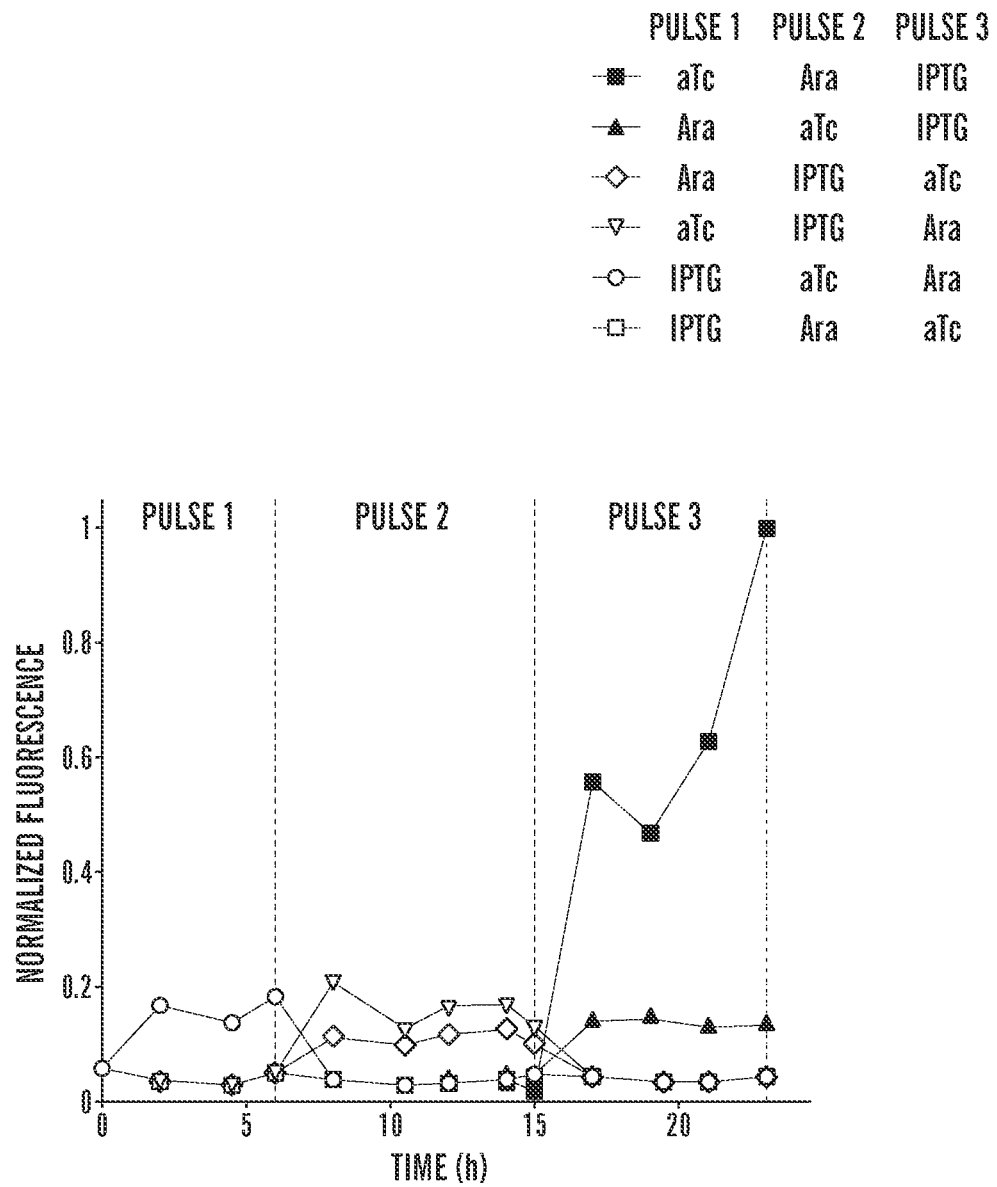
FIG. 2B shows mean fluorescence of multiple-inducer DIC 3-Counter cell populations over time, measured by a flow cytometer.
Figure 2D:
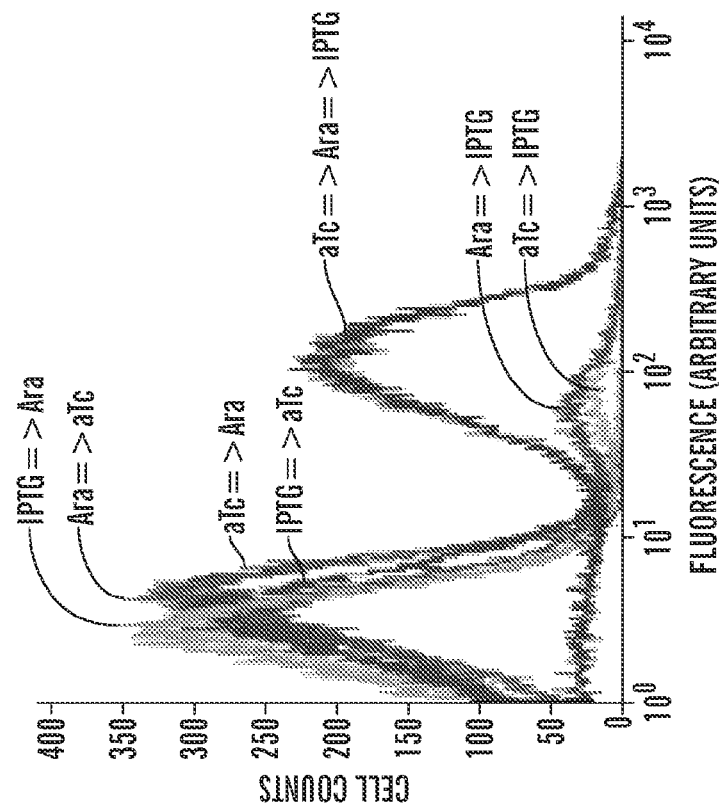
FIG. 2D depicts flow cytometry population data showing a multiple-inducer DIC 3-Counter when exposed to its desired sequence of three inducers and to all pairwise permutations of inducers.
Figure 2C:
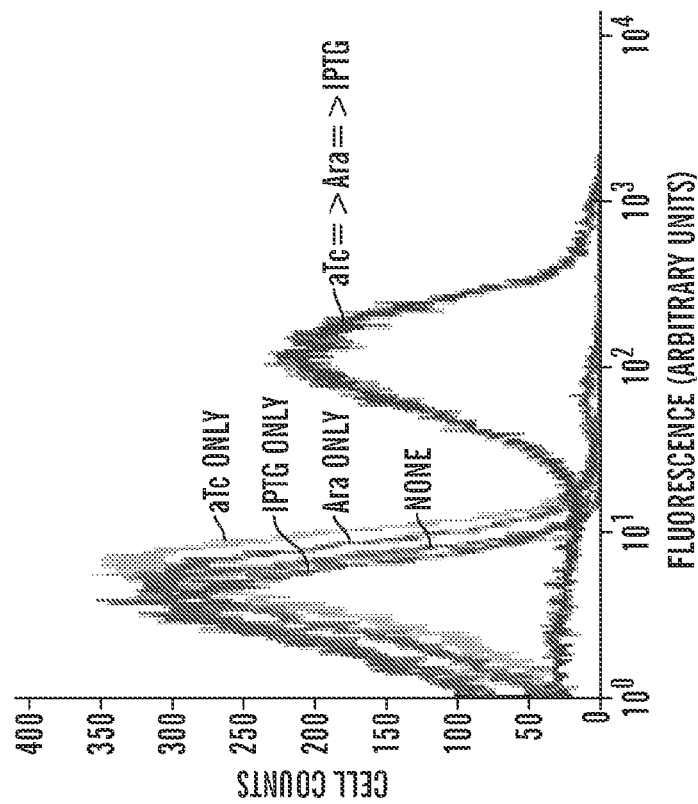
FIG. 2C depicts flow cytometry population data showing a multiple-inducer DIC 3-Counter when exposed to its desired sequence of three inducers and to single inducers only.
Figure 8:
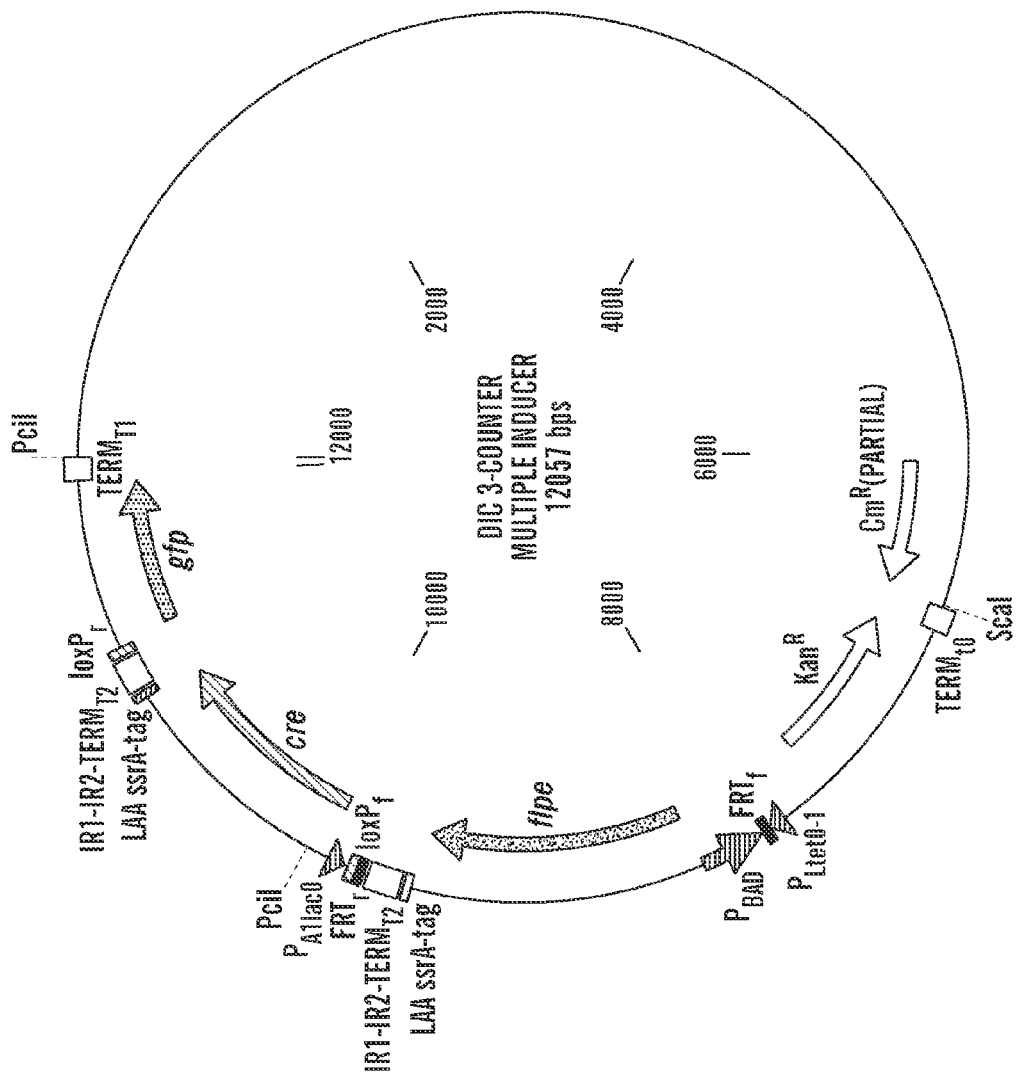
FIG. 8 depicts a multiple-inducer DIC 3-Counter Plasmid. Genes are denoted by arrows within the plasmid circle, promoters by arrows on the plasmid circle, transcriptional terminators by light rectangles, ssrA-based degradation tags by darker rectangles, and recombinase recognition sites by rectangles of other shades.

We also developed a multiple-inducer DIC 3-Counter by replacing the $P_{BAD}$ promoters in the single-inducer DIC 3-Counter with the inducible promoters P LtetO-1, $P_{BAD}$, and $P_{A1lacO}$ (FIG. 2A and FIG. 8). These promoters respond to anhydrotetracycline (aTc), arabinose, and isopropyl β-D-1-thiogalactopyranoside (IPTG), respectively (FIG. 2A). When exposed to aTc followed by arabinose followed by IPTG, the multiple-inducer DIC 3-Counter produced a high GFP output (FIG. 2B). No other permutations of the three inducers produced a high output, though some did exhibit a small amount of leakage (FIGS. 2C-2D). These results demonstrate that the circuit can be programmed to only record a desired sequence of events.

Figure 9B:
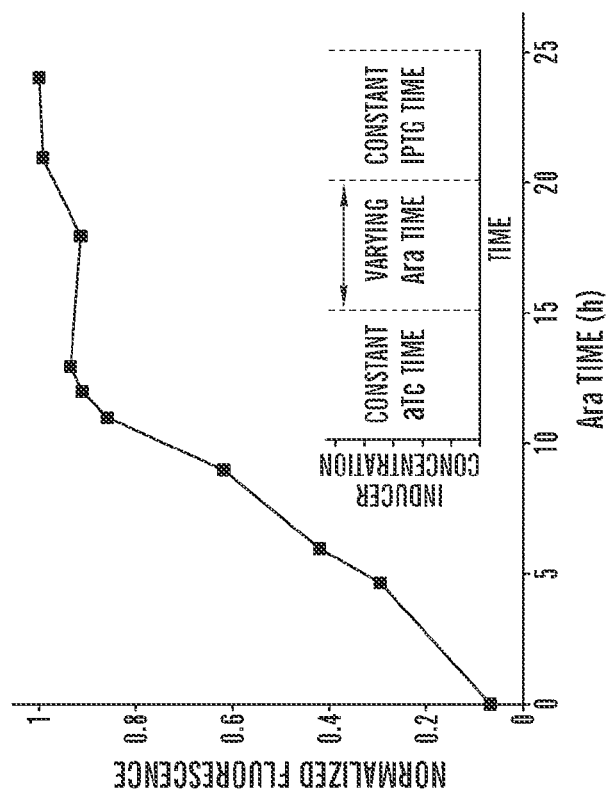
FIG. 9B shows that a second SIMM stage begins to respond to Ara within 9 hours of exposure. Very long arabinose exposure times did not result in increased GFP fluorescence.
Figure 9A:
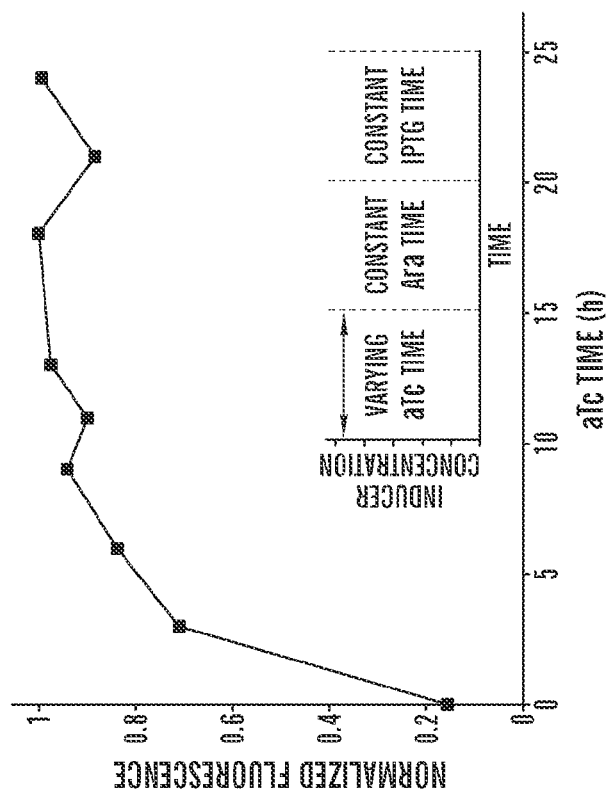
FIG. 9A shows that a first SIMM stage responds to aTc within 6 hours of exposure. Very long aTc exposure times did not result in increased GFP fluorescence.

We have constructed and validated two complementary designs for synthetic counters that operate across a range of time scales. These counters are both highly modular and are capable of functioning with any inducer-promoter pairs, as demonstrated by the different promoters used in the multiple-inducer DIC 3-Counter. Additionally, the architectures of both counters allow for the tunable output expression of any protein species of interest at any number in the counting process. While the constructs described here were built to count up to three events, our engineered genetic counter designs are both extensible with the use of other unique polymerases or recombinases, of which many are known. In addition to these shared qualities, each counter comes with its own set of properties. Our RTC Counters demonstrate fast activation due to transcriptional and translational regulatory elements, making them useful for counting cellular events on the time scale of cell division. The DIC Counters operate on time scales of hours (FIG. 9) as a result of DNA recombination dynamics (S. W. Santoro and P. G. Schultz, Proc Natl Acad Sci USA 99, 4185 (2002)), and they are built with a novel SIMM design that memorizes counter state based on DNA orientation. Together, these features could enable the design of temporally sensitive, complex synthetic programs as well as other types of counters.

Previous synthetic gene networks have demonstrated the feasibility of constructing biological analogues of some aspects of digital circuits, such as inverters (Y. Yokobayashi et al., Proc Natl Acad Sci USA 99, 16587 (2002)), logic gates (K. Rinaudo et al., Nat Biotechnol 25, 795 (2007); G. Seelig et al., Science 314, 1585 (2006)), toggle switches (T. S. Gardner et al., Nature 403, 339 (2000)), oscillators (M. B. Elowitz, S. Leibler, Nature 403, 335 (2000)), and pulse generators (S. Basu et al., Proc Natl Acad Sci USA 101, 6355 (2004)).

Synthetic gene circuits have enlarged the molecular toolset available to bio-engineers and molecular biologists (Y. Yokobayashi et al., Proc Natl Acad Sci USA 99, 16587 (2002); (K. Rinaudo et al., Nat Biotechnol 25, 795 (2007); G. Seelig et al., Science 314, 1585 (2006); T. S. Gardner et al., Nature 403, 339 (2000); (M. B. Elowitz, S. Leibler, Nature 403, 335 (2000); S. Basu et al., Proc Natl Acad Sci USA 101, 6355 (2004); T. S. Bayer, C. D. Smolke, Nat Biotechnol 23, 337 (2005); E. A. Davidson, A. D. Ellington, Trends Biotechnol 23, 109 (2005); F. J. Isaacs et al., Nat Biotechnol 24, 545 (2006); M. Mandal, R. R. Breaker, Nat Rev Mol Cell Biol 5, 451 (2004); 0. Rackham, J. W. Chin, Nat Chem Biol 1, 159 (2005)), enabling them to program novel cellular behaviors (J. C. Anderson et al., J Mol Biol 355, 619 (2006); S. Basu et al., Nature 434, 1130 (2005); T. L. Deans et al., Cell 130, 363 (2007); J. Hasty et al., Nature 420, 224 (2002); H. Kobayashi et al., Proc Natl Acad Sci USA 101, 8414 (2004); A. Levskaya et al., Nature 438, 441 (2005)), learn more about the necessary design principles of synthetic biology (B. F. Pfleger et al., Nat Biotechnol 24, 1027 (2006); J. M. Pedraza, A. van Oudenaarden, Science 307, 1965 (2005); S. Hooshangi et al., Proc Natl Acad Sci USA 102, 3581 (2005); N. J. Guido et al., Nature 439, 856 (2006)), and construct therapeutic agents (T. K. Lu, J. J. Collins, Proc Natl Acad Sci USA 104, 11197 (2007)).

Our synthetic counters represent complementary designs that can be used in different settings for a variety of purposes across a range of time scales. For example, if inputs to our RTC Counter are coupled to the cell cycle, cell death is programmed to occur after a user-defined number of cell divisions as a safety mechanism in engineered strains, which is useful for biosensing, bioremediation, or medical purposes. In addition, the multiple-inducer DIC Counter are useful for studying sequential events that occur in settings such as developmental biology and gene cascades, as the single-inducer DIC counter can record events encountered in its environment (e.g., for biosensing), and our SIMM design can be used in other synthetic circuits to maintain genetic memory of low frequency events, for therapeutic or other applications such as studying neural circuits.

Materials and Methods

RTC Counter Plasmid Construction

RTC Counter plasmids were constructed using basic molecular cloning techniques (J. Sambrook et al., Molecular Cloning: A Laboratory Manual, (Cold Spring Harbor Laboratory Press, Plainview, N.Y., edn. 2, 1989). New England Biolab's restriction endonucleases, T4 DNA Ligase, and Taq Polymerase were used as well as Invitrogen's PCR SuperMix High Fidelity. PCRs were carried out with an MJ Research PTC-200 Peltier Thermal Cycler. Synthetic oligonucleotides were made by Integrated DNA Technologies. For cloning, plasmids were transformed into $E.$ $coli$ strain DH5α (F⁻ φ80lacZΔM15 Δ(lacZYA-argF)U169 deoR recA1 endA1 hsdR17($r_k^-$, $m_k^+$)phoA supE44 thi-1 gyrA96 relA1λ⁻) with a standard heat shock protocol (Ibid.), and isolated with Qiagen QIAprep Spin Miniprep Kits. Plasmid modifications were confirmed by restriction digests and sequencing by Agencourt.

RTC Counter Plasmid Design

Two plasmids—the RTC 2-Counter and RTC 3-Counter—were made, both derived from the riboregulator vector pZER21Y12α12G reported by Isaacs et al. (F. J. Isaacs et al., Nat Biotechnol 22, 841 (2004)), itself based strongly on the Lutz and Bujard pZE21 expression vector (R. Lutz, H. Bujard, Nucleic Acids Res 25, 1203 (1997)). These contain kanamycin resistance, ColE1 origin of replication, the $P_{BAD}$ promoter driving transcription of taRNA version taR12 (F. J. Isaacs et al., Nat Biotechnol 22, 841 (2004)), and the $P_{LtetO-1}$ promoter. Both constructs were modified to have the $P_{LtetO-1}$ promoter driving transcription of T7 RNA polymerase (NCBI Accession NC_001604.1). For the RTC 2-Counter construct, there is also the T7 promoter (SEQ ID NO: 136 TAATAC-GACTCACTATAGGGAGA) driving transcription of GFPmut3b (B. P. Cormack, R. H. Valdivia, S. Falkow, Gene 173, 33 (1996)); for the RTC 3-Counter construct, the T7 promoter drives transcription of T3 RNA polymerase (NCBI Accession NC_003298.1). The RTC 3-Counter additionally contains the T3 promoter 14.3m (SEQ ID NO: 150 ATTAAC-CCTCACTAAAGGGAGA) (D. Sengupta, D. Chakravarti, U. Maitra, J Biol Chem 264, 14246 (1989)), which drives transcription of GFPmut3b. All genes used in these constructs were engineered with the crR12 cis-repressor sequence upstream of the RBS (F. J. Isaacs et al., Nat Biotechnol 22, 841 (2004)). All promoters were paired with appropriate transcription terminators: $P_{BAD}$ with the $E.$ $coli$ rrnB terminator, $P_{LtetO-1}$ with the $E.$ $coli$ terminator T1 (of the rrnB terminator), $P_{T7}$ with T7 transcription terminator Tphi, and $P_{T3}$ with T3 transcription terminator Tphi.

RTC Counter Experimental Conditions

All experiments were conducted with the $E.$ $coli$ K-12pro strain (F⁺, $P_{N25}$/tetR, $P_{laciq}$/lacI, Sp^r). For both the RTC 2-Counter and 3-Counter experiments, cells containing the counting vector were grown overnight in a Luria-Bertani (DIFCO) medium containing 30 μg/mL kanamycin, then diluted 1:100 and grown between 5 and 6.5 hours to an OD between 1.1 and 1.6 before being aliquoted into clear-bottom 24-well assay plates, 1 mL per well. For the 2-Counter, cells pulsed with arabinose had arabinose added to their wells for a final concentration of 0.001% at 0 minutes (immediately following the aliquot) and/or at 50 minutes. Pulses were left in the media for 10 minutes before cells were transferred into 1.5 mL tubes and spun for 1 minute at 8,000 rpm. Media was aspirated out of these tubes, and cells were resuspended in fresh media and transferred back to the plate. The 3-Counter experiments had 0.01% (final concentration) arabinose pulses delivered at varying times. All cells in 24-well plates were maintained at 37° C. throughout the course of the experiments, with shaking in between measurements. Experiments were performed in triplicate, and all data points shown are the mean values of these replicates.

RTC Counter Flow Cytometer Measurements

Data were collected with a Becton Dickinson FACSCalibur flow cytometer. Fluorescence was calibrated with Calibrite Beads (Becton Dickinson) and measured with a 488-nm argon laser excitation and a 515-nm to 545-nm emission filter. At each time point, 8 μL of cells were taken from the plate wells and diluted into 1 mL of filtered PBS, pH 7.2. Mean fluorescence measurements were calculated by BD Biosciences' Cellquest Pro software, from samples containing at least 100,000 cells. No filters or gates were used on the cell populations.

RTC Counter Spectrophotometer Measurements

Data was collected with a Tecan SPECTRAFluor Plus spectrophotometer. Excitation and emission wavelengths were 485 nm and 535 nm, respectively, with a fixed gain set at 40.

RTC Counter Mathematical Modeling

Mathematical modeling was used to verify the logic-based predictions of our design, to investigate the effects of pulse frequency and pulse length on the performance of the RTC counters, and to explore the possibility of counting to higher numbers. We used ordinary differential equations (ODE) to describe the temporal trajectories of population averages for all biochemical species. Stochastic modeling was not included because of the population homogeneity. Details for the modeling of each of the two constructs are described herein.

The RTC 2-Counter Model

Based on the design of the RTC 2-Counter, we approximated the system dynamics using the following biochemical reactions described below, where Eqs. (1)-(3) represent the synthesis and degradation of trans-activator (taRNA), T7 RNA polymerase transcripts in cis-repressed form (mT7cr), and GFP transcripts in cis-repressed form (mGFPcr), respectively. Transcripts in cis-repressed form are indicated by "cr". Kinetic parameters are as indicated in the equations. Eqs. (4) and (5) represent the binding of taRNA with mT7cr and mGFPcr so that the transcripts can be translated; these repression-relieved transcripts are denoted as mT7 and mGFP. Eqs. (6) and (7) represent the translations of mT7 and mGFP, respectively, with pT7 and pGFP as notations for these two proteins. Finally, Eqs. (8) and (9) represent the degradation of proteins. These biochemical reactions were sufficient to describe the system dynamics with high accuracy

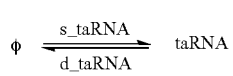
(1)

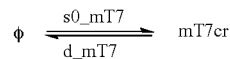
(2)

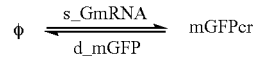
(3)

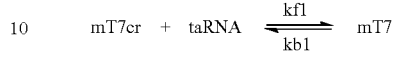
(4)

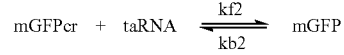
(5)

(6)

(7)

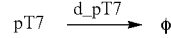
(8)

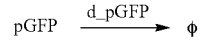
(9)

Based on these reactions, we wrote down the differential equations that describe the temporal evolution of all the species. Some of the parameters in the biochemical reactions are lumped parameters that are expanded to their explicit forms in the differential equations. The notations for all chemical species in this model (and the RTC 3-Counter model) are simplified and listed in Table 74, with all parameter values listed in Table 75. The square brackets in these equations indicate chemical species concentration. Because the fluorescence data to which we directly fit the model (see below for details) have arbitrary units, GFP protein concentrations in the model are considered nondimensional. All other parameter values, except for degradation rates (min$^{-1}$) and k_ara (concentration), are nondimensional as well.

The following five equations were used to capture the temporal dynamics of the system, $$\frac{d[taRNA]}{dt} = sT \cdot \frac{[ara]}{[ara] + k\_ara} + s0\_taRNA - d\_taRNA \cdot [taRNA] \quad (10)$$

$$\frac{d[mT7cr]}{dt} = s0\_mT7cr - d\_mT7cr \cdot [mT7cr] \quad (11)$$

$$\frac{d[pT7]}{dt} = s_0\_pT7 \cdot [mT7cr] + s\_pT7k \cdot [taRNA] \cdot [mT7cr] - d\_pt7 \cdot [pT7] \quad (12)$$

$$\frac{d[mGFPcr]}{dt} = s0\_mGFPcr + k\_PT7 \cdot \frac{[pT7]^n}{km7^n + [pT7]^n} - d\_mGFP \cdot [mGFPcr] \quad (13)$$

$$\frac{d[pGFP]}{dt} = s_0\_pGFP \cdot [mGFPcr] + s\_pGFPk \cdot [taRNA] \cdot [mGFPcr] - d\_pGFP \cdot [pGFP] \quad (14)$$

where on the right-hand side of Eq. (10), taRNA synthesis rate has two parts: the first part (s$_0$_taRNA) represents the basal production rate without any induction, and the second part (sT*ara/(ara+kara)) represents the synthesis rate induced by arabinose. To simplify the system, we assumed that the arabinose induction effect has a Hill function form with a Hill coefficient equal to 1. The third term of Eq. (10) represents taRNA degradation using a simple exponential decay with rate d_taRNA. In Eq. (11), cis-repressed T7 RNA polymerase transcripts (mT7cr) are constitutively expressed, with a constant production rate (s0_mT7cr) and exponential decay. Similarly, in Eq. (12), T7 RNA polymerase protein synthesis rate has two parts: $s_{0\_}pT7*mT7cr$ represents the translation rate of mT7cr without taRNA binding, and $s\_pT7k*taRNA*mT7cr$ represents the translation rate of mT7cr with taRNA binding. Here we assumed that taRNA binding and dissociation with mRNA [Eqs. (4) and (5)] have a much faster time scale than other reactions and reach equilibrium instantly. Thus, the parameter s_pT7k, for example, is also a lumped parameter with information about the binding reaction in Eq. (4) included. In Eq. (13), GFP mRNA synthesis depends on the basal transcription rate and on T7 RNA polymerase protein abundance. We used a general Hill function to describe this dependency: $k\_pT7*pT7^n/(pT7^n+km7^n)$, where n accounts for any type of cooperativity caused by T7 RNA polymerase activation. In Eq. (14), GFP protein dynamics parallel that of the T7 RNA polymerase protein in Eq. (12)

Extension to the RTC 3-Counter

The RTC 3-Counter construct is similar to the RTC 2-Counter in design and topology, and they have a number of components in common. So for the RTC 3-Counter model we used many of the same equations used for the RTC 2-Counter model. Besides the reactions in Eqs. (1)-(9), there are four additional reactions, where Eq. (10) represents the synthesis and degradation of cis-repressed T3 RNA polymerase transcripts (mT3cr) and Eq. (11) represents the binding of taRNA with mT3cr. Eqs. (12) and (13) represent translation and degradation of T3 RNA polymerase protein, respectively.

$$\phi \underset{d\_mT3}{\overset{s\ T3mRNA}{\rightleftarrows}} mT3cr \tag{15}$$

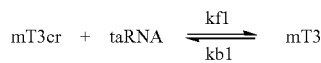

$$mT3 \xrightarrow{sT3} mT3 + pT3 \tag{17}$$

$$pT3 \xrightarrow{d\_pT3} \phi \tag{18}$$

The differential equations describing the RTC 3-Counter construct are similar to the RTC 2-Counter differential equations, except Eq. (13) changes to:

$$\frac{d[mGFPcr]}{dt} = s0\_mGFPcr + k\_pT3 \cdot \frac{[pT3]^n}{km3^n + [pT3]^n} - d\_mGFP \cdot [mGFPcr] \tag{19}$$

and the following two equations are added:

$$\frac{d[mT3cr]}{dt} = s0\_mT3cr + k\_pT7 \cdot \frac{[pT7]^n}{km7^n + [pT7]^n} - d\_mT3 \cdot [mT3cr] \tag{20}$$

$$\frac{d[pT3]}{dt} = s_{0\_}pT3 \cdot [mT3cr] + s\_pT3k \cdot [taRNA] \cdot [mT3cr] - d\_pT3 \cdot [mT3cr] \tag{21}$$

Eqs. (20) and (21) describe the change of T3 RNA polymerase transcripts and proteins over time. They have the same forms as Eqs. (13) and (14), respectively, with similar parameter implications.

RTC Counter Arabinose Induction

Different counter strains were induced by different numbers of external arabinose pulses to test and verify the counting behavior. To account for the arabinose pulse dynamics, we modeled it with two differential equations. The first equation describes arabinose when it is present in the medium:

$$\frac{d[ara]}{dt} = -cAra \tag{22}$$

This represents a constant consumption rate of arabinose, when it is present in abundance. The second equation describes arabinose after the cells have been spun and resuspended in arabinose-free media. The leftover, mainly intracellular arabinose is modeled as an exponentially decaying chemical species:

$$\frac{d[ara]}{dt} = -dAra \cdot [ara] \tag{23}$$

In the simulations, Eqs. (22) and (23) were used alternately so as to be consistent with actual experimental conditions.

RTC Counter Fitting of Experimental Data

Matlab function lsqcurvefit was used to narrow down the model parameters by fitting the model equations to experimental measurements. The parameter set that resulted in the most optimal data fitting among two hundred runs was chosen, with fluorescence levels of uninduced samples subtracted from all other experimental data. Parameters values used for these figures are listed in Table 75. The experimental arabinose doses used in the RTC 3-Counter experiments were ten-fold higher than those in the RTC 2-Counter experiments; thus parameters k_ara and cAra were adjusted ten-fold higher (as written in Table 75) for the RTC 3-Counter model to match the experimental results.

DIC Counter Plasmid Construction

DIC Counter plasmids were constructed using basic molecular cloning techniques (S1). New England Biolab's restriction endonucleases, T4 DNA Ligase, and NEB's Phusion PCR kits were used. PCRs were carried out with an MJ Research PTC-200 Peltier Thermal Cycler. Synthetic oligonucleotides were made by Integrated DNA Technologies. Single-inducer DIC Counter plasmids were transformed into *E. coli* strain DH5α (F⁻ φ80lacZΔM15 Δ(lacZYA-argF)U169 deoR recA1 endA1 hsdR17($r_k^-$, $m_k^+$) phoA supE44 thi-1 gyrA96 relA1 λ⁻). Multiple-inducer DIC Counter plasmids were transformed into *E. coli* strain DH5αPRO (F⁻ φ80lacZΔM15 Δ(lacZYA-argF)U169 deoR recA1 endA1 hsdR17($r_k^-$, $m_k^+$) phoA supE44 thi-1 gyrA96 relA1 λ⁻, $P_{N25}$/tetR, $P_{lacIq}$/lacI, Sp$^r$). Transformations were carried out using standard electroporationprotocols (J. Sambrook et al., Molecular Cloning: A Laboratory Manual, (Cold Spring Harbor Laboratory Press, Plainview, N.Y., edn. 2, 1989)) and isolated with Qiagen QIAprep Spin Miniprep Kits. Plasmid modifications were confirmed by restriction digests.

DIC Counter Plasmid Design

The single-inducer DIC 2-Counter (FIG. 4) and 3-Counter (FIG. 5) and multiple-inducer DIC 3-Counter (FIG. 8) were based off of the single-copy pBAC platform (D. A. Wright et al., Nat Protoc 1, 1637 (2006)). pBAC-lacZ (Addgene plasmid 13422) was obtained from Addgene (Cambridge, Mass.). We cloned all components for the DIC Counters in between ScaI and PciI restriction sites in pBAC-lacZ. Custom sequences, including recombinase recognition sites, were constructed using sequential PCR with DNA obtained from Integrated DNA Technologies (Coralville, Iowa). Promoters $P_{LtetO-1}$ and $P_{A1lacO}$ and terminators were obtained from R. Lutz, H. Bujard, Nucleic Acids Res 25, 1203 (1997), while $P_{BAD}$ was obtained from F. J. Isaacs et al., Nat Biotechnol 22, 841 (2004). The cre gene was obtained from A. Levskaya et al., Nature 438, 441 (2005). The $flp_e$ gene was derived from pCAG-Flpe (Addgene plasmid 13787) and based off of F. Buchholz et al., Nature biotechnology 16, 657 (July, 1998). The ribosome-binding sequences used in each stage were derived from S. Basu et al., Proc Natl Acad Sci USA 101, 6355 (2004), while ssrA-based degradation tags were designed according to J. B. Andersen et al., Appl Environ Microbiol 64, 2240 (June, 1998).

DIC Counter Experimental Conditions

All experiments were performed in Luria-Bertani media containing 30 µg/mL kanamycin. Prior to performing flow cytometer measurements on the DIC Counters, cells were grown overnight. To initiate experiments, cells were diluted 1:2000 in fresh media and grown at 37° C. and 300 rpm with inducers as indicated in the specific figures. Inducer concentrations were anhydrotetracycline=700 ng/mL, arabinose=0.1%, and IPTG=10 mM except for FIG. 2B in which anhydrotetracycline=100 ng/mL, arabinose=$10^{-3}$%, and IPTG=10 mM. At all inducer transitions (i.e., transitions from media with inducer to media without inducer, transitions from media without inducer to media with inducer, or transitions from media with one inducer to media with another inducer), cells were diluted 1:2000 in fresh media. Only in FIG. 1C with pulse intervals 2 h and 4 h were cells not diluted 1:2000 in fresh media for transitions from media without inducer to media with inducer due to low optical density of the cultures. Instead, inducer was added directly into the media; however, cells were still diluted 1:2000 in fresh media for transitions from media with inducer to media without inducer.

DIC Counter Flow Cytometer Measurements

Data for FIGS. 1, 2, 6, 7, and 9 were collected with a Becton Dickinson FACSCalibur flow cytometer. Fluorescence was calibrated with Calibrite Beads (Becton Dickinson) and measured with a 488-nm argon laser excitation and a 515-nm to 545-nm emission filter. Before analysis, cells were diluted in sterile phosphate-buffered saline. Becton Dickinson Calibrite Beads were used for instrument calibration. 50,000 cells were collected for each sample, gated to ensure consistency between samples, and processed with MATLAB to calculate mean fluorescence data points (Mathworks, Natick, Mass.).

RTC Counter Characteristics and Improvements

Whole Population Measurements

To verify the counting behavior, we also analyzed the RTC 2-Counter and the RTC 3-Counter with a spectrophotometer, which measures the total fluorescence in a given cell population. These spectrophotometer results corroborate the data from the flow cytometer. In the case of the RTC 2-Counter, the uninduced population similarly shows no increase in fluorescence, while populations that received either the first or the second arabinose pulse exhibit only some fluorescence. Cells that receive both pulses show a striking increase in fluorescence at 50 minutes, validating our design. The spectrophotometer measurements of the RTC 3-Counter reveal a similar corroboration, in which only cells that are pulsed three times respond with sharp increases in fluorescence.

Flow cytometer and spectrophotometer data sets do diverge qualitatively, where flow cytometer measurements exhibit a peak in fluorescence and then decrease whereas spectrophotometer measurements exhibit a fluorescence plateau. The decrease is likely due to external factors such as cell division (J. Roostalu et al., BMC Microbiol. 8, 68 (2008)), and is revealed in single-cell measurements of the flow cytometer. This effect is not seen in the spectrophotometer, where measurements are made on whole populations. Data presented are the mean of three replicates, and smoothed with a rolling window average.

Flow Cytometry Population Analysis

The data presented are mean fluorescence values of RTC counter cell populations, measured by a flow cytometer. We show the fluorescence profile of the entire RTC 3-Counter population when it is uninduced, after the second pulse, and after the third pulse. It is clear that the entire population shifts homogeneously following induction, with the greatest shift occurring as a result of the third pulse.

Verification of Discrete Counting

To verify that the counting response is driven by discrete induction pulses and not simply a summation of induction length, we took a fixed total length of induction and split it into two and three pulses. RTC 3-Counter cells were either given two short pulses followed by a long pulse or two long pulses, with total induction time equal for both sets of cells. It can be seen in that cells receiving three pulses (dark) generate significantly more GFP than cells receiving two pulses (light), demonstrating a true counting mechanism and not simply a summing effect. This supports our claim that the counter is able to distinguish between different numbers of pulses, even when total induction time is held constant. Additionally, our mathematical model accurately predicted the experimental results for both scenarios.

Higher Number Counters

Figure 10A:
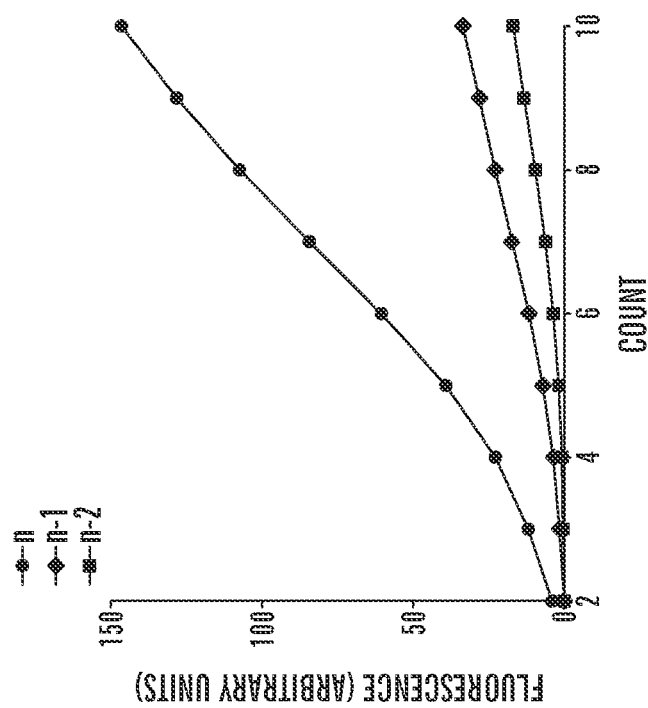
In FIG. 10A, the numbers on the x-axis represent counters with n nodes, and for each counter the fluorescence output was plotted due to n, n−1, and n−2 pulses. The best-fit parameter values are used in this figure, the same as those used for FIG. 2.

To investigate the possibility of expanding our design to count higher numbers, we expanded our system using mathematical modeling. We added extra genes to the cascade, each one an RNA polymerase whose downstream promoter regulates the transcription of the gene at the next node. We modeled cascades with up to ten nodes; in each case the first node is T7 RNA polymerase, the last node is GFP, and all nodes in between are polymerases with exactly the same kinetic properties as T3 RNA polymerase. With two additional differential equations for each node, we use mathematical modeling to predict the behavior of these higher number counters by comparing the fluorescence readout of n, n−1, and n−2 arabinose pulses for each n-node counter. As shown in FIG. 10A, the top line is the fluorescence result of n pulses, the middle line of n−1 pulses, and the bottom line n−2 pulses. It can be seen that the absolute difference in fluorescence levels between n and n−1 pulses increases with cascade length, suggesting the design can better distinguish different numbers of pulses as it is extended. Additionally, all three lines increase as the construct is extended, due to signal propagation and the accumulation of long-lived proteins as more pulses are delivered.

Figure 10B:
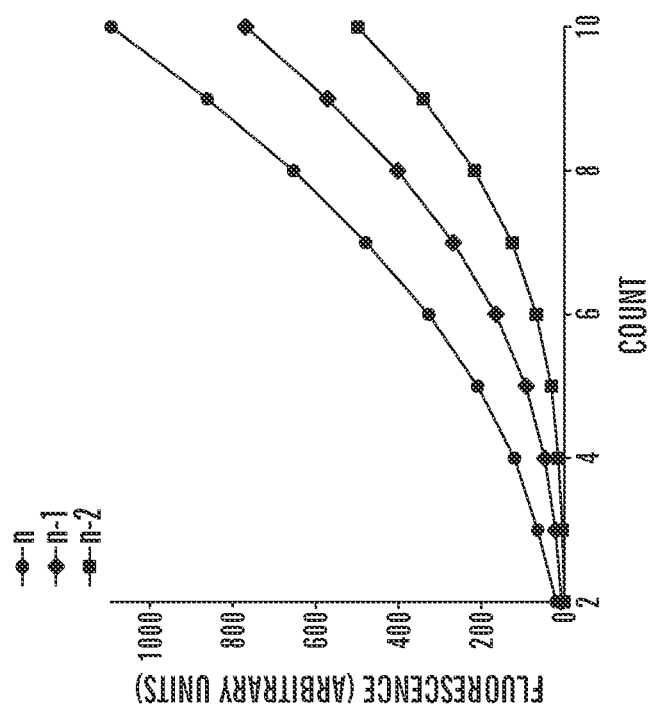
FIG. 10B is similar to FIG. 10A, except that the GFP protein half-life has been reduced from 231 minutes to 8 minutes.

This predicted accumulation effect results in the failure of this system to perform digitally as n increases, with ones and zeros no longer represented by high and low protein concentrations. However, by examining the temporal dynamics of all the chemical species in the cascades, we identified that it is the long half-life of GFP protein that causes the signal increase after n−1 and n−2 pulses. FIG. 10B is the predicted counter output in which GFP protein has its half-life shortened to 8 minutes instead of the 231 minute half life used for FIG. 10A. FIG. 10B illustrates that when the final output protein has a shortened half-life, the counter performance is remarkably robust as n increases. Counting from 2 to 10, output from n pulses increases almost exponentially while output from n−1 and n−2 pulses increases only marginally.

In some embodiments, if shortening the final protein's half-life is not possible or desirable, an alternative method for digitizing the output signal would be to couple the counter to a toggle switch (S. Basu et al., Proc Natl Acad Sci USA 101, 6355 (2004)). By placing one of the toggle repressor proteins at the final node of the counter cascade, it would be possible to flip a toggle from one state to the other with expression from the counter. The sharp and tunable switching threshold of a toggle switch may be used to filter out counter leakage due to n−1 or n−2 pulses, switching states only when n pulses produces a concentration of repressor proteins in excess of the switching threshold.

Extending the DIC Counter

Each of our individual counting units requires only a single recombinase whereas the protein-based toggle switch utilizes two proteins (T. S. Gardner et al., Nature 403, 339 (2000)). This allows our design to be extendable in a modular fashion using >100 identified recombinases to count to higher numbers (A. C. Groth, M. P. Calos, J Mol Biol 335, 667 (2004)). Recombinases can also be mutagenized to have altered site preferences or thermostabilities, allowing for increased diversity to create synthetic gene circuits. The availability of additional recombinases enables the DIC counter to be extended more readily than other systems that require rarer or more specialized components.

RTC and DIC Counter Designs: Further Embodiments

Compared to electronic counters, our biological counters are in an early stage of development. Our counters scale linearly instead of exponentially as is the case with digital electronic circuits that count in binary (P. Horowitz, W. Hill, The Art of Electronics. (Cambridge University Press, Cambridge, United Kingdom, ed. 2nd, 1989)). Counter designs which count in binary require the addition of bit reset and carry operations (Ibid.). The DIC counter is amenable to being adapted with advanced digital designs due to the ability of SIMMs to maintain memory and invert in both orientations. Reset operations could be carried out by downstream promoters which drive the transition of inverted SIMMs back to their original orientations. Carry operations could be achieved by components that act in trans to affect DNA orientation, insertions, or deletions on many different SIMMs or DIC counters; these trans-based components may include bacteriophage integrases and excisionases (A. C. Groth, M. P. Calos, J Mol Biol 335, 667 (2004)) or transcriptional activators. The development of biological counters with exponential scaling greatly expands the potential applications of biological counters.

Though there will invariably be upper limits to pulse frequencies that can be detected by counters, such as those described herein, those limits can be improved by combining synthetic counters with pulse-generating circuits that can detect edge transitions with greater rapidity (E. A. Davidson, A. D. Ellington, Trends Biotechnol 23, 109 (2005)) and/or with amplifiers that can enhance the magnitude of inputs. Pulse-generating circuits (Ibid.) can also enable the RTC counter and the single-inducer DIC counter to record low-frequency events with greater fidelity.

TABLE 74

A summary of chemical species represented in the RTC Counter model and their notations.

| Notation | Chemical species |
|---|---|
| taRNA | trans-activator |
| mT7cr | cis-repressed T7 RNA polymerase mRNA |
| mT7 | T7 RNA polymerase mRNA |
| pT7 | T7 RNA polymerase protein |
| mGFPcr | cis-repressed GFP mRNA |
| mGFP | GFP mRNA |
| pGFP | GFP protein |
| mT3cr | cis-repressed T3 RNA polymerase mRNA |
| mT3 | T3 RNA polymerase mRNA |
| pT3 | T3 RNA polymerase protein |
| ara | Arabinose |

TABLE 75

A list of all parameter values used in the RTC Counter models

| | |
|---|---|
| k_ara* | 0.0571 |
| s0_taRNA | 0.0008 |
| d_taRNA | 0.1177 |
| s0_mT7cr | 0.0252 |
| d_mT7 | 0.0706 |
| k_pT7 | 3.8009 |
| s0_mGFPcr | 0.0123 |
| d_mGFP | 0.07 |
| s_pT7k | 0.0766 |
| d_pT7 | 0.0056 |
| s_pGFPk | 0.9923 |
| d_pGFP | 0.003 |
| dAra | 0.1201 |
| s0_pT7 | 0.0003 |
| s0_pGFP | 0.1007 |
| sT | 0.8467 |
| cAra* | 0.0003 |
| n7 | 2.602 |
| km7 | 3.0455 |
| k_pT3 | 3.006 |
| s0_mT3cr | 0.0003 |
| d_mT3 | 0.0701 |
| s0_pT3 | 0 |
| s_pT3k | 0.0115 |
| d_pT3 | 0.0069 |
| n3 | 0.8892 |
| km3 | 7.9075 |

We claim:

1. A single invertase memory module (SIMM) engineered nucleic acid molecule comprising a nucleic acid sequence encoding: a forward recombinase recognition site (RRS$_{for}$), an inverted promoter sequence (iP$_{inv}$), a recombinase sequence (RC) and a reverse recombinase recognition site (RRS$_{rev}$), [RRS$_{for}$ - iP$_{inv}$ -RC -RRS$_{rev}$], where the recombinase encoded by the recombinase sequence is specific for the forward and reverse recombination recognition sites.

2. The single invertase memory module engineered nucleic acid molecule of claim 1, further comprising a nucleic acid sequence encoding a ribosome binding site (RBS).

3. The single invertase memory module engineered nucleic acid molecule of claim 1, further comprising a nucleic acid sequence encoding a transcriptional terminator sequence (T).

4. The single invertase memory module engineered nucleic acid molecule of claim 1, further comprising a nucleic acid sequence encoding a protein degradation tag sequence (D).

5. The single invertase memory module engineered nucleic acid molecule of claim 1, further comprising a nucleic acid sequence encoding a ribosome binding site (RBS) and a transcriptional terminator sequence (T).

6. The single invertase memory module engineered nucleic acid molecule of claim 1, further comprising a nucleic acid sequence encoding a ribosome binding site (RBS) and a protein degradation tag sequence (D).

7. The single invertase memory module engineered nucleic acid molecule of claim 1, further comprising a nucleic acid sequence encoding a protein degradation tag sequence (D) and a transcriptional terminator sequence (T).

8. The single invertase memory module engineered nucleic acid molecule of claim 1, further comprising an output nucleic acid sequence encoding an output product.

9. The single invertase memory module engineered nucleic acid molecule of claim 8, wherein the output product is a reporter protein, a transcriptional repressor, a transcriptional activator, a selection marker, an enzyme, a receptor protein, a ligand protein, an RNA, a riboswitch or a short-hairpin RNA.

10. An inducer engineered genetic counter nucleic acid molecule comprising a nucleic acid sequence encoding: an inducible promoter sequence ($iP_A$), at least one single invertase memory module (SIMM), and an output product (OP), where the SIMM comprises a nucleic acid sequence encoding: a forward recombinase recognition sequence ($RRS_{for}$), an inverted inducible promoter sequence ($iP_{1,inv}$), a ribosome binding site (RBS), a recombinase gene sequence (RC), a degradation tag sequence (D), a transcriptional terminator sequence (T), and a reverse recombinase recognition sequence ($RRS_{rev}$), such that the inducer engineered genetic counter nucleic acid molecule comprises a nucleic acid sequence encoding the following components:

$iP_A$-[$RRS_{1,for}$- $iP_{1,inv}$-RBS-$RC_1$-D-T-$RRS_{1,rev}$]$_n$-OP, wherein $iP_A$ and the $iP_1$ of each SIMM are responsive to the same inducer, wherein the recombinase encoded by each at least one SIMM is specific for the forward and reverse recombinase recognition site of that SIMM, and wherein n is an integer value ≥1.

11. The inducer engineered genetic counter nucleic acid molecule of claim 10, wherein the recombinase encoded by each at least one SIMM is a different recombinase from each other SIMM.

12. The inducer engineered genetic counter nucleic acid molecule of claim 10, further comprising an inverted promoter nucleic acid sequence downstream of the reverse recombination recognition site of at least one SIMM.

13. The inducer engineered genetic counter nucleic acid molecule of claim 10, further comprising an output nucleic acid sequence encoding an output product downstream of the recombinase sequence of at least one SIMM.

14. The inducer engineered genetic counter nucleic acid molecule of claim 10, further comprising an inverted output nucleic acid sequence encoding an output product downstream of the transcriptional terminator sequence of at least one SIMM.

15. The inducer engineered genetic counter nucleic acid molecule of claim 10, wherein the output product encoded by the output nucleic acid sequence is a reporter protein, a transcriptional repressor, a transcriptional activator, a selection marker, an enzyme, a receptor protein, a ligand protein, an RNA, a riboswitch or a short-hairpin RNA.

16. The inducer engineered genetic counter nucleic acid molecule of claim 10, further comprising an RBS nucleic acid sequence upstream of the output nucleic acid sequence.

17. The inducer engineered genetic counter nucleic acid molecule of claim 10, wherein n is an integer value selected from the group consisting of 1, 2, 3, 4, 5, 6, 7, 8, 9, 10, 11, 12, 13, 14, 15, 16, 17, 18, 19, and 20.

18. The inducer engineered genetic counter nucleic acid molecule of claim 10, further comprising a nucleic acid sequence encoding at least two SIMMs, where each one of the at least two SIMMs comprises a nucleic acid sequence encoding: a forward recombinase recognition sequence ($RRS_{for}$), an inverted inducible promoter sequence ($iP_{inv}$), a ribosome binding site (RBS), a recombinase gene sequence (RC), a degradation tag sequence (D), a transcriptional terminator sequence (T), and a reverse recombinase recognition sequence ($RRS_{rev}$), such that the inducer engineered genetic counter nucleic acid molecule comprises a nucleic acid sequence encoding the following components:

$iP_A$-[$RRS_{1,for}$-$iP_{inv}$-RBS-$RC_1$-D-T-$RRS_{1,rev}$]$_n$-OP, and wherein $iP_A$ and the $iP_1$ of the at least two SIMMs are each responsive to a different inducer from each other, wherein the recombinase encoded by each at least two SIMMs is specific for the forward and reverse recombinase recognition site of that SIMMs, and wherein n is an integer value ≥1.

19. The inducer engineered genetic counter nucleic acid molecule of claim 18, wherein the recombinase encoded by each at least two SIMMs is a different recombinase from each other SIMM.

20. The inducer engineered genetic counter nucleic acid molecule of claim 18, further comprising an inverted promoter nucleic acid sequence downstream of the reverse recombination recognition site of at least one SIMM.

21. The inducer engineered genetic counter nucleic acid molecule of claim 18, further comprising an output nucleic acid sequence encoding an output product downstream of the recombinase sequence of at least one SIMM.

22. The inducer engineered genetic counter nucleic acid molecule of claim 18, further comprising an inverted output nucleic acid sequence encoding an output product downstream of the transcriptional terminator sequence of at least one SIMM.

23. A method for counting at least one event in a cellular system comprising introducing the inducer engineered genetic counter nucleic acid molecule of claim 10 into a cellular or non-cellular system for use in counting events in the cellular or non-cellular system.

24. The method of claim 23, wherein the inducer engineered genetic counter nucleic acid molecule is introduced into the cellular or non-cellular system using a vector.

25. A single-inducer engineered genetic counter nucleic acid molecule comprising a nucleic acid sequence encoding: an inducible promoter sequence ($iP_A$), one single invertase memory module (SIMM), and an output product (OP), where the SIMM comprises a nucleic acid sequence encoding: a forward recombinase recognition sequence ($RRS_{for}$), an inverted inducible promoter sequence ($iP_{1,inv}$), a ribosome binding site (RBS), a recombinase gene sequence (RC), a degradation tag sequence (D), a transcriptional terminator sequence (T), and a reverse recombinase recognition sequence ($RRS_{rev}$), such that the single-inducer engineered genetic counter nucleic acid molecule comprises a nucleic acid sequence encoding the following components:

$iP_A$-[$RRS_{1,for}$-$iP_{1,inv}$-RBS-$RC_1$-D-T-$RRS_{1,rev}$]-OP,
wherein $iP_A$ and $iP_1$ are responsive to the same inducer, and wherein the recombinase encoded by the SIMM is specific for the forward and reverse recombinase recognition site of the SIMM.

26. A single-inducer engineered genetic counter nucleic acid molecule comprising a nucleic acid sequence encoding: an inducible promoter sequence ($iP_A$), two single invertase memory modules (SIMMs), and an output product (OP), where each SIMM comprises a nucleic acid sequence encoding: a forward recombinase recognition sequence ($RRS_{for}$), an inverted inducible promoter sequence ($iP_{inv}$), a ribosome binding site (RBS), a recombinase gene sequence (RC), a degradation tag sequence (D), a transcriptional terminator sequence (T), and a reverse recombinase recognition sequence ($RRS_{rev}$), such that the single-inducer engineered genetic counter nucleic acid molecule comprises a nucleic acid sequence encoding the following components:

$iP_A$-[$RRS_{1,for}$-$iP_{1,inv}$-RBS-$RC_1$-D-T-$RRS_{1,rev}$]-[$RRS_{2,for}$-$iP_{1,inv}$-RBS-$RC_2$-D-T-$RRS_{2,rev}$]-OP,
wherein $iP_A$ and $iP_1$ are responsive to the same inducer, and wherein the recombinase encoded by each SIMM is specific for the forward and reverse recombinase recognition site of that SIMM.

27. A multiple-inducer engineered genetic counter nucleic acid molecule comprising a nucleic acid sequence encoding: an inducible promoter sequence ($iP_A$), one single invertase memory module (SIMM), and an output product (OP), where the SIMM comprises a nucleic acid sequence encoding: a forward recombinase recognition sequence ($RRS_{for}$), an inverted inducible promoter sequence ($iP_{1,inv}$), a ribosome binding site (RBS), a recombinase gene sequence (RC), a degradation tag sequence (D), a transcriptional terminator sequence (T), and a reverse recombinase recognition sequence ($RRS_{rev}$), such that the multiple-inducer engineered genetic counter nucleic acid molecule comprises a nucleic acid sequence encoding the following components:

$iP_A$-[$RRS_{1,for}$-$iP_{1,inv}$-RBS-$RC_1$-D-T-$RRS_{1,rev}$]-OP,
wherein $iP_A$ and the $iP_1$ of the SIMM are responsive to different inducers from each other, and wherein the recombinase encoded by the SIMM is specific for the forward and reverse recombinase recognition site of the SIMM.

28. A multiple-inducer engineered genetic counter nucleic acid molecule comprising a nucleic acid sequence encoding: an inducible promoter sequence ($iP_A$), two single invertase memory modules (SIMMs), and an output product (OP), where each SIMM comprises a nucleic acid sequence encoding: a forward recombinase recognition sequence ($RRS_{for}$), an inverted inducible promoter sequence ($iP_{inv}$), a ribosome binding site (RBS), a recombinase gene sequence (RC), a degradation tag sequence (D), a transcriptional terminator sequence (T), and a reverse recombinase recognition sequence ($RRS_{rev}$), such that the multiple-inducer engineered genetic counter nucleic acid molecule comprises a nucleic acid sequence encoding the following components:

$iP_A$-[$RRS_{1,for}$-$iP_{1,inv}$-RBS-$RC_1$-D-T-$RRS_{1,rev}$]-[$RRS_{2,for}$-$iP_{2,inv}$-RBS-$RC_2$-D-T-$RRS_{2,rev}$] OP,
wherein $iP_A$ and the iP of at least one SIMM are responsive to different inducers from each other, and wherein the recombinase encoded by each SIMM is specific for the forward and reverse recombinase recognition site of that SIMM.

* * * * *

UNITED STATES PATENT AND TRADEMARK OFFICE
CERTIFICATE OF CORRECTION

PATENT NO. : 8,645,115 B2
APPLICATION NO. : 13/141165
DATED : February 4, 2014
INVENTOR(S) : Collins et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 155 days.

Signed and Sealed this

Twenty-ninth Day of September, 2015

Michelle K. Lee
*Director of the United States Patent and Trademark Office*

SEQUENCE LISTING

<160> NUMBER OF SEQ ID NOS: 1004

<210> SEQ ID NO 1
<211> LENGTH: 34
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 1
ataacttcgt atagcataca ttatacgaag ttat                                    34

<210> SEQ ID NO 2
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 2
ataacttcgt ataatgtatg ctatacgaag ttat                                    34

<210> SEQ ID NO 3
<211> LENGTH: 1272
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 3
atgagccaat tgatatatt atgtaaaaca ccacctaagg tcctggttcg tcagtttgtg         60
gaaaggtttg aaagaccttc aggggaaaaa atagcatcat gtgctgctga actaacctat       120
ttatgttgga tgattactca taacggaaca gcaatcaaga gagccacatt catgagctat       180
aatactatca taagcaattc gctgagtttc gatattgtca acaaatcact ccagttttaaa      240 tacaagacgc aaaaagcaac aattctggaa gcctcattaa agaaattaat tcctgcttgg      300
gaatttacaa ttattcctta caatggacaa aaacatcaat ctgatatcac tgatattgta       360
agtagtttgc aattacagtt cgaatcatcg gaagaagcag ataagggaaa tagccacagt      420
aaaaaaatgc ttaaagcact tctaagtgag ggtgaaagca tctgggagat cactgagaaa      480
atactaaatt cgtttgagta tacctcgaga tttacaaaaa caaaaacttt ataccaattc       540
ctcttcctag ctactttcat caattgtgga agattcagcg atattaagaa cgttgatccg      600
aaatcattta aattagtcca aaataagtat ctgggagtaa taatccagtg tttagtgaca       660
gagacaaaga caagcgttag taggcacata tacttcttta gcgcaagggg taggatcgat       720
ccacttgtat atttggatga attttttgagg aactctgaac cagtcctaaa acgagtaaat      780
aggaccggca attcttcaag caacaaacag gaataccaat tattaaaaga taacttagtc       840
agatcgtaca acaaggcttt gaagaaaaat gcgccttatc caatctttgc tataaagaat      900
ggcccaaaat ctcacattgg aagacatttg atgacctcat ttctgtcaat gaagggccta      960
acggagttga ctaatgttgt gggaaattgg agcgataagc gtgcttctgc cgtggccagg     1020
acaacgtata ctcatcagat aacagcaata cctgatcact acttcgcact agtttctcgg     1080
tactatgcat atgatccaat atcaaaggaa atgatagcat tgaaggatga gactaatcca     1140
attgaggagt ggcagcatat agaacagcta aagggtagtg ctgaaggaag catacgatac     1200
cccgcatgga atgggataat atcacaggag gtactagact acctttcatc ctacataaat     1260
agacgcatat aa                                                         1272
```

-continued

```
<210> SEQ ID NO 4
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 4
gaagttccta ttccgaagtt cctattctct agaaagtata ggaacttc                48

<210> SEQ ID NO 5
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5
gaagttccta ttctctagaa agtataggaa cttc                                34

<210> SEQ ID NO 6
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 6
ttgatgaaag aatacgttat tctttcatca a                                   31

<210> SEQ ID NO 7
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7
aatacaagac aattggggcc aaactgtcca tatcat                              36

<210> SEQ ID NO 8
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 8
ctctatgagt caaaatggcc ccaaatgttt catcttttg                           39

<210> SEQ ID NO 9
<211> LENGTH: 603
<212> TYPE: DNA
<213> ORGANISM: Escherichia coli

<400> SEQUENCE: 9
atgaagaata aggctgataa caaaaaaagg aacttcctga cccatagtga aatcgaatca    60
ctccttaaag cagcaaatac cgggcctcat gcagcacgta attattgtct gactttgctt    120
```

```
tgttttattc atggtttccg ggcgagtgaa atttgtcgat tgaggatttc ggatattgat    180
cttaaggcaa agtgtatata tatccatcga ttaaaaaaag gcttttcaac aacgcacccg    240
ctattgaata aagaagttca ggctttaaaa aactggttga gtatccgtac ttcgtacccg    300
catgctgaga gcgagtgggt atttttatca cgtaagggga atccgctttc tcggcaacag    360
ttttaccata ttatctcgac ttccggtggt aatgccgggt tgtcactgga gattcatccg    420
cacatgttac gccattcgtg tggttttgct ttggcgaata tgggaataga tacgcgactt    480
atccaggatt atcttgggca tcgcaatatt cgtcatactg tctggtatac cgccagcaat    540
gcagggcgtt tttacggcat ctgggataga gccagaggac gacagcgtca cgctgtttta    600
tag                                                                   603
```

<210> SEQ ID NO 10
<211> LENGTH: 597
<212> TYPE: DNA
<213> ORGANISM: Escherichia coli

<400> SEQUENCE: 10

```
gtgagtaaac gtcgttatct taccggtaaa gaagttcagg ccatgatgca ggcggtttgt     60
tacggggcaa cgggagccag agattattgt cttattctgt tggcatatcg gcatgggatg    120
cgtattagtg aactgcttga tctgcattat caggaccttg accttaatga aggtagaata    180
aatattcgcc gactgaagaa cggattttct accgttcacc cgttacgttt tgatgagcgt    240
gaagccgtgg aacgctggac ccaggaacgt gctaactgga aaggcgctga ccggactgac    300
gctatattta tttctcgccg cgggagtcgg ctttctcgcc agcaggccta tcgcattatt    360
cgcgatgccg gtattgaagc tggaaccgta acgcagactc atcctcatat gttaaggcat    420
gcttgcggtt atgaattggc ggagcgtggt gcagatactc gtttaattca ggattatctc    480
gggcatcgaa atattcgcca tactgtgcgt tataccgcca gtaatgctgc tcgttttgcc    540
ggattatggg aaagaaataa tctcataaac gaaaaattaa aaagagaaga ggtttga       597
```

<210> SEQ ID NO 11
<211> LENGTH: 912
<212> TYPE: DNA
<213> ORGANISM: Yersina pseudotuberculosis

<400> SEQUENCE: 11

```
atgaccgagt tcagtgcttc actggctcca caggtagagg cttttctccg ttatctcagt     60
attgagcgtc agcttagtcc actgaccgtc accagttatc gccgtcagtt gtctgcgcta    120
atggaaatag gcgaacagat gggcttggct cactggcaga cgctggatgc tgctcaggtc    180
cgttcgttgg tctcccgcag caaacgtgcg ggtttacatg cttcaagcct ggcattacgg    240
ctctccgcat tacgcagttt tctcaactgg ttggtcagcc agggcgtgct gccagccaac    300
cccgctaaag ggtcagtac gccacgctcg ggccgccacc tgccaaaaaa tattgatgtt     360
gatgaagtca ataaactgct gagtattgat ctgaatgatc cgctggcggt acgtgaccgg    420
gccatgctgg aggtgatgta cggcgcgggg ctgcgtttat ctgaattggt tggcatgaac    480
tgtaaacatg tggatctggc gagcggcgat gtctgggtga tggggaaggg cagtaaagag    540
cgcaaggtgc cgttaggtaa aacggcggtg acctggttac agcattggct ggcgttacgt    600
gagttattcg aaccgcaaga tgacgctatt tttctggcca ataccggcaa gcgtatttca    660
gcccgtaatg tgcagaagcg ctttgccgaa tggggggtga agcagggggt cagtagccac    720
attcacccac ataaattacg tcactctttt gccacgcaca tgctggaatc cagtggtgat    780
```

```
ctacgcgcag tacaagagct actgggccat gccaacctga ccaccacgca aatttataca    840
catctcgact ttcaacatct ggcgacagtg tatgatgctg ctcatccacg ggccaaacga    900
ggcaaatcct ga                                                        912
```

```
<210> SEQ ID NO 12
<211> LENGTH: 573
<212> TYPE: DNA
<213> ORGANISM: Salmonella enterica

<400> SEQUENCE: 12
atggctacta ttgggtatat tcgggtgtca acaattgacc aaaatatcga tttacagcgt     60
aatgcgctta ctagtgcaaa ttgtgaccgc attttttgagg accgtatcag tggcaagatt   120
gcaaaccgcc ccggcctgaa acgagcgtta aagtatgtaa ataaaggcga tactcttgtc   180
gtctggaaat tagacagact gggccgcagc gtgaaaaacc tggtggcgtt aatatcagaa   240
ttacatgaac gtggagctca cttccattct ttaaccgata gtattgatac cagtagcgcg   300
atggggcgat tctttttttca tgtaatgtca gcactggccg agatggagcg agaattaatt   360
gtcgagcgaa cccttgccgg actggctgcc gccagagcgc aaggacgact gggagggcgc   420
cctcgggcga tcaacaaaca tgaacaggaa cagattagtc ggctattaga gaaaggccat   480
cctcggcagc aactagctat tattttggt attggcgtat ctaccttata cagatatttt   540
ccggcaagcc gcataaaaaa acgaatgaat taa                                573
```

```
<210> SEQ ID NO 13
<211> LENGTH: 34
<212> TYPE: DNA
<213> ORGANISM: Escherichia coli

<400> SEQUENCE: 13
ataacttcgt atagtataca ttatacgaag ttat                                34
```

```
<210> SEQ ID NO 14
<211> LENGTH: 34
<212> TYPE: DNA
<213> ORGANISM: Escherichia coli

<400> SEQUENCE: 14
acaacttcgt ataatgtatg ctatacgaag ttat                                34
```

```
<210> SEQ ID NO 15
<211> LENGTH: 30
<212> TYPE: DNA
<213> ORGANISM: Escherichia coli

<400> SEQUENCE: 15
cttggtatag catacattat acgaacggta                                     30
```

```
<210> SEQ ID NO 16
<211> LENGTH: 30
<212> TYPE: DNA
<213> ORGANISM: Escherichia coli

<400> SEQUENCE: 16
gttcgtatac gatacattat acgaagttat                                     30
```

```
<210> SEQ ID NO 17
<211> LENGTH: 30
<212> TYPE: DNA
<213> ORGANISM: Escherichia coli
```

<400> SEQUENCE: 17
cttcgtataa tgtatgctat acgaagttat                                    30

<210> SEQ ID NO 18
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 18
gaagttccta ttctctagaa agtataggaa cttc                               34

<210> SEQ ID NO 19
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 19
ctttctagtg caaattgtga ccgcattttg                                    30

<210> SEQ ID NO 20
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 20
ttatcaaaaa ccatggtttt tgataa                                        26

<210> SEQ ID NO 21
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 21
accactttgt acaagaaagc tgggt                                         25

<210> SEQ ID NO 22
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 22
tcactatcag tcaaaataaa atcattattt                                    30

<210> SEQ ID NO 23
<211> LENGTH: 30
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 23
gttcagcttt cttgtacaaa gtggttgatc                                            30

<210> SEQ ID NO 24
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 24
aacacaacat atccagtcac tatggtcgac                                            30

<210> SEQ ID NO 25
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 25
acgaccttcg cattacgaat gcgctgc                                               27

<210> SEQ ID NO 26
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 26
gggacatatt tgggacagaa gtaccaaaaa                                            30

<210> SEQ ID NO 27
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 27
ttcctatact ttttagagaa taggaacttc                                            30

<210> SEQ ID NO 28
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 28
ttcctatact ttctagagaa taggaacttc                                            30
```

```
<210> SEQ ID NO 29
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 29
tcggtgcgca taatgtatat tatgttaaat                                     30

<210> SEQ ID NO 30
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 30
tcatttaaca taatatacat tatgcgcacc                                     30

<210> SEQ ID NO 31
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 31
gaaacatttg gggccaaact gtccatatta                                     30

<210> SEQ ID NO 32
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 32
gagtcaaaat ggcccaatt gtcttgtatt                                      30

<210> SEQ ID NO 33
<211> LENGTH: 84
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 33
gcatgctccc tatcagtgat agagattgac atccctatca gtgatagaga tactgagcac    60
atcagcagga cgcactgacc agga                                           84

<210> SEQ ID NO 34
<211> LENGTH: 286
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 34

```
aagaaaccaa ttgtccatat tgcatcagac attgccgtca ctgcgtcttt tactggctct    60
tctcgctaac caaaccggta accccgctta ttaaaagcat tctgtaacaa agcgggacca   120
aagccatgac aaaaacgcgt aacaaaagtg tctataatca cggcagaaaa gtccacattg   180
attatttgca cggcgtcaca ctttgctatg ccatagcatt tttatccata agattagcgg   240
atcctacctg acgcttttta tcgcaactct ctactgtttc tccata                 286
```

<210> SEQ ID NO 35
<211> LENGTH: 90
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 35

```
ccatcgaatg gctgaaatga gctgttgaca attaatcatc cggctcgtat aatgtgtgga    60
attgtgagcg gataacaatt tcacacagga                                    90
```

<210> SEQ ID NO 36
<211> LENGTH: 74
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 36

```
ataaatgtga gcggataaca ttgacattgt gagcggataa caagatactg agcactcagc    60
aggacgcact gacc                                                     74
```

<210> SEQ ID NO 37
<211> LENGTH: 84
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 37

```
aaaatttatc aaaaagagtg ttgacttgtg agcggataac aatgatactt agattcaatt    60
gtgagcggat aacaatttca caca                                          84
```

<210> SEQ ID NO 38
<211> LENGTH: 102
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 38

```
catagcattt ttatccataa gattagcgga tcctaagctt tacaattgtg agcgctcaca    60
attatgatag attcaattgt gagcggataa caatttcaca ca                     102
```

<210> SEQ ID NO 39
<211> LENGTH: 102

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 39
gcatgcacag ataaccatct gcggtgataa attatctctg gcggtgttga cataaatacc    60
actggcggtt ataatgagca catcagcagg gtatgcaaag ga                     102

<210> SEQ ID NO 40
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 40
gtttatacat aggcgagtac tctgttatgg                                     30

<210> SEQ ID NO 41
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 41
agaggttcca actttcacca taatgaaaca                                     30

<210> SEQ ID NO 42
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 42
taaacaacta acggacaatt ctacctaaca                                     30

<210> SEQ ID NO 43
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 43
acatcaagcc aaattaaaca ggattaacac                                     30

<210> SEQ ID NO 44
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 44
```

```
gaggtaaaat agtcaacacg cacggtgtta                                              30
```

<210> SEQ ID NO 45
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 45

```
caggccggaa taactcccta taatgcgcca                                              30
```

<210> SEQ ID NO 46
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 46

```
ggctagctca gtcctaggta cagtgctagc                                              30
```

<210> SEQ ID NO 47
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 47

```
agctagctca gtcctaggta ttatgctagc                                              30
```

<210> SEQ ID NO 48
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 48

```
agctagctca gtcctaggta ctgtgctagc                                              30
```

<210> SEQ ID NO 49
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 49

```
agctagctca gtcctaggga ttatgctagc                                              30
```

<210> SEQ ID NO 50
<211> LENGTH: 30
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 50
agctagctca gtcctaggta ttgtgctagc                                    30

<210> SEQ ID NO 51
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 51
ggctagctca gtcctaggta ctatgctagc                                    30

<210> SEQ ID NO 52
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 52
ggctagctca gtcctaggta tagtgctagc                                    30

<210> SEQ ID NO 53
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 53
ggctagctca gccctaggta ttatgctagc                                    30

<210> SEQ ID NO 54
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 54
agctagctca gtcctaggta taatgctagc                                    30

<210> SEQ ID NO 55
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 55
agctagctca gtcctaggga ctgtgctagc                                    30

<210> SEQ ID NO 56
<211> LENGTH: 30
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 56
ggctagctca gtcctaggta caatgctagc                                          30

<210> SEQ ID NO 57
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 57
ggctagctca gtcctaggta tagtgctagc                                          30

<210> SEQ ID NO 58
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 58
agctagctca gtcctaggga ttatgctagc                                          30

<210> SEQ ID NO 59
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 59
ggctagctca gtcctaggga ttatgctagc                                          30

<210> SEQ ID NO 60
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 60
ggctagctca gtcctaggta caatgctagc                                          30

<210> SEQ ID NO 61
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 61
agctagctca gcccttggta caatgctagc                                          30
```

<210> SEQ ID NO 62
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 62
agctagctca gtcctaggga ctatgctagc                                    30

<210> SEQ ID NO 63
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 63
agctagctca gtcctaggga ttgtgctagc                                    30

<210> SEQ ID NO 64
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 64
ggctagctca gtcctaggta ttgtgctagc                                    30

<210> SEQ ID NO 65
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 65
agctagctca gtcctaggta taatgctagc                                    30

<210> SEQ ID NO 66
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 66
ggctagctca gtcctaggta ttatgctagc                                    30

<210> SEQ ID NO 67
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 67
ggctagctca gtcctaggta caatgctagc                                      30

<210> SEQ ID NO 68
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 68
aaagtgtgac gccgtgcaaa taatcaatgt                                      30

<210> SEQ ID NO 69
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 69
gacgaatact taaaatcgtc atacttattt                                      30

<210> SEQ ID NO 70
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 70
aaacctttcg cggtatggca tgatagcgcc                                      30

<210> SEQ ID NO 71
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 71
tgatagcgcc cggaagagag tcaattcagg                                      30

<210> SEQ ID NO 72
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 72
ttatttaccg tgacgaacta attgctcgtg                                      30

<210> SEQ ID NO 73
<211> LENGTH: 30
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 73
catacgccgt tatacgttgt ttacgctttg                                      30

<210> SEQ ID NO 74
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 74
ttatgcttcc ggctcgtatg ttgtgtggac                                      30

<210> SEQ ID NO 75
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 75
ttatgcttcc ggctcgtatg gtgtgtggac                                      30

<210> SEQ ID NO 76
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 76
atatatatat atatataatg gaagcgtttt                                      30

<210> SEQ ID NO 77
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 77
atatatatat atatataatg gaagcgtttt                                      30

<210> SEQ ID NO 78
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 78
ccccgaaagc ttaagaatat aattgtaagc                                      30
```

```
<210> SEQ ID NO 79
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 79
ccccgaaagc ttaagaatat aattgtaagc                                         30

<210> SEQ ID NO 80
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 80
tgacaatata tatatatata taatgctagc                                         30

<210> SEQ ID NO 81
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 81
acaatatata tatatatata taatgctagc                                         30

<210> SEQ ID NO 82
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 82
aatatatata tatatatata taatgctagc                                         30

<210> SEQ ID NO 83
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 83
tatatatata tatatatata taatgctagc                                         30

<210> SEQ ID NO 84
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 84
```

```
tatatatata tatatatata taatgctagc                                              30
```

<210> SEQ ID NO 85
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 85

```
aaaaaaaaaa aaaaaaaata taatgctagc                                              30
```

<210> SEQ ID NO 86
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 86

```
aaaaaaaaaa aaaaaaaata taatgctagc                                              30
```

<210> SEQ ID NO 87
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 87

```
caccttcggg tgggcctttc tgcgtttata                                              30
```

<210> SEQ ID NO 88
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 88

```
caccttcggg tgggcctttc tgcgtttata                                              30
```

<210> SEQ ID NO 89
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 89

```
caccttcggg tgggcctttc tgcgtttata                                              30
```

<210> SEQ ID NO 90
<211> LENGTH: 30
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 90
caccttcggg tgggcctttc tgcgtttata                                      30

<210> SEQ ID NO 91
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 91
ggctagctca gtcctaggta cagtgctagc                                      30

<210> SEQ ID NO 92
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 92
tgctagctac tagagattaa agaggagaaa                                      30

<210> SEQ ID NO 93
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 93
cctgttttta tgttattctc tctgtaaagg                                      30

<210> SEQ ID NO 94
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 94
aaatatttgc ttatacaatc ttcctgtttt                                      30

<210> SEQ ID NO 95
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 95
gctgataaac cgatacaatt aaaggctcct                                      30

<210> SEQ ID NO 96
<211> LENGTH: 30
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 96
ctcttctcag cgtcttaatc taagctatcg                                          30

<210> SEQ ID NO 97
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 97
atgagccagt tcttaaaatc gcataaggta                                          30

<210> SEQ ID NO 98
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 98
ctattgattg tgacaaaata aacttattcc                                          30

<210> SEQ ID NO 99
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 99
gtttcgcgct tggtataatc gctggggtc                                           30

<210> SEQ ID NO 100
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 100
ctttgcttct gactataata gtcagggtaa                                          30

<210> SEQ ID NO 101
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 101
aaaccgatac aattaaaggc tcctgctagc                                          30
```

<210> SEQ ID NO 102
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 102
gccggaataa ctccctataa tgcgccacca                                        30

<210> SEQ ID NO 103
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 103
gccggaataa ctccctataa tgcgccacca                                        30

<210> SEQ ID NO 104
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 104
ttgacaagct tttcctcagc tccgtaaact                                        30

<210> SEQ ID NO 105
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 105
ttgacagcta gctcagtcct aggtataatg ctagc                                  35

<210> SEQ ID NO 106
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 106
ttgacggcta gctcagtcct aggtacagtg ctagc                                  35

<210> SEQ ID NO 107
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

```
<400> SEQUENCE: 107
tttacagcta gctcagtcct aggtattatg ctagc                                    35

<210> SEQ ID NO 108
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 108
ttgacagcta gctcagtcct aggtactgtg ctagc                                    35

<210> SEQ ID NO 109
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 109
ctgatagcta gctcagtcct agggattatg ctagc                                    35

<210> SEQ ID NO 110
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 110
ttgacagcta gctcagtcct aggtattgtg ctagc                                    35

<210> SEQ ID NO 111
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 111
tttacggcta gctcagtcct aggtactatg ctagc                                    35

<210> SEQ ID NO 112
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 112
tttacggcta gctcagtcct aggtatagtg ctagc                                    35

<210> SEQ ID NO 113
<211> LENGTH: 35
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 113
tttacggcta gctcagccct aggtattatg ctagc                                35

<210> SEQ ID NO 114
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 114
ctgacagcta gctcagtcct aggtataatg ctagc                                35

<210> SEQ ID NO 115
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 115
tttacagcta gctcagtcct agggactgtg ctagc                                35

<210> SEQ ID NO 116
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 116
tttacggcta gctcagtcct aggtacaatg ctagc                                35

<210> SEQ ID NO 117
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 117
ttgacggcta gctcagtcct aggtatagtg ctagc                                35

<210> SEQ ID NO 118
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 118
ctgatagcta gctcagtcct agggattatg ctagc                                35
```

<210> SEQ ID NO 119
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 119
ctgatggcta gctcagtcct agggattatg ctagc                                35

<210> SEQ ID NO 120
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 120
tttatggcta gctcagtcct aggtacaatg ctagc                                35

<210> SEQ ID NO 121
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 121
tttatagcta gctcagccct tggtacaatg ctagc                                35

<210> SEQ ID NO 122
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 122
ttgacagcta gctcagtcct agggactatg ctagc                                35

<210> SEQ ID NO 123
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 123
ttgacagcta gctcagtcct agggattgtg ctagc                                35

<210> SEQ ID NO 124
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 124

```
ttgacggcta gctcagtcct aggtattgtg ctagc                                  35

<210> SEQ ID NO 125
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 125
ggtttcaaaa ttgtgatcta tatttaacaa                                        30

<210> SEQ ID NO 126
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 126
ggtttcaaaa ttgtgatcta tatttaacaa                                        30

<210> SEQ ID NO 127
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 127
tctattccaa taaagaaatc ttcctgcgtg                                        30

<210> SEQ ID NO 128
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 128
aaaaatgggc tcgtgttgta caataaatgt                                        30

<210> SEQ ID NO 129
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 129
aaaaaaagcg cgcgattatg taaaatataa                                        30

<210> SEQ ID NO 130
<211> LENGTH: 30
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"

<400> SEQUENCE: 130
atccttatcg ttatgggtat tgtttgtaat                                            30

<210> SEQ ID NO 131
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 131
taaaagaatt gtgagcggga atacaacaac                                            30

<210> SEQ ID NO 132
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 132
aaaaaaagcg cgcgattatg taaaatataa                                            30

<210> SEQ ID NO 133
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 133
tacaaaataa ttcccctgca aacattatca                                            30

<210> SEQ ID NO 134
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 134
tacaaaataa ttcccctgca aacattatcg                                            30

<210> SEQ ID NO 135
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 135
agggaataca agctacttgt tcttttttgca                                           30

<210> SEQ ID NO 136
<211> LENGTH: 23
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 136
taatacgact cactataggg aga                                            23

<210> SEQ ID NO 137
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 137
gaatttaata cgactcacta tagggaga                                       28

<210> SEQ ID NO 138
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 138
taatacgact cactatagg                                                 19

<210> SEQ ID NO 139
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 139
gagtcgtatt aatacgactc actatagggg                                     30

<210> SEQ ID NO 140
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 140
agtgagtcgt actacgactc actatagggg                                     30

<210> SEQ ID NO 141
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 141
gagtcgtatt aatacgactc tctatagggg                                     30
```

<210> SEQ ID NO 142
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 142
taatacgact cactataggg aga                                            23

<210> SEQ ID NO 143
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 143
ttatacgact cactataggg aga                                            23

<210> SEQ ID NO 144
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 144
gaatacgact cactataggg aga                                            23

<210> SEQ ID NO 145
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 145
taatacgtct cactataggg aga                                            23

<210> SEQ ID NO 146
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 146
tcatacgact cactataggg aga                                            23

<210> SEQ ID NO 147
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 147
taatacgact cactataggg agaccacaac                                      30

<210> SEQ ID NO 148
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 148
taattgaact cactaaaggg agaccacagc                                      30

<210> SEQ ID NO 149
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 149
cgaagtaata cgactcacta ttagggaaga                                      30

<210> SEQ ID NO 150
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 150
attaaccctc actaaaggga ga                                              22

<210> SEQ ID NO 151
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 151
atttaggtga cactataga                                                  19

<210> SEQ ID NO 152
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 152
acaaacacaa atacacacac taaattaata                                      30

<210> SEQ ID NO 153
<211> LENGTH: 30
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 153
ccaagcatac aatcaactat ctcatataca                                          30

<210> SEQ ID NO 154
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 154
gatacaggat acagcggaaa caacttttaa                                          30

<210> SEQ ID NO 155
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 155
tttcaagcta taccaagcat acaatcaact                                          30

<210> SEQ ID NO 156
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 156
cctttgcagc ataaattact atacttctat                                          30

<210> SEQ ID NO 157
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 157
cctttgcagc ataaattact atacttctat                                          30

<210> SEQ ID NO 158
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 158
cctttgcagc ataaattact atacttctat                                          30
```

<210> SEQ ID NO 159
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 159
cctttgcagc ataaattact atacttctat                                    30

<210> SEQ ID NO 160
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 160
cctttgcagc ataaattact atacttctat                                    30

<210> SEQ ID NO 161
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 161
ttatctactt tttacaacaa atataaaaca                                    30

<210> SEQ ID NO 162
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 162
acaaacacaa atacacacac taaattaata                                    30

<210> SEQ ID NO 163
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 163
gtttcgaata aacacacata aacaaacaaa                                    30

<210> SEQ ID NO 164
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 164
accatcaaag gaagctttaa tcttctcata                                          30

<210> SEQ ID NO 165
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 165
agaacccact gcttactggc ttatcgaaat                                          30

<210> SEQ ID NO 166
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 166
ggccgttttt ggcttttttg ttagacgaag                                          30

<210> SEQ ID NO 167
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 167
tgttatagtc gaatacctct ggcggtgata                                          30

<210> SEQ ID NO 168
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 168
ttttggtaca ctccctatca gtgatagaga                                          30

<210> SEQ ID NO 169
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 169 cttttggta cactacctct ggcggtgata                                           30

<210> SEQ ID NO 170
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 170
tacgcaagaa aatggtttgt tatagtcgaa                                    30

<210> SEQ ID NO 171
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 171
cgtgcgtgtt gataacaccg tgcgtgttga                                    30

<210> SEQ ID NO 172
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 172
agattgtact aaatcgtata atgacagtga                                    30

<210> SEQ ID NO 173
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 173
gtgttgatgc ttttatcacc gccagtggta                                    30

<210> SEQ ID NO 174
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 174
agtgtgtgga attgtgagcg gataacaatt                                    30

<210> SEQ ID NO 175
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 175
acatcttaaa agttttagta tcatattcgt                                    30

<210> SEQ ID NO 176
<211> LENGTH: 30

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 176
tacgcaagaa aatggtttgt tatagtcgaa                                      30

<210> SEQ ID NO 177
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 177
atcctccttt agtcttcccc ctcatgtgtg                                      30

<210> SEQ ID NO 178
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 178
taaaattatg aaatttgcat aaattcttca                                      30

<210> SEQ ID NO 179
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 179
gtgttgacta ttttacctct ggcggtgata                                      30

<210> SEQ ID NO 180
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 180
gaaatctggc agttttggt acacgaaagc                                       30

<210> SEQ ID NO 181
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 181
acaccgtgcg tgttgatata gtcgaataaa                                      30
```

<210> SEQ ID NO 182
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 182
aaaattatga aatttgtata aattcttcag                                    30

<210> SEQ ID NO 183
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 183
ggttcttttt ggtacctctg gcggtgataa                                    30

<210> SEQ ID NO 184
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 184
tgtaggatcg tacaggtata aattcttcag                                    30

<210> SEQ ID NO 185
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 185
caagaaaatg gtttgttata gtcgaataaa                                    30

<210> SEQ ID NO 186
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 186
ctatctcatt tgctagtata gtcgaataaa                                    30

<210> SEQ ID NO 187
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 187
tagtttataa tttaagtgtt ctttaatttc                                   30

<210> SEQ ID NO 188
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 188
caccttcggg tgggcctttc tgcgtttata                                   30

<210> SEQ ID NO 189
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 189
aataactctg atagtgctag tgtagatctc                                   30

<210> SEQ ID NO 190
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 190
caccttcggg tgggcctttc tgcgtttata                                   30

<210> SEQ ID NO 191
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 191
caccttcggg tgggcctttc tgcgtttata                                   30

<210> SEQ ID NO 192
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 192
ttgacacctg taggatcgta caggtataat                                   30

<210> SEQ ID NO 193
<211> LENGTH: 30
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 193
caagaaaatg gtttgttata gtcgaataaa                                          30

<210> SEQ ID NO 194
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 194
cacgcaaaac ttgcgacaaa caataggtaa                                          30

<210> SEQ ID NO 195
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 195
gttagctttc gaattggcta aaaagtgttc                                          30

<210> SEQ ID NO 196
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 196
ccattctgct ttccacgaac ttgaaaacgc                                          30

<210> SEQ ID NO 197
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 197
ggccgcgggt tcttttggt acacgaaagc                                           30

<210> SEQ ID NO 198
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 198
aagaaaatgg tttgttgata ctcgaataaa                                          30
```

```
<210> SEQ ID NO 199
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 199
gaaaaccttg tcaatgaaga gcgatctatg                                           30

<210> SEQ ID NO 200
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 200
ttctcgttcg actcatagct gaacacaaca                                           30

<210> SEQ ID NO 201
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 201
atgacaaaat tgtcat                                                          16

<210> SEQ ID NO 202
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 202
accaatgctg ggaacggcca gggcacctaa                                           30

<210> SEQ ID NO 203
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 203
ctgaaagcgc ataccgctat ggaggggtt                                            30

<210> SEQ ID NO 204
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 204
```
tagatatgcc tgaaagcgca taccgctatg                                30

<210> SEQ ID NO 205
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 205
agggaataca agctacttgt tctttttgca                                30

<210> SEQ ID NO 206
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 206
taatacgact cactataggg aga                                       23

<210> SEQ ID NO 207
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 207
gaatttaata cgactcacta tagggaga                                  28

<210> SEQ ID NO 208
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 208
taatacgact cactatagg                                            19

<210> SEQ ID NO 209
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 209
atttaggtga cactataga                                            19

<210> SEQ ID NO 210
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 210
gagtcgtatt aatacgactc actatagggg                                    30

<210> SEQ ID NO 211
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 211
agtgagtcgt actacgactc actatagggg                                    30

<210> SEQ ID NO 212
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 212
gagtcgtatt aatacgactc tctatagggg                                    30

<210> SEQ ID NO 213
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 213
taatacgact cactataggg aga                                           23

<210> SEQ ID NO 214
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 214
ttatacgact cactataggg aga                                           23

<210> SEQ ID NO 215
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 215
gaatacgact cactataggg aga                                           23

<210> SEQ ID NO 216
<211> LENGTH: 23

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 216
taatacgtct cactataggg aga                                            23

<210> SEQ ID NO 217
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 217
tcatacgact cactataggg aga                                            23

<210> SEQ ID NO 218
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 218 atagggaat tgtgagcgga taacaattcc                                      30

<210> SEQ ID NO 219
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 219 atagggaat tgtgagcgga taacaattcc                                      30

<210> SEQ ID NO 220
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 220 atagggaat tgtgagcgga taacaattcc                                      30

<210> SEQ ID NO 221
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 221 atagggaat tgtgagcgga taacaattcc                                      30
```

```
<210> SEQ ID NO 222
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 222
taatacgact cactataggg agaccacaac                                  30

<210> SEQ ID NO 223
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 223
taattgaact cactaaaggg agaccacagc                                  30

<210> SEQ ID NO 224
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 224
cgaagtaata cgactcacta ttagggaaga                                  30

<210> SEQ ID NO 225
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 225
ttgtgagcgg ataacaagat actgagcaca                                  30

<210> SEQ ID NO 226
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 226
ttgtgagcgg ataacaattc tgaagaacaa                                  30

<210> SEQ ID NO 227
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 227
ttgtgagcgg ataacaattc tgataaaaca                                    30

<210> SEQ ID NO 228
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 228
ttgtgagcgg ataacatcta accctttaga                                    30

<210> SEQ ID NO 229
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 229
ttgtgagcgg ataacatagc agataagaaa                                    30

<210> SEQ ID NO 230
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 230
gtttgagcga gtaacgccga aaatcttgca                                    30

<210> SEQ ID NO 231
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 231
gtgtgagcga gtaacgacga aaatcttgca                                    30

<210> SEQ ID NO 232
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 232
tttgagcgag taacagccga aaatcttgca                                    30

<210> SEQ ID NO 233
<211> LENGTH: 30
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 233
tgtgagcgag taacagccga aaatcttgca                                          30

<210> SEQ ID NO 234
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 234
ttgtgagcga gtggcaccat taagtacgta                                          30

<210> SEQ ID NO 235
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 235
ttgtgagcga gtgacaccat taagtacgta                                          30

<210> SEQ ID NO 236
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 236
ttgtgagcga gtaacaccat taagtacgta                                          30

<210> SEQ ID NO 237
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 237
ttgtgagcga gtaacaccat taagtacgta                                          30

<210> SEQ ID NO 238
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 238
cagtgagcga gtaacaacta cgctgtttta                                          30
```

```
<210> SEQ ID NO 239
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 239
cagtgagcga gtaacaacta cgctgtttta                                              30

<210> SEQ ID NO 240
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 240
atgtgagcgg ataacactat aattaataga                                              30

<210> SEQ ID NO 241
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 241
atgtgagcgg ataacactat aattaataga                                              30

<210> SEQ ID NO 242
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 242
gaattgtgag cggataacaa ttggatccgg                                              30

<210> SEQ ID NO 243
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 243
ggaattgtga gcgctcacaa ttggatccgg                                              30

<210> SEQ ID NO 244
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 244
```
ggaattgtaa gcgcttacaa ttggatccgg                                               30

<210> SEQ ID NO 245
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 245
ggaattgtaa acgtttacaa ttggatccgg                                               30

<210> SEQ ID NO 246
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 246
ggaattgtga acgttcacaa ttggatccgg                                               30

<210> SEQ ID NO 247
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 247
ggaattttga gcgctcaaaa ttggatccgg                                               30

<210> SEQ ID NO 248
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 248
ggaattatga gcgctcataa ttggatccgg                                               30

<210> SEQ ID NO 249
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 249
gggacgactg tatacagtcg tcggatccgg                                               30

<210> SEQ ID NO 250
<211> LENGTH: 30
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 250
ggaattgtga gcgcttacaa ttggatccgg                                          30

<210> SEQ ID NO 251
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 251
ggaattgtga gcgctcataa ttggatccgg                                          30

<210> SEQ ID NO 252
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 252
ggaattgtga gctacagtcg tcggatccgg                                          30

<210> SEQ ID NO 253
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 253
ggaattgtaa gcgctcacaa ttggatccgg                                          30

<210> SEQ ID NO 254
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 254
ggaattgtaa gcgttcacaa ttggatccgg                                          30

<210> SEQ ID NO 255
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 255
ggaattgtaa gcgctcataa ttggatccgg                                          30

<210> SEQ ID NO 256
<211> LENGTH: 30
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 256
ggaattgtaa gctacagtcg tcggatccgg                                          30

<210> SEQ ID NO 257
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 257
ggaattgtga acgctcataa ttggatccgg                                          30

<210> SEQ ID NO 258
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 258
ggaattgtga actacagtcg tcggatccgg                                          30

<210> SEQ ID NO 259
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 259
ggaattatga gcgctcacaa ttggatccgg                                          30

<210> SEQ ID NO 260
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 260
ggaattgtga gcgctcataa ttggatccgg                                          30

<210> SEQ ID NO 261
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 261
ggaattgtga gctacagtcg tcggatccgg                                          30
```

<210> SEQ ID NO 262
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 262
ggaattgtga acgctcataa ttggatccgg         30

<210> SEQ ID NO 263
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 263
ggaattgtga actacagtcg tcggatccgg         30

<210> SEQ ID NO 264
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 264
taaattgtga acgctcataa ttggatccgg         30

<210> SEQ ID NO 265
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 265
gaaattgtaa gcgcttacaa ttggatccgg         30

<210> SEQ ID NO 266
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 266
gaaattgtaa gcgcttacaa ttggatccgg         30

<210> SEQ ID NO 267
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 267
ggaattgtaa gcgcttacaa ttggatccgg                                    30

<210> SEQ ID NO 268
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 268
gccaaattaa acaggattaa caggatccgg                                    30

<210> SEQ ID NO 269
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 269
gccaaattaa acaggattaa caggatccgg                                    30

<210> SEQ ID NO 270
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 270
gccaaattaa acaggattaa caggatccgg                                    30

<210> SEQ ID NO 271
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 271
gccaaattaa acaggattaa caggatccgg                                    30

<210> SEQ ID NO 272
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 272
gccaaattaa acaggattaa caggatccgg                                    30

<210> SEQ ID NO 273
<211> LENGTH: 30
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 273
gccaaattaa acaggattaa caggatccgg                                          30

<210> SEQ ID NO 274
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 274
gccaaattaa acaggattaa caggatccgg                                          30

<210> SEQ ID NO 275
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 275
gaaattgtaa gcgcttacaa ttggatccgg                                          30

<210> SEQ ID NO 276
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 276
taaattgtaa gcgcttacaa ttggatccgg                                          30

<210> SEQ ID NO 277
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 277
gtaattgtaa gcgcttacaa ttggatccgg                                          30

<210> SEQ ID NO 278
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 278
tcaattgtaa gcgcttacaa ttggatccgg                                          30
```

-continued

<210> SEQ ID NO 279
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 279
aaaattgtaa gcgcttacaa ttggatccgg                                       30

<210> SEQ ID NO 280
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 280
caaattgtaa gcgcttacaa ttggatccgg                                       30

<210> SEQ ID NO 281
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 281
gaaattgtaa gcgcttacaa ttggatccgg                                       30

<210> SEQ ID NO 282
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 282
taaattgtaa gcgcttacaa ttggatccgg                                       30

<210> SEQ ID NO 283
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 283
gtaattgtaa gcgcttacaa ttggatccgg                                       30

<210> SEQ ID NO 284
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 284
tcaattgtaa gcgcttacaa ttggatccgg    30

<210> SEQ ID NO 285
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 285
aaaattgtaa gcgcttacaa ttggatccgg    30

<210> SEQ ID NO 286
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 286
caaattgtaa gcgcttacaa ttggatccgg    30

<210> SEQ ID NO 287
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 287
gaaattgtaa gcgcttacaa ttggatccgg    30

<210> SEQ ID NO 288
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 288
taaattgtaa gcgcttacaa ttggatccgg    30

<210> SEQ ID NO 289
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 289
gtaattgtaa gcgcttacaa ttggatccgg    30

<210> SEQ ID NO 290
<211> LENGTH: 30
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 290
tcaattgtaa gcgcttacaa ttggatccgg                                      30

<210> SEQ ID NO 291
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 291
aaaattgtaa gcgcttacaa ttggatccgg                                      30

<210> SEQ ID NO 292
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 292
caaattgtaa gcgcttacaa ttggatccgg                                      30

<210> SEQ ID NO 293
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 293
gaaattgtaa gcgcttacaa ttggatccgg                                      30

<210> SEQ ID NO 294
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 294
taaattgtaa gcgcttacaa ttggatccgg                                      30

<210> SEQ ID NO 295
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 295
gtaattgtaa gcgcttacaa ttggatccgg                                      30

<210> SEQ ID NO 296
<211> LENGTH: 30
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 296
tcaattgtaa gcgcttacaa ttggatccgg                                    30

<210> SEQ ID NO 297
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 297
aaaattgtaa gcgcttacaa ttggatccgg                                    30

<210> SEQ ID NO 298
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 298
caaattgtaa gcgcttacaa ttggatccgg                                    30

<210> SEQ ID NO 299
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 299
gaaattgtaa gcgcttacaa ttggatccgg                                    30

<210> SEQ ID NO 300
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 300
taaattgtaa gcgcttacaa ttggatccgg                                    30

<210> SEQ ID NO 301
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 301
gtaattgtaa gcgcttacaa ttggatccgg                                    30
```

<210> SEQ ID NO 302
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 302
tcaattgtaa gcgcttacaa ttggatccgg                                       30

<210> SEQ ID NO 303
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 303
aaaattgtaa gcgcttacaa ttggatccgg                                       30

<210> SEQ ID NO 304
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 304
caaattgtaa gcgcttacaa ttggatccgg                                       30

<210> SEQ ID NO 305
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 305
gaaattgtaa gcgcttacaa ttggatccgg                                       30

<210> SEQ ID NO 306
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 306
taaattgtaa gcgcttacaa ttggatccgg                                       30

<210> SEQ ID NO 307
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 307
gtaattgtaa gcgcttacaa ttggatccgg                                     30

<210> SEQ ID NO 308
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 308
tcaattgtaa gcgcttacaa ttggatccgg                                     30

<210> SEQ ID NO 309
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 309
aaaattgtaa gcgcttacaa ttggatccgg                                     30

<210> SEQ ID NO 310
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 310
caaattgtaa gcgcttacaa ttggatccgg                                     30

<210> SEQ ID NO 311
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 311
gaaattgtaa gcgcttacaa ttggatccgg                                     30

<210> SEQ ID NO 312
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 312
taaattgtaa gcgcttacaa ttggatccgg                                     30

<210> SEQ ID NO 313
<211> LENGTH: 30
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 313
gtaattgtaa gcgcttacaa ttggatccgg                                          30

<210> SEQ ID NO 314
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 314
tcaattgtaa gcgcttacaa ttggatccgg                                          30

<210> SEQ ID NO 315
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 315
aaaattgtaa gcgcttacaa ttggatccgg                                          30

<210> SEQ ID NO 316
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 316
caaattgtaa gcgcttacaa ttggatccgg                                          30

<210> SEQ ID NO 317
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 317
gccaaattaa acaggattaa caggatccgg                                          30

<210> SEQ ID NO 318
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 318
gccaaattaa acaggattaa caggatccgg                                          30
```

```
<210> SEQ ID NO 319
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 319
caaattatga gcgctcacaa ttggatccgg                                    30

<210> SEQ ID NO 320
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 320
gtttctccat acccgttttt ttgggctagc                                    30

<210> SEQ ID NO 321
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 321
tgttatagtc gaatacctct ggcggtgata                                    30

<210> SEQ ID NO 322
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 322
attacaaact ttcttgtata gatttaacgt                                    30

<210> SEQ ID NO 323
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 323
atttataaat agtggtgata gatttaacgt                                    30

<210> SEQ ID NO 324
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 324
```
tttcttgtat agatttacaa tgtatcttgt                                    30

<210> SEQ ID NO 325
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 325
tttcttgtag atacttacaa tgtatcttgt                                    30

<210> SEQ ID NO 326
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 326
ctttatgctt ccggctcgta tgttgtgtgg                                    30

<210> SEQ ID NO 327
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 327 tttttttgggc tagcaagctt taccatggat                                   30

<210> SEQ ID NO 328
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 328
tgtttctcca taccgttttt ttgggctagc                                    30

<210> SEQ ID NO 329
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 329
ttttggtaca ctccctatca gtgatagaga                                    30

<210> SEQ ID NO 330
<211> LENGTH: 30
<212> TYPE: DNA
<213> ORGANISM: Artificial Sequence
<220> FEATURE:
<221> NAME/KEY: source -continued

```
<223> OTHER INFORMATION: /note="Description of Artificial Sequence:
      Synthetic oligonucleotide"

<400> SEQUENCE: 330 cttttggta cactacctct ggcggtgata                                    30

<210> SEQ ID NO 331
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 331
tacgcaagaa aatggtttgt tatagtcgaa                                   30

<210> SEQ ID NO 332
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 332
gaaaaccttg tcaatgaaga gcgatctatg                                   30

<210> SEQ ID NO 333
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 333
ctcaaagcgg gccagccgta gccgttacgc                                   30

<210> SEQ ID NO 334
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 334
ttctcgttcg actcatagct gaacacaaca                                   30

<210> SEQ ID NO 335
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 335
gttctttaat tatttaagtg ttctttaatt                                   30

<210> SEQ ID NO 336
<211> LENGTH: 30
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 336
cgtgcgtgtt gataacaccg tgcgtgttga                                      30

<210> SEQ ID NO 337
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 337
gttacgttta tcgcggtgat tgttacttat                                      30

<210> SEQ ID NO 338
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 338
gcaaaataaa atggaatgat gaaactgggt                                      30

<210> SEQ ID NO 339
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 339
gttacgttta tcgcggtgat tgttacttat                                      30

<210> SEQ ID NO 340
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 340
atttcacact gctattgaga taattcacaa                                      30

<210> SEQ ID NO 341
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 341
agattgtact aaatcgtata atgacagtga                                      30
```

<210> SEQ ID NO 342
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 342
gacatctccg gcgcaactga aaataccact                                    30

<210> SEQ ID NO 343
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 343
gaggatgcgc atcgtcggga aactgatgcc                                    30

<210> SEQ ID NO 344
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 344
catccgggac tgatggcgga ggatgcgcat                                    30

<210> SEQ ID NO 345
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 345
aacttttata tattgtgcaa tctcacatgc                                    30

<210> SEQ ID NO 346
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 346
tgttgtccgg tgtacgtcac aattttctta                                    30

<210> SEQ ID NO 347
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 347
aatggctgtg tgttttttgt tcatctccac                                           30

<210> SEQ ID NO 348
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 348
gtgttgatgc ttttatcacc gccagtggta                                           30

<210> SEQ ID NO 349
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 349
agtgtgtgga attgtgagcg gataacaatt                                           30

<210> SEQ ID NO 350
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 350
atgacaaaat tgtcat                                                          16

<210> SEQ ID NO 351
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 351
acatcttaaa agttttagta tcatattcgt                                           30

<210> SEQ ID NO 352
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 352
ctgaaagcgc ataccgctat ggaggggggtt                                          30

<210> SEQ ID NO 353
<211> LENGTH: 30
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 353
ctgaaagcgc ataccgctat ggaggggggtt                                30

<210> SEQ ID NO 354
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 354
aacgaatata acaggtggga gatgagagga                                 30

<210> SEQ ID NO 355
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 355
aatatttcct cattttccac agtgaagtga                                 30

<210> SEQ ID NO 356
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 356
tacgcaagaa aatggtttgt tatagtcgaa                                 30

<210> SEQ ID NO 357
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 357
atttaattgt tttgatcaat tatttttctg                                 30

<210> SEQ ID NO 358
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 358
attattctgc attttggggg agaatggact                                 30
```

```
<210> SEQ ID NO 359
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 359
ccttgctgga aggtttaacc tttatcacag                                          30

<210> SEQ ID NO 360
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 360
atgatgtgtc catggatta                                                      19

<210> SEQ ID NO 361
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 361
atgatagacg atgtgcggac aacgtg                                              26

<210> SEQ ID NO 362
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 362
cattagccgc caccatgggg ttaagtagca                                          30

<210> SEQ ID NO 363
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 363
atttataaat agtggtgata gatttaacgt                                          30

<210> SEQ ID NO 364
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 364
```
ataaagccat cacgagtacc atagaggatc                                              30

<210> SEQ ID NO 365
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 365
tttgtctttt cttgcttaat aatgttgtca                                              30

<210> SEQ ID NO 366
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 366
tttgtctttt cttgcttaat aatgttgtca                                              30

<210> SEQ ID NO 367
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 367
atcctccttt agtcttcccc ctcatgtgtg                                              30

<210> SEQ ID NO 368
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 368
taaaattatg aaatttgcat aaattcttca                                              30

<210> SEQ ID NO 369
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 369
gaaatctggc agtttttggt acacgaaagc                                              30

<210> SEQ ID NO 370
<211> LENGTH: 30
<212> TYPE: DNA
<213> ORGANISM: Artificial Sequence
<220> FEATURE:
<221> NAME/KEY: source -continued
<223> OTHER INFORMATION: /note="Description of Artificial Sequence:
      Synthetic oligonucleotide"

<400> SEQUENCE: 370
tgccagttct ggcaggtcta aaaagtgttc                                30

<210> SEQ ID NO 371
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 371
cacagaactt gcatttatat aaagggaaag                                30

<210> SEQ ID NO 372
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 372
acaccgtgcg tgttgatata gtcgaataaa                                30

<210> SEQ ID NO 373
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 373
aaaattatga aatttgtata aattcttcag                                30

<210> SEQ ID NO 374
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 374
ggttcttttt ggtacctctg gcggtgataa                                30

<210> SEQ ID NO 375
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 375
tgtaggatcg tacaggtata aattcttcag                                30

<210> SEQ ID NO 376
<211> LENGTH: 30

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 376
caagaaaatg gtttgttata gtcgaataaa                                     30

<210> SEQ ID NO 377
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 377
ctatctcatt tgctagtata gtcgaataaa                                     30

<210> SEQ ID NO 378
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 378
gttacgttta tcgcggtgat tgttacttat                                     30

<210> SEQ ID NO 379
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 379
gttacgttta tcgcggtgat tgttacttat                                     30

<210> SEQ ID NO 380
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 380
gttacgttta tcgcggtgat tgttacttat                                     30

<210> SEQ ID NO 381
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 381
ataaatgctt gactctgtag cgggaaggcg                                     30
```

<210> SEQ ID NO 382
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 382
aaaactggta gtaggactgg agattggtac                                         30

<210> SEQ ID NO 383
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 383
gggacacaaa catcaagagg atatgagatt                                         30

<210> SEQ ID NO 384
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 384
gtcaaaatga ccgaaacggg tggtaacttc                                         30

<210> SEQ ID NO 385
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 385
agtaatctta tcgccagttt ggtctggtca                                         30

<210> SEQ ID NO 386
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 386
agtaatctta tcgccagttt ggtctggtca                                         30

<210> SEQ ID NO 387
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 387
aattctgaac aacatccgta ctcttcgtgc                                    30

<210> SEQ ID NO 388
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 388
tcgataagat taccgatctt acctgaagct                                    30

<210> SEQ ID NO 389
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 389
cgatctattc acctgaaaga gaaataaaaa                                    30

<210> SEQ ID NO 390
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 390
atcgcaacct atttattaca acactagtgc                                    30

<210> SEQ ID NO 391
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 391
aaacgttagt ttgaatggaa agatgcctgc                                    30

<210> SEQ ID NO 392
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 392
tttgcacgaa ccatatgtaa gtatttcctt                                    30

<210> SEQ ID NO 393
<211> LENGTH: 30
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 393
taacacttat ttaattaaaa agaggagaaa                                       30

<210> SEQ ID NO 394
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 394
tagaaacaaa atgtaacatc tctatggaca                                       30

<210> SEQ ID NO 395
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 395
acaggaaaca gctatgacca tgattacgcc                                       30

<210> SEQ ID NO 396
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 396
agcgacgtct gatgacgtaa tttctgcctc                                       30

<210> SEQ ID NO 397
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 397
gttcactcta taccgctgaa ggtgtaatgg                                       30

<210> SEQ ID NO 398
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 398
tagtttataa tttaagtgtt ctttaatttc                                       30
```

```
<210> SEQ ID NO 399
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 399
cgagcacttc accaacaagg accatagcat                                     30

<210> SEQ ID NO 400
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 400
caccttcggg tgggcctttc tgcgtttata                                     30

<210> SEQ ID NO 401
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 401
catggcatgg atgaactata caaataataa                                     30

<210> SEQ ID NO 402
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 402
caccttcggg tgggcctttc tgcgtttata                                     30

<210> SEQ ID NO 403
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 403
caccttcggg tgggcctttc tgcgtttata                                     30

<210> SEQ ID NO 404
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 404
```
caccttcggg tgggcctttc tgcgtttata                                              30

<210> SEQ ID NO 405
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 405
caccttcggg tgggcctttc tgcgtttata                                              30

<210> SEQ ID NO 406
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 406
caccttcggg tgggcctttc tgcgtttata                                              30

<210> SEQ ID NO 407
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 407
caccttcggg tgggcctttc tgcgtttata                                              30

<210> SEQ ID NO 408
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 408
caccttcggg tgggcctttc tgcgtttata                                              30

<210> SEQ ID NO 409
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 409
caccttcggg tgggcctttc tgcgtttata                                              30

<210> SEQ ID NO 410
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 410
caccttcggg tgggccttc tgcgtttata                                        30

<210> SEQ ID NO 411
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 411
caccttcggg tgggccttc tgcgtttata                                        30

<210> SEQ ID NO 412
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 412
caccttcggg tgggccttc tgcgtttata                                        30

<210> SEQ ID NO 413
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 413
caccttcggg tgggccttc tgcgtttata                                        30

<210> SEQ ID NO 414
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 414
caccttcggg tgggccttc tgcgtttata                                        30

<210> SEQ ID NO 415
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 415
caccttcggg tgggccttc tgcgtttata                                        30

<210> SEQ ID NO 416
<211> LENGTH: 30

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 416
caccttcggg tgggcctttc tgcgtttata                              30

<210> SEQ ID NO 417
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 417
tgtttctcca taccgttttt ttgggctagc                              30

<210> SEQ ID NO 418
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 418
tgtttctcca taccgttttt ttgggctagc                              30

<210> SEQ ID NO 419
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 419
ttttatcgca actctctact gtttctccat                              30

<210> SEQ ID NO 420
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 420
gtttctccat tactagagaa agaggggaca                              30

<210> SEQ ID NO 421
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 421
caccttcggg tgggcctttc tgcgtttata                              30
```

```
<210> SEQ ID NO 422
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 422 ataactctg atagtgctag tgtagatctc                                       30

<210> SEQ ID NO 423
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 423
caccttcggg tgggcctttc tgcgtttata                                      30

<210> SEQ ID NO 424
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 424
caccttcggg tgggcctttc tgcgtttata                                      30

<210> SEQ ID NO 425
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 425
gggacacaaa catcaagagg atatgagatt                                      30

<210> SEQ ID NO 426
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 426
ataataagcg aagttagcga gatgaatgcg                                      30

<210> SEQ ID NO 427
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 427
agttggcaca gatttcgctt tatctttttt                                30

<210> SEQ ID NO 428
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 428
caagaaaatg gtttgttata gtcgaataaa                                30

<210> SEQ ID NO 429
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 429
gtgttgacta ttttacctct ggcggtgata                                30

<210> SEQ ID NO 430
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 430
gttagctttc gaattggcta aaaagtgttc                                30

<210> SEQ ID NO 431
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 431
ccattctgct ttccacgaac ttgaaaacgc                                30

<210> SEQ ID NO 432
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 432
ggccgcgggt tcttttggt acacgaaagc                                 30

<210> SEQ ID NO 433
<211> LENGTH: 30
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 433
ttttatcgca actctctact gtttctccat                                          30

<210> SEQ ID NO 434
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 434
attattctgc attttggggg agaatggact                                          30

<210> SEQ ID NO 435
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 435
attattctgc attttggggg agaatggact                                          30

<210> SEQ ID NO 436
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 436
aacgttagtt tgaatggaaa gatgcctgca                                          30

<210> SEQ ID NO 437
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 437
aagaaaatgg tttgttgata ctcgaataaa                                          30

<210> SEQ ID NO 438
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 438
aacgcagtcg ttaagttcta caaagtcggt                                          30
```

```
<210> SEQ ID NO 439
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 439
gtcggtgaca gataacagga gtaagtaatg                                     30

<210> SEQ ID NO 440
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 440
tattggctga ctataataag cgcaaattca                                     30

<210> SEQ ID NO 441

<400> SEQUENCE: 441

000

<210> SEQ ID NO 442
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 442
cgaaacggga accctatatt gatctctact                                     30

<210> SEQ ID NO 443
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 443
aagttggcac gcatcgtgct ttatacagat                                     30

<210> SEQ ID NO 444
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 444
gaggaaacta gacccgccgc caccatggag                                     30

<210> SEQ ID NO 445
<211> LENGTH: 30
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 445
gagtaaccaa aaccaaaaca gatttcaacc                                         30

<210> SEQ ID NO 446
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 446
aaagtaagaa tttttgaaaa ttcaatataa                                         30

<210> SEQ ID NO 447
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 447
atacggtcaa cgaactataa ttaactaaac                                         30

<210> SEQ ID NO 448
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 448
cacaaataca cacactaaat taataactag                                         30

<210> SEQ ID NO 449
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 449
cacaaataca cacactaaat taataactag                                         30

<210> SEQ ID NO 450
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 450
cacaaataca cacactaaat taataactag                                         30
```

```
<210> SEQ ID NO 451
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 451
atactttaac gtcaaggaga aaaaactata                                      30

<210> SEQ ID NO 452
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 452
accgttaaga accatatcca agaatcaaaa                                      30

<210> SEQ ID NO 453
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 453
cttcatatat aaaccgccag aaatgaatta                                      30

<210> SEQ ID NO 454
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 454
atcttcatac aacaataact accaaccttta                                     30

<210> SEQ ID NO 455
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 455
tttcatacac aatataaacg attaaaagaa                                      30

<210> SEQ ID NO 456
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

<400> SEQUENCE: 456
aaattccagt aaattcacat attggagaaa                              30

<210> SEQ ID NO 457
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 457
gggagccaga acgcttctgg tggtgtaaat                              30

<210> SEQ ID NO 458
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 458
gcacagactt agattggtat atatacgcat                              30

<210> SEQ ID NO 459
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 459
aagtgcaaga aagaccagaa acgcaactca                              30

<210> SEQ ID NO 460
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 460
taaaaaaaaa aaaaaaaaaa aaaaaaaaaa                              30

<210> SEQ ID NO 461
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 461
ggggcgaggg ccccgcctcc ggaggcgggg                              30

<210> SEQ ID NO 462
<211> LENGTH: 30
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 462 gagggggacgg ctccggcccc ggggccggag                                    30

<210> SEQ ID NO 463
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 463
ggggcgaggg ctccggcccc ggggccggag                                     30

<210> SEQ ID NO 464
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 464
gaggggacgg ccccgcctcc ggaggcgggg                                     30

<210> SEQ ID NO 465
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 465
tgttatagtc gaatacctct ggcggtgata                                     30

<210> SEQ ID NO 466
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 466
gatttaacgt atcagcacaa aaaagaaacc                                     30

<210> SEQ ID NO 467
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 467
attacaaact ttcttgtata gatttaacgt                                     30

<210> SEQ ID NO 468
```

```
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 468
tttcttgtat agatttacaa tgtatcttgt                                      30

<210> SEQ ID NO 469
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 469
tttcttgtag atacttacaa tgtatcttgt                                      30

<210> SEQ ID NO 470
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 470
actctgtcaa tgatagagtg gattcaaaaa                                      30

<210> SEQ ID NO 471
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 471
ttttggtaca ctccctatca gtgatagaga                                      30

<210> SEQ ID NO 472
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 472 cttttggta cactacctct ggcggtgata                                       30

<210> SEQ ID NO 473
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 473
```

```
aaacctttcg cggtatggca tgatagcgcc                                            30
```

<210> SEQ ID NO 474
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 474

```
tattttacct ctggcggtga taatggttgc                                            30
```

<210> SEQ ID NO 475
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 475

```
actctcggca tggacgagct gtacaagtaa                                            30
```

<210> SEQ ID NO 476
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 476

```
ttgtgagcgg ataacaatat gttgagcaca                                            30
```

<210> SEQ ID NO 477
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 477

```
cattgagaca cttgtttgca cagaggatgg                                            30
```

<210> SEQ ID NO 478
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 478

```
ttctcgttcg actcatagct gaacacaaca                                            30
```

<210> SEQ ID NO 479
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:

-continued

Synthetic oligonucleotide"

<400> SEQUENCE: 479
gaattgtgag cggataacaa ttggatccgg          30

<210> SEQ ID NO 480
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 480
ggaattgtga gcgctcacaa ttggatccgg          30

<210> SEQ ID NO 481
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 481
ggaattgtaa gcgcttacaa ttggatccgg          30

<210> SEQ ID NO 482
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 482
ggaattgtaa acgtttacaa ttggatccgg          30

<210> SEQ ID NO 483
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 483
ggaattgtga acgttcacaa ttggatccgg          30

<210> SEQ ID NO 484
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 484
ggaattttga gcgctcaaaa ttggatccgg          30

<210> SEQ ID NO 485
<211> LENGTH: 30
<212> TYPE: DNA

<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 485
ggaattatga gcgctcataa ttggatccgg                          30

<210> SEQ ID NO 486
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 486
gggacgactg tatacagtcg tcggatccgg                          30

<210> SEQ ID NO 487
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 487
ggaattgtga gcgcttacaa ttggatccgg                          30

<210> SEQ ID NO 488
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 488
ggaattgtga gcgctcataa ttggatccgg                          30

<210> SEQ ID NO 489
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 489
ggaattgtga gctacagtcg tcggatccgg                          30

<210> SEQ ID NO 490
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 490
ggaattgtaa gcgctcacaa ttggatccgg                          30

```
<210> SEQ ID NO 491
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 491
ggaattgtaa gcgttcacaa ttggatccgg                                      30

<210> SEQ ID NO 492
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 492
ggaattgtaa gcgctcataa ttggatccgg                                      30

<210> SEQ ID NO 493
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 493
ggaattgtaa gctacagtcg tcggatccgg                                      30

<210> SEQ ID NO 494
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 494
ggaattgtga acgctcataa ttggatccgg                                      30

<210> SEQ ID NO 495
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 495
ggaattgtga actacagtcg tcggatccgg                                      30

<210> SEQ ID NO 496
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 496
ggaattatga gcgctcacaa ttggatccgg                                    30

<210> SEQ ID NO 497
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 497
ggaattgtga gcgctcataa ttggatccgg                                    30

<210> SEQ ID NO 498
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 498
ggaattgtga gctacagtcg tcggatccgg                                    30

<210> SEQ ID NO 499
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 499
ggaattgtga acgctcataa ttggatccgg                                    30

<210> SEQ ID NO 500
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 500
ggaattgtga actacagtcg tcggatccgg                                    30

<210> SEQ ID NO 501
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 501
taaattgtga acgctcataa ttggatccgg                                    30

<210> SEQ ID NO 502
<211> LENGTH: 30
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 502
gaaattgtaa gcgcttacaa ttggatccgg                                    30

<210> SEQ ID NO 503
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 503
gaaattgtaa gcgcttacaa ttggatccgg                                    30

<210> SEQ ID NO 504
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 504
ggaattgtaa gcgcttacaa ttggatccgg                                    30

<210> SEQ ID NO 505
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 505
gccaaattaa acaggattaa caggatccgg                                    30

<210> SEQ ID NO 506
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 506
gccaaattaa acaggattaa caggatccgg                                    30

<210> SEQ ID NO 507
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 507
gccaaattaa acaggattaa caggatccgg                                    30

<210> SEQ ID NO 508
```

```
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 508
gccaaattaa acaggattaa caggatccgg                                        30

<210> SEQ ID NO 509
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 509
gccaaattaa acaggattaa caggatccgg                                        30

<210> SEQ ID NO 510
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 510
gccaaattaa acaggattaa caggatccgg                                        30

<210> SEQ ID NO 511
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 511
gccaaattaa acaggattaa caggatccgg                                        30

<210> SEQ ID NO 512
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 512
gaaattgtaa gcgcttacaa ttggatccgg                                        30

<210> SEQ ID NO 513
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 513
```
taaattgtaa gcgcttacaa ttggatccgg        30

<210> SEQ ID NO 514
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 514
gtaattgtaa gcgcttacaa ttggatccgg        30

<210> SEQ ID NO 515
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 515
tcaattgtaa gcgcttacaa ttggatccgg        30

<210> SEQ ID NO 516
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 516
aaaattgtaa gcgcttacaa ttggatccgg        30

<210> SEQ ID NO 517
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 517
caaattgtaa gcgcttacaa ttggatccgg        30

<210> SEQ ID NO 518
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 518
gaaattgtaa gcgcttacaa ttggatccgg        30

<210> SEQ ID NO 519
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 519
taaattgtaa gcgcttacaa ttggatccgg					30

<210> SEQ ID NO 520
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 520
gtaattgtaa gcgcttacaa ttggatccgg					30

<210> SEQ ID NO 521
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 521
tcaattgtaa gcgcttacaa ttggatccgg					30

<210> SEQ ID NO 522
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 522
aaaattgtaa gcgcttacaa ttggatccgg					30

<210> SEQ ID NO 523
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 523
caaattgtaa gcgcttacaa ttggatccgg					30

<210> SEQ ID NO 524
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 524
gaaattgtaa gcgcttacaa ttggatccgg					30

<210> SEQ ID NO 525
<211> LENGTH: 30
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 525
taaattgtaa gcgcttacaa ttggatccgg                                    30

<210> SEQ ID NO 526
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 526
gtaattgtaa gcgcttacaa ttggatccgg                                    30

<210> SEQ ID NO 527
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 527
tcaattgtaa gcgcttacaa ttggatccgg                                    30

<210> SEQ ID NO 528
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 528
aaaattgtaa gcgcttacaa ttggatccgg                                    30

<210> SEQ ID NO 529
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 529
caaattgtaa gcgcttacaa ttggatccgg                                    30

<210> SEQ ID NO 530
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 530
gaaattgtaa gcgcttacaa ttggatccgg                                    30
```

<210> SEQ ID NO 531
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 531
taaattgtaa gcgcttacaa ttggatccgg                                    30

<210> SEQ ID NO 532
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 532
gtaattgtaa gcgcttacaa ttggatccgg                                    30

<210> SEQ ID NO 533
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 533
tcaattgtaa gcgcttacaa ttggatccgg                                    30

<210> SEQ ID NO 534
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 534
aaaattgtaa gcgcttacaa ttggatccgg                                    30

<210> SEQ ID NO 535
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 535
caaattgtaa gcgcttacaa ttggatccgg                                    30

<210> SEQ ID NO 536
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 536
gaaattgtaa gcgcttacaa ttggatccgg                                          30

<210> SEQ ID NO 537
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 537
taaattgtaa gcgcttacaa ttggatccgg                                          30

<210> SEQ ID NO 538
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 538
gtaattgtaa gcgcttacaa ttggatccgg                                          30

<210> SEQ ID NO 539
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 539
tcaattgtaa gcgcttacaa ttggatccgg                                          30

<210> SEQ ID NO 540
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 540
aaaattgtaa gcgcttacaa ttggatccgg                                          30

<210> SEQ ID NO 541
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 541
caaattgtaa gcgcttacaa ttggatccgg                                          30

<210> SEQ ID NO 542
<211> LENGTH: 30
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 542
gaaattgtaa gcgcttacaa ttggatccgg                                    30

<210> SEQ ID NO 543
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 543
taaattgtaa gcgcttacaa ttggatccgg                                    30

<210> SEQ ID NO 544
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 544
gtaattgtaa gcgcttacaa ttggatccgg                                    30

<210> SEQ ID NO 545
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 545
tcaattgtaa gcgcttacaa ttggatccgg                                    30

<210> SEQ ID NO 546
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 546
aaaattgtaa gcgcttacaa ttggatccgg                                    30

<210> SEQ ID NO 547
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 547
caaattgtaa gcgcttacaa ttggatccgg                                    30

<210> SEQ ID NO 548
```

```
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 548
gaaattgtaa gcgcttacaa ttggatccgg                                       30

<210> SEQ ID NO 549
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 549
taaattgtaa gcgcttacaa ttggatccgg                                       30

<210> SEQ ID NO 550
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 550
gtaattgtaa gcgcttacaa ttggatccgg                                       30

<210> SEQ ID NO 551
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 551
tcaattgtaa gcgcttacaa ttggatccgg                                       30

<210> SEQ ID NO 552
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 552
aaaattgtaa gcgcttacaa ttggatccgg                                       30

<210> SEQ ID NO 553
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 553
```
caaattgtaa gcgcttacaa ttggatccgg 30

<210> SEQ ID NO 554
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 554
gccaaattaa acaggattaa caggatccgg 30

<210> SEQ ID NO 555
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 555
gccaaattaa acaggattaa caggatccgg 30

<210> SEQ ID NO 556
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 556
caaattatga gcgctcacaa ttggatccgg 30

<210> SEQ ID NO 557
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 557
tgatagagat tccctatcag tgatagagat 30

<210> SEQ ID NO 558
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 558
tgatagagat tccctatcag tgatagagat 30

<210> SEQ ID NO 559
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:

-continued

Synthetic oligonucleotide"

<400> SEQUENCE: 559
gttctttaat tatttaagtg ttctttaatt                                     30

<210> SEQ ID NO 560
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 560
gttctttaat tatttaagtg ttctttaatt                                     30

<210> SEQ ID NO 561
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 561
cgtgcgtgtt gataacaccg tgcgtgttga                                     30

<210> SEQ ID NO 562
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 562
gtgttcttta atatttaagt gttctttaat                                     30

<210> SEQ ID NO 563
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 563
ggaattgtga gcggataaca atttcacaca                                     30

<210> SEQ ID NO 564
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 564
tgtgtgtaat tgtgagcgga taacaattaa                                     30

<210> SEQ ID NO 565
<211> LENGTH: 30
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 565
ttttacctct ggcggtgata atggttgcag                                           30

<210> SEQ ID NO 566
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 566
gtgttgatgc ttttatcacc gccagtggta                                           30

<210> SEQ ID NO 567
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 567
agtgtgtgga attgtgagcg gataacaatt                                           30

<210> SEQ ID NO 568
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 568 aggggggtggg ggcgcgttgg cgcgccacac                                          30

<210> SEQ ID NO 569
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 569
acatcttaaa agttttagta tcatattcgt                                           30

<210> SEQ ID NO 570
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 570
tattttacct ctggcggtga taatggttgc                                           30
```

```
<210> SEQ ID NO 571
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 571
atttataaat agtggtgata gatttaacgt                                    30

<210> SEQ ID NO 572
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 572
acccttctcg ttcgactcat agctgaacac                                    30

<210> SEQ ID NO 573
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 573
tgacttatcc gcttcgaaga gagacactac                                    30

<210> SEQ ID NO 574
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 574
aggtgttaaa ttgatcacgt tttagaccat                                    30

<210> SEQ ID NO 575
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 575
caatttggta aaggctccat catgtaataa                                    30

<210> SEQ ID NO 576
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 576
gagaaacaat ttggtaaagg ctccatcatg                                    30

<210> SEQ ID NO 577
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 577
aacgcgcggg gagaggcggt ttgcgtattg                                    30

<210> SEQ ID NO 578
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 578
cagtgataga gatactgagc acatcagcac                                    30

<210> SEQ ID NO 579
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 579
ttatgcttcc ggctcgtata atgtttcaaa                                    30

<210> SEQ ID NO 580
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 580
ggctcgtatg ttgtgtcgac cgagctgcgc                                    30

<210> SEQ ID NO 581
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 581
aaacctttcg cggtatggca tgatagcgcc                                    30

<210> SEQ ID NO 582
<211> LENGTH: 30
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 582
atttgtcact gtcgttacta tatcggctgc                                          30

<210> SEQ ID NO 583
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 583
gtccaatcaa taaccgcttt aatagataaa                                          30

<210> SEQ ID NO 584
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 584
actttattat caataagtta aatcggtacc                                          30

<210> SEQ ID NO 585
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 585
gtgttgacta ttttacctct ggcggtgata                                          30

<210> SEQ ID NO 586
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 586
gtgttgacta ttttacctct ggcggtgata                                          30

<210> SEQ ID NO 587
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 587
atacctctgg cggtgatata taatggttgc                                          30

<210> SEQ ID NO 588
```

```
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 588
gtgttgacta ttttacctct ggcggtgata                                    30

<210> SEQ ID NO 589
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 589
gaaatctggc agttttggt acacgaaagc                                     30

<210> SEQ ID NO 590
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 590
tgccagttct ggcaggtcta aaaagtgttc                                    30

<210> SEQ ID NO 591
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 591
agcgctcaca atttaatacg actcactata                                    30

<210> SEQ ID NO 592
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 592
taataattgt gagcgctcac aattttgaca                                    30

<210> SEQ ID NO 593
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 593
```
atccctatca gtgatagaga tactgagcac                                30

<210> SEQ ID NO 594
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 594
ttgtgagcgg ataacaagat actgagcaca                                30

<210> SEQ ID NO 595
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 595
ggaattgtga gcggataaca atttcacaca                                30

<210> SEQ ID NO 596
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 596
ggaattgtga gcggataaca atttcacaca                                30

<210> SEQ ID NO 597
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 597
ggaattgtga gcggataaca atttcacaca                                30

<210> SEQ ID NO 598
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 598
agaactgtaa tccctatcag tgatagagat                                30

<210> SEQ ID NO 599
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:

-continued

Synthetic oligonucleotide"

<400> SEQUENCE: 599
tgttgattta tctaacaccg tgcgtgttga                30

<210> SEQ ID NO 600
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 600
acaccgtgcg tgttgatata gtcgaataaa                30

<210> SEQ ID NO 601
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 601
cctttcgcgg tatggcatga tagcgcccgg                30

<210> SEQ ID NO 602
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 602
cctttcgcgg tatggcatga tagcgcccgg                30

<210> SEQ ID NO 603
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 603
cctttcgcgg tatggcatga tagcgcccgg                30

<210> SEQ ID NO 604
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 604 ggttctttttt ggtacctctg gcggtgataa               30

<210> SEQ ID NO 605
<211> LENGTH: 30
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 605
tgtaggatcg tacaggtata aattcttcag                                 30

<210> SEQ ID NO 606
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 606
ctatctcatt tgctagtata gtcgaataaa                                 30

<210> SEQ ID NO 607
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 607
gtatatatat acagtataat tgcttcaaca                                 30

<210> SEQ ID NO 608
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 608
cacaatgtca attgttatcc gctcacaatt                                 30

<210> SEQ ID NO 609
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 609
aattgtgagc ggataacaat ttcacacaga                                 30

<210> SEQ ID NO 610
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 610
ccggaagaga gtcaattcag ggtggtgaat                                 30
```

```
<210> SEQ ID NO 611
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 611
acggtgacct agatctccga tactgagcac                                          30

<210> SEQ ID NO 612
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 612
tggaattgtg agcggataaa atttcacaca                                          30

<210> SEQ ID NO 613
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 613
tagtagataa tttaagtgtt ctttaatttc                                          30

<210> SEQ ID NO 614
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 614
ccaacgcgtt cacagcgtac aattactagt                                          30

<210> SEQ ID NO 615
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 615
aacaaaaaaa cggatcctct agttgcggcc                                          30

<210> SEQ ID NO 616
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

```
<400> SEQUENCE: 616
ataaatgctt gactctgtag cgggaaggcg                                      30

<210> SEQ ID NO 617
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 617
atttcatgat gatacgtgag cggatagaag                                      30

<210> SEQ ID NO 618
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 618
caaacagaaa gcgttggcgg cagcactggg                                      30

<210> SEQ ID NO 619
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 619
gtcaaaatga ccgaaacggg tggtaacttc                                      30

<210> SEQ ID NO 620
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 620
agtaatctta tcgccagttt ggtctggtca                                      30

<210> SEQ ID NO 621
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 621
agtaatctta tcgccagttt ggtctggtca                                      30

<210> SEQ ID NO 622
<211> LENGTH: 30
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 622
aattctgaac aacatccgta ctcttcgtgc                                       30

<210> SEQ ID NO 623
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 623
tttacgttat cattcacttt acatcagagt                                       30

<210> SEQ ID NO 624
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 624
gtttctccat acccgttttt ttgggctagc                                       30

<210> SEQ ID NO 625
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 625
cgatctattc acctgaaaga gaaataaaaa                                       30

<210> SEQ ID NO 626
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 626
aaacgttagt ttgaatggaa agatgcctgc                                       30

<210> SEQ ID NO 627
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 627
attgccgaat taatactaag aattattatc                                       30

<210> SEQ ID NO 628
```

<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 628
acaggaaaca gctatgacca tgattacgcc                                           30

<210> SEQ ID NO 629
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 629
actggcggtt ataatgagca catcagcagg                                           30

<210> SEQ ID NO 630
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 630
caccgacaaa caacagataa aacgaaaggc                                           30

<210> SEQ ID NO 631
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 631
agtgttatta agctactaaa gcgtagtttt                                           30

<210> SEQ ID NO 632
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 632
gaataagaag gctggctctg caccttggtg                                           30

<210> SEQ ID NO 633
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 633
ttagcgactt gatgctcttg atcttccaat            30

<210> SEQ ID NO 634
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 634
acatctaaaa cttttagcgt tattacgtaa            30

<210> SEQ ID NO 635
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 635
ttccgacctc attaagcagc tctaatgcgc            30

<210> SEQ ID NO 636
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 636
caatttttaa acctgtagga tcgtacaggt            30

<210> SEQ ID NO 637
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 637
caatttttaa aattaaaggc gttacccaac            30

<210> SEQ ID NO 638
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 638
tagtttataa tttaagtgtt ctttaatttc            30

<210> SEQ ID NO 639
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:

-continued

Synthetic oligonucleotide"

<400> SEQUENCE: 639
gaaaatgtga gcgagtaaca acctcacaca           30

<210> SEQ ID NO 640
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 640
caccttcggg tgggcctttc tgcgtttata           30

<210> SEQ ID NO 641
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 641
ttttatcgca actctctact gtttctccat           30

<210> SEQ ID NO 642
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 642
gtttctccat tactagagaa agaggggaca           30

<210> SEQ ID NO 643
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 643
caccttcggg tgggcctttc tgcgtttata           30

<210> SEQ ID NO 644
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 644
caccttcggg tgggcctttc tgcgtttata           30

<210> SEQ ID NO 645
<211> LENGTH: 30
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 645
caccttcggg tgggcctttc tgcgtttata                                  30

<210> SEQ ID NO 646
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 646
aataactctg atagtgctag tgtagatctc                                  30

<210> SEQ ID NO 647
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 647
caccttcggg tgggcctttc tgcgtttata                                  30

<210> SEQ ID NO 648
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 648
caccttcggg tgggcctttc tgcgtttata                                  30

<210> SEQ ID NO 649
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 649
ttgtgagcgg ataacaagat actgagcaca                                  30

<210> SEQ ID NO 650
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 650
actgagcaca tactagagaa agaggagaaa                                  30
```

```
<210> SEQ ID NO 651
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 651
actgagcaca tactagagaa agaggagaaa                                          30

<210> SEQ ID NO 652
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 652
tcacacatac tagagattaa agaggagaaa                                          30

<210> SEQ ID NO 653
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 653
ggaattgtga gcggataaca atttcacaca                                          30

<210> SEQ ID NO 654
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 654
ggaattgtga gcggataaca atttcacaca                                          30

<210> SEQ ID NO 655
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 655
ttgtgagcgg ataacaagat actgagcaca                                          30

<210> SEQ ID NO 656
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 656
atccctatca gtgatagaga tactgagcac                                      30

<210> SEQ ID NO 657
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 657
ccgtcataat atgaaccata agttcaccac                                      30

<210> SEQ ID NO 658
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 658
tattttacct ctggcggtga taatggttgc                                      30

<210> SEQ ID NO 659
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 659
attgtatgaa aatacaagaa agtttgttga                                      30

<210> SEQ ID NO 660
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 660
tagtagataa tttaagtgtt ctttaatttc                                      30

<210> SEQ ID NO 661
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 661
ttgacacctg taggatcgta caggtataat                                      30

<210> SEQ ID NO 662
<211> LENGTH: 30
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 662
cacgcaaaac ttgcgacaaa caataggtaa                                          30

<210> SEQ ID NO 663
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 663
gtgttgacta ttttacctct ggcggtgata                                          30

<210> SEQ ID NO 664
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 664
tagatctcct atagtgagtc gtattaattt                                          30

<210> SEQ ID NO 665
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 665
tactttcaaa gactacattt gtaagatttg                                          30

<210> SEQ ID NO 666
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 666
cataaagttc atgaaacgtg aactgaaatt                                          30

<210> SEQ ID NO 667
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 667
ccgtgatact atgaaccata agttcaccac                                          30

<210> SEQ ID NO 668
```

```
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 668
aattttacct ctggcggtga tactggttgc                                          30

<210> SEQ ID NO 669
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 669
attgtatgat actacaagaa agtttgttga                                          30

<210> SEQ ID NO 670
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 670
tagtagatac tttaagtgtt ctttaatttc                                          30

<210> SEQ ID NO 671
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 671
tggtcccacg cgcgtgggat actacgtcag                                          30

<210> SEQ ID NO 672
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 672
attacggtga gatactccca cgcgcgtggg                                          30

<210> SEQ ID NO 673
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 673
```
acgcgcgtgg gatactccca cgcgcgtggg                          30

<210> SEQ ID NO 674
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 674
gattagattc ataaatttga gagaggagtt                          30

<210> SEQ ID NO 675
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 675
acttagattc ataaatttga gagaggagtt                          30

<210> SEQ ID NO 676
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 676
ggttagattc ataaatttga gagaggagtt                          30

<210> SEQ ID NO 677
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 677
acttagattc ataaatttga gagaggagtt                          30

<210> SEQ ID NO 678
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 678
aattagattc ataaatttga gagaggagtt                          30

<210> SEQ ID NO 679
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:

-continued

Synthetic oligonucleotide"

<400> SEQUENCE: 679
acttagattc ataaatttga gagaggagtt                              30

<210> SEQ ID NO 680
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 680
atttagattc ataaatttga gagaggagtt                              30

<210> SEQ ID NO 681
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 681
cacgcgcgtg ggaatgttat aatacgtcag                              30

<210> SEQ ID NO 682
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 682
actgagcaca tactagagaa agaggagaaa                              30

<210> SEQ ID NO 683
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 683
cagtgagcga gtaacaacta cgctgtttta                              30

<210> SEQ ID NO 684
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 684
cagtgagcga gtaacaacta cgctgtttta                              30

<210> SEQ ID NO 685
<211> LENGTH: 30
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 685
atgtgagcgg ataacactat aattaataga                                   30

<210> SEQ ID NO 686
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 686
atgtgagcgg ataacactat aattaataga                                   30

<210> SEQ ID NO 687
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 687
atttcatgat gatacgtgag cggatagaag                                   30

<210> SEQ ID NO 688
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 688
ttgtgagcga gtggcaccat taagtacgta                                   30

<210> SEQ ID NO 689
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 689
ttgtgagcga gtgacaccat taagtacgta                                   30

<210> SEQ ID NO 690
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 690
ttgtgagcga gtaacaccat taagtacgta                                   30
```

<210> SEQ ID NO 691
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 691
ttgtgagcga gtaacaccat taagtacgta                                   30

<210> SEQ ID NO 692
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 692
agttggcaca gatttcgctt tatcttttt                                    30

<210> SEQ ID NO 693
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 693
tggaattgtg agcggataac aattaagctt                                   30

<210> SEQ ID NO 694
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 694
agtttgttta aacaacaaac taataggtga                                   30

<210> SEQ ID NO 695
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 695
aatgtgtgta attgtgagcg gataacaatt                                   30

<210> SEQ ID NO 696
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 696 atagggaat tgtgagcgga taacaattcc                                30

<210> SEQ ID NO 697
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 697 atagggaat tgtgagcgga taacaattcc                                30

<210> SEQ ID NO 698
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 698 atagggaat tgtgagcgga taacaattcc                                30

<210> SEQ ID NO 699
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 699 atagggaat tgtgagcgga taacaattcc                                30

<210> SEQ ID NO 700
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 700
aaacaaacaa acaaaaaaaa aaaaaaaaaa                                30

<210> SEQ ID NO 701
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 701
atactttaac gtcaaggaga aaaaactata                                30

<210> SEQ ID NO 702
<211> LENGTH: 30
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 702
tagatacaat tctattaccc ccatccatac                                      30

<210> SEQ ID NO 703
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 703
ttagtgaacc gtcagatcac tagtctgcag                                      30

<210> SEQ ID NO 704
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 704
ttagtgaacc gtcagatcac tagtctgcag                                      30

<210> SEQ ID NO 705
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 705
ggaaaggacg aaacaccgac tagtctgcag                                      30

<210> SEQ ID NO 706
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 706
attgtttgtg tattttagac tagtctgcag                                      30

<210> SEQ ID NO 707
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 707
attgtttgtg tattttagac tagtctgcag                                      30

<210> SEQ ID NO 708
```

```
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 708
attgtttgtg tattttagac tagtctgcag                                         30

<210> SEQ ID NO 709
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 709
ttagtgaacc gtcagatcac tagtctgcag                                         30

<210> SEQ ID NO 710
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 710
tgttatagtc gaatacctct ggcggtgata                                         30

<210> SEQ ID NO 711
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 711
attacaaact ttcttgtata gatttaacgt                                         30

<210> SEQ ID NO 712
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 712
tttcttgtat agatttacaa tgtatcttgt                                         30

<210> SEQ ID NO 713
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 713
```
tttcttgtag atacttacaa tgtatcttgt                                              30

<210> SEQ ID NO 714
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 714
ttttggtaca ctccctatca gtgatagaga                                              30

<210> SEQ ID NO 715
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 715 cttttttggta cactacctct ggcggtgata                                             30

<210> SEQ ID NO 716
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 716
actctcggca tggacgagct gtacaagtaa                                              30

<210> SEQ ID NO 717
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 717
ttctcgttcg actcatagct gaacacaaca                                              30

<210> SEQ ID NO 718
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 718
ggaattgtga gcgctcataa ttggatccgg                                              30

<210> SEQ ID NO 719
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:

-continued

Synthetic oligonucleotide"

<400> SEQUENCE: 719
ggaattgtga gctacagtcg tcggatccgg　　　　　　　　　　　　　　　30

<210> SEQ ID NO 720
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 720
ggaattgtga acgctcataa ttggatccgg　　　　　　　　　　　　　　　30

<210> SEQ ID NO 721
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 721
ggaattgtga actacagtcg tcggatccgg　　　　　　　　　　　　　　　30

<210> SEQ ID NO 722
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 722
taaattgtga acgctcataa ttggatccgg　　　　　　　　　　　　　　　30

<210> SEQ ID NO 723
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 723
gaaattgtaa gcgcttacaa ttggatccgg　　　　　　　　　　　　　　　30

<210> SEQ ID NO 724
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 724
gaaattgtaa gcgcttacaa ttggatccgg　　　　　　　　　　　　　　　30

<210> SEQ ID NO 725
<211> LENGTH: 30
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 725
ggaattgtaa gcgcttacaa ttggatccgg                                    30

<210> SEQ ID NO 726
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 726
gccaaattaa acaggattaa caggatccgg                                    30

<210> SEQ ID NO 727
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 727
gccaaattaa acaggattaa caggatccgg                                    30

<210> SEQ ID NO 728
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 728
gccaaattaa acaggattaa caggatccgg                                    30

<210> SEQ ID NO 729
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 729
gccaaattaa acaggattaa caggatccgg                                    30

<210> SEQ ID NO 730
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 730
gccaaattaa acaggattaa caggatccgg                                    30
```

```
<210> SEQ ID NO 731
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 731
gccaaattaa acaggattaa caggatccgg                                         30

<210> SEQ ID NO 732
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 732
gccaaattaa acaggattaa caggatccgg                                         30

<210> SEQ ID NO 733
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 733
gaaattgtaa gcgcttacaa ttggatccgg                                         30

<210> SEQ ID NO 734
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 734
taaattgtaa gcgcttacaa ttggatccgg                                         30

<210> SEQ ID NO 735
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 735
gtaattgtaa gcgcttacaa ttggatccgg                                         30

<210> SEQ ID NO 736
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 736
tcaattgtaa gcgcttacaa ttggatccgg                                              30

<210> SEQ ID NO 737
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 737
aaaattgtaa gcgcttacaa ttggatccgg                                              30

<210> SEQ ID NO 738
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 738
caaattgtaa gcgcttacaa ttggatccgg                                              30

<210> SEQ ID NO 739
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 739
gaaattgtaa gcgcttacaa ttggatccgg                                              30

<210> SEQ ID NO 740
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 740
taaattgtaa gcgcttacaa ttggatccgg                                              30

<210> SEQ ID NO 741
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 741
gtaattgtaa gcgcttacaa ttggatccgg                                              30

<210> SEQ ID NO 742
<211> LENGTH: 30
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 742
tcaattgtaa gcgcttacaa ttggatccgg                                        30

<210> SEQ ID NO 743
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 743
aaaattgtaa gcgcttacaa ttggatccgg                                        30

<210> SEQ ID NO 744
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 744
caaattgtaa gcgcttacaa ttggatccgg                                        30

<210> SEQ ID NO 745
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 745
gaaattgtaa gcgcttacaa ttggatccgg                                        30

<210> SEQ ID NO 746
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 746
taaattgtaa gcgcttacaa ttggatccgg                                        30

<210> SEQ ID NO 747
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 747
gtaattgtaa gcgcttacaa ttggatccgg                                        30

<210> SEQ ID NO 748
```

```
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 748
tcaattgtaa gcgcttacaa ttggatccgg                                    30

<210> SEQ ID NO 749
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 749
aaaattgtaa gcgcttacaa ttggatccgg                                    30

<210> SEQ ID NO 750
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 750
caaattgtaa gcgcttacaa ttggatccgg                                    30

<210> SEQ ID NO 751
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 751
gaaattgtaa gcgcttacaa ttggatccgg                                    30

<210> SEQ ID NO 752
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 752
taaattgtaa gcgcttacaa ttggatccgg                                    30

<210> SEQ ID NO 753
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 753
```

-continued gtaattgtaa gcgcttacaa ttggatccgg					30

<210> SEQ ID NO 754
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 754
tcaattgtaa gcgcttacaa ttggatccgg					30

<210> SEQ ID NO 755
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 755
aaaattgtaa gcgcttacaa ttggatccgg					30

<210> SEQ ID NO 756
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 756
caaattgtaa gcgcttacaa ttggatccgg					30

<210> SEQ ID NO 757
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 757
gaaattgtaa gcgcttacaa ttggatccgg					30

<210> SEQ ID NO 758
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 758
taaattgtaa gcgcttacaa ttggatccgg					30

<210> SEQ ID NO 759
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 759
gtaattgtaa gcgcttacaa ttggatccgg                                    30

<210> SEQ ID NO 760
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 760
tcaattgtaa gcgcttacaa ttggatccgg                                    30

<210> SEQ ID NO 761
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 761
aaaattgtaa gcgcttacaa ttggatccgg                                    30

<210> SEQ ID NO 762
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 762
caaattgtaa gcgcttacaa ttggatccgg                                    30

<210> SEQ ID NO 763
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 763
gaaattgtaa gcgcttacaa ttggatccgg                                    30

<210> SEQ ID NO 764
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 764
taaattgtaa gcgcttacaa ttggatccgg                                    30

<210> SEQ ID NO 765
<211> LENGTH: 30
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 765
gtaattgtaa gcgcttacaa ttggatccgg                                      30

<210> SEQ ID NO 766
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 766
tcaattgtaa gcgcttacaa ttggatccgg                                      30

<210> SEQ ID NO 767
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 767
aaaattgtaa gcgcttacaa ttggatccgg                                      30

<210> SEQ ID NO 768
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 768
caaattgtaa gcgcttacaa ttggatccgg                                      30

<210> SEQ ID NO 769
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 769
gaaattgtaa gcgcttacaa ttggatccgg                                      30

<210> SEQ ID NO 770
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 770
taaattgtaa gcgcttacaa ttggatccgg                                      30
```

```
<210> SEQ ID NO 771
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 771
gtaattgtaa gcgcttacaa ttggatccgg                                      30

<210> SEQ ID NO 772
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 772
tcaattgtaa gcgcttacaa ttggatccgg                                      30

<210> SEQ ID NO 773
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 773
aaaattgtaa gcgcttacaa ttggatccgg                                      30

<210> SEQ ID NO 774
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 774
caaattgtaa gcgcttacaa ttggatccgg                                      30

<210> SEQ ID NO 775
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 775
gccaaattaa acaggattaa caggatccgg                                      30

<210> SEQ ID NO 776
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

<400> SEQUENCE: 776
gccaaattaa acaggattaa caggatccgg                                    30

<210> SEQ ID NO 777
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 777
caaattatga gcgctcacaa ttggatccgg                                    30

<210> SEQ ID NO 778
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 778
tgatagagat tccctatcag tgatagagat                                    30

<210> SEQ ID NO 779
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 779
gttctttaat tatttaagtg ttctttaatt                                    30

<210> SEQ ID NO 780
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 780
gttctttaat tatttaagtg ttctttaatt                                    30

<210> SEQ ID NO 781
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 781
cgtgcgtgtt gataacaccg tgcgtgttga                                    30

<210> SEQ ID NO 782
<211> LENGTH: 30
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 782 gtgttctttta atatttaagt gttctttaat                                       30

<210> SEQ ID NO 783
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 783
ggaattgtga gcggataaca atttcacaca                                        30

<210> SEQ ID NO 784
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 784
gttacgttta tcgcggtgat tgttacttat                                        30

<210> SEQ ID NO 785
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 785
gcaaaataaa atggaatgat gaaactgggt                                        30

<210> SEQ ID NO 786
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 786
aacgcgcggg gagaggcggt ttgcgtattg                                        30

<210> SEQ ID NO 787
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 787
gtgttgatgc ttttatcacc gccagtggta                                        30

<210> SEQ ID NO 788
```

```
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 788
agtgtgtgga attgtgagcg gataacaatt                                    30

<210> SEQ ID NO 789
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 789
acatcttaaa agttttagta tcatattcgt                                    30

<210> SEQ ID NO 790
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 790
ctgaaagcgc ataccgctat ggaggggtt                                     30

<210> SEQ ID NO 791
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 791
tattttacct ctggcggtga taatggttgc                                    30

<210> SEQ ID NO 792
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 792
atttataaat agtggtgata gatttaacgt                                    30

<210> SEQ ID NO 793
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 793
```

```
atttataaat agtggtgata gatttaacgt                                      30
```

<210> SEQ ID NO 794
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 794

```
gaaatctggc agtttttggt acacgaaagc                                      30
```

<210> SEQ ID NO 795
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 795

```
tgccagttct ggcaggtcta aaaagtgttc                                      30
```

<210> SEQ ID NO 796
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 796

```
cacagaactt gcatttatat aaagggaaag                                      30
```

<210> SEQ ID NO 797
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 797

```
agttggcaca gatttcgctt tatcttttt                                       30
```

<210> SEQ ID NO 798
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 798

```
agcgctcaca atttaatacg actcactata                                      30
```

<210> SEQ ID NO 799
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:

-continued

Synthetic oligonucleotide"

<400> SEQUENCE: 799
ggaattgtga gcggataaca atttcacaca                                    30

<210> SEQ ID NO 800
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 800
ggaattgtga gcggataaca atttcacaca                                    30

<210> SEQ ID NO 801
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 801
ggaattgtga gcggataaca atttcacaca                                    30

<210> SEQ ID NO 802
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 802
agaactgtaa tccctatcag tgatagagat                                    30

<210> SEQ ID NO 803
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 803
tgttgattta tctaacaccg tgcgtgttga                                    30

<210> SEQ ID NO 804
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 804
acaccgtgcg tgttgatata gtcgaataaa                                    30

<210> SEQ ID NO 805
<211> LENGTH: 30
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 805
ggttcttttt ggtacctctg gcggtgataa                                        30

<210> SEQ ID NO 806
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 806
tgtaggatcg tacaggtata aattcttcag                                        30

<210> SEQ ID NO 807
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 807
ctatctcatt tgctagtata gtcgaataaa                                        30

<210> SEQ ID NO 808
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 808
aattgtgagc ggataacaat ttcacacaga                                        30

<210> SEQ ID NO 809
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 809
gttacgttta tcgcggtgat tgttacttat                                        30

<210> SEQ ID NO 810
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 810
acggtgacct agatctccga tactgagcac                                        30
```

<210> SEQ ID NO 811
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 811
tggaattgtg agcggataaa atttcacaca                                      30

<210> SEQ ID NO 812
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 812
tagtagataa tttaagtgtt ctttaatttc                                      30

<210> SEQ ID NO 813
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 813
aacaaaaaaa cggatcctct agttgcggcc                                      30

<210> SEQ ID NO 814
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 814
ataaatgctt gactctgtag cgggaaggcg                                      30

<210> SEQ ID NO 815
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 815
atttcatgat gatacgtgag cggatagaag                                      30

<210> SEQ ID NO 816
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

-continued

<400> SEQUENCE: 816
gggacacaaa catcaagagg atatgagatt                                30

<210> SEQ ID NO 817
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 817
gtcaaaatga ccgaaacggg tggtaacttc                                30

<210> SEQ ID NO 818
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 818
agtaatctta tcgccagttt ggtctggtca                                30

<210> SEQ ID NO 819
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 819
agtaatctta tcgccagttt ggtctggtca                                30

<210> SEQ ID NO 820
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 820
aattctgaac aacatccgta ctcttcgtgc                                30

<210> SEQ ID NO 821
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 821
cgatctattc acctgaaaga gaaataaaaa                                30

<210> SEQ ID NO 822
<211> LENGTH: 30
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 822
aaacgttagt ttgaatggaa agatgcctgc                                    30

<210> SEQ ID NO 823
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 823
acaggaaaca gctatgacca tgattacgcc                                    30

<210> SEQ ID NO 824
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 824
gttcactcta taccgctgaa ggtgtaatgg                                    30

<210> SEQ ID NO 825
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 825
tagtttataa tttaagtgtt ctttaatttc                                    30

<210> SEQ ID NO 826
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 826
gaaaatgtga gcgagtaaca acctcacaca                                    30

<210> SEQ ID NO 827
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 827
ttttatcgca actctctact gtttctccat                                    30

<210> SEQ ID NO 828
```

```
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 828
gtttctccat tactagagaa agagggaca                                     30

<210> SEQ ID NO 829
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 829
aataactctg atagtgctag tgtagatctc                                    30

<210> SEQ ID NO 830
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 830
caccttcggg tgggcctttc tgcgtttata                                    30

<210> SEQ ID NO 831
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 831
caccttcggg tgggcctttc tgcgtttata                                    30

<210> SEQ ID NO 832
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 832
gtgttgacta ttttacctct ggcggtgata                                    30

<210> SEQ ID NO 833
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 833
```

```
cgaaacggga accctatatt gatctctact                                          30
```

<210> SEQ ID NO 834
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 834

```
accgttaaga accatatcca agaatcaaaa                                          30
```

<210> SEQ ID NO 835
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 835

```
accgttaaga accatatcca agaatcaaaa                                          30
```

<210> SEQ ID NO 836
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 836

```
cacaaataca cacactaaat taataactag                                          30
```

<210> SEQ ID NO 837
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 837

```
atacggtcaa cgaactataa ttaactaaac                                          30
```

<210> SEQ ID NO 838
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 838

```
tagatacaat tctattaccc ccatccatac                                          30
```

<210> SEQ ID NO 839
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:

-continued

Synthetic oligonucleotide"

<400> SEQUENCE: 839
ggggcgaggg ccccgcctcc ggaggcgggg            30

<210> SEQ ID NO 840
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 840
gaggggacgg ctccggcccc ggggccggag            30

<210> SEQ ID NO 841
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 841
ggggcgaggg ctccggcccc ggggccggag            30

<210> SEQ ID NO 842
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 842
gaggggacgg ccccgcctcc ggaggcgggg            30

<210> SEQ ID NO 843
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 843
aggaggaaaa aaatg            15

<210> SEQ ID NO 844
<211> LENGTH: 13
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 844
aggaatttaa atg            13

<210> SEQ ID NO 845
<211> LENGTH: 15
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 845
aggaaacaga ccatg                                                    15

<210> SEQ ID NO 846
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 846
aggaaaccgg ttcgatg                                                  17

<210> SEQ ID NO 847
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 847
aggaaaccgg ttatg                                                    15

<210> SEQ ID NO 848
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 848
aggacggttc gatg                                                     14

<210> SEQ ID NO 849
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 849
aggaaaggcc tcgatg                                                   16

<210> SEQ ID NO 850
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 850
aggacggccg gatg                                                     14
```

```
<210> SEQ ID NO 851
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (13)..(15)
<223> OTHER INFORMATION: a, c, t, g, unknown or other
<220> FEATURE:
<221> NAME/KEY: modified_base
<222> LOCATION: (18)..(20)
<223> OTHER INFORMATION: a, c, t, g, unknown or other

<400> SEQUENCE: 851
tctagagaaa gannngannn actagatg                                              28

<210> SEQ ID NO 852
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 852
tctagagaaa gagggacaa actagatg                                               28

<210> SEQ ID NO 853
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 853
tctagagaaa gacaggaccc actagatg                                              28

<210> SEQ ID NO 854
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 854
tctagagaaa gatccgatgt actagatg                                              28

<210> SEQ ID NO 855
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 855
tctagagaaa gattagacaa actagatg                                              28

<210> SEQ ID NO 856
```

```
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 856
tctagagaaa gaagggacag actagatg                                        28

<210> SEQ ID NO 857
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 857
tctagagaaa gacatgacgt actagatg                                        28

<210> SEQ ID NO 858
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 858
tctagagaaa gataggagac actagatg                                        28

<210> SEQ ID NO 859
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 859
tctagagaaa gaagagactc actagatg                                        28

<210> SEQ ID NO 860
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 860
tctagagaaa gacgagatat actagatg                                        28

<210> SEQ ID NO 861
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 861
```
tctagagaaa gactggagac actagatg                                          28

<210> SEQ ID NO 862
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 862
tctagagaaa gaggcgaatt actagatg                                          28

<210> SEQ ID NO 863
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 863
tctagagaaa gaggcgatac actagatg                                          28

<210> SEQ ID NO 864
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 864
tctagagaaa gaggtgacat actagatg                                          28

<210> SEQ ID NO 865
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 865
tctagagaaa gagtggaaaa actagatg                                          28

<210> SEQ ID NO 866
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 866
tctagagaaa gatgagaaga actagatg                                          28

<210> SEQ ID NO 867
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:

-continued

Synthetic oligonucleotide"

<400> SEQUENCE: 867
tctagagaaa gaagggatac actagatg                28

<210> SEQ ID NO 868
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 868
tctagagaaa gacatgaggc actagatg                28

<210> SEQ ID NO 869
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 869
tctagagaaa gacatgagtt actagatg                28

<210> SEQ ID NO 870
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 870
tctagagaaa gagacgaatc actagatg                28

<210> SEQ ID NO 871
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 871
tctagagaaa gatttgatat actagatg                28

<210> SEQ ID NO 872
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 872
tctagagaaa gacgcgagaa actagatg                28

<210> SEQ ID NO 873
<211> LENGTH: 28
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 873
tctagagaaa gagacgagtc actagatg                                          28

<210> SEQ ID NO 874
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 874
tctagagaaa gagaggagcc actagatg                                          28

<210> SEQ ID NO 875
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 875
tctagagaaa gagatgacta actagatg                                          28

<210> SEQ ID NO 876
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 876
tctagagaaa gagccgacat actagatg                                          28

<210> SEQ ID NO 877
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 877
tctagagaaa gagccgagtt actagatg                                          28

<210> SEQ ID NO 878
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 878
tctagagaaa gaggtgactc actagatg                                          28
```

```
<210> SEQ ID NO 879
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 879
tctagagaaa gagtggaact actagatg                                         28

<210> SEQ ID NO 880
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 880
tctagagaaa gataggactc actagatg                                         28

<210> SEQ ID NO 881
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 881
tctagagaaa gattggacgt actagatg                                         28

<210> SEQ ID NO 882
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 882
tctagagaaa gaaacgacat actagatg                                         28

<210> SEQ ID NO 883
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 883
tctagagaaa gaaccgaatt actagatg                                         28

<210> SEQ ID NO 884
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 884
tctagagaaa gacaggatta actagatg                                          28

<210> SEQ ID NO 885
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 885
tctagagaaa gacccgagac actagatg                                          28

<210> SEQ ID NO 886
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 886
tctagagaaa gaccggaaat actagatg                                          28

<210> SEQ ID NO 887
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 887
tctagagaaa gaccggagac actagatg                                          28

<210> SEQ ID NO 888
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 888
tctagagaaa gagctgagca actagatg                                          28

<210> SEQ ID NO 889
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 889
tctagagaaa gagtagatca actagatg                                          28

<210> SEQ ID NO 890
<211> LENGTH: 28
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 890
tctagagaaa gatatgaata actagatg                                   28

<210> SEQ ID NO 891
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 891
tctagagaaa gattagagtc actagatg                                   28

<210> SEQ ID NO 892
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 892
tctagagttc acacaggaaa cctactagat g                               31

<210> SEQ ID NO 893
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 893
tctagagatt aaagaggaga aatactagat g                               31

<210> SEQ ID NO 894
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 894
tctagagtca cacaggaaac ctactagatg                                 30

<210> SEQ ID NO 895
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 895
tctagagtca cacaggaaag tactagatg                                  29

<210> SEQ ID NO 896
```

```
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 896
tctagagtca cacaggacta ctagatg                                        27

<210> SEQ ID NO 897
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 897
tctagagaaa gaggagaaat actagatg                                       28

<210> SEQ ID NO 898
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 898
tctagagatt aaagaggaga atactagatg                                     30

<210> SEQ ID NO 899
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 899
tctagagaaa gagggaaat actagatg                                        28

<210> SEQ ID NO 900
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 900 gtgtg                                                                 5

<210> SEQ ID NO 901
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 901
```

-continued gtgtgtctag                                                                                           10

<210> SEQ ID NO 902
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 902
tcacacagga aaccggttcg atg                                                                            23

<210> SEQ ID NO 903
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 903
tcacacagga aaggcctcga tg                                                                             22

<210> SEQ ID NO 904
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 904
tcacacagga cggccggatg                                                                                20

<210> SEQ ID NO 905
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 905
tctcacgtgt gtcaag                                                                                    16

<210> SEQ ID NO 906
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 906
tctcacgtgt gt                                                                                        12

<210> SEQ ID NO 907
<211> LENGTH: 7
<212> TYPE: DNA
<213> ORGANISM: Artificial Sequence
<220> FEATURE:
<221> NAME/KEY: source
<223> OTHER INFORMATION: /note="Description of Artificial Sequence:

-continued

Synthetic oligonucleotide"

<400> SEQUENCE: 907 catccct                                                                 7

<210> SEQ ID NO 908
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 908
tcacatccct                                                             10

<210> SEQ ID NO 909
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 909
tcacatccct cc                                                          12

<210> SEQ ID NO 910
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 910
actgcacgag gtaacacaag                                                  20

<210> SEQ ID NO 911
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 911
tacgaggagg atgaagagta                                                  20

<210> SEQ ID NO 912
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 912
actttactta tgagggagta                                                  20

<210> SEQ ID NO 913
<211> LENGTH: 20
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 913
acgaagacgg agacttctaa                                              20

<210> SEQ ID NO 914
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 914
aaccctcagg aggtaaacca                                              20

<210> SEQ ID NO 915
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 915
aagacatgga gacacattta                                              20

<210> SEQ ID NO 916
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 916
gcacgaggta acacaagatg tgaagagctg                                   30

<210> SEQ ID NO 917
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 917
gaggaggatg aagagtaatg tgaagagctg                                   30

<210> SEQ ID NO 918
<211> LENGTH: 11
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 918
aggaggtcat c                                                       11
```

```
<210> SEQ ID NO 919
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 919
gcaagctctt ttttcagttg tctc                                              24

<210> SEQ ID NO 920
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 920
ctgatagtta aaatcaccag catga                                             25

<210> SEQ ID NO 921
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 921
taaaaacaag aggaaaacaa                                                   20

<210> SEQ ID NO 922
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 922
tctcctcttt                                                              10

<210> SEQ ID NO 923
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 923
acggagaagc agcgaa                                                       16

<210> SEQ ID NO 924
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 924
gaggttggga caag                                                    14

<210> SEQ ID NO 925
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 925
taaatgtatc cgtttataag gacagcccga                                   30

<210> SEQ ID NO 926
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 926
ctcttaagtg ggagcggct                                               19

<210> SEQ ID NO 927
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 927
ctctaccgga gaaatt                                                  16

<210> SEQ ID NO 928
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 928
ctcatcgtta aagagcgact ac                                           22

<210> SEQ ID NO 929
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 929
ctcagcctgt acctggagag cctttc                                       26

<210> SEQ ID NO 930
<211> LENGTH: 10
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 930
ctcaaggagg                                                                  10

<210> SEQ ID NO 931
<211> LENGTH: 6
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 931 gagagg                                                                       6

<210> SEQ ID NO 932
<211> LENGTH: 13
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 932
aggaggatta caa                                                              13

<210> SEQ ID NO 933
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 933
aaagaggaga aa                                                               12

<210> SEQ ID NO 934
<211> LENGTH: 13
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 934
tcacacagga aag                                                              13

<210> SEQ ID NO 935
<211> LENGTH: 8
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 935 ggaagagg                                                                     8

<210> SEQ ID NO 936
```

```
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 936
tttctcctct ttaat                                                          15

<210> SEQ ID NO 937
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 937
tcacacagga aaggcctcg                                                      19

<210> SEQ ID NO 938
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 938
attaaagagg agaaattaag c                                                   21

<210> SEQ ID NO 939
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 939
tcgtttctga aaaattttcg tttctgaaaa                                          30

<210> SEQ ID NO 940
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 940
tggctaacat agggt                                                          15

<210> SEQ ID NO 941
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 941
```
tggctaactg aggat                                                   15

<210> SEQ ID NO 942
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 942
tggctaaccc agggt                                                   15

<210> SEQ ID NO 943
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 943
tggctaactc aggtg                                                   15

<210> SEQ ID NO 944
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 944
tggctaaccc tggta                                                   15

<210> SEQ ID NO 945
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 945
tggctaactt gggac                                                   15

<210> SEQ ID NO 946
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 946
tggctaacgc aggtc                                                   15

<210> SEQ ID NO 947
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 947
tggctaacat cggtg    15

<210> SEQ ID NO 948
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 948
ttaattaagg aaaagatct    19

<210> SEQ ID NO 949
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 949
cagaagagga tattaata    18

<210> SEQ ID NO 950
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 950
ttgataagga attgta    16

<210> SEQ ID NO 951
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 951
tcagaggaga taattta    17

<210> SEQ ID NO 952
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 952
tgacacgttg agcggtatga    20

<210> SEQ ID NO 953
<211> LENGTH: 20
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 953
acagataaca ggagtaagta                                                     20

<210> SEQ ID NO 954
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 954
taaagggaga aaaat                                                          15

<210> SEQ ID NO 955
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 955
gagtcttgag gtaactat                                                       18

<210> SEQ ID NO 956
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 956
tcaggaatat taaaaacgct                                                     20

<210> SEQ ID NO 957
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 957
atttgaagga aaatatt                                                        17

<210> SEQ ID NO 958
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 958
caaaaacata ctgcaggaat                                                     20
```

```
<210> SEQ ID NO 959
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 959
tgccattgca aaggagaaga ct                                              22

<210> SEQ ID NO 960
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 960 aaggggaat tcaaat                                                      16

<210> SEQ ID NO 961
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 961
aaggggtgca gaat                                                       14

<210> SEQ ID NO 962
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 962
aggtggaatc acag                                                       14

<210> SEQ ID NO 963
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 963
atagataaaa atggtaacaa t                                               21

<210> SEQ ID NO 964
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 964
gggatatagc ctgaggggcc tgta                                          24

<210> SEQ ID NO 965
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 965
cggcaataac agaggcgatt t                                             21

<210> SEQ ID NO 966
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 966
attaaagagg agaaata                                                  17

<210> SEQ ID NO 967
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 967
tcacacagga aagta                                                    15

<210> SEQ ID NO 968
<211> LENGTH: 11
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 968
aaaggaggtg t                                                        11

<210> SEQ ID NO 969
<211> LENGTH: 11
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 969
agaggtggtg t                                                        11

<210> SEQ ID NO 970
<211> LENGTH: 6
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 970 aggagg                                                                     6

<210> SEQ ID NO 971
<211> LENGTH: 4
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 971 gagg                                                                       4

<210> SEQ ID NO 972
<211> LENGTH: 11
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 972
taaaggagga a                                                              11

<210> SEQ ID NO 973
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 973
aaaggtggtg aa                                                             12

<210> SEQ ID NO 974
<211> LENGTH: 13
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 974
aggaaacaga acc                                                            13

<210> SEQ ID NO 975
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 975
gattgggata aataat                                                         16

<210> SEQ ID NO 976
```

```
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 976
atcaaccggg gtacat                                                   16

<210> SEQ ID NO 977
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 977
tttggagatt ttcaac                                                   16

<210> SEQ ID NO 978
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 978
aaaaaaggta attcaa                                                   16

<210> SEQ ID NO 979
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 979
cataaggtaa ttcaca                                                   16

<210> SEQ ID NO 980
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 980
ataaggagtc ttaatc                                                   16

<210> SEQ ID NO 981
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 981
```

-continued gttccggcta agtaac  16

<210> SEQ ID NO 982
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 982
taatggaaac ttcctc  16

<210> SEQ ID NO 983
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 983
tcgctggggg tcaaag  16

<210> SEQ ID NO 984
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 984
atttgagggg gattca  16

<210> SEQ ID NO 985
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 985
aatttaggtc agaag  15

<210> SEQ ID NO 986
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 986
aatcaatagg agaaatcaat  20

<210> SEQ ID NO 987
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 987
ttaaagagga gaaatactag                                          20

<210> SEQ ID NO 988
<211> LENGTH: 56
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 988
tctagagaac tagaatcacc tcttggattt gggtattaaa gaggagatac tagatg    56

<210> SEQ ID NO 989
<211> LENGTH: 56
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 989
tctagagaac tagaatcacc tcttgctttt gggtaagaaa gaggagatac tagatg    56

<210> SEQ ID NO 990
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 990
cccgccgcca ccatggag                                            18

<210> SEQ ID NO 991
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 991
cccgccgcca ccatggag                                            18

<210> SEQ ID NO 992
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 992
tctagagcac cactactaga tg                                       22

<210> SEQ ID NO 993
<211> LENGTH: 25
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 993
tctagagtca caccactact agatg                                           25

<210> SEQ ID NO 994
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 994
tctagagtca caccaccta ctagatg                                          27

<210> SEQ ID NO 995
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 995

Arg Pro Ala Ala Asn Asp Glu Asn Tyr Ala Leu Ala Ala
1               5                   10

<210> SEQ ID NO 996
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 996

Arg Pro Ala Ala Asn Asp Glu Asn Tyr Ala Leu Val Ala
1               5                   10

<210> SEQ ID NO 997
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 997

Arg Pro Ala Ala Asn Asp Glu Asn Tyr Ala Ala Ala Val
1               5                   10

<210> SEQ ID NO 998
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 998
```

Arg Pro Ala Ala Asn Asp Glu Asn Tyr Ala Ala Ser Val
1               5                   10

<210> SEQ ID NO 999
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 999
gcagcaaacg acgaaaacta cgctttagca gcttaa                                   36

<210> SEQ ID NO 1000
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1000
gcagcaaacg acgaaaacta cgctgcagca gtttaa                                   36

<210> SEQ ID NO 1001
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1001
gcagcaaacg acgaaaacta cgctgcatca gtttaa                                   36

<210> SEQ ID NO 1002
<211> LENGTH: 1032
<212> TYPE: DNA
<213> ORGANISM: Enterobacteria phage P1

<400> SEQUENCE: 1002
atgtccaatt tactgaccgt acaccaaaat ttgcctgcat taccggtcga tgcaacgagt          60
gatgaggttc gcaagaacct gatggacatg ttcagggatc gccaggcgtt ttctgagcat         120
acctggaaaa tgcttctgtc cgtttgccgg tcgtgggcgg catggtgcaa gttgaataac         180
cggaaatggt tcccgcagaa acctgaagat gttcgcgatt atcttctata tcttcaggcg         240
cgcggtctgg cagtaaaaac tatccagcaa catttgggcc agctaaacat gcttcatcgt         300
cggtccgggc tgccacgacc aagtgacagc aatgctgttt cactggttat gcggcggatc         360
cgaaaagaaa acgttgatgc cggtgaacgt gcaaacagg ctctagcgtt cgaacgcact          420
gatttcgacc aggttcgttc actcatgaa atagcgatc gctgccagga tatacgtaat          480
ctggcatttc tggggattgc ttataacacc ctgttacgta tagccgaaat tgccaggatc         540
agggttaaag atatctcacg tactgacggt gggagaatgt taatccatat tggcagaacg         600
aaaacgctgg ttagcaccgc aggtgtagag aaggcactta gcctgggggt aactaaactg         660
gtcgagcgat ggatttccgt ctctggtgta gctgatgatc cgaataacta cctgttttgc         720
cgggtcagaa aaatggtgt tgccgcgcca tctgccacca gccagctatc aactcgcgcc         780

| | |
|---|---|
| ctggaaggga tttttgaagc aactcatcga ttgatttacg gcgctaagga tgactctggt | 840 |
| cagagatacc tggcctggtc tggacacagt gcccgtgtcg gagccgcgcg agatatggcc | 900 |
| cgcgctggag tttcaatacc ggagatcatg caagctggtg gctggaccaa tgtaaatatt | 960 |
| gtcatgaact atatccgtaa cctggatagt gaaacagggg caatggtgcg cctgctggaa | 1020 |
| gatggcgatt ag | 1032 |

<210> SEQ ID NO 1003
<211> LENGTH: 4543
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 1003

| | |
|---|---|
| atgaccatga ttacgccaag cttgcatgcc tgcaggtcga ctctagaatt cgctgtctgc | 60 |
| gagggccggc tgttggggtg agtactccct ctcaaaagcg ggcatgactt ctgcgctaag | 120 |
| attgtcagtt tccaaaaacg aggaggattt gatattcacc tggcccgcgg tgatgccttt | 180 |
| gagggtggcc gcgtccatct ggtcagaaaa gacaatcttt ttgttgtcaa gcttgaggtg | 240 |
| tggcaggctt gagatctggc catacacttg agtgacaatg acatccactt tgcctttctc | 300 |
| tccacaggtg tccactccca ggtccaactg cagcccaagc ttccaccatg ccacaatttg | 360 |
| atatattatg taaacacca cctaaggtgc ttgttcgtca gtttgtggaa aggtttgaaa | 420 |
| gaccttcagg tgagaaaata gcattatgtg ctgctgaact aacctattta tgttggatga | 480 |
| ttacacataa cggaacagca atcaagagag ccacattcat gagctataat actatcataa | 540 |
| gcaattcgct gagtttggat attgtcaaca agtcactgca gtttaaatac aagacgcaaa | 600 |
| aagcaacaat tctggaagcc tcattaaaga aattgattcc tgcttgggaa tttacaatta | 660 |
| ttccttacta tggacaaaaa catcaatctg atatcactga tattgtaagt agtttgcaat | 720 |
| tacagttcga atcatcggaa gaagcagata agggaaatag ccacagtaaa aaatgctta | 780 |
| aagcacttct aagtgagggt gaaagcatct gggagatcac tgagaaaata ctaaattcgt | 840 |
| ttgagtatac ttcgagattt acaaaaacaa aaactttata ccaattcctc ttcctagcta | 900 |
| cttttcatcaa ttgtggaaga ttcagcgata ttaagaacgt tgatccgaaa tcatttaaat | 960 |
| tagtccaaaa taagtatctg ggagtaataa tccagtgttt agtgacagag acaaagacaa | 1020 |
| gcgttagtag gcacatatac ttctttagcg caaggggtag gatcgatcca cttgtatatt | 1080 |
| tggatgaatt tttgaggaat tctgaaccag tcctaaaacg agtaaatagg accggcaatt | 1140 |
| cttcaagcaa caagcaggaa taccaattat taaaagataa cttagtcaga tcgtacaaca | 1200 |
| aagctttgaa gaaaaatgcg ccttattcaa tctttgctat aaaaaatggc ccaaaatctc | 1260 |
| acattggaag acatttgatg acctcatttc tttcaatgaa gggcctaacg gagttgacta | 1320 |
| atgttgtggg aaattggagc gataagcgtg cttctgccgt ggccaggaca acgtatactc | 1380 |
| atcagataac agcaatacct gatcactact tcgcactagt ttctcggtac tatgcatatg | 1440 |
| atccaatatc aaaggaaatg atagcattga aggatgagac taatccaatt gaggagtggc | 1500 |
| agcatataga acagctaaag ggtagtgctg aaggaagcat acgataccc gcatggaatg | 1560 |
| ggataatatc acaggaggta ctagactacc tttcatccta cataaataga cgcatataag | 1620 |
| tacgcattta agcataaaca cgcactatgc cgttcttctc atgtatatat atatacaggc | 1680 |
| aacacgcaga tataggtgcg acgtgaacag tgagctgtat gtgcgggtac cgagctcctc | 1740 |

```
gaggatcaga catgataaga tacattgatg agtttggaca aaccacaact agaatgcagt    1800
gaaaaaaatg ctttatttgt gaaatttgtg atgctattgc tttatttgta accattataa    1860
agctgcaata aacaagttat cctcgaggag ctcatgagcg cttgtttcgg cgtgggtatg    1920
gtggcaggcc cgtggccggg ggactgttgg gcgccatctc cttgcatgca ccattccttg    1980
cggcggcggt gctcaacggc ctcaacctac tactgggctg cttcctaatg caggagtcgc    2040
ataagggaga gcgtcgacct actagtcggc cgtacgggcc ctttcgtctc gcgcgtttcg    2100
gtgatgacgg tgaaaacctc tgacacatgc agctcccgga gacggtcaca gcttgtctgt    2160
aagcggatgc cgggagcaga caagcccgtc agggcgcgtc agcgggtgtt ggcgggtgtc    2220
ggggctggct taactatgcg gcatcagagc agattgtact gagagtgcac catatgcggt    2280
gtgaaatacc gcacagatgc gtaaggagaa aataccgcat caggcggcct aagggcctc     2340 gtgatacgcc tatttttata ggttaatgtc atgataataa tggtttctta gacgtcaggt    2400
ggcacttttc ggggaaatgt gcgcggaacc cctatttgtt tatttttcta aatacattca    2460
aatatgtatc cgctcatgag acaataaccc tgataaatgc ttcaataata ttgaaaaagg    2520
aagagtatga gtattcaaca tttccgtgtc gcccttattc ccttttttgc ggcattttgc    2580
cttcctgttt ttgctcaccc agaaacgctg gtgaaagtaa aagatgctga agatcagttg    2640
ggtgcacgag tgggttacat cgaactggat ctcaacagcg gtaagatcct tgagagtttt    2700
cgccccgaag aacgttttcc aatgatgagc acttttaaag ttctgctatg tggcgcggta    2760
ttatcccgta ttgacgccgg gcaagagcaa ctcggtcgcc gcatacacta ttctcagaat    2820
gacttggttg agtactcacc agtcacagaa aagcatctta cggatggcat gacagtaaga    2880
gaattatgca gtgctgccat aaccatgagt gataacactg cggccaactt acttctgaca    2940
acgatcggag gaccgaagga gctaaccgct tttttgcaca acatggggga tcatgtaact    3000
cgccttgatc gttgggaacc ggagctgaat gaagccatac caaacgacga gcgtgacacc    3060
acgatgcctg tagcaatggc aacaacgttg cgcaaactat taactggcga actacttact    3120
ctagcttccc ggcaacaatt aatagactgg atggaggcgg ataaagttgc aggaccactt    3180
ctgcgctcgg cccttccggc tggctggttt attgctgata atctggagc cggtgagcgt    3240 gggtctcgcg gtatcattgc agcactgggg ccagatggta agccctcccg tatcgtagtt    3300
atctacacga cggggagtca ggcaactatg gatgaacgaa atagacagat cgctgagata    3360
ggtgcctcac tgattaagca ttggtaactg tcagaccaag tttactcata tatactttag    3420
attgatttaa aacttcattt ttaatttaaa aggatctagg tgaagatcct ttttgataat    3480
ctcatgacca aaatccctta acgtgagttt tcgttccact gagcgtcaga ccccgtagaa    3540
aagatcaaag gatcttcttg agatcctttt tttctgcgcg taatctgctg cttgcaaaca    3600
aaaaaaccac cgctaccagc ggtggtttgt ttgccggatc aagagctacc aactctttt    3660 ccgaaggtaa ctggcttcag cagagcgcag ataccaaata ctgtccttct agtgtagccg    3720
tagttaggcc accacttcaa gaactctgta gcaccgccta catacctcgc tctgctaatc    3780
ctgttaccag tggctgctgc cagtggcgat aagtcgtgtc ttaccgggtt ggactcaaga    3840
cgatagttac cggataaggc gcagcggtcg ggctgaacgg ggggttcgtg cacacagccc    3900
agcttggagc gaacgaccta caccgaactg agatacctac agcgtgagca ttgagaaagc    3960
gccacgcttc ccgaagggag aaaggcggac aggtatccgg taagcggcag ggtcggaaca    4020
ggagagcgca cgagggagct tccaggggga aacgcctggt atctttatag tcctgtcggg    4080
tttcgccacc tctgacttga gcgtcgattt ttgtgatgct cgtcaggggg gcggagccta    4140
```

-continued

```
tggaaaaacg ccagcaacgc ggccttttta cggttcctgg cctttgctg gcctttgct      4200 cacatgttct ttcctgcgtt atccctgat tctgtggata accgtattac cgcctttgag      4260
tgagctgata ccgctcgccg cagccgaacg accgagcgca gcgagtcagt gagcgaggaa    4320
gcggaagagc gcccaatacg caaaccgcct ctccccgcgc gttggccgat tcattaatgc    4380
agctggcacg acaggtttcc cgactggaaa gcgggcagtg agcgcaacgc aattaatgtg    4440
agttagctca ctcattaggc accccaggct ttacactta tgcttccggc tcgtatgttg     4500
tgtggaattg tgagcggata caatttcac acaggaaaca gct                      4543
```

<210> SEQ ID NO 1004
<211> LENGTH: 6251
<212> TYPE: DNA
<213> ORGANISM: Zygosaccharomyces rouxii

<400> SEQUENCE: 1004

```
gaattcaaaa cataaagaag agcatgaaaa gactattagt gaacatgtca ccaatcgaag      60
gactggaaga attgtttttt caggcaagat cgttgggagt accttcccat ttggtagaga    120
gtgtacgacc acctgtcgat attcatagcg gtaacatgca caggacaggt attagtccga    180
ggaagcgaac cttacctgaa ccgttcgatg aatcaaacac cataagccac cggagaacta    240
gaagaaatac caaacaataa cctaaacctg ctatggctaa tagattagga ttgagctact    300
ggacgggaat tgtggagggg tattgtggaa tggagtgttg tgttgtggaa cggggttaat    360
tgtaatgata atgataatga taacggtggg ttatagagca ttgcatctgt cgagttacga    420
tgatagagtt gtaagggcgg cagcgggtat ggcctaaata atttagttta gcttaatata    480
atttagtttt tctaggcgag atcatatcac tgtggacgtt gatgaaagaa tacgttattc    540
tttcatcaaa tcgttctttc attaattcgt tctttcatca aatcgttctt tcatcaagtc    600 gttcttcat caaccgtac cgcgcagaag ggagcctgcg caggcggttg ctacagaaat      660
taaaccatta ctctatcgaa taaacatttg actacgagaa gcaatgattg gtccagttga    720
tacaccctga cagttactat gctcttgtat ttttattttg ttcctctaaa ctacccgctt    780
gttcctcgta ccttcttgct gaaagtaaag atctacactc aaaatgtaaa ttcttgaaaa    840
taaaataata acccaataaa accctctcta tattgctacc atacaccatc ttgcttcttg    900
gacctcgcct ccgaatttga tttggacatt attgcaatac aaatttatca ttatacccat    960
gatttttata cccttaccta ttacctactg ttacaataag aaaaattaat agtacacggt   1020
ctcaatagtc ttacagaaag gcttaaatta gcaaatgagt ctatccactg gactcagttt   1080
cactttgatc ctcaggatcc ttctcagagc ctcctcttct gttggtgtct ttacctagaa   1140
tgtcacacct gacttgtaac cgaatatcat ccaaagtgtt accttgtgag gtcattttga   1200
tattcaccca aaatccggag aggtgaccag aattgcttgg tttaaggctt acttttaatt   1260
gcccattttg cttgcatctg acacctctat atatgctaaa tttccagctg ctcccaaggc   1320
accctttgag atctagatat agccgagcac gggtatcctt cgtttgcata aaaaaatctt   1380
cttgttcgcg cttatgactc aataaatagc ttgcaagctt cctgcattgt ccagctgag    1440 ccttagcgga atctgggtca tcctgaagtg cggaaacaat cttatcaaat aactgtgagg   1500
atgtctctgg tgcctctggt gccctttgag cctcttgatc ttgaccagga atgcagatt    1560 gtgagttctg tacttccaca gaactgccct catcgtcgtc ccctcctccc tcatcaaaac   1620
cataatctgt ttcgttggtg atcatattac acaccatctc tcctacccag agctcccgga   1680
cattggcggc cataatttga agtttgaagg attgtcctaa cattgctttg gatgatacga   1740
```

```
ggatctcaac tttacacaaa ccaacctcga gatttcaac caatgtgcca ttatgaagtt    1800
tttcaaagaa tcgctgcaat cgaggccttg cattcacagg atcaaggaag ttctcattaa    1860
tcgttttggt gacaactcgt tccttcttct gttgacccaa aatttcgtct ttcctcgatt    1920
caggaatgct tacatcagga gcaattaact tatgaagcct ttcagcaaag tcttctttgt    1980
ctttatttgc aaagaactta tgttctttta ggcgcttaag gatagtattt aataccacat    2040
aaggctccgg ccattccaag ttcactggaa ttaccccgta tggtaacttt ttcattaggt    2100
atttcacata gaatattgct aagataggat agtctcggta attctcggct atgttgacca    2160
tacccttagc tgttgaaagc atattctgtg ctggtaggtg tataacagtg taaggatatg    2220
tcataagcac atcgttcatc attctcagct ctctatcggg tctggagtcc ctagcatcct    2280
gactagtaaa catatttaca acatcgccac ttataatcgc cgtttctaaa tgaaatcaga    2340
atccttatgc tttagatttg agaaagtctg agaaaatgat ctgggggatg ttccttttat    2400
atagtcggta cccgtagcat atgacagagt gagaattttg cagagaggat atcccctttt    2460
cgttttaaa cctcagaaaa gttttctttt gtccgcagag cgcacaggga gctcattttc    2520
gtacgtagat atcagaagag gttttcgcgg atagtgcttt ccattttgg atctactaag    2580
gcattgagca agttcattca taaaaccctc agcaaatatt tctgtatttg tgaagcctat    2640
agaagatcta gaactgtctg taaagctcat atggtattta tgtttattaa tagaactcac    2700
agtaaattaa agtgtgttta aagatcctac aaaatatgta atgctattct tagattccca    2760
cgagaggctt gcttttgtac atagaccctc cagaaaacat agtgctgttt atgcagcaca    2820
cagaaggttt ataggtgtga gctacacttt ataggccggg taagtatagt aagatatgtg    2880
caaattagcc gcggagccat aaacaatcat ctttttaaatt agatgcacag ccttaaacca    2940
agcaattctg gtcacctctc cggatttttgg gtgaatatca aaatgacctc acaaggtaac    3000
actttggatg atattcggtt acaagtcagg tgtgacattc taggtaaaga caccaacaga    3060
agaggaggct ctgagaagga tcctgaggat caaagtgaaa ctgagtccag tggatagact    3120
catttgctaa tttaagcctt tctgtaagac tattgagacc gtgtactatt aattttttctt    3180
attgtaacag taggtaatag gtaagggtat aaaaatcatg ggtataatga taaatttgta    3240
ttgcaataat gtccaaatca aattcggagg cgaggtccaa gaagcaagat ggtgtatggt    3300
agcaatatag agagggtttt attgggttat tattttattt tcaagaattt acattttgag    3360
tgtagatctt tactttcagc aagaaggtac gaggaacaag cgggtagttt agaggaacaa    3420
aataaaaata caagagcata gtaactgtca gggtgtatca actggaccaa tcattgcttc    3480
tcgtagtcaa atgtttattc gatagagtaa tggtttaatt tctgtagcaa ccgcctgcgc    3540
aggctcccctt ctgcgcggta cgggttgatg aaagaacgac ttgatgaaag aacgatttga    3600
tgaaagaacg aattaatgaa agaacgattt gatgaaagaa taacgtattc tttcatcaac    3660
gtccacagtg atatgatctc gcctagaaaa actaaattat attaagctaa actaaattat    3720
ttaggccata cccgctgccg cccttacaac tctatcatcg taactcgaca gatgcaatgc    3780
tctataaccc accgttatca ttatcattat cattacaatt aaccccgttc cacaacacaa    3840
cactccattc cacaataccc ctccacaatt cccgtccagt agctcaaatc tagtgtagaa    3900
tcttaaaaca ttgaatcata aatcgtatat cttacatgac attacattac attacattac    3960
gtgtatatca ttatccagcc tatttaagac gagtctcctg atatatcagg gcatctgttg    4020
aaagataatt cttgagagag caccaacgag cctgtatttg agcaagttac gtcaatgctt    4080
gaaatagagt ccgagtccgg tggtgtgttc ggaggatgtg aaggcttaat cttgtcagga    4140
```

```
ggtgtcagga ggtgtcgatg gatcgtccga cgacaatgct aatctttcgg cgcttcacat   4200
gtgccgctgt taacgcgtta taaagtgcag ttctcccatt atccggaaaa tctgggacgc   4260
ctcgggaact tcttgcttgt aacttatact ctttaccttc gttattcttg aacctggcat   4320
agctgctcaa aaaaaccaat acatccattg gtattatttc tgcattcttt ccataccgag   4380
ccatcaatgt ctcgatatct gatatcatag gaatattctt gtcttgttca caagggttgc   4440
tatttggatc aaccaactca cacgcccttt cggctgtgat attataaaac cccgatagaa   4500
acgcaaataa ataagaaggc ggactctttt ctatcgtgtg catgtatcga gccttagcca   4560
cacggctaac accttcttcc cgcgcggcag accaattacc atagagcgtg gcttctttat   4620
ccatctcatt atttgaaaga tatgaagctg tcacatgcct gcctaaatgc gctttcggtc   4680
cattgggtat tttaaagatg ctctcatccg attgtttaga gataaacccg tcatatgagc   4740
ctaacagact gttcctgaga agctggtaat catagcgtgc atcctcatca gtagttcgag   4800
ttttgggaat aggatctgtc cattggaggt atgaatctag tgccaacagc gggtcgcatc   4860
gtcctttaca agggaagaaa tagacaaaac gagtaccagt cttagtctct gggacaaaag   4920
cacgtagcat gcggccaagg tgcttgtctg gaataacttc aaatgtcttg atatcggtat   4980
tctttaagtc gtctgctcta caacaattca taaaagtcgc ctgaagcaaa agattgtacg   5040
cggcttttgt tgtaggccga gtagttctag cttctattaa gtccatagtc ttcccgacaa   5100
acccccaaat agtttcctgt gtttcagcga ttttagtgat ttcatcatta atcttgttac   5160
ccaaatctct tttccgacct gcttcctttc tcatatgtac agcagataaa tgactcatta   5220
catcatcagg cttttcgtgt acccccacaa caaatctata gggcgataca acatcttcga   5280 gtcctttat tagcttactt gggtctttca aatggtattc aaaggatacc gttttagtgg    5340
aagaatcgta ttgcaatgtt tttgaaatag acctctggta tttcaagaaa gtggagcgct   5400
tgacaggaac gtcctttctt ttctgactcg ccaaattggc catcaaaatt atcatcgtca   5460
gatgggaggc tagttttcc ttaggtaaag ggttctcatt ctccaaaatg tcttttattt    5520
tagagatctg gtgtaaggga aggatttgac taagctcgct gaagtctgac atttgtctat   5580
taattgttga aatttcagta tccttggtca attgcattca aatgcaatta atcgttgctg   5640
tgagcgctcg aattttttgc gtgccatgat gggccgcctc tatgaccctg atttacgaag   5700
aggaggaaat tcgtccacgg ccaaaaatga agctgtgaga aaaaaaaaaa catagtactg   5760
tagtatacca gctgggatta acaaaactaa aagggcagac tattgccaga tgcaaataca   5820
aaacagtatt agggccacac tggaatctaa tcatggctta ttagacgttg actatgtggc   5880
taacctgctc gaaaatttat tgagaacttg gaaacatggt aaacccacta ttaaagtcag   5940
ggaagctatt cagttagctc atgcaaaaag cattaaggta atttcattat ggcctcagga   6000
aacctgtagc ttccgaaatt ttgatggaaa tccagaagac gatccaaatg tgccctggct   6060
tgtaaggagg gagaattcgt cggggccttt cacacagccg ggatcagaaa cgtcttcctt   6120
ggaacagttg ctaaatggac tgggatgcat tgcacgtatt ctgcgggaga ataccaacac   6180
agtggaagct aggagagcga tagatgacca cttttgtaag attaaaaaac ctgcaaaact   6240
cacaatggtt g                                                       6251
```